(12) United States Patent
Boudreaux et al.

(10) Patent No.: US 11,291,444 B2
(45) Date of Patent: *Apr. 5, 2022

(54) SURGICAL STAPLING ASSEMBLY WITH CARTRIDGE BASED RETAINER CONFIGURED TO UNLOCK A CLOSURE LOCKOUT

(71) Applicant: Cilag GmbH International, Zug (CH)

(72) Inventors: Chad P. Boudreaux, Cincinnati, OH (US); Gregory J. Bakos, Mason, OH (US); Richard W. Timm, Cincinnati, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 23 days.

This patent is subject to a terminal disclaimer.

(21) Appl. No.: 16/453,289

(22) Filed: Jun. 26, 2019

(65) Prior Publication Data
US 2020/0261082 A1 Aug. 20, 2020

Related U.S. Application Data

(60) Provisional application No. 62/866,208, filed on Jun. 25, 2019, provisional application No. 62/807,310, (Continued)

(51) Int. Cl.
*A61B 17/072* (2006.01)
*A61B 34/30* (2016.01)
(Continued)

(52) U.S. Cl.
CPC ...... *A61B 17/07207* (2013.01); *A61B 17/068* (2013.01); *A61B 17/0684* (2013.01);
(Continued)

(58) Field of Classification Search
CPC .......... A61B 17/0684; A61B 17/07207; A61B 17/07257; A61B 17/07271; A61B 17/105;
(Continued)

(56) References Cited

U.S. PATENT DOCUMENTS 1,853,416 A 4/1932 Hall
2,222,125 A 11/1940 Stehlik
(Continued)

FOREIGN PATENT DOCUMENTS

AU 2015201140 A1 3/2015
CA 2795323 A1 5/2014
(Continued)

OTHER PUBLICATIONS

US 10,504,709 B2, 12/2019, Karancsi et al. (withdrawn)
(Continued)

*Primary Examiner* — Stephen F. Gerrity
*Assistant Examiner* — Linda J Hodge

(57) ABSTRACT

A surgical stapling assembly is disclosed that comprises a retainer that is configured to be removably mounted to a staple cartridge that is configured to be operably seated in a stapling device. The retainer comprises an authentication key that is configured to defeat a first jaw lockout of the stapling device that is configured to prevent the jaws of the stapling device from closing. The stapling device further comprises a second lockout that is configured to prevent a firing member of the stapling device from advancing through a staple firing stroke when a spent staple cartridge is seated in one of the jaws.

25 Claims, 82 Drawing Sheets

Related U.S. Application Data filed on Feb. 19, 2019, provisional application No. 62/807,319, filed on Feb. 19, 2019, provisional application No. 62/807,309, filed on Feb. 19, 2019.

(51) Int. Cl.

| | |
|---|---|
| *A61B 17/068* | (2006.01) |
| *A61B 50/00* | (2016.01) |
| *A61B 50/20* | (2016.01) |
| *A61B 90/00* | (2016.01) |
| *A61B 17/29* | (2006.01) |
| *A61B 17/00* | (2006.01) |

(52) U.S. Cl.
CPC ............ *A61B 17/072* (2013.01); *A61B 17/29* (2013.01); *A61B 34/30* (2016.02); *A61B 50/00* (2016.02); *A61B 50/20* (2016.02); *A61B 90/06* (2016.02); *A61B 90/08* (2016.02); *A61B 2017/00017* (2013.01); *A61B 2017/00039* (2013.01); *A61B 2017/00389* (2013.01); *A61B 2017/00398* (2013.01); *A61B 2017/00477* (2013.01); *A61B 2017/00482* (2013.01); *A61B 2017/00734* (2013.01); *A61B 2017/00876* (2013.01); *A61B 2017/00982* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2926* (2013.01); *A61B 2050/007* (2016.02); *A61B 2090/067* (2016.02); *A61B 2090/0808* (2016.02); *A61B 2090/0811* (2016.02); *A61B 2090/0814* (2016.02)

(58) Field of Classification Search
CPC ......... A61B 17/115; A61B 34/32; B25C 5/00; B25C 5/1637
USPC ............................... 227/176.1, 180.1, 175.1
See application file for complete search history.

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |
| 4,202,722 A | 5/1980 | Paquin |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,849,752 A | 7/1989 | Bryant |
| D303,787 S | 10/1989 | Messenger et al. |
| 4,892,244 A | 1/1990 | Fox et al. |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,766,186 A | 6/1998 | Faraz et al. |
| 5,769,791 A | 6/1998 | Benaron et al. |
| 5,775,331 A | 7/1998 | Raymond et al. |

(56) References Cited

U.S. PATENT DOCUMENTS

| | | |
|---|---|---|
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |

(56) References Cited

U.S. PATENT DOCUMENTS

| | | |
|---|---|---|
| 7,407,074 B2 | 8/2008 | Ortiz et al. |
| 7,408,439 B2 | 8/2008 | Wang et al. |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,951,148 B2 | 5/2011 | McClurken |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |

(56) References Cited

U.S. PATENT DOCUMENTS

| | | |
|---|---|---|
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| D687,146 S | 7/2013 | Juzkiw et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |

(56) References Cited

U.S. PATENT DOCUMENTS

| | | |
|---|---|---|
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,429 B2 | 2/2016 | St. Pierre et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | Von Grvon Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Durie |
| 9,364,231 B2 | 6/2016 | Wenchell |

(56) References Cited

U.S. PATENT DOCUMENTS

| | | |
|---|---|---|
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 * | 7/2016 | Aronhalt .......... A61B 17/07292 |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,563 B2 | 9/2017 | Shikhman et al. |
| 9,753,135 B2 | 9/2017 | Bosch |
| 9,753,568 B2 | 9/2017 | McMillen |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |

(56) References Cited

U.S. PATENT DOCUMENTS

| | | |
|---|---|---|
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondon et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |

(56) References Cited

U.S. PATENT DOCUMENTS

| | | |
|---|---|---|
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonitas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |

(56) References Cited

U.S. PATENT DOCUMENTS

| | | |
|---|---|---|
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |

(56) References Cited

U.S. PATENT DOCUMENTS

| | | |
|---|---|---|
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,454 B2 | 10/2020 | Kopp |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,580 B2 | 2/2021 | Green et al. |
| 10,912,619 B2 | 2/2021 | Jarc et al. |

(56) References Cited

U.S. PATENT DOCUMENTS

| | | |
|---|---|---|
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,705 B2 | 3/2021 | Muhsin et al. |
| 10,932,772 B2 | 3/2021 | Shelton, IV et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,950,982 B2 | 3/2021 | Regnier et al. |
| 10,952,708 B2 | 3/2021 | Scheib et al. |
| 10,954,935 B2 | 3/2021 | O'Shea et al. |
| 11,000,276 B2 | 5/2021 | Shelton, IV et al. |
| 11,051,817 B2 | 7/2021 | Shelton, IV et al. |
| 11,058,501 B2 | 7/2021 | Tokarchuk et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2003/0009111 A1 | 1/2003 | Cory et al. |
| 2003/0018329 A1 | 1/2003 | Hooven |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0078236 A1 | 4/2004 | Stoodley et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0192633 A1 | 9/2005 | Montpetit |
| 2005/0203384 A1 | 9/2005 | Sati et al. |
| 2005/0203504 A1 | 9/2005 | Wham et al. |
| 2005/0222631 A1 | 10/2005 | Dalal et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0049947 A1 | 3/2007 | Menn et al. |
| 2007/0078678 A1 | 4/2007 | DiSilvestro et al. |
| 2007/0084896 A1 | 4/2007 | Doll et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0191713 A1 | 8/2007 | Eichmann et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0299214 A1 | 12/2009 | Wu et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0292535 A1 | 11/2010 | Paskar |
| 2010/0292684 A1 | 11/2010 | Cybulski et al. |
| 2011/0022032 A1 | 1/2011 | Zemlok et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |

(56) References Cited

U.S. PATENT DOCUMENTS

| | | |
|---|---|---|
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0264000 A1 | 10/2011 | Paul et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203785 A1 | 8/2012 | Awada |
| 2012/0211542 A1 | 8/2012 | Racenet |
| 2012/0245958 A1 | 9/2012 | Lawrence et al. |
| 2012/0253329 A1 | 10/2012 | Zemlok et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0144284 A1 | 6/2013 | Behnke, II et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William et al. |
| 2014/0148729 A1 | 5/2014 | Schmitz et al. |
| 2014/0166724 A1 | 6/2014 | Schellin et al. |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0276749 A1 | 9/2014 | Johnson |
| 2014/0303660 A1 | 10/2014 | Boyden et al. |
| 2014/0303990 A1 | 10/2014 | Schoenefeld et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051617 A1 | 2/2015 | Takemura et al. |
| 2015/0053737 A1 | 2/2015 | Leimbach et al. |
| 2015/0057675 A1 | 2/2015 | Akeel et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0133945 A1 | 5/2015 | Dushyant et al. |
| 2015/0140982 A1 | 5/2015 | Postrel |
| 2015/0145682 A1 | 5/2015 | Harris |
| 2015/0148830 A1 | 5/2015 | Stulen et al. |
| 2015/0173673 A1 | 6/2015 | Toth et al. |
| 2015/0173756 A1 | 6/2015 | Baxter, III et al. |
| 2015/0196295 A1 | 7/2015 | Shelton, IV et al. |
| 2015/0199109 A1 | 7/2015 | Lee |
| 2015/0208934 A1 | 7/2015 | Sztrubel et al. |
| 2015/0237502 A1 | 8/2015 | Schmidt et al. |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272576 A1* | 10/2015 | Cappola ............... A61B 17/072 227/175.2 |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0289874 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0158468 A1 | 6/2016 | Tang et al. |
| 2016/0174998 A1 | 6/2016 | Lal et al. |
| 2016/0180045 A1 | 6/2016 | Syed |
| 2016/0184054 A1 | 6/2016 | Lowe |
| 2016/0192960 A1 | 7/2016 | Bueno et al. |

(56) References Cited

U.S. PATENT DOCUMENTS

| | | |
|---|---|---|
| 2016/0206202 A1 | 7/2016 | Frangioni |
| 2016/0224760 A1 | 8/2016 | Petak et al. |
| 2016/0225551 A1 | 8/2016 | Shedletsky |
| 2016/0228204 A1 | 8/2016 | Quaid et al. |
| 2016/0235303 A1 | 8/2016 | Fleming et al. |
| 2016/0249910 A1 | 9/2016 | Shelton, IV et al. |
| 2016/0249929 A1* | 9/2016 | Cappola ............... A61B 17/068 227/176.1 |
| 2016/0278841 A1 | 9/2016 | Panescu et al. |
| 2016/0287312 A1 | 10/2016 | Tegg et al. |
| 2016/0287912 A1 | 10/2016 | Warnking |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0361070 A1 | 12/2016 | Ardel et al. |
| 2016/0367305 A1 | 12/2016 | Hareland |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0312456 A1 | 11/2017 | Phillips |
| 2017/0325813 A1 | 11/2017 | Aranyi et al. |
| 2017/0325876 A1 | 11/2017 | Nakadate et al. |
| 2017/0325878 A1 | 11/2017 | Messerly et al. |
| 2017/0360439 A1 | 12/2017 | Chen et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0042659 A1 | 2/2018 | Rupp et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168606 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168621 A1 | 6/2018 | Shelton, IV et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0177383 A1 | 6/2018 | Noonan et al. |
| 2018/0206884 A1 | 7/2018 | Beaupre |
| 2018/0206905 A1 | 7/2018 | Batchelor et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0296286 A1 | 10/2018 | Peine et al. |

(56) References Cited

U.S. PATENT DOCUMENTS

| | | |
|---|---|---|
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0315492 A1 | 11/2018 | Bishop et al. |
| 2018/0333207 A1 | 11/2018 | Moctezuma De la Barrera |
| 2018/0351987 A1 | 12/2018 | Patel et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000478 A1 | 1/2019 | Messerly et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125384 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159777 A1 | 5/2019 | Ehrenfels et al. |
| 2019/0159778 A1 | 5/2019 | Shelton, IV et al. |
| 2019/0167296 A1 | 6/2019 | Tsubuku et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |

(56) References Cited

U.S. PATENT DOCUMENTS

| | | |
|---|---|---|
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cut et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0214699 A1 | 7/2020 | Shelton, IV et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |

(56) References Cited

U.S. PATENT DOCUMENTS

| | | | |
|---|---|---|---|
| 2020/0305945 A1 | 10/2020 | Morgan et al. | |
| 2020/0314569 A1 | 10/2020 | Morgan et al. | |
| 2020/0405375 A1 | 12/2020 | Shelton, IV et al. | |
| 2021/0000555 A1 | 1/2021 | Shelton, IV et al. | |
| 2021/0007760 A1 | 1/2021 | Reisin | |
| 2021/0015568 A1 | 1/2021 | Liao et al. | |
| 2021/0022731 A1 | 1/2021 | Eisinger | |
| 2021/0022738 A1 | 1/2021 | Weir et al. | |
| 2021/0022809 A1 | 1/2021 | Crawford et al. | |
| 2021/0059674 A1 | 3/2021 | Shelton, IV et al. | |
| 2021/0068834 A1 | 3/2021 | Shelton, IV et al. | |
| 2021/0128149 A1 | 5/2021 | Whitfield et al. | |
| 2021/0153889 A1 | 5/2021 | Nott et al. | |
| 2021/0169516 A1 | 6/2021 | Houser et al. | |
| 2021/0176179 A1 | 6/2021 | Shelton, IV | |
| 2021/0177452 A1 | 6/2021 | Nott et al. | |
| 2021/0177489 A1 | 6/2021 | Yates et al. | |
| 2021/0192914 A1 | 6/2021 | Shelton, IV et al. | |
| 2021/0201646 A1 | 7/2021 | Shelton, IV et al. | |
| 2021/0205020 A1 | 7/2021 | Shelton, IV et al. | |
| 2021/0205021 A1 | 7/2021 | Shelton, IV et al. | |
| 2021/0205028 A1 | 7/2021 | Shelton, IV et al. | |
| 2021/0205029 A1 | 7/2021 | Wiener et al. | |
| 2021/0205030 A1 | 7/2021 | Shelton, IV et al. | |
| 2021/0205031 A1 | 7/2021 | Shelton, IV et al. | |
| 2021/0212602 A1 | 7/2021 | Shelton, IV et al. | |
| 2021/0212694 A1 | 7/2021 | Shelton, IV et al. | |
| 2021/0212717 A1 | 7/2021 | Yates et al. | |
| 2021/0212719 A1 | 7/2021 | Houser et al. | |
| 2021/0212770 A1 | 7/2021 | Messerly et al. | |
| 2021/0212771 A1 | 7/2021 | Shelton, IV et al. | |
| 2021/0212774 A1 | 7/2021 | Shelton, IV et al. | |
| 2021/0212775 A1 | 7/2021 | Shelton, IV et al. | |
| 2021/0212782 A1 | 7/2021 | Shelton, IV et al. | |
| 2021/0219976 A1 | 7/2021 | DiNardo et al. | |
| 2021/0220058 A1 | 7/2021 | Messerly et al. | |
| 2021/0240852 A1 | 8/2021 | Shelton, IV et al. | |
| 2021/0241898 A1 | 8/2021 | Shelton, IV et al. | |
| 2021/0249125 A1 | 8/2021 | Morgan et al. | |
| 2021/0251487 A1 | 8/2021 | Shelton, IV et al. | |
| 2021/0259697 A1 | 8/2021 | Shelton, IV et al. | |
| 2021/0259698 A1 | 8/2021 | Shelton, IV et al. | |
| 2021/0282780 A1 | 9/2021 | Shelton, IV et al. | |
| 2021/0282781 A1 | 9/2021 | Shelton, IV et al. | |
| 2021/0315579 A1 | 10/2021 | Shelton, IV et al. | |
| 2021/0315580 A1 | 10/2021 | Shelton, IV et al. | |
| 2021/0315581 A1 | 10/2021 | Shelton, IV et al. | |
| 2021/0315582 A1 | 10/2021 | Shelton, IV et al. | |
| 2021/0322014 A1 | 10/2021 | Shelton, IV et al. | |
| 2021/0322015 A1 | 10/2021 | Shelton, IV et al. | |
| 2021/0322017 A1 | 10/2021 | Shelton, IV et al. | |
| 2021/0322018 A1 | 10/2021 | Shelton, IV et al. | |
| 2021/0322019 A1 | 10/2021 | Shelton, IV et al. | |
| 2021/0322020 A1 | 10/2021 | Shelton, IV et al. | |

FOREIGN PATENT DOCUMENTS

| | | | |
|---|---|---|---|
| CN | 101617950 A | 1/2010 | |
| CN | 104490448 B | 3/2017 | |
| CN | 206097107 U | 4/2017 | |
| CN | 108652695 A | 10/2018 | |
| DE | 2037167 A1 | 7/1980 | |
| DE | 3016131 A1 | 10/1981 | |
| DE | 3824913 A1 | 2/1990 | |
| DE | 4002843 C1 | 4/1991 | |
| DE | 102005051367 A1 | 4/2007 | |
| DE | 102016207666 A1 | 11/2017 | |
| EP | 0000756 B1 | 10/1981 | |
| EP | 0408160 A1 | 1/1991 | |
| EP | 0473987 A1 | 3/1992 | |
| EP | 0929263 B1 | 7/1999 | |
| EP | 1214913 A2 | 6/2002 | |
| EP | 2732772 A1 | 5/2014 | |
| EP | 2774550 A2 * | 9/2014 | ......... A61B 17/0682 |
| EP | 2942023 A2 | 11/2015 | |
| EP | 3047806 A1 | 7/2016 | |
| EP | 3056923 A1 | 8/2016 | |
| EP | 3095399 A2 | 11/2016 | |
| EP | 3120781 A2 | 1/2017 | |
| EP | 3135225 A2 | 3/2017 | |
| EP | 3141181 A1 | 3/2017 | |
| FR | 2838234 A1 | 10/2003 | |
| GB | 2509523 A | 7/2014 | |
| JP | S5373315 A | 6/1978 | |
| JP | 2001029353 A | 2/2001 | |
| JP | 2007123394 A | 5/2007 | |
| JP | 2017513561 A | 6/2017 | |
| KR | 20140104587 A | 8/2014 | |
| KR | 101587721 B1 | 1/2016 | |
| WO | WO-9734533 A1 | 9/1997 | |
| WO | WO-0024322 A1 | 5/2000 | |
| WO | WO-0108578 A1 | 2/2001 | |
| WO | WO-0112089 A1 | 2/2001 | |
| WO | WO-0120892 A2 | 3/2001 | |
| WO | WO-03079909 A2 | 10/2003 | |
| WO | WO-2007137304 A2 | 11/2007 | |
| WO | WO-2008053485 A1 | 5/2008 | |
| WO | WO-2008056618 A2 | 5/2008 | |
| WO | WO-2008069816 A1 | 6/2008 | |
| WO | WO-2008147555 A2 | 12/2008 | |
| WO | WO-2011112931 A1 | 9/2011 | |
| WO | WO-2013143573 A1 | 10/2013 | |
| WO | WO-2014031800 A1 | 2/2014 | |
| WO | WO-2014071184 A1 | 5/2014 | |
| WO | WO-2014134196 A1 | 9/2014 | |
| WO | WO-2015129395 A1 | 9/2015 | |
| WO | WO-2016100719 A1 | 6/2016 | |
| WO | WO-2016206015 A1 | 12/2016 | |
| WO | WO-2017011382 A1 | 1/2017 | |
| WO | WO-2017011646 A1 | 1/2017 | |
| WO | WO-2017058617 | 4/2017 | |
| WO | WO-2017058695 A1 | 4/2017 | |
| WO | WO-2017151996 A1 | 9/2017 | |
| WO | WO-2017189317 A1 | 11/2017 | |
| WO | WO-2017205308 A1 | 11/2017 | |
| WO | WO-2017210499 A1 | 12/2017 | |
| WO | WO-2017210501 A1 | 12/2017 | |
| WO | WO-2018116247 A1 | 6/2018 | |
| WO | WO-2018152141 A1 | 8/2018 | |
| WO | WO-2018176414 A1 | 10/2018 | |

OTHER PUBLICATIONS

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Slocinski et al., "Distance measure for impedance spectra for quantified evaluations," Lecture Notes on Impedance Spectroscopy, vol. 3, Taylor and Francis Group (Jul. 2012)—Book Not Attached.

Zoccali, Bruno, "A Method for Approximating Component Temperatures at Altitude Conditions Based on CFD Analysis at Sea Level Conditions," (white paper), www.tdmginc.com, Decembers, 2018 (9 pages).

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

(56) References Cited

OTHER PUBLICATIONS

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.
Benkmann et al., "Concept of iterative optimization of minimally invasive surgery," 2017 22nd International Conference on Methods and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIII, pp. 1-10, Jul. 12, 2017.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trend-based methods," Computers in Biology and Medic, New York, NY, vol. 27, No. 5, pp. 389-409 (1997).
Stacey et al., "Temporal abstraction in intelligent clinical data analysis: A survey," Artificial Intelligence in Medicine, vol. 39, No. 1, pp. 1-24 (2006).
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.
Hsiao-Wei Tang, "ARCM", Video, Sep. 2012, YouTube, 5 screenshots, Retrieved from Internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
IEEE Std No. 177, "Standard Definitions and Methods of Measurement for Piezoelectric Vibrators," published May 1966, The Institute of Electrical and Electronics Engineers, Inc., New York, N.Y.
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Phumzile Malindi, "5. QoS in Telemedicine," "Telemedicine," Jun. 20, 2011, IntechOpen, pp. 119-138.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas forTM0n0 operating mode,"Article, Oct. 8, 2010, pp. 1-9, Microwave Journal.
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgicai_devices.pdf.
Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).

(56) References Cited

OTHER PUBLICATIONS

Nabil Simaan et al., "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

\* cited by examiner

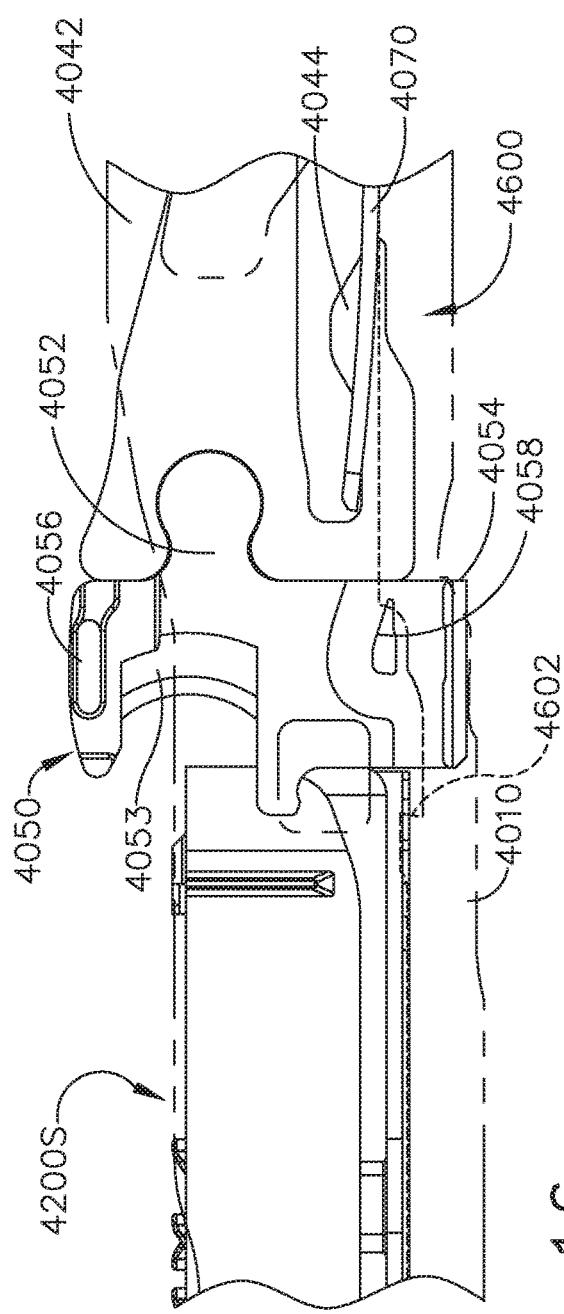
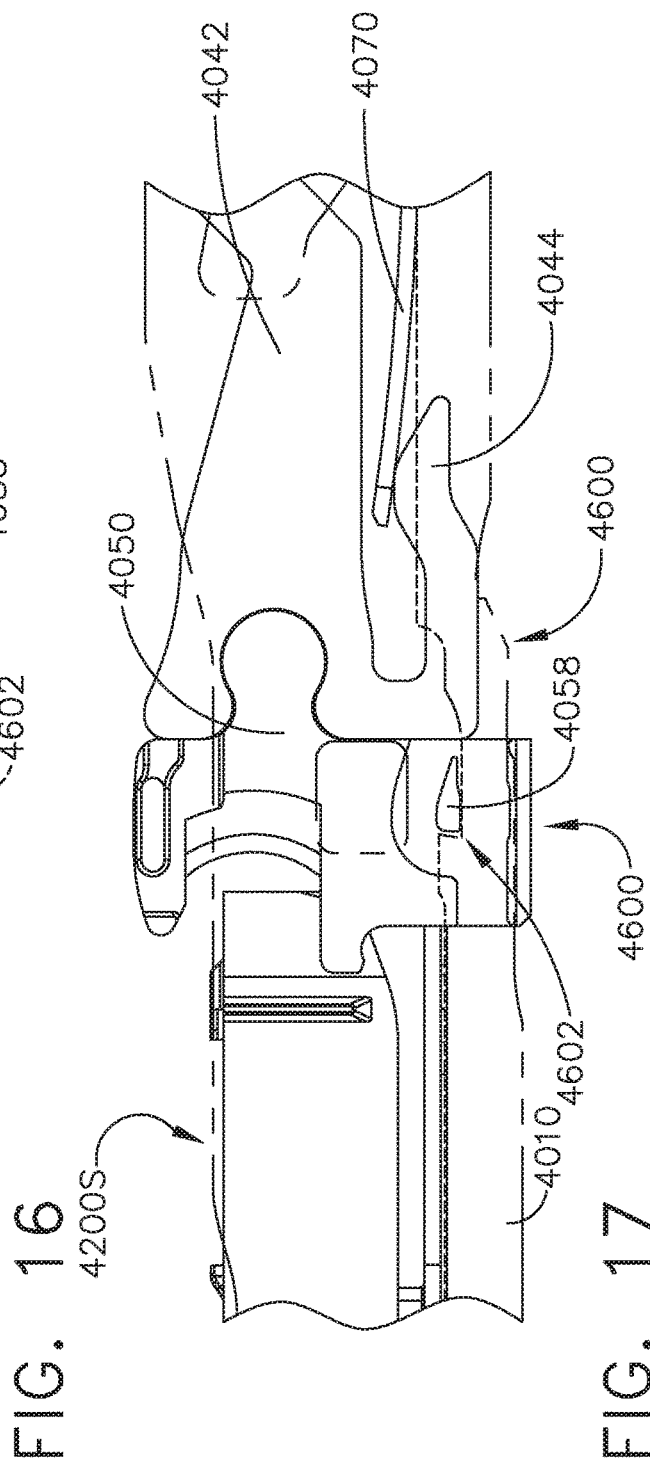
FIG. 16
FIG. 17

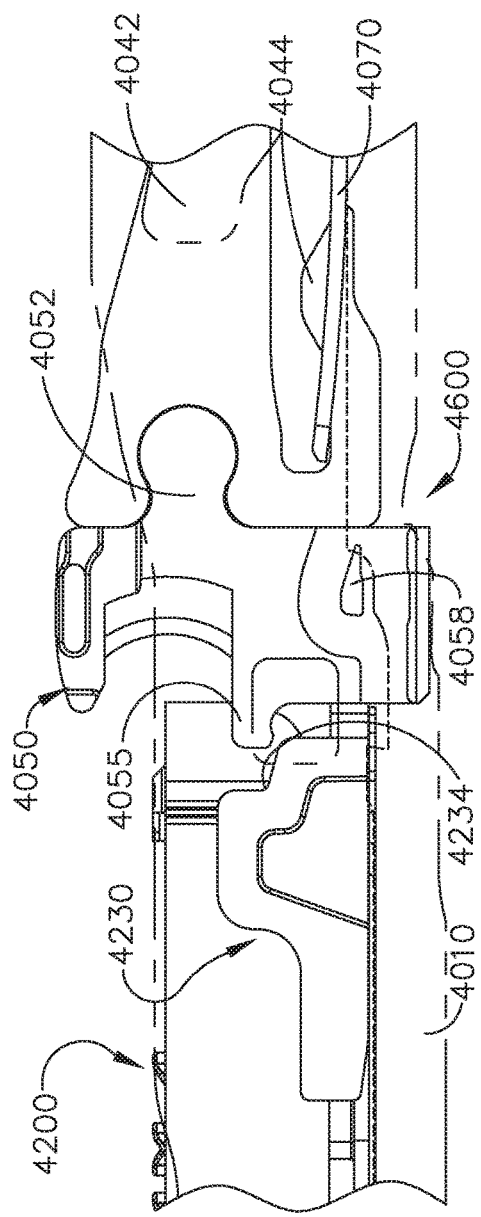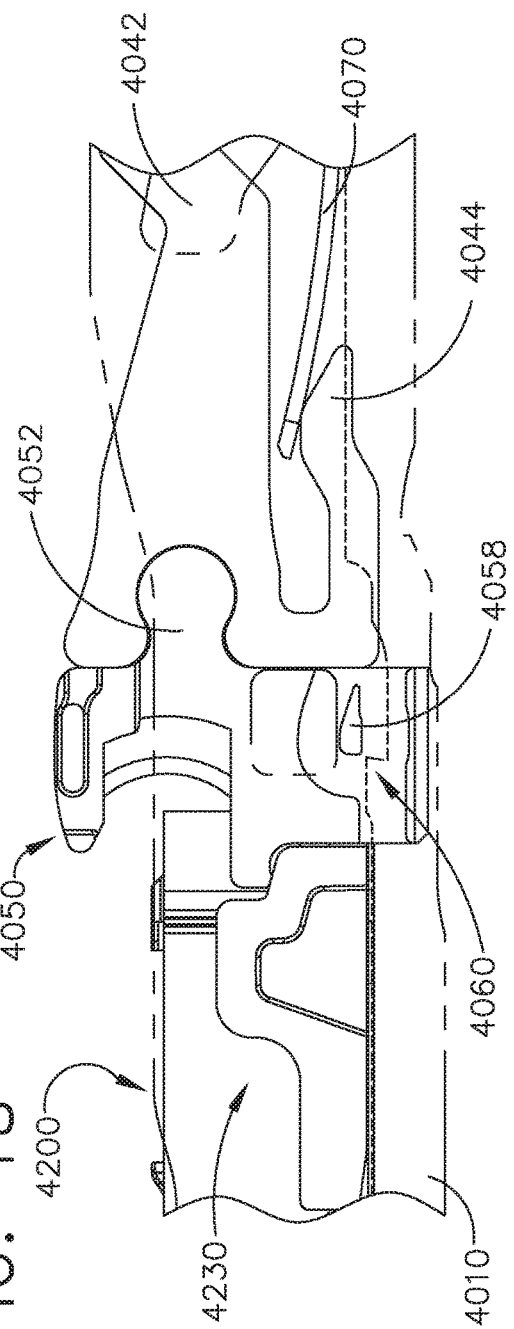

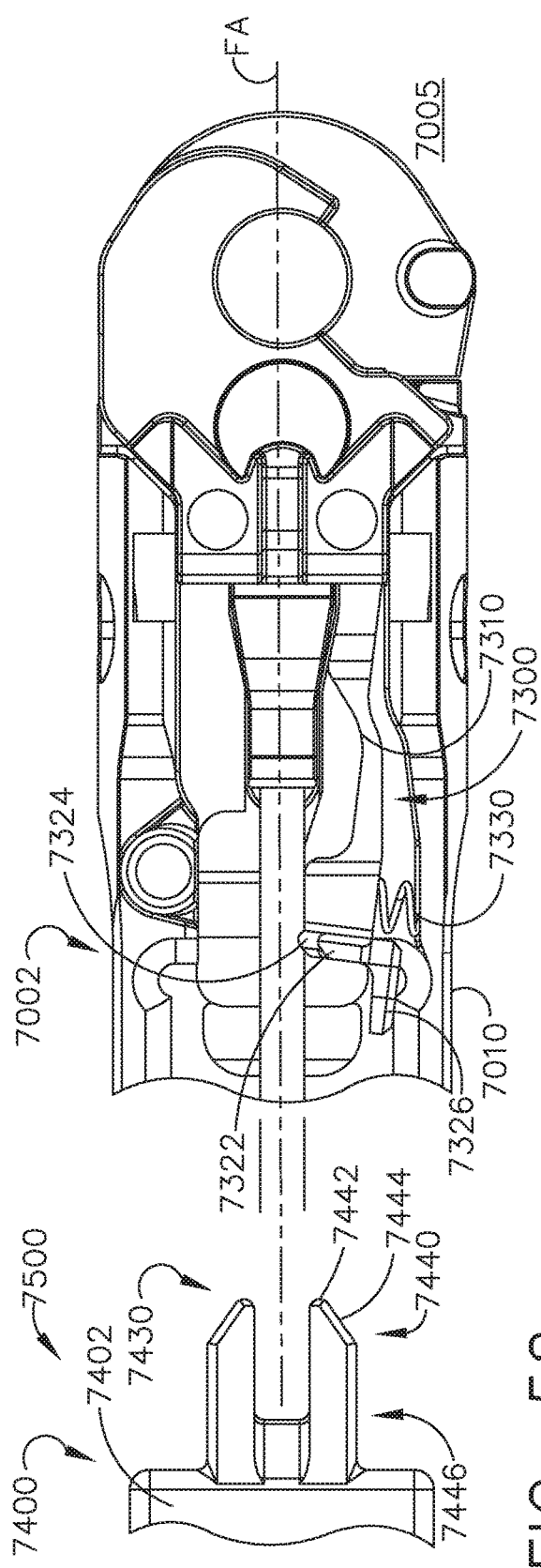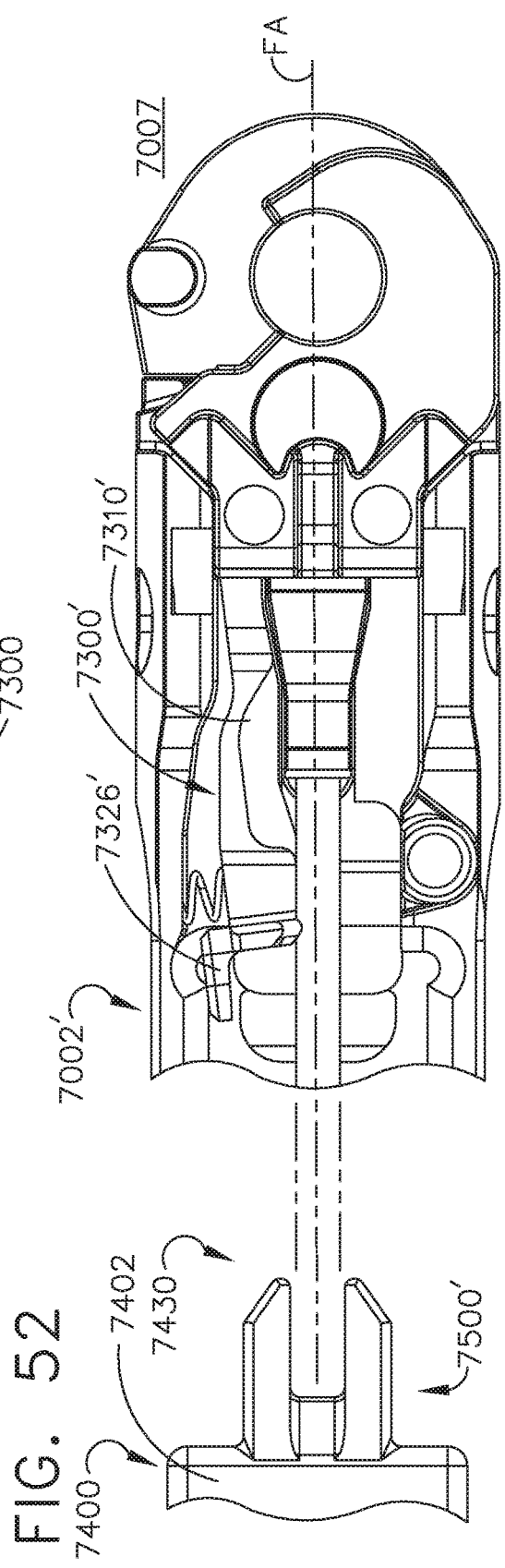

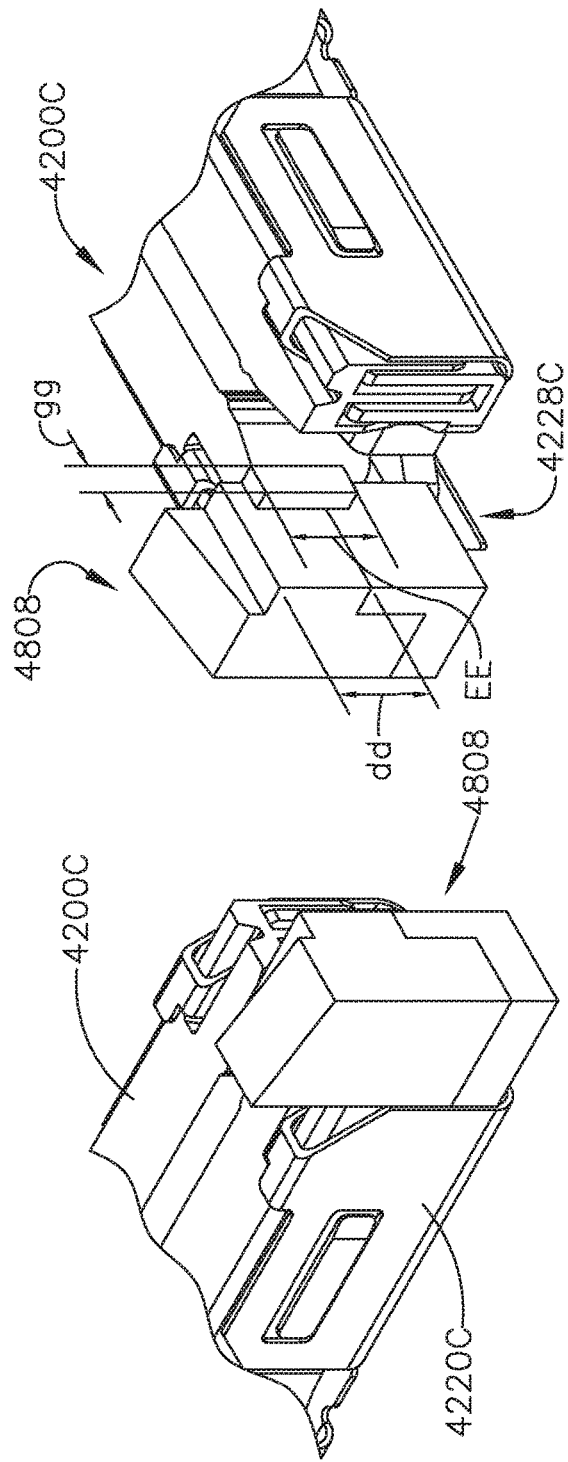
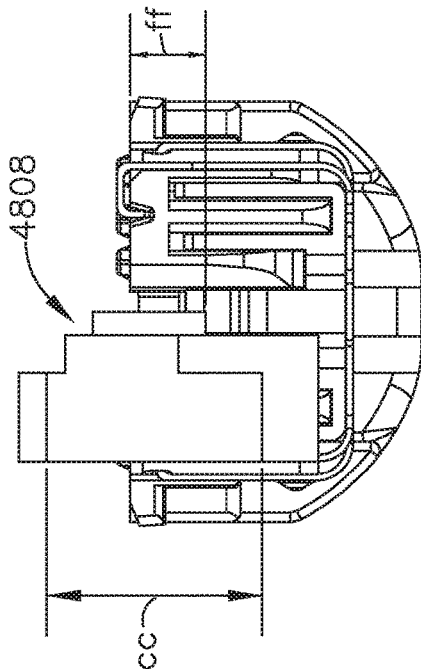
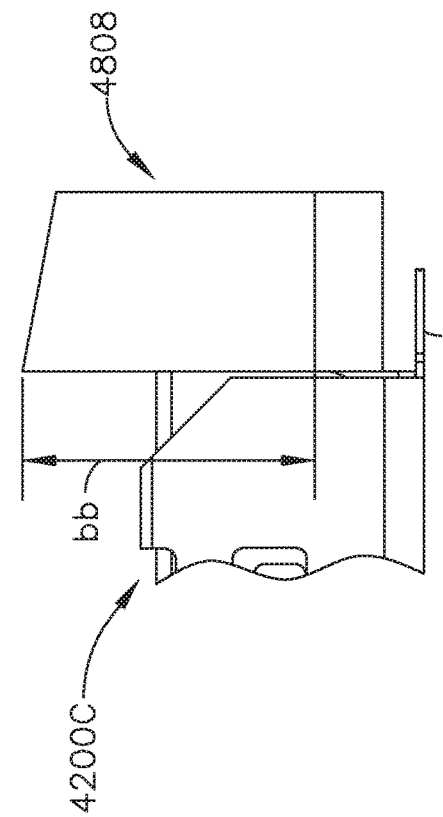

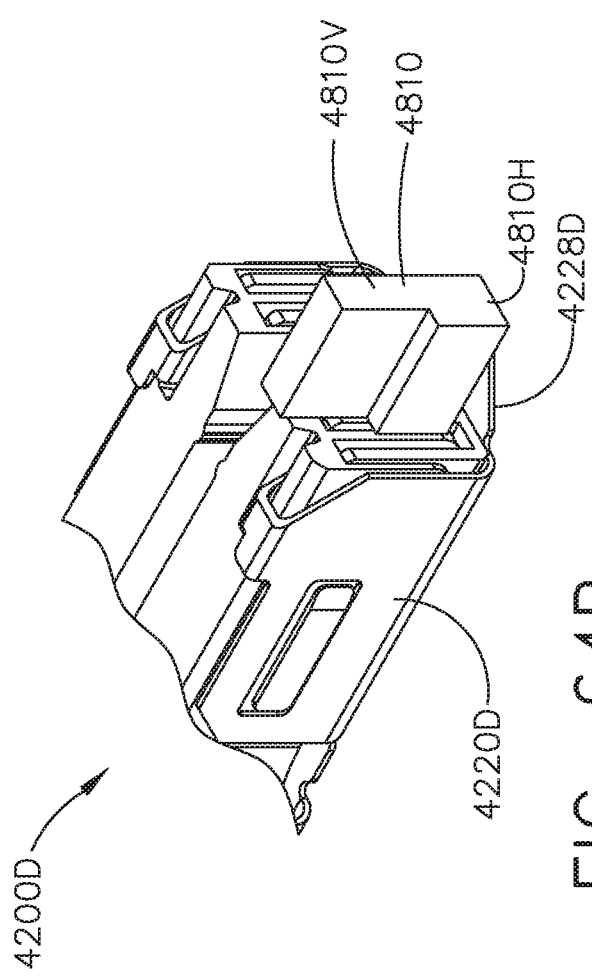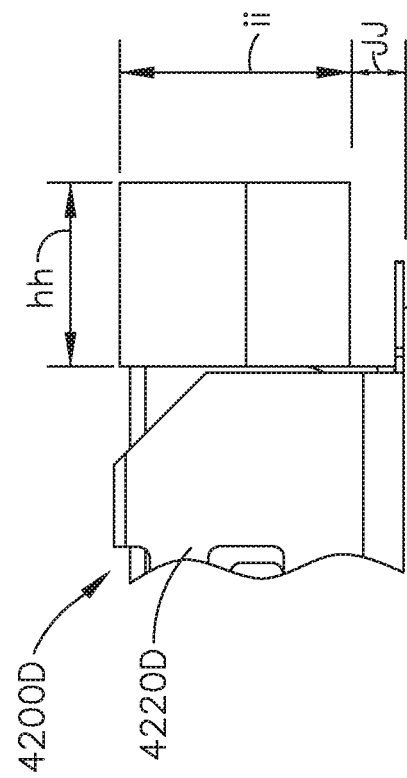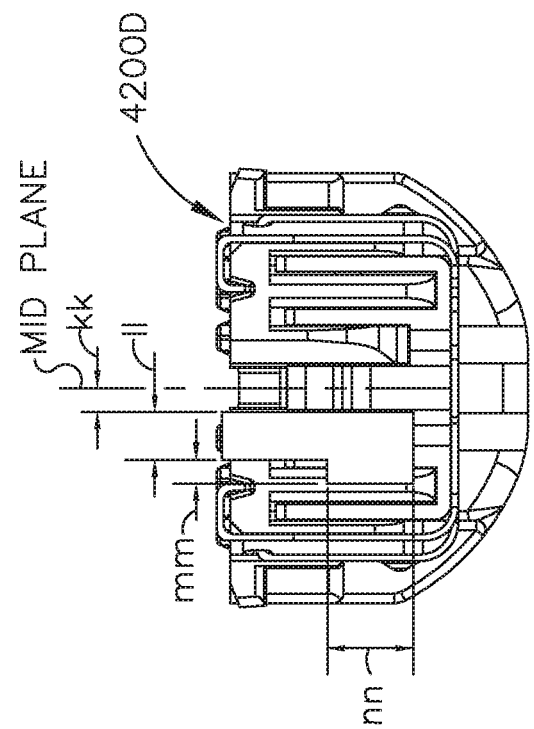
FIG. 64R
FIG. 64S
FIG. 64T

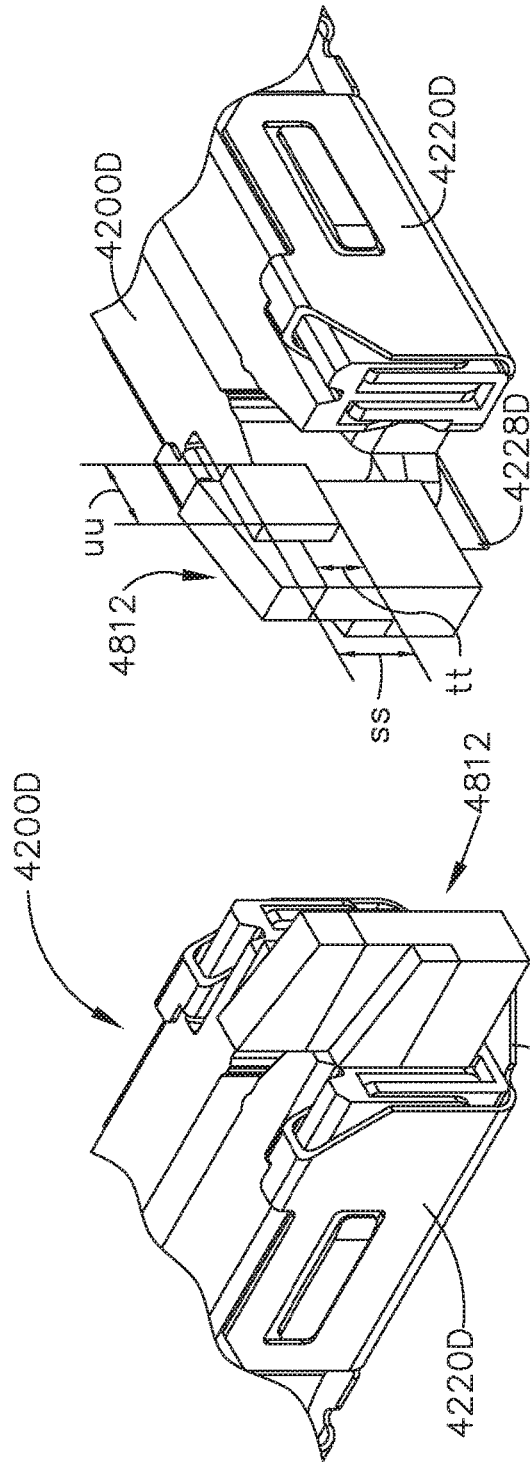
FIG. 64U
FIG. 64W
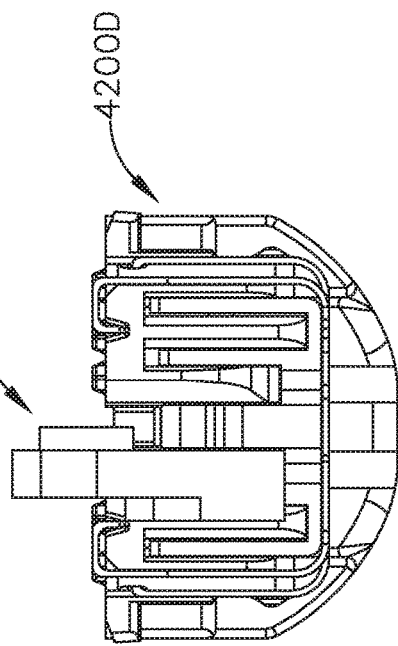
FIG. 64X
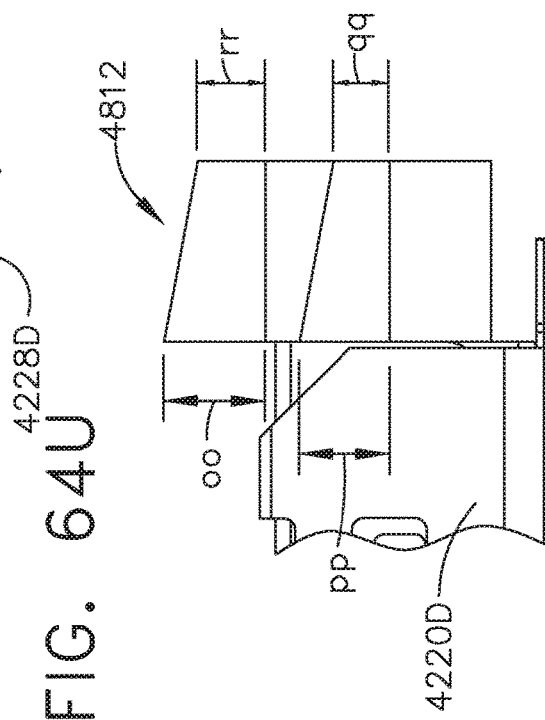
FIG. 64V

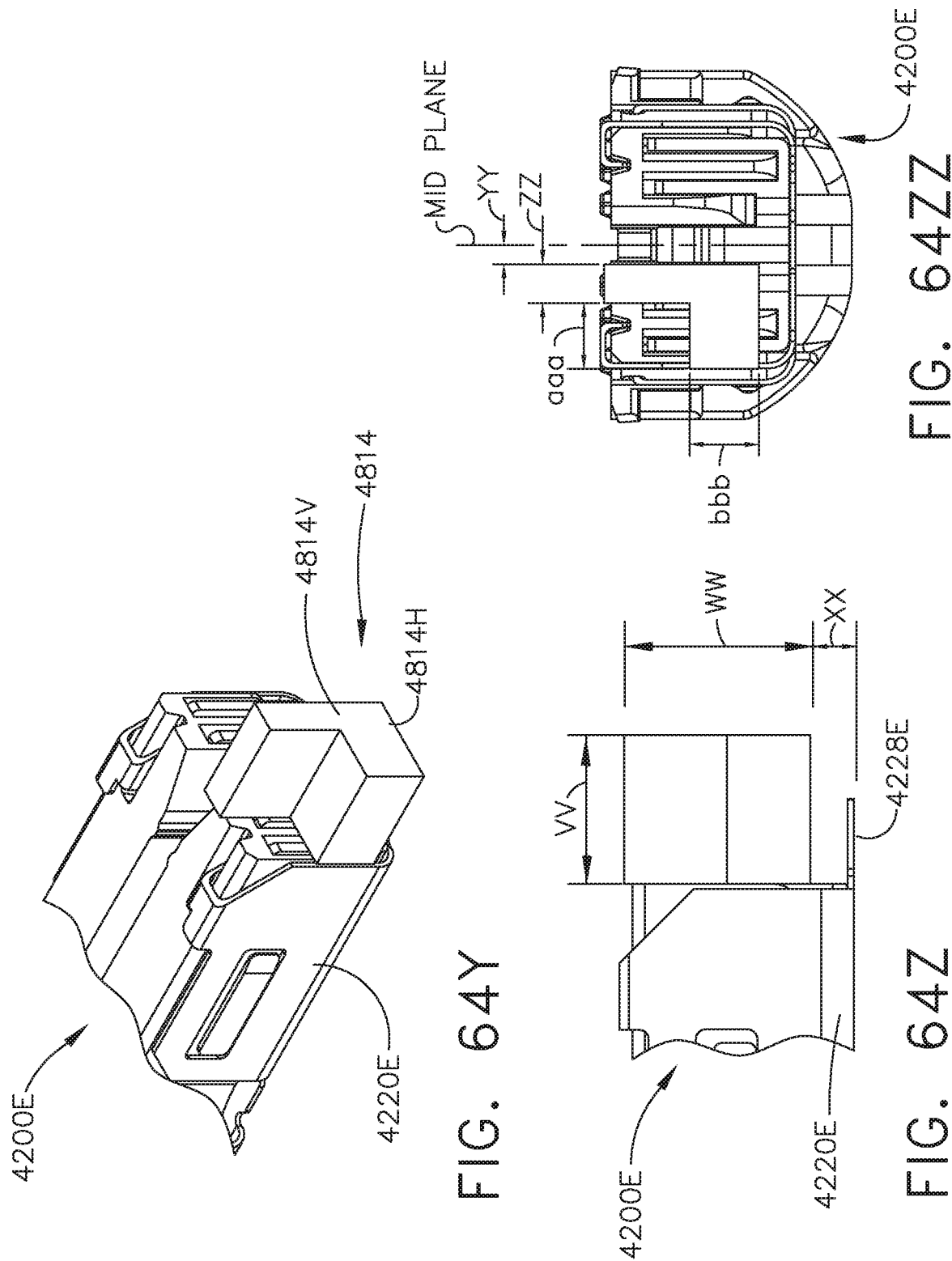

SURGICAL STAPLING ASSEMBLY WITH CARTRIDGE BASED RETAINER CONFIGURED TO UNLOCK A CLOSURE LOCKOUT

CROSS-REFERENCE TO RELATED APPLICATIONS

This application claims the benefit of U.S. Provisional Patent Application Ser. No. 62/866,208, entitled STAPLE CARTRIDGES WITH FEATURES FOR DEFEATING LOCKOUTS IN SURGICAL STAPLING DEVICES, filed Jun. 25, 2019, of U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS, filed Feb. 19, 2019, of U.S. Provisional Patent Application Ser. No. 62/807,319, entitled SURGICAL STAPLING DEVICES WITH IMPROVED LOCKOUT SYSTEMS, filed Feb. 19, 2019, and of U.S. Provisional Patent Application Ser. No. 62/807,309, entitled SURGICAL STAPLING DEVICES WITH IMPROVED ROTARY DRIVEN CLOSURE SYSTEMS, filed Feb. 19, 2019, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 16 is a side elevational view of a portion of the surgical stapling device of FIG. 6 with a spent staple cartridge seated in the first jaw and the firing member in a starting position;

FIG. 17 is another side elevational view of the surgical stapling device and spent staple cartridge of FIG. 16 showing a second firing member lockout in a locked position, wherein the firing member is prevented from moving distally during a staple firing stroke;

FIG. 18 is a side elevational view of a portion of the surgical stapling device of FIG. 6 with an unfired staple cartridge seated in the first jaw and the firing member in a starting position;

FIG. 19 is another side elevational view of the surgical stapling device and unfired staple cartridge of FIG. 18 showing the second firing member lockout in an unlocked position, wherein a sled in the staple cartridge is in unlocking engagement with the firing member;

FIG. 52 is another top view of the surgical stapling device of FIG. 49 illustrating an initial insertion of a cartridge assembly comprising a retainer attached to a staple cartridge into the surgical stapling device;

FIG. 56 is a top view of another surgical stapling device wherein a first lockout arm is supported in an opposite side of the surgical stapling device and during an initial insertion of the cartridge assembly of FIG. 52 therein;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
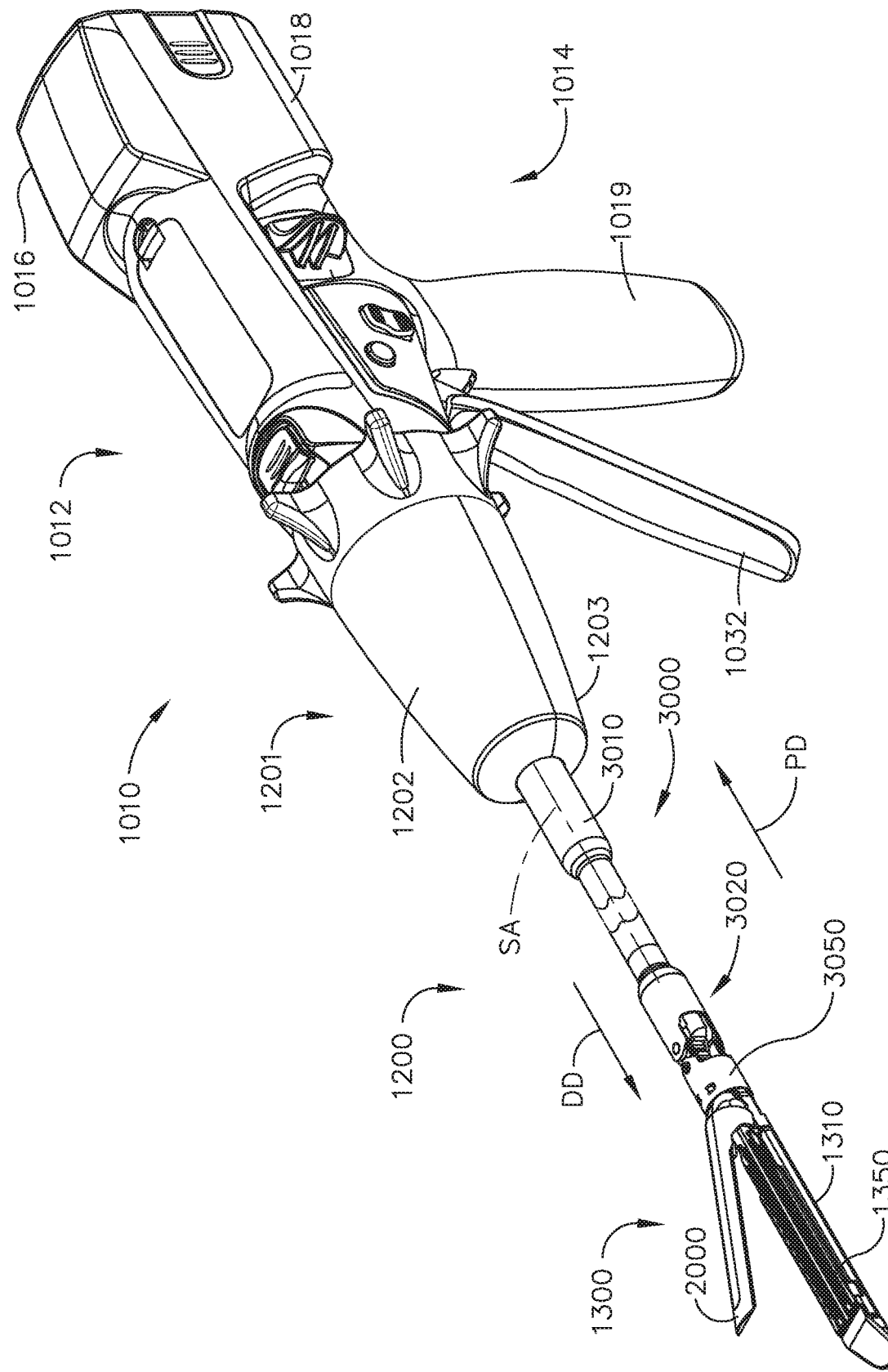
FIG. 1 is a perspective view of a powered surgical stapling system.

Applicant of the present application owns the following U.S. Patent Applications that were filed on Jun. 26, 2019 and which are each herein incorporated by reference in their respective entireties:

U.S. patent application Ser. No. 16/453,273, entitled METHOD FOR PROVIDING AN AUTHENTICATION LOCKOUT IN A SURGICAL STAPLER WITH A REPLACEABLE CARTRIDGE, now U.S. Patent Application Publication No. 2020-0261080;

U.S. patent application Ser. No. 16/453,283, entitled SURGICAL STAPLING ASSEMBLY WITH CARTRIDGE BASED RETAINER CONFIGURED TO UNLOCK A FIRING LOCKOUT; now U.S. Patent Application Publication No. 2020-0261081;

U.S. patent application Ser. No. 16/453,302, entitled UNIVERSAL CARTRIDGE BASED KEY FEATURE THAT UNLOCKS MULTIPLE LOCKOUT ARRANGEMENTS IN DIFFERENT SURGICAL STAPLERS, now U.S. Patent Application Publication No. 2020-0261075

U.S. patent application Ser. No. 16/453,310, entitled STAPLE CARTRIDGE RETAINERS WITH FRANGIBLE RETENTION FEATURES AND METHODS OF USING SAME, now U.S. Patent Application Publication No. 2020-0261083;

U.S. patent application Ser. No. 16/453,330, entitled STAPLE CARTRIDGE RETAINER WITH FRANGIBLE AUTHENTICATION KEY, now U.S. Patent Application Publication No. 2020-0261084;

U.S. patent application Ser. No. 16/453,335, entitled STAPLE CARTRIDGE RETAINER WITH RETRACTABLE AUTHENTICATION KEY, now U.S. Patent Application Publication No. 2020-0261078;

U.S. patent application Ser. No. 16/453,343, entitled STAPLE CARTRIDGE RETAINER SYSTEM WITH AUTHENTICATION KEYS, now U.S. Patent Application Publication No. 2020-0261085;

U.S. patent application Ser. No. 16/453,355, entitled INSERTABLE DEACTIVATOR ELEMENT FOR SURGICAL STAPLER LOCKOUTS, now U.S. Patent Application Publication No. 2020-0261086;

U.S. patent application Ser. No. 16/453,369, entitled DUAL CAM CARTRIDGE BASED FEATURE FOR UNLOCKING A STAPLER LOCKOUT, now U.S. Patent Application Publication No. 2020-0261076;

U.S. patent application Ser. No. 16/453,391, entitled STAPLE CARTRIDGES WITH CAM SURFACES CONFIGURED TO ENGAGE PRIMARY AND SECONDARY PORTIONS OF A LOCKOUT OF A SURGICAL STAPLING DEVICE, now U.S. Patent Application Publication No. 2020-0261077;

U.S. patent application Ser. No. 16/453,413, entitled SURGICAL STAPLE CARTRIDGES WITH MOVABLE AUTHENTICATION KEY ARRANGEMENTS, now U.S. Patent Application Publication No. 2020-0261087;

U.S. patent application Ser. No. 16/453,423, entitled DEACTIVATOR ELEMENT FOR DEFEATING SURGICAL STAPLING DEVICE LOCKOUTS, now U.S. Patent Application Publication No. 2020-0261088; and U.S. patent application Ser. No. 16/453,429, entitled SURGICAL STAPLE CARTRIDGES WITH INTEGRAL AUTHENTICATION KEYS, now U.S. Patent Application Publication No. 2020-0261089.

Applicant of the present application owns the following U.S. Design Patent Applications that were filed on Jun. 25, 2019 which are each herein incorporated by reference in their respective entireties:

U.S. Design Patent Application Ser. No. 29/696,066, entitled SURGICAL STAPLE CARTRIDGE RETAINER WITH FIRING SYSTEM AUTHENTICATION KEY;

U.S. Design Patent Application Ser. No. 29/696,067, entitled SURGICAL STAPLE CARTRIDGE RETAINER WITH CLOSURE SYSTEM AUTHENTICATION KEY; and U.S. Design Patent Application Ser. No. 29/696,072, entitled SURGICAL STAPLE CARTRIDGE.

Applicant of the present application owns the following U.S. Patent Applications that were filed on Feb. 21, 2019 which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,670, entitled STAPLE CARTRIDGE COMPRISING A LOCKOUT KEY CONFIGURED TO LIFT A FIRING MEMBER;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled SURGICAL INSTRUMENT COMPRISING A DEACTIVATABLE LOCKOUT, U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,660, entitled SURGICAL STAPLE CARTRIDGE WITH FIRING MEMBER DRIVEN CAMMING ASSEMBLY THAT HAS AN ONBOARD TISSUE CUTTING FEATURE;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND FRAME ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working frame through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
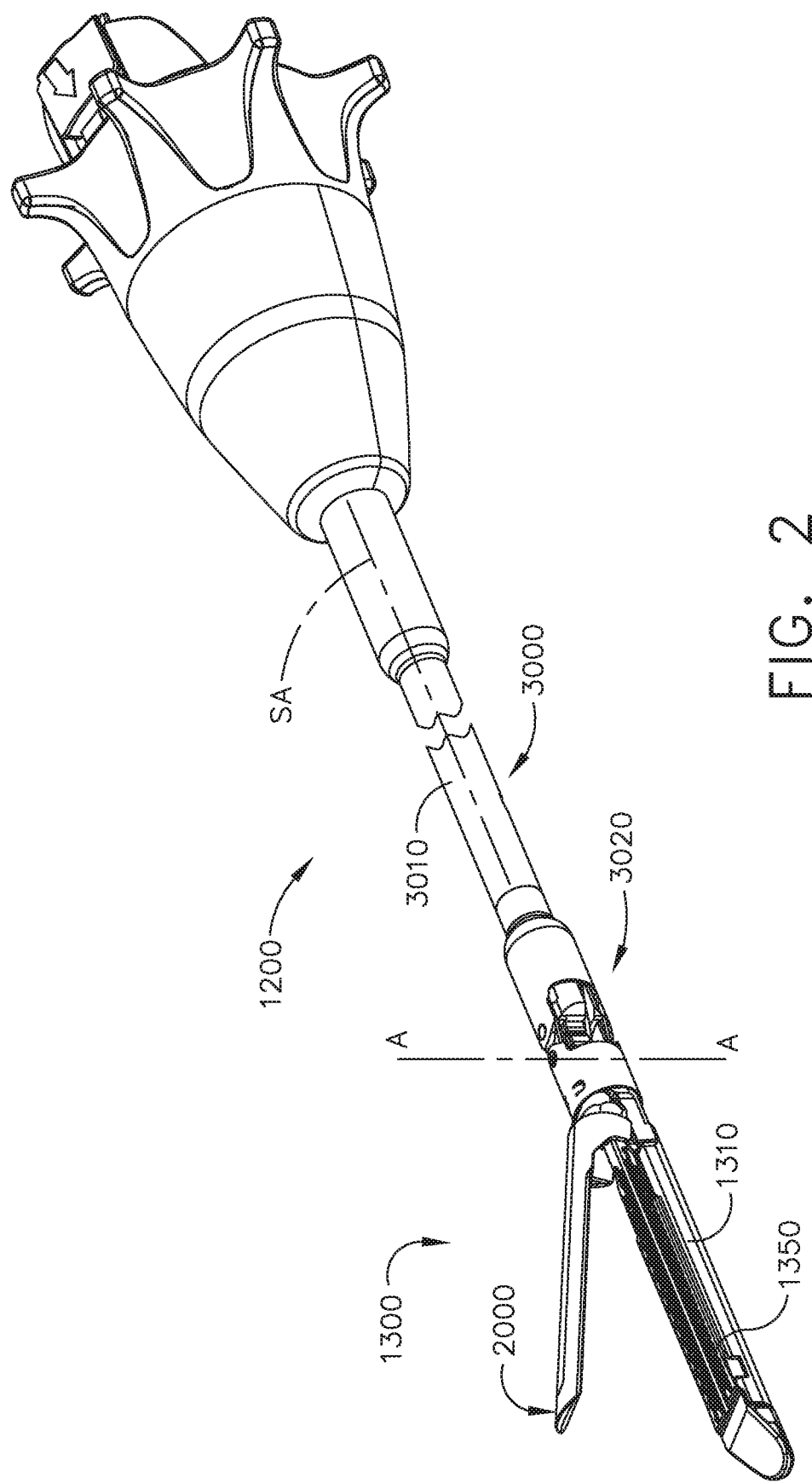
FIG. 2 is a perspective view of an interchangeable surgical shaft assembly of the powered surgical stapling system of FIG. 1.
Figure 3:
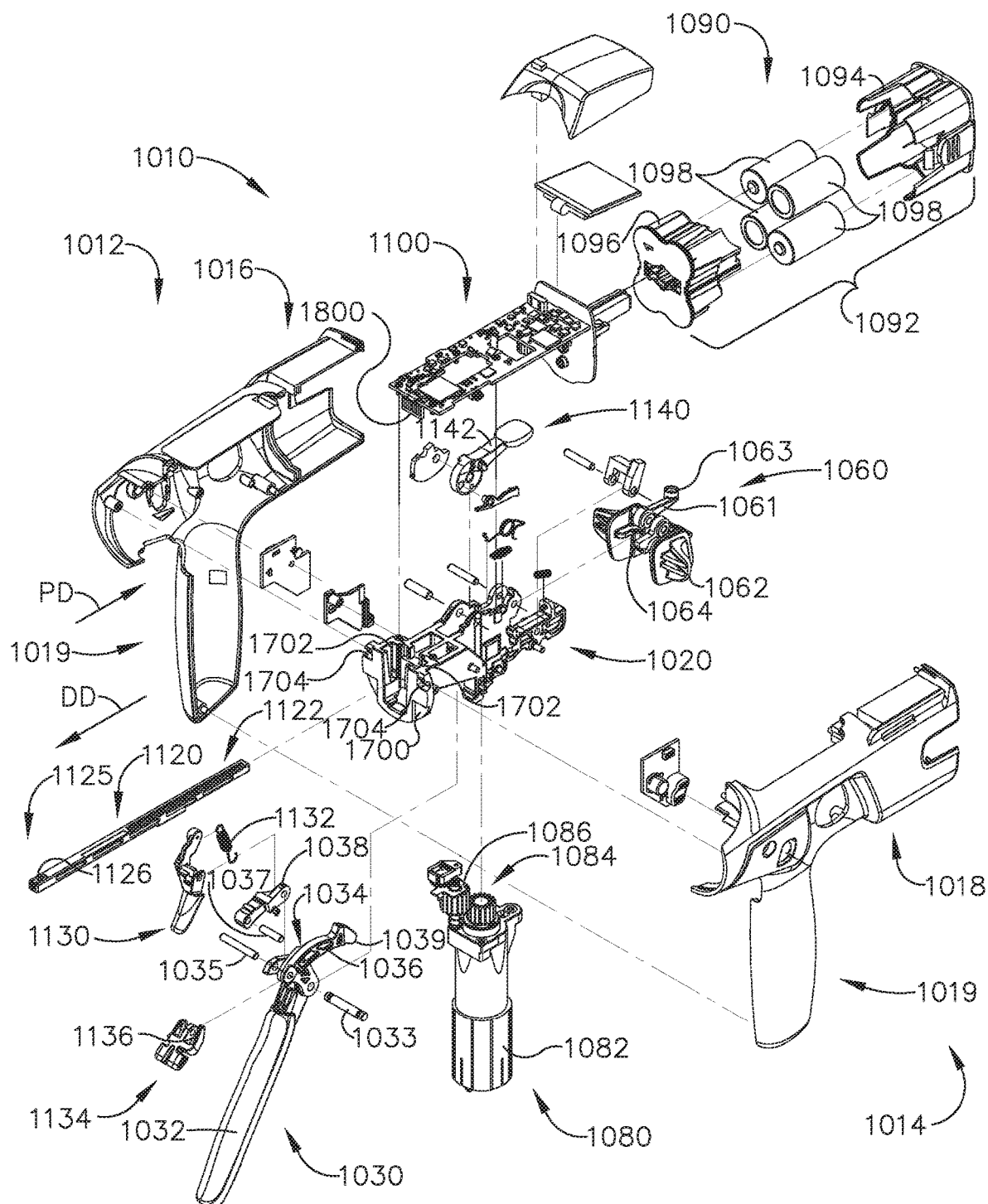
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a previous housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The previous housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 1350 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the release button assembly 1062. A magnetic element 1063, such as a permanent magnet, for example, may be mounted to the arm 1061. When the release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally-movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 82 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. See FIG. 3. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with the rack of teeth 1122 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
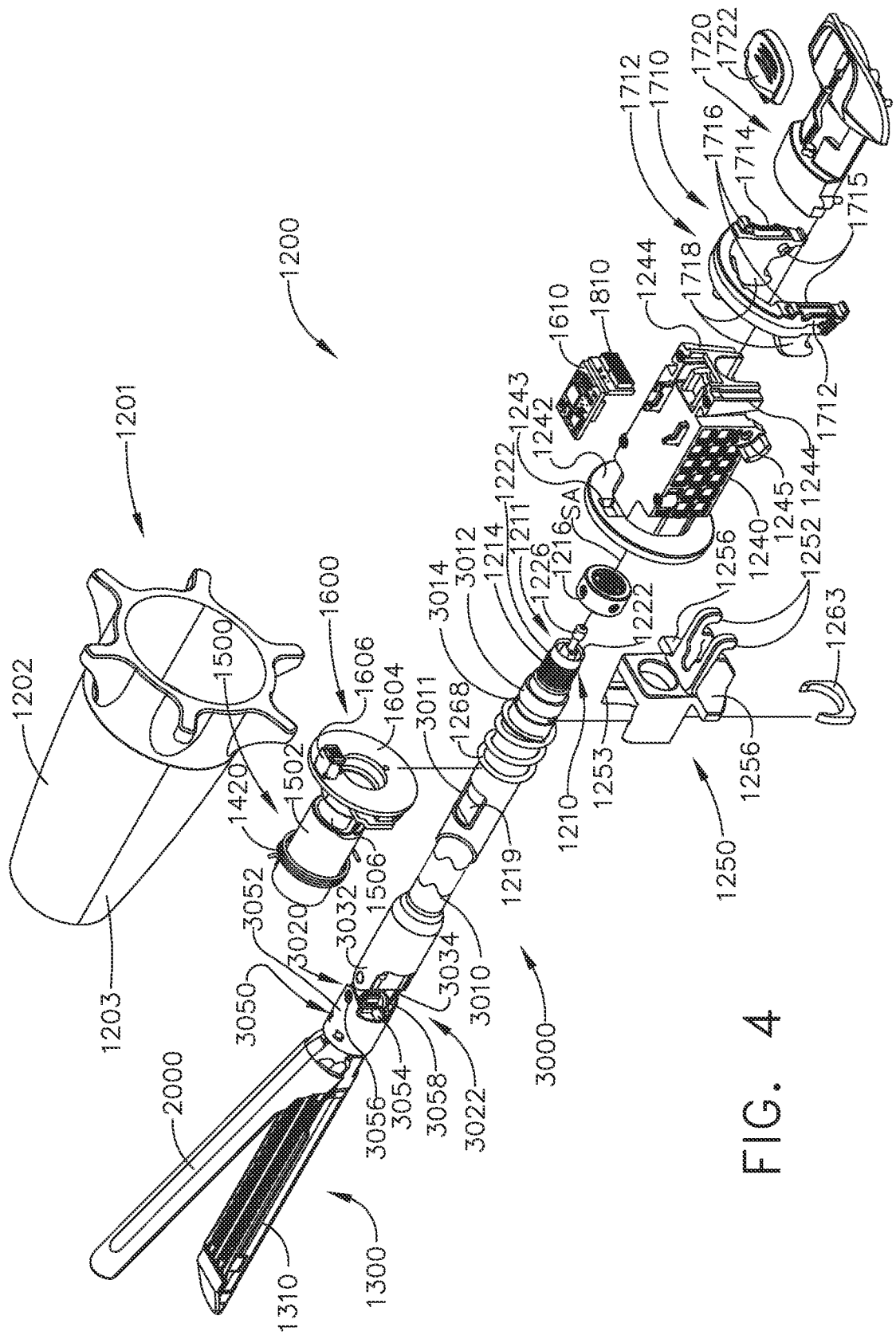
FIG. 4 is an exploded assembly view of the interchangeable surgical shaft assembly of FIG. 2.
Figure 5:
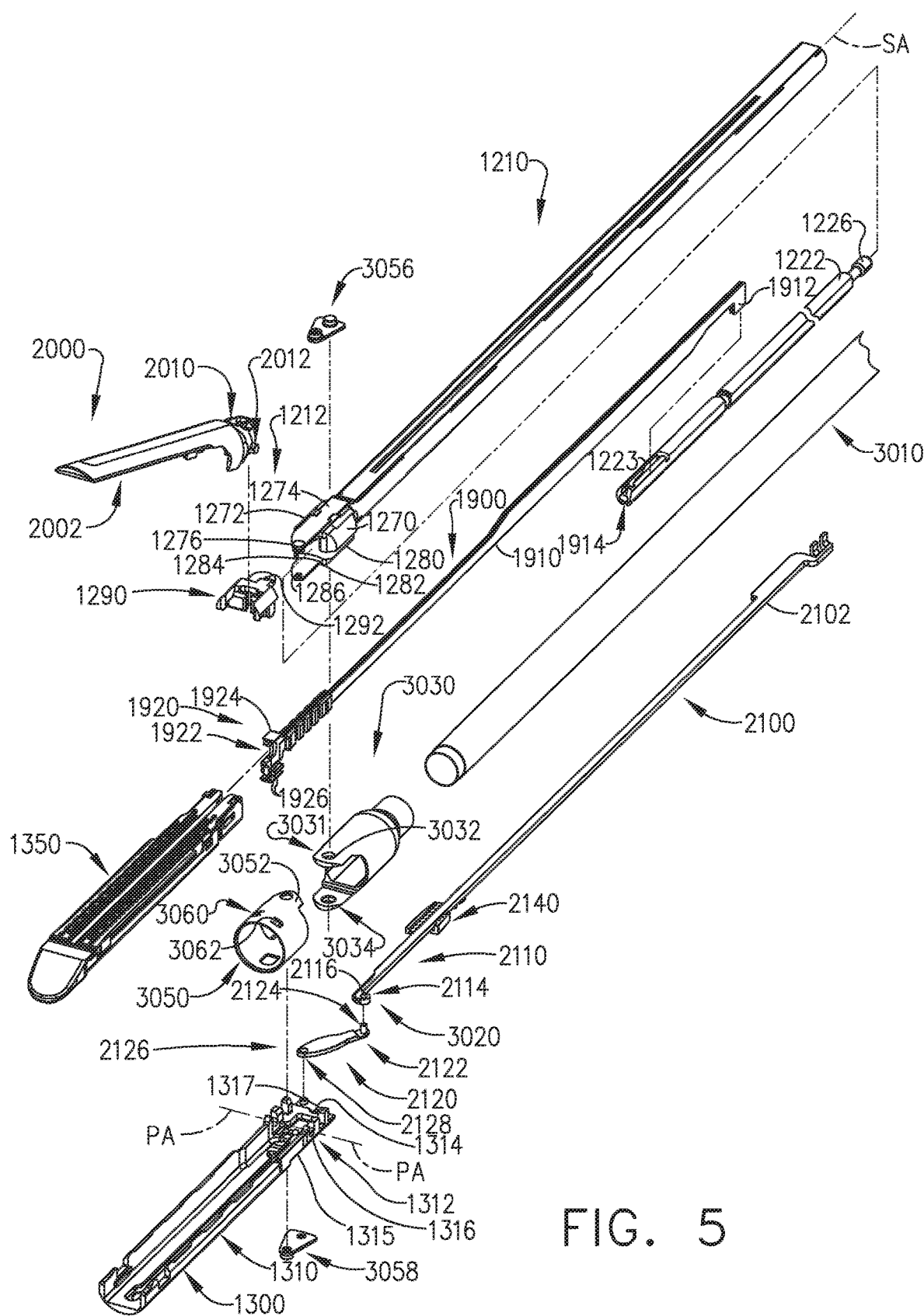
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate frame 1310 that is configured to operably support a staple cartridge 1350 therein. The end effector 1300 may further include an anvil 2000 that is pivotally supported relative to the elongate frame 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a frame cap or anvil retainer 1290 that is attached to a proximal end portion 1312 of the elongate frame 1310. The lower mounting link 1284 includes lower pivot pin 1286 that adapted to be received within a pivot hole 1314 formed in the proximal end portion 1312 of the elongate frame 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a frame pin 1317 formed on the proximal end portion 1312 of the elongate frame 1310. Thus, axial movement of proximal articulation driver 2102 will thereby apply articulation motions to the elongate frame 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower proximally projecting tangs 3052, 3054. An upper double pivot link 3056 includes upwardly projecting distal and proximal pivot pins that engage respectively an upper distal pin hole in the upper proximally projecting tang 3052 and an upper proximal pin hole 3032 in an upper distally projecting tang 3031 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure tube 3050 to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 1350 positioned within the frame 1310. The knife bar 1910 includes a knife portion 1920 that includes a blade or tissue cutting edge 1922 and includes an upper anvil engagement tab 1924 and lower frame engagement tabs 1926. Various firing member configurations and operations are disclosed in various other references incorporated herein by reference.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receive an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle 1201 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, now U.S. Patent Application Publication No. 2014/0263541, entitled ARTICULATABLE SURGICAL INSTRUMENT COMPRISING AN ARTICULATION LOCK and U.S. Pat. No. 9,913,642, entitled SURGICAL INSTRUMENT COMPRISING A SENSOR SYSTEM, the entire disclosures of each being hereby incorporated by reference herein. For example, when the closure member segment 3010 is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail receiving slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame or spine of the shaft assembly 1200 with the frame 1020 of the handle 1014. Another system can comprise a closure drive system 1030 which can operably connect the closure trigger 1032 of the handle 1014 and the closure tube 3050 and the anvil 2000 of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the control circuit board 1100. Further details regaining the circuitry and control systems may be found in U.S. patent application Ser. No. 13/803,086, now U.S. Patent Application Publication No. 2014/0263541, and U.S. patent application Ser. No. 14/226,142, now U.S. Pat. No. 9,913,642, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate frame 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate frame 1310. The anvil trunnions 2012 are pivotally retained in their corresponding trunnion cradle 1316 by the frame cap or anvil retainer 1290. The frame cap or anvil retainer 1290 includes a pair of attachment lugs that are configured to be retainingly received within corresponding lug grooves or notches formed in the upstanding walls 1315 of the proximal end portion 1312 of the elongate frame 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

The disclosures of U.S. Patent Application Publication No. 2004/0232200, entitled SURGICAL STAPLING INSTRUMENT HAVING A SPENT CARTRIDGE LOCKOUT, filed on May 20, 2003, U.S. Patent Application Publication No. 2004/0232199, entitled SURGICAL STAPLING INSTRUMENT HAVING A FIRING LOCKOUT FOR AN UNCLOSED ANVIL, U.S. Patent Application Publication No. 2004/0232197, entitled SURGICAL STAPLING INSTRUMENT INCORPORATING AN E-BEAM FIRING MECHANISM, filed on May 20, 2003, U.S. Patent Application Publication No. 2004/0232196, entitled SURGICAL STAPLING INSTRUMENT HAVING SEPARATE DISTINCT CLOSING AND FIRING SYSTEMS, filed on May 20, 2003, U.S. Patent Application Publication No. 2004/0232195, entitled SURGICAL STAPLING INSTRUMENT HAVING A SINGLE LOCKOUT MECHANISM FOR PREVENTION OF FIRING, filed on May 20, 3003, and U.S. Patent Application Publication No. 2018/0085123, entitled ARTICULATING SURGICAL STAPLING INSTRUMENT INCORPORATING A TWO-PIECE E-BEAM FIRING MECHANISM, filed on Aug. 17, 2017 are incorporated by reference in their entireties.

Figure 6:
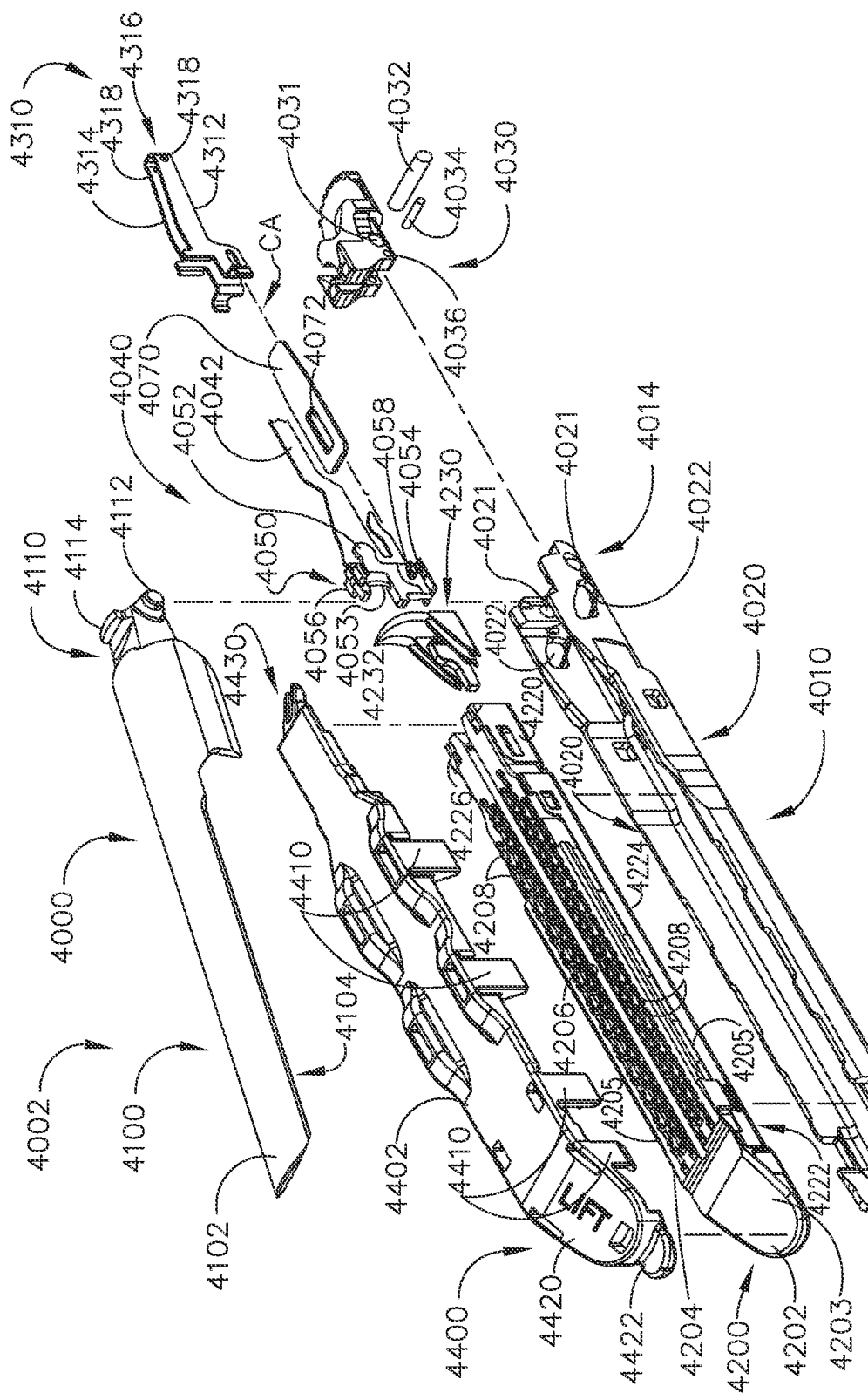
FIG. 6 is an exploded perspective assembly view of a surgical stapling device and staple cartridge of a surgical stapling assembly.

Referring to FIG. 6, an example of a surgical stapling assembly 4000 is shown. The surgical stapling assembly 4000 may be employed in connection with the surgical instrument 1010 described above or in connection with a variety of other surgical instruments described in various disclosures that have been incorporated by reference herein. The surgical stapling assembly 4000 may be employed in connection with electrically controlled, battery powered, manually powered, and/or robotically-controlled surgical instruments in the various forms disclosed in the aforementioned incorporated disclosures, for example. As can be seen in FIG. 6, the surgical stapling assembly 4000 comprises a surgical stapling device generally designated as 4002 that comprises a first jaw, or frame 4010 that is configured to operably support a staple cartridge 4200 therein. The first jaw 4010 may be attached to a spine of the shaft assembly of a surgical instrument or robot in the various manners described herein as well as in the various disclosures which have been herein incorporated by reference. In the illustrated example, the first jaw 4010 is attached to the spine portion of the shaft assembly (not shown in FIG. 6), by a shaft mount flange 4030 that is pinned by a pin 4032 or otherwise attached to a proximal end 4014 of the first jaw 4010. In particular, pin 4032 is configured to pass through aligned holes 4021 in upstanding sidewalls 4020 of the first jaw 4010 as well as through hole 4031 in the shaft mount flange 4030. The shaft mount flange 4030 is configured to interface with an articulation joint arrangement (not shown) that is configured to facilitate articulation of the first jaw 4010 relative to the shaft assembly in various known configurations. Other methods of attaching and operably interfacing the surgical device 4002 with a shaft of a surgical instrument may also be employed. For example, the stapling device 4002 may be attached to the shaft assembly such that the stapling device (sometimes also referred to as an "end effector") is not capable of articulating relative to the shaft assembly.

Still referring to FIG. 6, the surgical stapling device 4002 further comprises a firing member assembly 4040 that comprises a knife bar 4042 that is attached to a knife member or "firing member" 4050. The knife bar 4042 also interfaces with corresponding components and firing systems in the surgical instrument to receive firing motions which can distally advance the knife bar 4042 and firing member 4050 through a staple firing stroke from a starting position to an ending position and also retract the knife bar 4042 and firing member 4050 proximally to a starting position. In the illustrated arrangement, the firing member 4050 comprises a firing member body 4052 that supports a cutting edge or knife edge 4053. The firing member 4050 further comprises a foot 4054 that is formed on the bottom of the firing member body 4052 and extends laterally from each side of the firing member body 4052. The firing member 4050 further comprises a pair of top pins or tabs 4056 that extend laterally from the firing member body 4052 that are adapted to engage ledges on an anvil as will be discussed further herein. Additionally, the firing member 4050 comprises a pair of central pins or tabs 4058 that protrude laterally from each side of the firing member body 4052. In some of the disclosures incorporated by reference herein, the firing member 4050 may also be referred to as an "E-Beam" firing member or cutting member.

Further to the above, the surgical stapling device 4002 comprises a second jaw or anvil 4100 that is movable relative to the first jaw or frame 4010. The anvil 4100 comprises an anvil body 4102 and an anvil mounting portion 4110. The anvil body 4102 comprises a staple forming undersurface or tissue contacting surface 4104 that has a series of staple forming pockets formed therein (not shown) that are arranged to form corresponding staples as they are driven into forming contact therewith. The anvil mounting portion 4110 comprises a pair of laterally extending anvil pins or trunnion pins 4112 that are configured to be received in corresponding trunnion slots 4022 in the upstanding sidewalls 4020 of the first jaw 4010. In the illustrated arrangement, the trunnion slots 4022 are somewhat "kidney-shaped" and facilitate pivotal as well as axial travel of the corresponding trunnion pins 4112 therein. Such pivotal and axial movement of the anvil 4100 may be referred to as "translation" of the anvil during an anvil closure sequence.

As discussed above, as well as in several of the disclosures which have been incorporated by reference herein, the anvil 4100 may be movable from an open position wherein a used or spent surgical staple cartridge may either be removed from the first jaw or frame 4010 or an unfired surgical staple cartridge may be operably seated therein to a closed position. The anvil 4100 may be movable between the open and closed positions by an axially movable closure member which may comprise an end effector closure tube (not shown) that is part of the shaft assembly of the surgical instrument to which the surgical device 4002 is operably attached. For example, as the closure member is moved distally from a proximal position by actuating a closure control system in the surgical instrument, the closure member may operably engage a cam surface on the anvil mounting portion 4110. Such interaction between the closure member and the anvil mounting portion 4110 causes the anvil mounting portion 4110 and the anvil trunnion pins 4112 to pivot and translate up the trunnion slots 4022 until the closure member moves the anvil 4100 to a fully closed position. When in the fully closed position, the staple-forming pockets in the anvil 4100 are properly aligned with the staples in a corresponding compatible surgical staple cartridge that has been operably seated in the first jaw or frame 4010. When the axially movable closure member is thereafter moved in a proximal direction, the closure member interfaces with an upstanding tab 4114 on the anvil mounting portion 4110 to return the anvil 4100 to the open position.

One form of surgical staple cartridge 4200 that may be compatible with the surgical stapling device 4002 comprises a cartridge body 4202 that defines a cartridge deck surface or tissue contacting surface 4204. The cartridge body 4202 further comprises a longitudinal slot 4206 that bisects the cartridge deck surface 4204 and is configured to accommodate axial passage of the firing member 4050 therein between its starting position and an ending position within the cartridge body 4202 during a staple firing stroke. The longitudinal slot 4206 lies along a center axis CA of the cartridge 4200. The surgical staple cartridge 4200 further comprises a series of staple pockets 4208 that are formed in the cartridge body 4202. The staple pockets 4208 may be formed in offset "lines" located on each side of the longitudinal slot 4206. Each staple pocket 4208 may have a staple driver (not shown) associated therewith that supports a surgical staple or fastener (not shown) thereon. In at least one example, the cartridge body 4202 is molded from a polymer material with the staple pockets 4208 molded or machined therein. In one arrangement, the staple pockets 4208 also open through a bottom of the cartridge body 4202 to facilitate installation of the drivers and fasteners into their respective staple pockets 4208. Once the drivers and fasteners are inserted into their respective staple pockets 4208, a cartridge pan 4220 is attached to the cartridge body 4202. In one form, the cartridge pan 4220 is fabricated from a metal material and includes a bottom 4222 that spans across the bottom of the cartridge body 4202. The cartridge pan 4220 also includes two upstanding sidewalls 4224 that correspond to each side of the cartridge body 4202. The cartridge pan 4220 may be removably affixed to the cartridge body 4202 by hooks 4226 that are formed on the sidewalls 4224 and configured to hookingly engage corresponding portions of the cartridge body 4202. In addition, the cartridge body 4202 may also have lugs or attachment formations protruding therefrom that are configured to retainingly engage corresponding portions of the cartridge pan 4220. When installed, the cartridge pan 4220 may, among other things, prevent the drivers and fasteners from falling out of the bottom of the cartridge body 4202 during handling and installation of the staple cartridge into the first jaw or frame 4010.

Some of the staple drivers operably support a single surgical staple thereon and other staple drivers support more than one surgical staple thereon depending upon the particular cartridge design. Each surgical staple comprises a staple crown and two upstanding staple legs. The staple crown is typically supported on a cradle arrangement formed in a corresponding staple driver such that the legs are vertically oriented toward the anvil when the cartridge is operably seated in the frame 4010. In some arrangements, surgical staples have a somewhat V-shape, wherein the ends of the legs flare slightly outward. Such arrangement may serve to retain the staple in its corresponding staple pocket due to frictional engagement between the legs and the sides of the staple pocket should the cartridge be inadvertently inverted or turned upside down during use. Other surgical staples are roughly U-shaped (the ends of the legs do not flare outward) and may be more susceptible to falling out of the staple pocket should the cartridge be inverted prior to use.

The surgical staple cartridge 4200 further comprises a sled or camming member 4230 that is configured to be axially advanced through the cartridge body 4202 during a staple firing stroke. In a "new", "fresh" or "unfired" surgical staple cartridge, the sled 4230 is in its proximal-most, "unfired" position. The sled 4230 comprises a plurality of wedges or cam members 4232 that are configured to drivingly engage the corresponding lines of staple drivers in the cartridge body. During the staple firing stroke, the firing member 4050 abuts and pushes the sled 4230 distally into camming contact with the staple drivers thereby sequentially driving the staple drivers upward toward the anvil 4100 as the sled 4230 is driven from its unfired position to its distal-most fully fired position within the cartridge body 4202. As the staple drivers are driven upwardly, the staples are driven through the tissue that is clamped between the deck surface 4204 of the staple cartridge 4200 and the anvil 4100 and into forming contact with the staple-forming undersurface 4104 of the anvil 4100. The tissue-cutting knife 4053 on the firing member 4050 cuts through the stapled tissue as the firing member 4050 is driven distally. After the staple firing stroke has been completed, and/or after a sufficient length of the staple firing stroke has been completed, the firing member 4050 is retracted proximally. However, the sled 4230 is not retracted proximally with the firing member 4050. Instead, the sled 4230 is left behind at the distal-most position in which it was pushed by the firing member 4050.

After a staple cartridge has been fired, or at least partially fired, it is removed from the frame and then replaced with another replaceable staple cartridge, if desired. At such point, the stapling device can be re-used to continue stapling and incising the patient tissue. In some instances, however, a previously-fired staple cartridge can be accidentally loaded into the frame. If the firing member were to be advanced distally within such a previously-fired staple cartridge, the stapling instrument would cut the patient tissue without stapling it. The stapling instrument would similarly cut the patient tissue without stapling it if the firing member were advanced distally through a staple firing stroke without a staple cartridge positioned in the cartridge jaw at all. In addition, various surgical staple cartridges may have different arrays of and/or orientations of staples/fasteners therein. The sizes of the staples or fasteners, as well as the number of fasteners may vary from cartridge type to cartridge type depending upon a particular surgical procedure or application. To ensure that the staples are properly crimped or formed, the surgical staple cartridges must be used in connection with corresponding, compatible anvils that have the proper array of staple-forming pockets therein as well as the proper cutting and firing components. Should a "non-compatible" cartridge be loaded into a surgical stapling device that has an anvil that is mismatched to the staple cartridge, the staples may not be properly formed during the firing process which could lead to catastrophic results. To this end, the surgical stapling assembly 4000 comprises one or more lockouts which prevents this from happening, as discussed in greater detail below.

Figure 7:
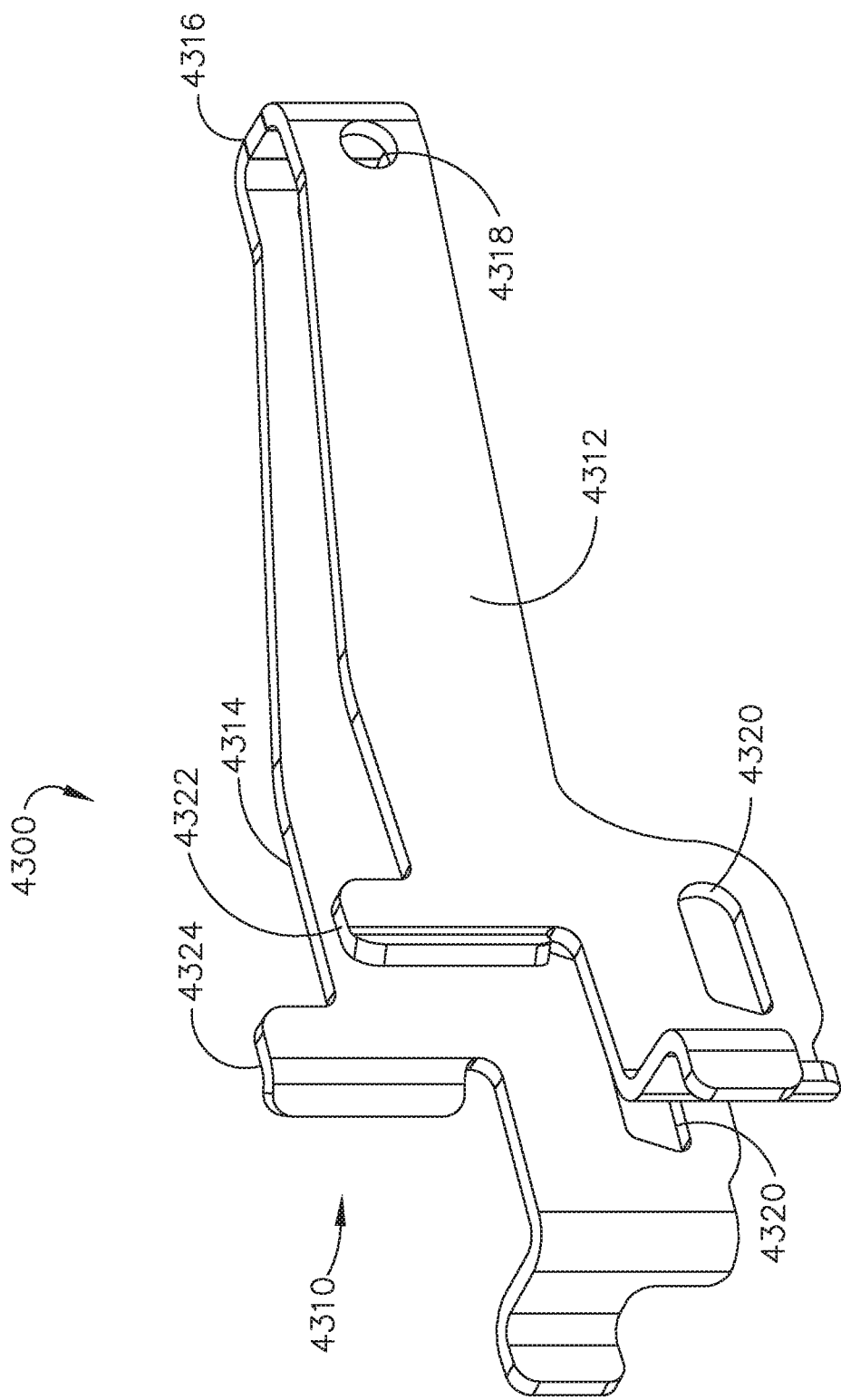
FIG. 7 is a perspective view of a first lockout spring of the surgical stapling device of FIG. 6.

Further to the above, the surgical stapling device 4002 comprises a first lockout 4300 that is configured to prevent the firing member 4050 from moving distally from its proximal-most, starting position unless an authorized or compatible staple cartridge is operably seated in the first jaw or frame 4010. The first lockout 4300 may also be referred to herein as an "authentication" lockout. In the illustrated arrangement, the first lockout 4300 comprises a single, bi-lateral first lockout spring 4310 that is supported in the proximal end 4014 of the frame 4010 and attached to the shaft mount flange 4030. In one arrangement for example, the first lockout spring 4310 comprises a first lockout arm 4312 that is located on one side of the cartridge axis CA and a second lockout arm 4314 that is located on an opposite side of the cartridge axis CA. The first and second lockout arms 4312, 4314 are attached to a central body portion 4316. See FIG. 7. The spring 4310 is supported in the first jaw or frame 4010 and affixed to the shaft mount flange 4030 by a pin 4034 that extends through holes 4036 in the shaft mount flange 4030 and through holes 4318 in the first lockout arm 4312 and the second lockout arm 4314. The first lockout arm 4312 and the second lockout arm 4314 each further comprise a lockout window or opening 4320. The lockout windows 4320 are each adapted to receive therein a corresponding central pin 4058 protruding from the adjacent first or second lateral side of the firing member 4050 when the firing member 4050 is in its proximal-most or starting position. See FIGS. 8 and 9.

Figure 8:
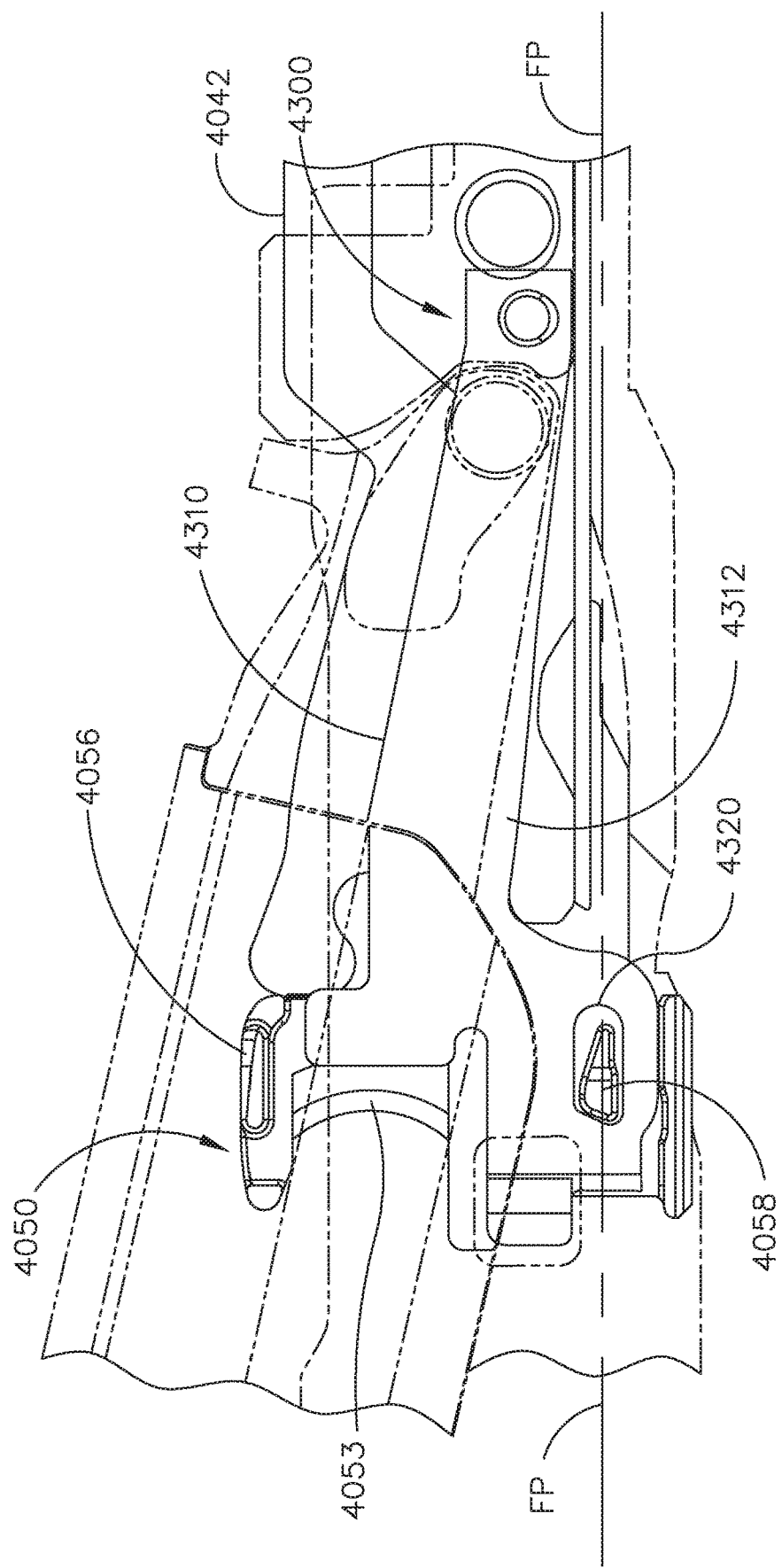
FIG. 8 is a partial side elevational view of a portion of the surgical stapling device of FIG. 6 showing the first lockout spring in retaining engagement with a firing member thereof and prior to insertion of a surgical staple cartridge into a first jaw of the surgical stapling device.
Figure 9:
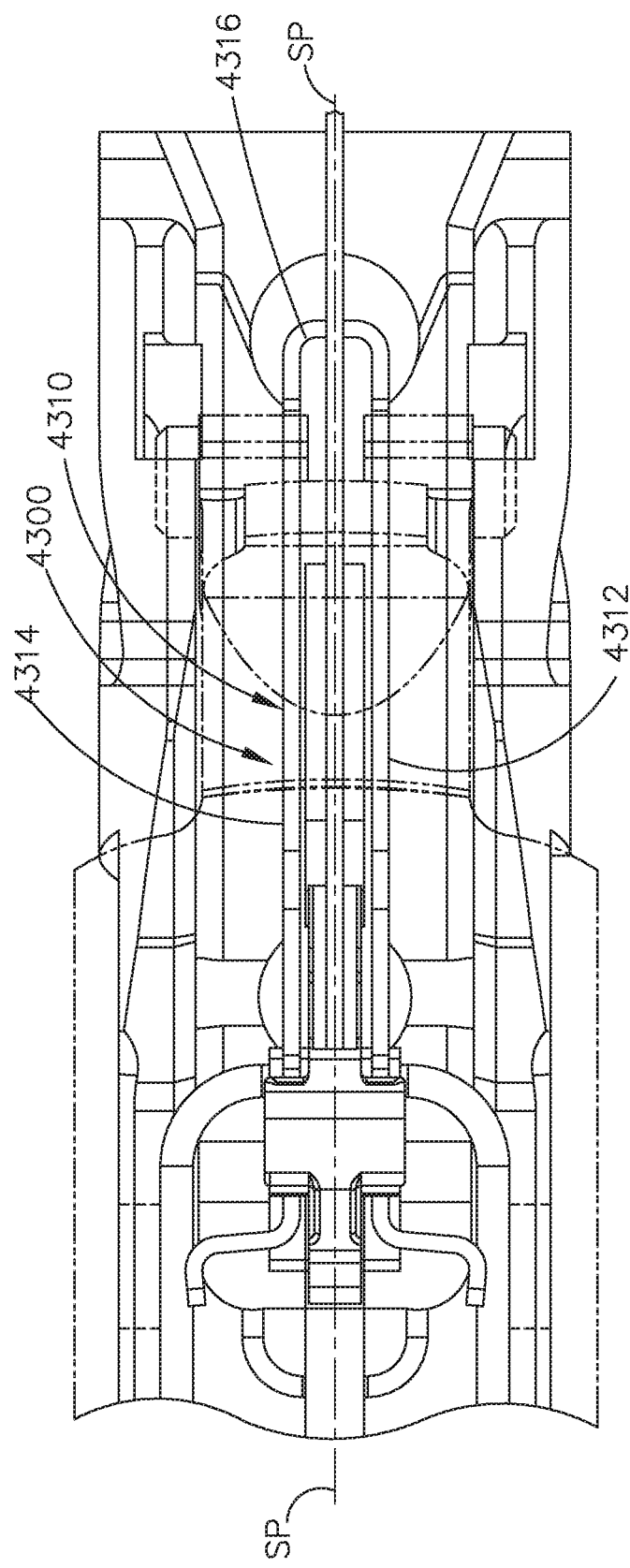
FIG. 9 is a top view of the portion of the surgical stapling device of FIG. 8.
Figure 10:
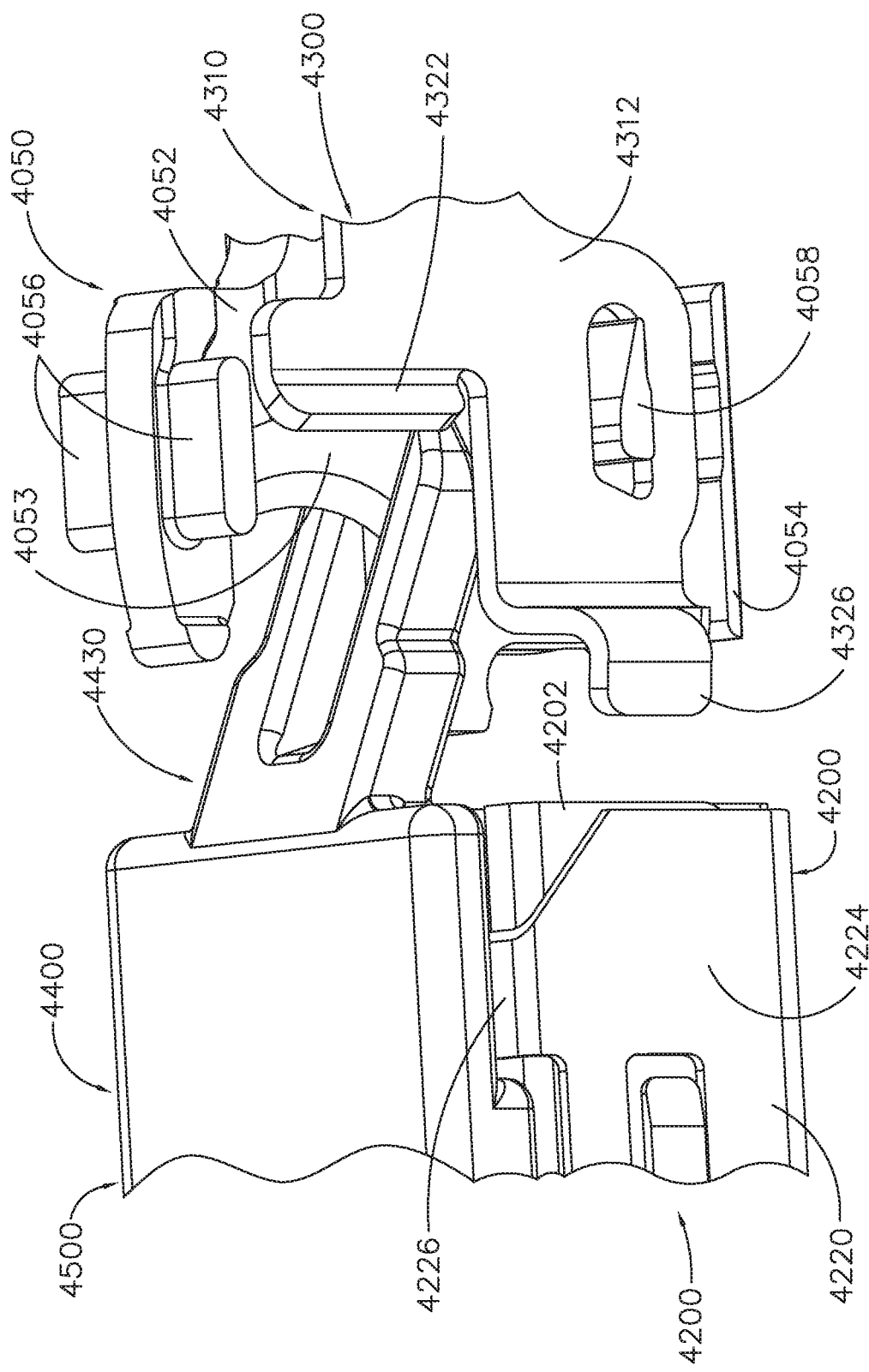
FIG. 10 is an exploded view of portions of the surgical stapling device of FIG. 8 showing an initial insertion of a cartridge assembly that comprises a retainer that is attached to a staple cartridge wherein an authentication key on the retainer is engaging the first lockout spring of the surgical stapling device.

FIGS. 8-10 illustrate the first lockout 4300 in the locked position wherein the central pins 4058 are received within the lockout windows 4320 in the first and second lockout arms 4312, 4314. In some arrangements, those staple cartridges that are compatible with the surgical stapling device 4002 or, stated another way, those staple cartridges that have the proper number, size, and arrangement of staples, may have one or more unlocking or "authorization" keys directly formed on the cartridge body and/or on the cartridge pan that are configured to defeat the first lockout when the compatible staple cartridge is operably seated in the first jaw or frame. Various staple cartridges that have unlocking keys protruding therefrom are disclosed below as well as in various disclosures which have been herein incorporated by reference. In certain instances, however, the clinician may wish to use staple cartridges that are compatible with the surgical stapling device, but otherwise lack the unlocking keys. In such instances, the clinician would be unable to otherwise use those compatible staple cartridges in the surgical stapling device. The surgical stapling device 4002 includes features designed to facilitate use of such compatible staple cartridges that otherwise lack unlocking key features.

Turning now to FIGS. 6 and 10, the stapling assembly 4000 further comprises a retainer 4400 that is configured to be removably coupled to the staple cartridge 4200 which is otherwise compatible with the surgical stapling device 4002. In the illustrated arrangement, the retainer 4400 comprises a top portion 4402 that is coextensive with, and configured to be received on, the deck surface 4204 of the cartridge body 4202. Thus, in at least one configuration, when the retainer 4400 is attached to the cartridge body 4202, the retainer 4400 covers all of the staple pockets 4208 in the cartridge body 4202. As such, when the retainer 4400 is attached to the staple cartridge 4200, the retainer 4400 may prevent the surgical staples stored within the staple pockets 4208 from falling out should the staple cartridge 4200 be inverted or turned upside down prior to use. The retainer 4400 also protects the deck surface from being contaminated during shipping and storage.

In one arrangement, the retainer 4400 may be molded from a polymer material and include a plurality of retainer lugs 4410 that are configured to latchingly engage outwardly extending deck ledge portions 4205 that are formed on the cartridge body 4202. The retainer 4400 may further comprise an angled nose portion 4420 and distal latch tab 4422 that that is configured to latching engage a distal nose 4203 of the cartridge body 4202. The retainer 4400 may be removably coupled to the surgical staple cartridge 4200 by engaging the distal latch tab 4422 with an end of the distal nose 4203 and aligning the retainer 4400 such that the underside of the top portion 4402 confronts the cartridge deck surface 4204 and the retainer lugs 4410 are located above the deck ledge portions 4205 on each side of the cartridge body 4202. Thereafter, the retainer 4400 may be pressed toward the staple cartridge 4200 causing the retainer lugs 4410 to flex laterally outward and snap into latching engagement with the corresponding deck ledge portions 4205. Other retainer latching arrangements disclosed herein may also be employed to removably affix the retainer 4400 to the staple cartridge 4200. The retainer 4400 may be removed from the staple cartridge 4200 by applying a prying motion to the distal latch tab 4422 until the retainer lugs 4410 disengage the deck ledge portions 4205. In the illustrated example, the term "LIFT" is molded, embossed, imprinted or otherwise provided on the nose portion 4420 to provide removal instructions to the user.

Figure 11:
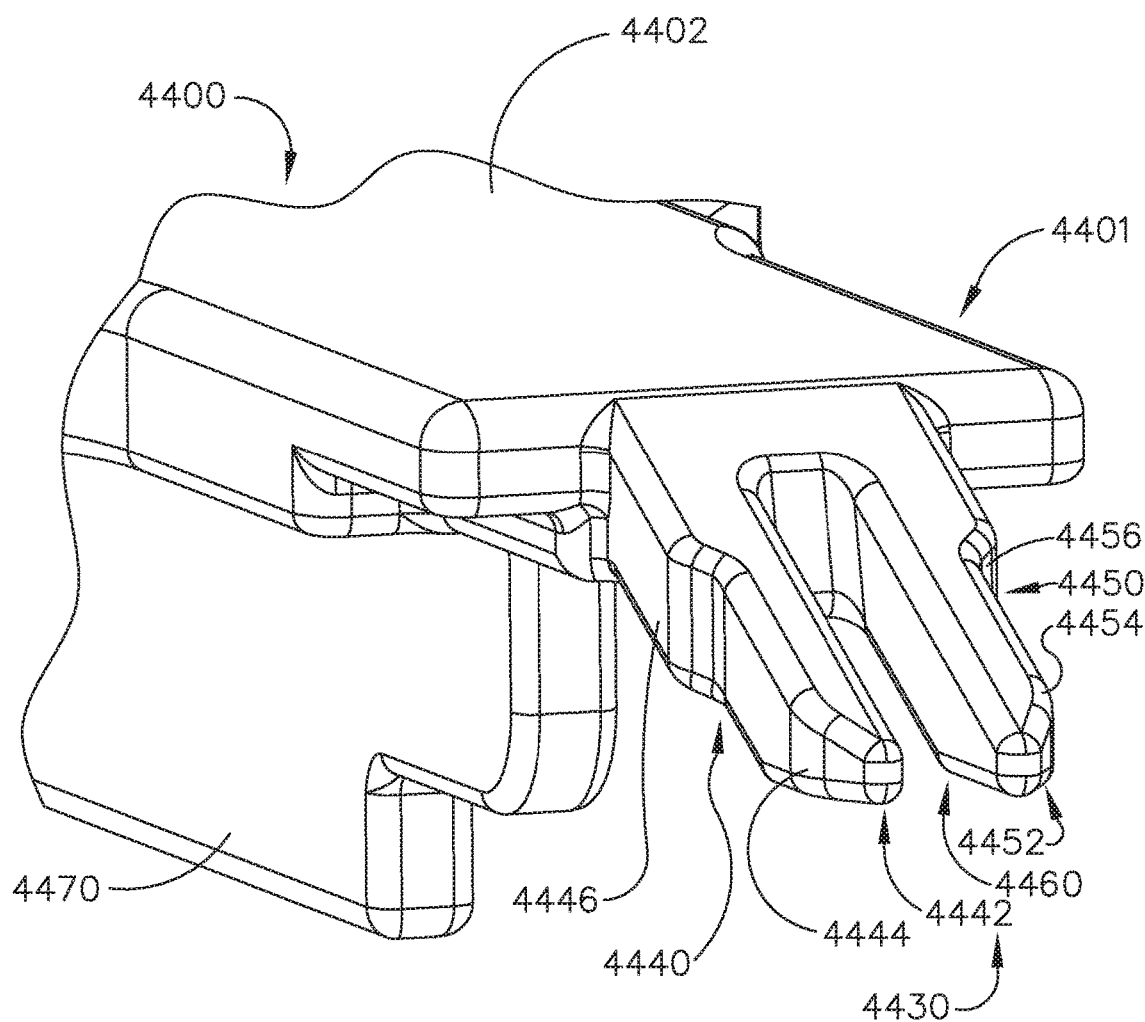
FIG. 11 is a perspective view of the authentication key of the retainer of FIG. 10.
Figure 12:
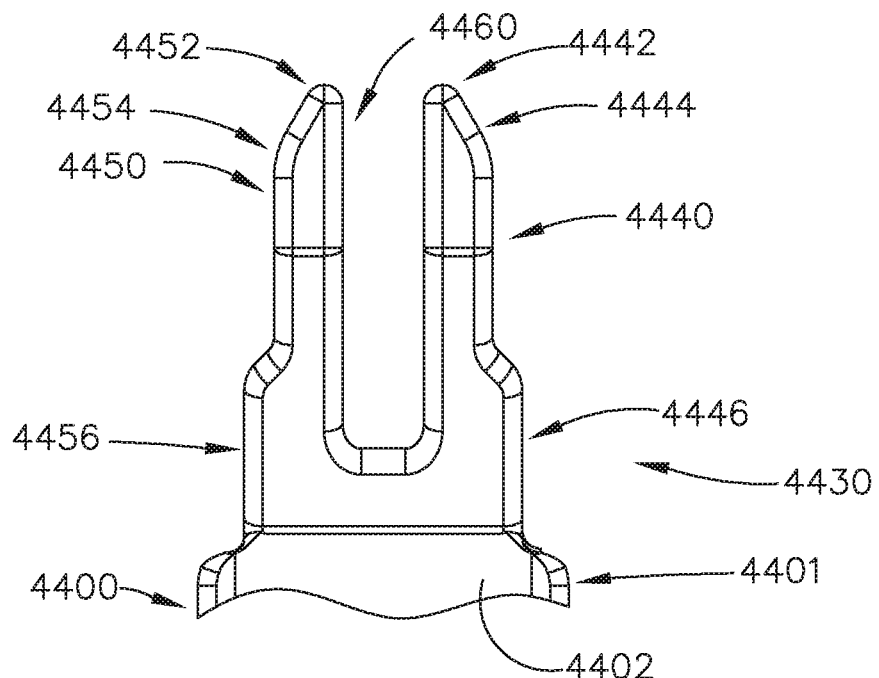
FIG. 12 is a top view of the authentication key of the retainer of FIG. 11.
Figure 13:
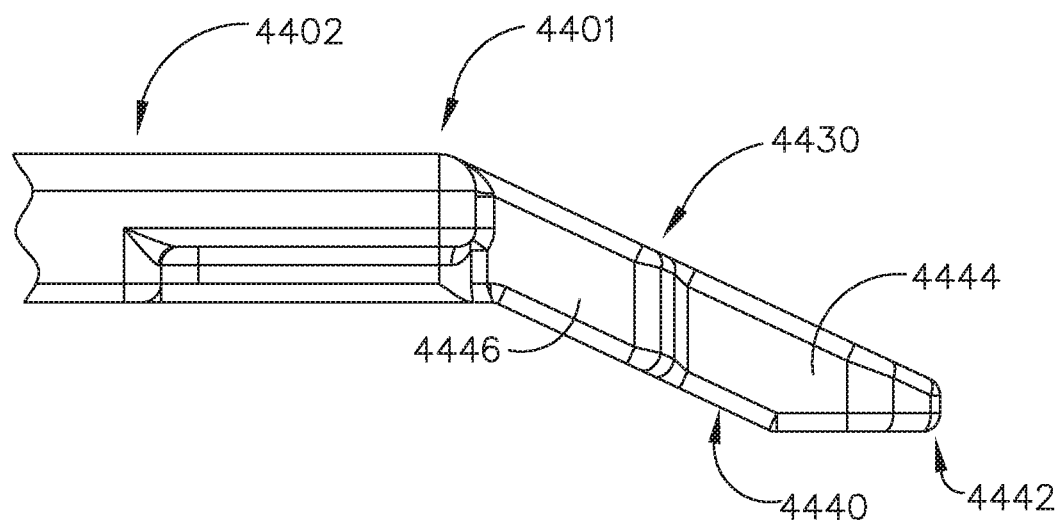
FIG. 13 is a side view of the authentication key of the retainer of FIG. 11.

Referring now to FIGS. 10-13, the retainer 4400 further comprises an authentication key 4430 that is configured to defeat, deactivate or unlatch the first lockout 4300 when the retainer 4400 is attached to the staple cartridge 4200 to form a cartridge assembly 4500 and the cartridge assembly 4500 has been operably seated in the first jaw or frame 4010. As can be seen in FIG. 11, the authentication key 4430 protrudes proximally from a proximal end 4401 of the top portion 4402 of the retainer 4400 and comprises a right ramp feature 4440 and a left ramp feature 4450 that are separated by a space 4460 that is sized to receive the firing member body 4052 therebetween. In the illustrated example, the right ramp feature 4440 angles downward from the top portion 4402 of the retainer 4400 and comprises a proximal right tip 4442. The proximal right tip 4442 defines a first right cam surface 4444 that angles inward at the tip and extends distally to a second right cam surface 4446. The second right cam surface 4446 extends from the first right cam surface 4444 to the top portion 4402. See FIG. 12. Similarly, the left ramp feature 4450 angles downward from the top portion 4402 of the retainer 4400 and comprises a proximal left tip 4452. The proximal left tip 4452 angles inward at the tip and extends distally to a second left cam surface 4456. The second left cam surface 4456 extends from the first left cam surface 4454 to the top portion 4402. The retainer 4400 additionally comprises a retainer keel 4470 that protrudes from the bottom surface of the top portion 4402 and is oriented to be received within the longitudinal slot 4206 in the surgical staple cartridge 4200. Retainer keel 4470 may serve to properly orient the retainer 4400 on the staple cartridge 4200 so that the right and left ramp features 4440 and 4450 extend on each side of the firing member 4050. In addition, the retainer keel 4470 may be configured to engage the sled 4230 in the staple cartridge 4200 and retain the sled 4230 in the unfired position while the retainer 4400 is attached to the staple cartridge 4200. The retainer keel 4470 may be sized relative to the longitudinal slot 4206 to establish a frictional fit therewith to retain the retainer 4400 on the staple cartridge 4200.

Figure 14:
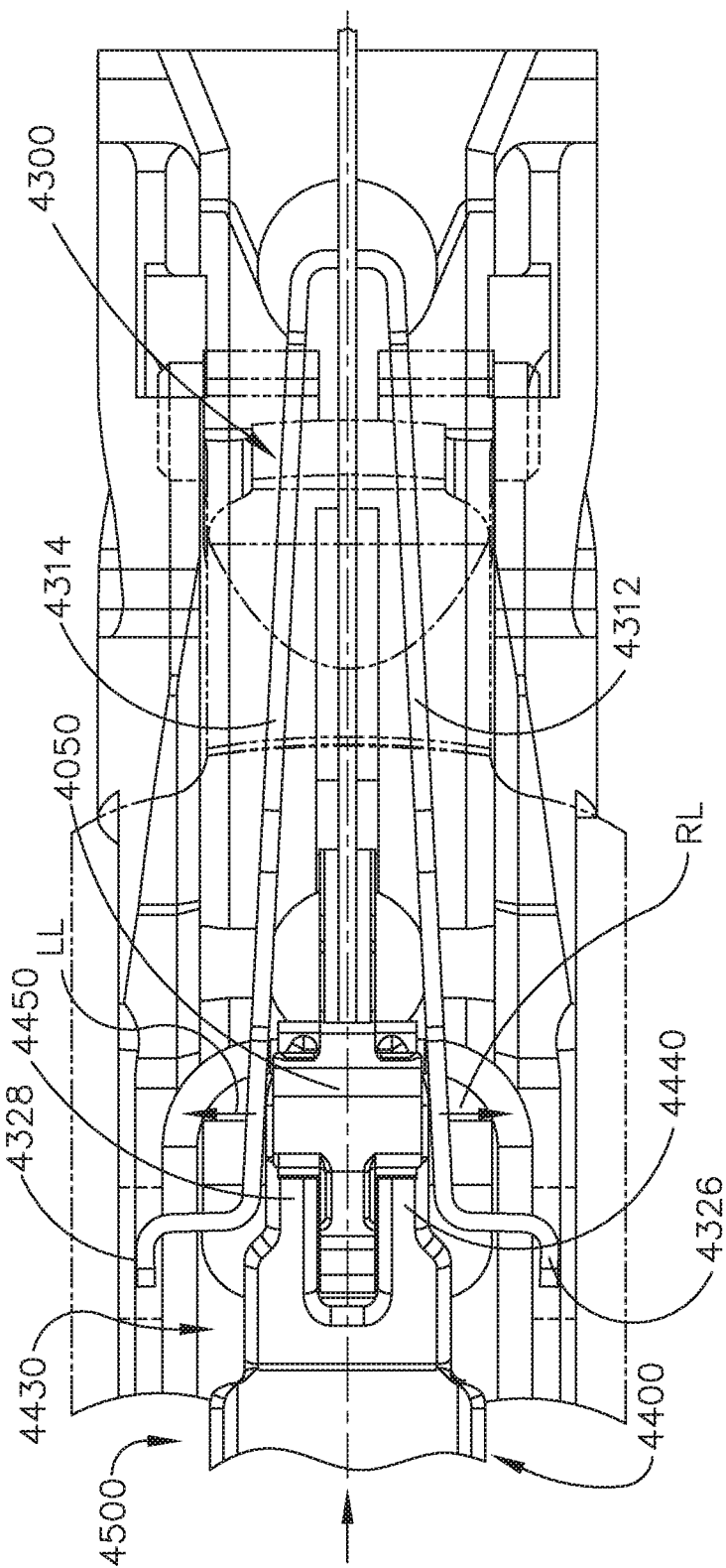
FIG. 14 is another top view of a portion of the surgical stapling device of FIG. 8 illustrating an initial insertion of the cartridge assembly of FIG. 8 into the first jaw of the surgical stapling device.
Figure 15:
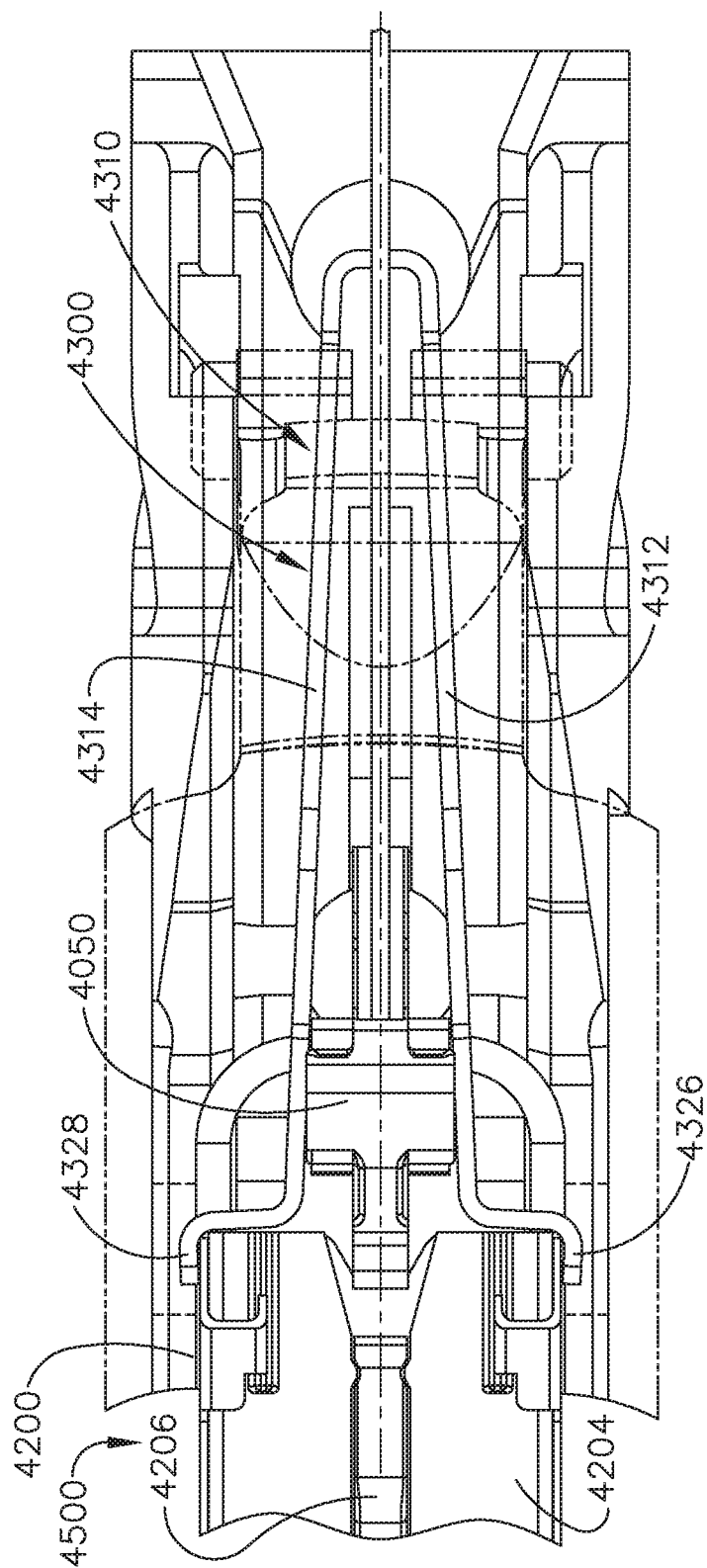
FIG. 15 is another top view of the portion of the surgical stapling device of FIG. 14 after the retainer has been removed from the staple cartridge that is operably seated in the first jaw of the surgical stapling device.

Referring now to FIGS. 10, 14, and 15, after the retainer 4400 has been attached to the staple cartridge 4200 to form the cartridge assembly 4500, the cartridge assembly 4500 may be longitudinally inserted into the first jaw or frame 4010 so as to bring the right tip 4442 of the right ramp feature 4440 of the authentication key 4430 into contact with an upstanding unlocking tab 4322 on the first lockout arm 4312 and the left tip 4452 of the left ramp 4450 into contact with an upstanding unlocking tab 4324 on the second lockout arm 4314 of the first lockout spring 4310. During the initial longitudinal insertion of the assembled cartridge arrangement 4500 in a proximal direction into the frame 4010, the first right cam surface 4444 biases the first lockout arm 4312 of the first lockout spring 4310 laterally outward (arrow RL in FIG. 14) and the first left cam surface 4454 biases the second lockout arm 4314 laterally outward (arrow LL). Further proximal advancement of the cartridge assembly 4500 into the first jaw or frame 4010 causes the first lockout arm 4312 to attain a first intermediate position wherein the first lockout arm 4312 disengages the corresponding central pin 4058 on the firing member 4050 and also causes the second lockout arm 4314 to attain a second intermediate position wherein the second lockout arm 4314 disengages the corresponding central pin 4058 on the firing member 4050. Continued longitudinal insertion of the assembled cartridge arrangement 4500 in a proximal direction into the first jaw or frame 4010 causes the second right cam surface 4446 to further bias the first lockout arm 4312 laterally outward and the second left cam surface 4456 to further bias the second lockout arm 4314 laterally outward until the cartridge assembly 4500 is completely operably seated in the first jaw or frame 4010. See FIG. 15. When the cartridge assembly 4500 has been operably seated in the first jaw or frame 4010, a distal first retention tab 4326 on the first lockout arm 4312 engages a corresponding side of the staple cartridge 4200 to retain the first lockout arm 4312 in that unlocked position. Likewise a distal second retention tab 4328 formed on the second lockout arm 4314 engages another corresponding side of the staple cartridge 4200 to retain the second lockout arm 4314 in that unlocked position. When in that position, the first lockout 4300 is in the unlocked position or, stated another way, is "defeated". During the unlocking process, the right and left ramps 4440, 4450 may be reinforced by the firing member 4050 in applications wherein the locking forces generated from the first spring 4310 are high.

The user may then remove the retainer 4400 from the staple cartridge 4200 by prying the up the distal latch tab 4422 and lifting the retainer 4400 upward until the retainer lugs 4410 disengage the deck ledge portions 4205 on the cartridge body 4202. With the first lockout 4300 defeated or unlocked, the firing member 4050 may be distally advanced from the starting position and is in a "ready state". After the staple cartridge 4200 has been fired, the firing member 4050 is retracted back to the starting position and the second jaw or anvil 4100 is pivoted back to the open position. The spent staple cartridge may then be removed from the first jaw or frame 4010. Once the spent staple cartridge 4200 has been removed from the first jaw or frame 4010, the first and second lockout arms 4312, 4314 spring back into engagement with the corresponding central pins 4058 on the firing member 4050 to once again retain the firing member 4050 in the starting position.

Other first lockout spring arrangements are contemplated. For example, a first lockout spring may only comprise one lateral lockout arm and engage only one side of the firing member. In such arrangements, an authentication key comprising only one ramp may be needed to unlock the lockout arm.

As discussed above, when the cartridge assembly 4500 is operably seated in the frame 4010, the first lockout 4300 is defeated or unlocked to permit the firing member 4050 to be distally advanced from that ready state during a staple firing stroke. When attached to the staple cartridge 4200, the retainer 4400 covers the cartridge deck surface 4204 and prevents staples from falling out of the staple pockets 4208 as well as prevents any debris or contamination from entering the longitudinal slot 4206 or staple pockets 4208 which could damage the staple cartridge or prevent it from operating properly. Other variations of the retainer 4400 are contemplated wherein only a portion of the cartridge deck surface 4204 is covered by the retainer. Other configurations may not cover any of staple pockets and/or any of the deck surface.

As was also discussed above, after a staple cartridge has been fired, or at least partially fired, it is removed from the first jaw or frame and then replaced with another compatible staple cartridge, if desired. At such point, the stapling device can be re-used to continue stapling and incising the patient tissue. In some instances, however, a previously-fired staple cartridge can be accidentally loaded into the frame. If the firing member were to be advanced distally within such a previously-fired staple cartridge (sometimes referred to herein as a "spent" cartridge), the stapling instrument would cut the patient tissue without stapling it. This could conceivably happen even if the retainer 4400 were inadvertently accidentally attached to the spent cartridge and the resulting cartridge assembly is then seated into the frame so as to defeat the first lockout. The surgical stapling device would similarly cut the patient tissue without stapling it if the firing member were advanced distally through a staple firing stroke without a staple cartridge positioned in the cartridge jaw at all. To prevent these occurrences from happening, the surgical stapling device 4002 further comprises a second lockout 4600 that is configured to prevent the firing member 4050 from distally advancing through the staple firing stroke when a spent staple cartridge is seated in the first jaw or frame 4010.

Referring now to FIGS. 6, and 16-19, the knife bar 4042, which may comprise a solid or laminated structure, comprises a spring tab 4044 that is configured to operably interface with a spring plate 4070 that is mounted or grounded in the bottom of the first jaw or frame 4010. The spring plate 4070 is provided with a hole 4072 that is configured to receive the spring tab 4044 therein when the firing member 4050 is in its proximal-most, "starting" position. When in that position, the spring tab 4044 extends into the hole 4072 and may serve to prevent any inadvertent distal movement of the firing member 4050 until desired by the operator. In the illustrated example, the second lockout 4600 further comprises blocking features or ledges 4602 that are formed in the bottom of the frame 4010. If the user were to attempt to distally advance the firing member 4050 before a cartridge has been operably seated into the frame 4010, the spring tab 4044 in cooperation with the spring plate 4070 will cause the firing member 4050 to dive downward bringing the central pins 4058 on the firing member 4050 into contact with the blocking features 4602 in the frame and thereby prevent the firing member 4050 from advancing distally.

FIGS. 16 and 17 illustrate operation of the second lockout 4600 when a spent staple cartridge 4200S has been seated into the frame 4010. As used in this context, the term "spent" staple cartridge may refer to a staple cartridge that has been previously fully fired or partially fired. In either case, the sled 4230 will have been distally advanced from its proximal-most, unfired position. FIG. 16 depicts the firing member 4050 in the proximal-most, starting position with the spent staple cartridge 4200S seated in the frame 4010. FIG. 17 illustrates the second lockout 4600 preventing the firing member 4050 from being distally advanced into the spent cartridge 4200S. As can be seen in FIG. 17, the spring tab 4044 in cooperation with the spring plate 4070 has caused the firing member 4050 to dive downward bringing the central pins 4058 on the firing member 4050 into contact with the blocking features 4602 in the frame to thereby prevent the firing member 4050 from advancing distally.

FIGS. 18 and 19 illustrate operation of the second lockout 4600 when an unfired staple cartridge 4200 has been seated into the first jaw or frame 4010. As can be seen in FIGS. 18 and 19, the sled 4230 is in its proximal-most, unfired position. The sled 4230 comprises an unlocking ledge 4234 that is configured to be engaged by an unlocking feature 4055 that is formed on the firing member body 4052. FIG. 18 illustrates the firing member 4050 in the proximal-most, starting position with the unfired staple cartridge 4200 seated in the first jaw or frame 4010. When the firing member 4050 is advanced distally, the unlocking feature 4055 on the firing member 4050 engages the unlocking ledge 4234 on the sled 4230 which causes the firing member 4050 to be lifted upward so that the central pins 4058 on the firing member 4050 clear the blocking features 4060 in the first jaw or frame 4010. The firing member 4050 is now free to continue its distal advancement into the staple cartridge 4200 to complete the staple firing stroke. As the firing member 4050 is distally advanced, the foot 4054 may engage corresponding surfaces on the bottom of the first jaw or frame 4010 and the top pins 4056 may engage a cam surface on the anvil 4100 of the surgical stapling device 4002 which co-operate to position the anvil 4100 and the staple cartridge 4200 relative to one another. That said, embodiments are envisioned without one or both of the foot 4054 and top pins 4056.

As can be appreciated from the foregoing, the first lockout 4300 is proximal to the second lockout 4600. The first lockout 4300 is positioned within the surgical stapling device 4002 such that the first lockout 4300 is proximal to the sled 4230 of an unfired staple cartridge 4200 that has been seated in the first jaw or frame 4010. The first lockout 4300 is configured to move laterally between engaged positions wherein the first lock prevents distal advancement of the firing member 4050 from a starting position and disengaged positions wherein the firing member 4050 may be distally advanced therefrom (sometimes referred to herein as a "ready state"). For example, the first and second lockout arms 4312 and 4314 are configured to move in a first horizontal plane FP between engaged and disengaged positions. See FIG. 8. With regard to the second lockout 4600, the firing member 4050 moves vertically between the unlocked and locked positions along a second plane SP. See FIG. 9. In the illustrated example, the second plane SP is orthogonal to the first plane FP. When the firing member 4050 is in the ready state, if firing motions are applied thereto, the firing member 4050 may move distally. However, unless a compatible staple cartridge that has a sled located in an unfired position therein is seated in the frame to unlock the second lockout, the firing member will be prevented from distally advancing through the staple firing stroke.

Figure 20:
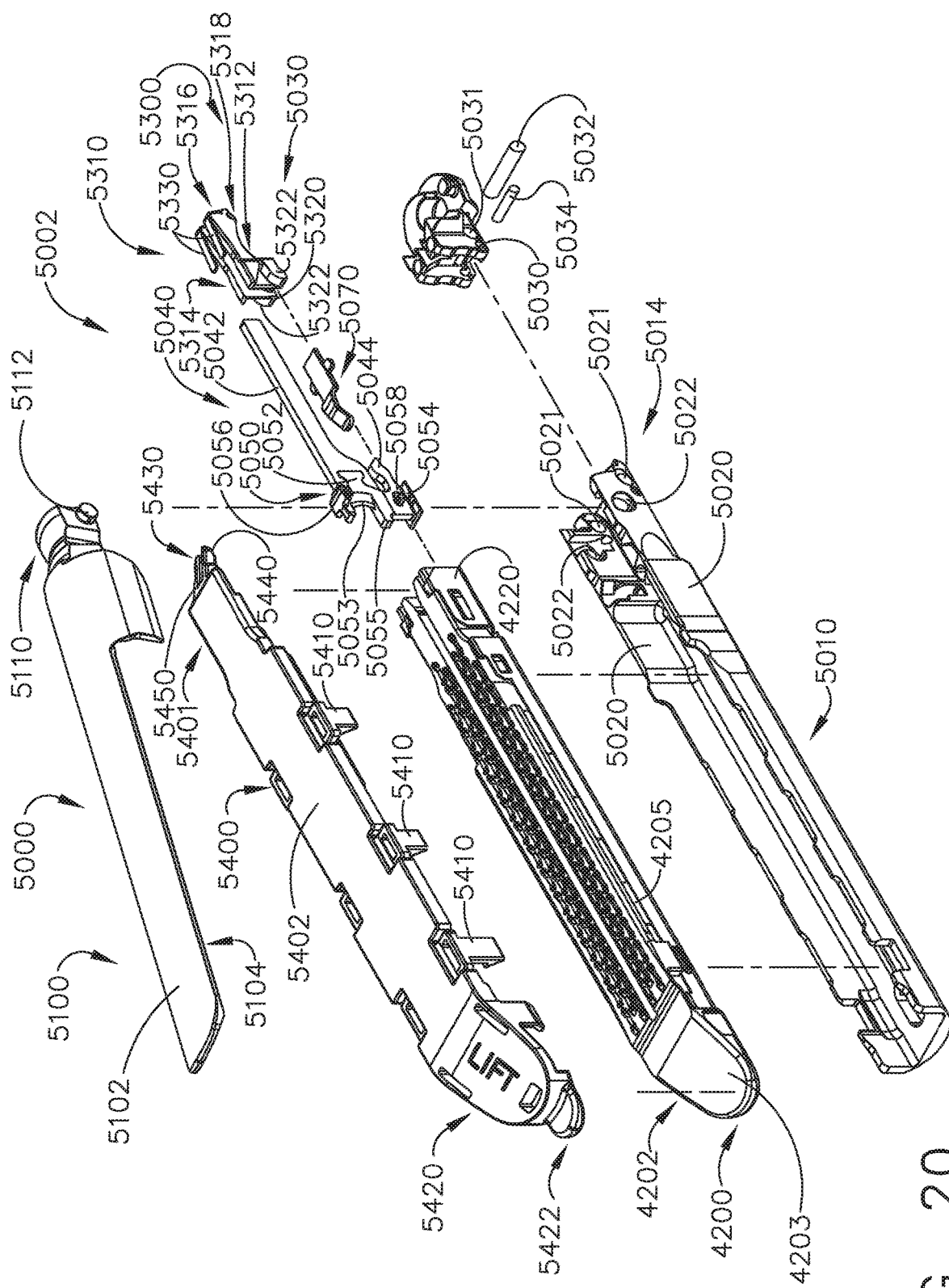
FIG. 20 is an exploded perspective assembly view of a surgical stapling device and staple cartridge of another surgical stapling assembly.

FIGS. 20-23 illustrate another surgical stapling assembly 5000 that is similar in many aspects to surgical stapling assembly 4000 discussed above. The surgical stapling assembly 5000 comprises a surgical stapling device 5002 that may be employed in connection with the surgical instrument 1010 described above or in connection with a variety of other surgical instruments described in various disclosures that have been incorporated by reference herein. As can be seen in FIG. 20, the surgical stapling device 5002 comprises a first jaw or frame 5010 that is configured to operably support a compatible staple cartridge 4200 therein. The first jaw or frame 5010 may be attached to a spine of a shaft assembly of a surgical instrument or robot in the various manners described herein and/or described in the various disclosures which have been incorporated by reference herein. In the illustrated example, the first jaw or frame 5010 is attached to the spine of a shaft assembly (not shown in FIG. 20), by a shaft mount flange 5030 that is pinned by a pin 5032 or otherwise attached to a proximal end 5014 of the first jaw 5010. In particular, pin 5032 is configured to pass through aligned holes 5021 in upstanding sidewalls 5020 of the first jaw or frame 5010 as well as through hole 5031 in the shaft mount flange 5030. The shaft mount flange 5030 is configured to interface with an articulation joint arrangement (not shown) that is configured to facilitate articulation of the first jaw 5010 relative to the shaft assembly in various known configurations. The surgical stapling device 5002 may also be used in connection with shaft assemblies that do not facilitate articulation of the surgical stapling device 5002.

Still referring to FIG. 20, the surgical stapling device 5002 further comprises a firing member assembly 5040 that comprises a knife bar 5042 that is attached to a knife member or firing member 5050. The knife bar 5042 also interfaces with corresponding components and firing systems in the surgical instrument or robot to receive firing motions which can distally advance the knife bar 5042 and firing member 5050 through a staple firing stroke from a starting position to an ending position and also retract the knife bar 5042 and firing member 5050 proximally to the starting position. In the illustrated arrangement, the firing member 5050 comprises a firing member body 5052 that supports a cutting edge or knife edge 5053. The firing member 5050 further comprises a foot 5054 that is formed on the bottom of the firing member body 5052 and extends laterally from each side thereof. The firing member 5050 further comprises a pair of top pins or tabs 5056 that extend laterally from the firing member body 5052 that are adapted to engage ledges on a second jaw or anvil as will be discussed further herein. Additionally, the firing member 5050 comprises a pair of central pins or tabs 5058 that protrude laterally from each side of the firing member body 5052. In some of the disclosures incorporated by reference herein, the firing member 5050 may also be referred to as an "E-Beam" firing member or cutting member.

Further to the above, the surgical stapling device 5002 further comprises a second jaw or anvil 5100 that is movable relative to the first jaw or frame 5010. The anvil 5100 comprises an anvil body 5102 and an anvil mounting portion 5110. The anvil body 5102 comprises a staple forming undersurface or tissue contacting surface 5104 that has a series of staple forming pockets (not shown) formed therein that are arranged to form corresponding staples as they are driven into forming contact therewith. The anvil mounting portion 5110 comprises a pair of laterally extending anvil pins or trunnion pins 5112 that are configured to be received in corresponding trunnion holes 5022 provided in the upstanding sidewalls 5020 of the first jaw or frame 5010. Unlike the anvil 4100 described above, the anvil 5100 is pivotally pinned to the frame 5010 for pivotal travel relative thereto about a fixed pivot axis. Stated another way, unlike anvil 4100, anvil 5100 does not materially move axially or translate during the anvil closure process. In various arrangements, the trunnion holes 5022 may be sized relative to the trunnion pins 5112 to facilitate installation therein and free pivotal travel of the trunnion pins such that the trunnion pins may have some slight axial movement therein, but any of such axial motion is much less than the axial translation of the anvil 4100.

As discussed above, as well as in several of the disclosures which have been incorporated by reference herein, the anvil 5100 may be movable from an open position wherein a used or spent staple cartridge may either be removed from the first jaw or frame 5010 or an unfired staple cartridge may be operably seated therein to a closed position by an axially movable closure member or end effector closure tube (not shown). For example, as the closure member is moved distally from a proximal position, the closure tube may operably engage a cam surface on the anvil mounting portion 5110. Such interaction between the closure member and the anvil mounting portion 5110 causes the anvil mounting portion 5110 and the anvil trunnion pins 5112 to pivot until the closure member moves the anvil 5100 to a fully closed position. When in the fully closed position, the staple-forming pockets in the anvil 5100 are properly aligned with the staples in a corresponding compatible surgical staple cartridge that has been operably seated in the first jaw or frame 5010. When the axially movable closure member is thereafter moved in a proximal direction, the closure member causes the anvil 5100 to pivot back to the open position.

Further to the above, the surgical stapling device 5002 comprises a first lockout 5300 that is configured to prevent the firing member 5050 from moving distally from its proximal-most, starting position when an authorized or compatible staple cartridge is not operably seated in the frame 5010. The first lockout 5300 may also be referred to herein as an "authentication" lockout. In the illustrated arrangement, the first lockout 5300 comprises a single, a pivotal first spring assembly 5310 that is supported in a proximal end 5014 of the first jaw or frame 5010 and is attached to the shaft mount flange 5030. In one arrangement for example, the first spring assembly 5310 comprises a first lockout arm 5312 and a second lockout arm 5314 that are attached to a central body portion 5316. The first spring assembly 5310 is attached to the shaft mount flange 5030 by a pin 5034 that extends through holes 5036 in the shaft mount flange 5030 and through holes 5318 in the first lockout arm 5312 and the second lockout arm 5314. The first lockout arm 5312 and the second lockout arm 5314 each further comprise a lockout latch feature 5320. Each lockout latch feature 5320 is adapted to releasably capture therein a corresponding central pin 5058 on the firing member 5050 when the firing member 5050 is in its proximal-most or starting position. See FIG. 21. Additionally, the first lockout spring assembly 5310 further comprises a pivot spring or springs 5330 that serve to bias or pivot the first spring assembly 5310 downwardly about the pin 5034 to bring the latch features 5320 into latching or locking engagement with the corresponding central pins 5058.

The surgical stapling assembly 5000 may further comprise a retainer 5400 that is similar to retainer 4400 described above. The retainer 5400 comprises a top portion 5402 that is coextensive with and configured to be received on the deck surface 4204 of the staple cartridge 4200 such that when the retainer 5400 is attached to the cartridge body 4202, the retainer 5400 covers all of the staple pockets 4208 in the cartridge body 4202. Thus, when the retainer 5400 is attached to the staple cartridge 4200, the retainer 5400 may prevent the surgical staples stored within the staple pockets 4208 from falling out should the surgical staple cartridge 4200 be inverted or turned upside down prior to use. Other retainer configurations are contemplated wherein the retainer top does not cover all or any of the staple pockets. In the illustrated arrangement, the retainer 5400 may be molded from a polymer material and include a plurality of retainer lugs 5410 that are configured to latchingly engage outwardly extending deck ledge portions 4205 on the staple cartridge body 4202. The retainer 5400 may further comprise an angled nose portion 5420 and a distal latch tab 5422 that that is configured to latchingly engage the distal nose 4203 of the cartridge body 4202. The retainer 5400 may be removably coupled to the staple cartridge 4200 by engaging the distal latch tab 5422 with the end of the staple cartridge distal nose 4203 and aligning the retainer 5400 such that the underside of the top portion 5402 confronts the cartridge deck surface 4204 and the retainer lugs 5410 are located above the deck ledge portions 4205 on each side of the staple cartridge body 4202. Thereafter, the retainer 5400 may be pressed toward the staple cartridge 4200 causing the retainer lugs 5410 to flex laterally outward and snap into latching engagement with the corresponding deck ledge portions 4205. Other retainer latching arrangements disclosed herein may also be employed to removably affix the retainer 5400 to the staple cartridge 4200.

The retainer 5400 further comprises an authentication key 5430 that is adapted to engage key pockets 5322 that are formed in the first lockout arm 5312 and the second lockout arm 5314. As can be seen in FIG. 20, the authentication key 5430 protrudes proximally from a proximal end 5401 of the top portion 5402 of the retainer 5400 and comprises a right ramp feature 5440 and a left ramp feature 5450 that are separated by a space that is sized to receive the firing member body 5052 therebetween. In the illustrated example, the ramps 5440 and 5450 angle downward from the top portion 5402 of the retainer 5400 and are configured to enter the key pockets 5322 in the first and second lockout arms 5312, 5314.

Figure 21:
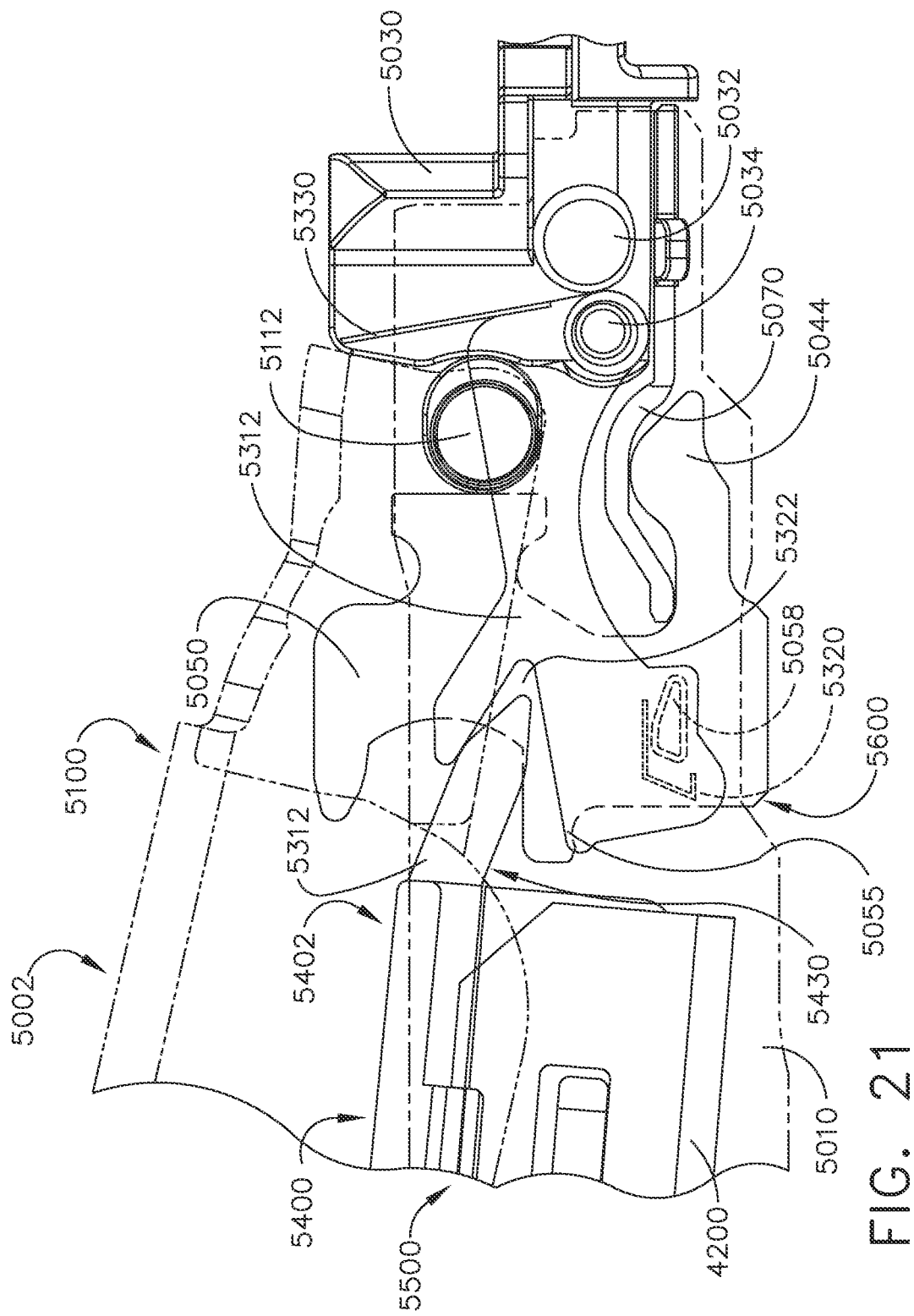
FIG. 21 is a partial side elevational view of a portion of the surgical stapling device of FIG. 20 during an initial insertion of a cartridge assembly comprising a retainer attached to a staple cartridge into the surgical stapling device.
Figure 22:
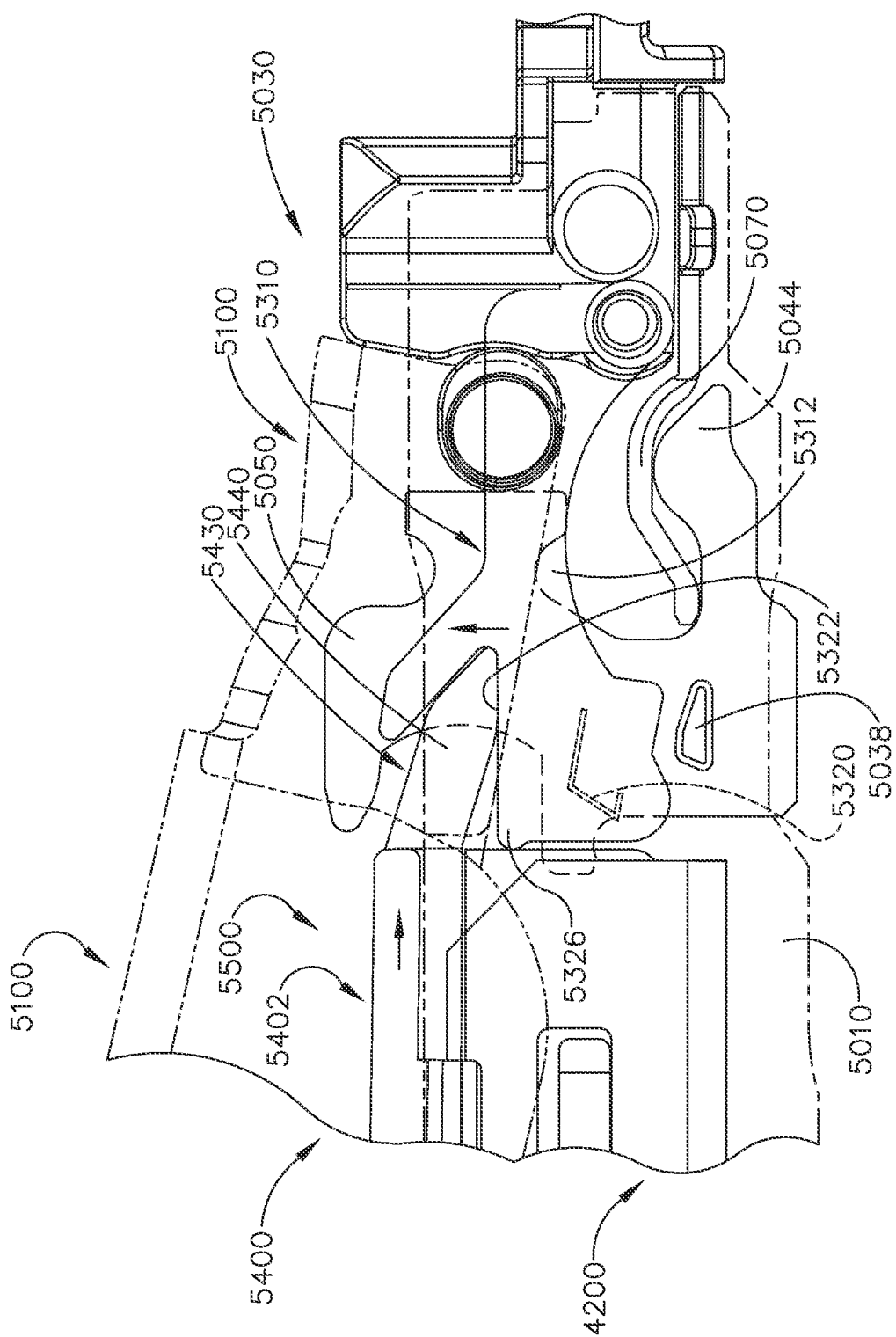
FIG. 22 is another partial side view of the surgical stapling device of FIG. 21 after the cartridge assembly has been seated in a first jaw of the surgical stapling device and prior to removal of the retainer from the staple cartridge.
Figure 23:
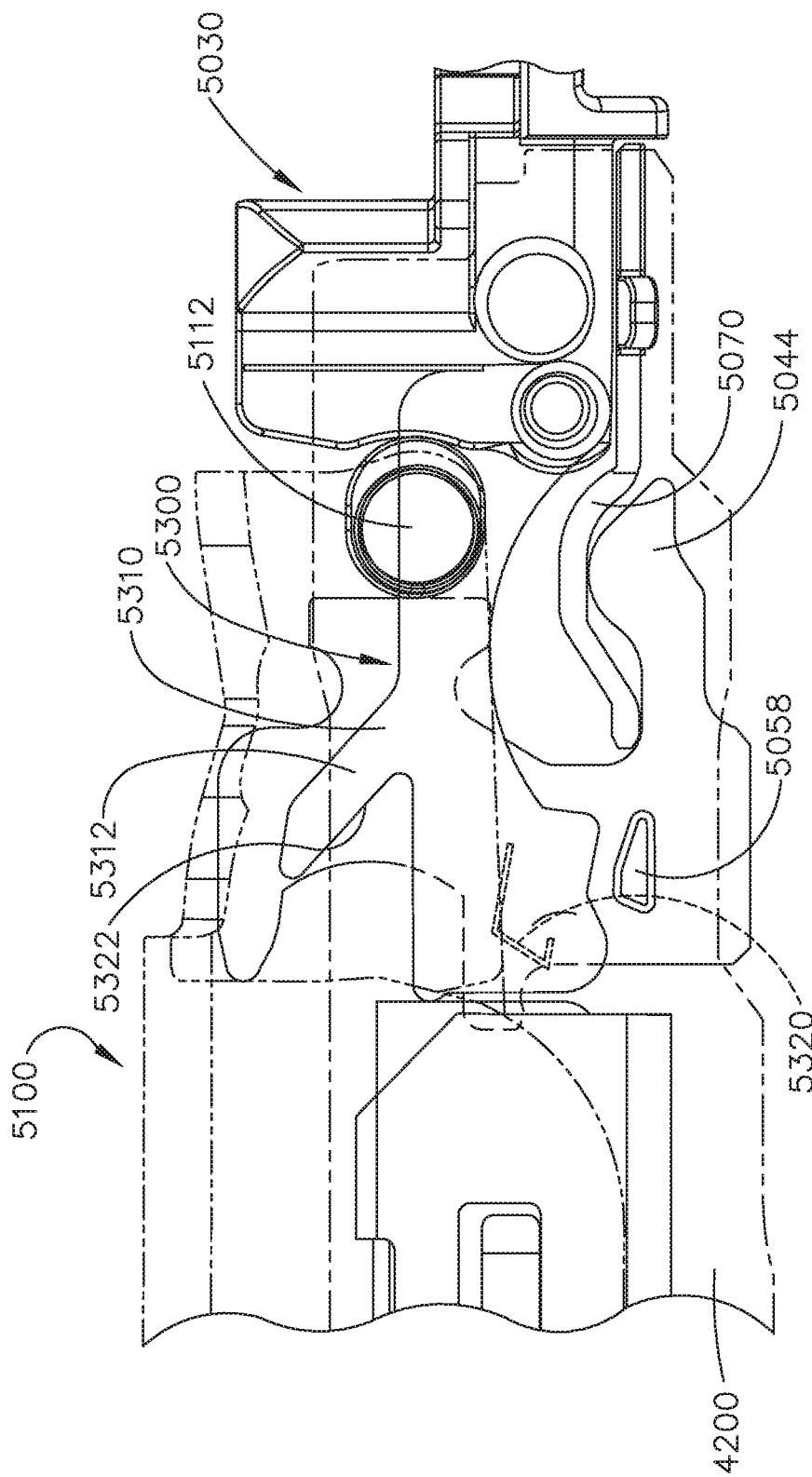
FIG. 23 is another partial side view of the surgical stapling assembly of FIG. 22 after the retainer has been removed from the staple cartridge.

In use, the retainer 5400 is removably attached to the staple cartridge 4200 to form a cartridge assembly 5500. Thereafter, the cartridge assembly is initially inserted into the first jaw or frame 5010 so as to insert the ramps 5440 and 5450 of the authentication key 5430 into the key pockets 5322 in the first and second lockout arms 5312, 5314. See FIG. 21. Further longitudinal advancement of the cartridge assembly 5500 into the first jaw or frame 5010 in a proximal direction causes the ramps 5440 and 5450 to pivot the first spring 5310 upward into a disengaged or unlocked position wherein the latch features 5320 have disengaged the corresponding central pins 5058. See FIG. 22. When the cartridge assembly 5500 has been operably seated in the first jaw or frame 5010, a distally facing detent 5326 that is formed on each of the first and second lockout arms 5312, 5314 retainingly engage a proximal end of the staple cartridge 4200 as shown in FIG. 22. Such arrangement serves to retain the first spring 5310 in the disengaged position. When in that position, the first lockout 5300 is in the unlocked position or stated another way is "defeated", unlocked or unlatched. The user may then remove the retainer 5400 from the staple cartridge 4200 by prying the up the distal latch tab 5422 and lifting the retainer 5400 upward until the retainer lugs 5410 disengage the deck ledge portions 4205. In the illustrated example, the term "LIFT" is molded, embossed, imprinted or otherwise provided on the nose portion 5420 to provide removal instructions to the user. The surgical staple cartridge 5200 remaining in the frame 5010 is ready to be fired. See FIG. 23.

The surgical stapling device 5002 also includes a second lockout 5600 that is very similar to the second lockout 4600 described above. Referring now to FIGS. 20 and 21, the knife bar 5042, which may comprise a solid or laminated structure, comprises a spring tab 5044 that is configured to operably interface with a spring plate 5070 that is mounted in the bottom of the first jaw 5010. The spring plate 5070 serves to pivot the firing member 5050 downward such that the central pins 5038 thereon contact the frame blocking or abutment features (not shown) in the bottom of the frame 5010 unless an unlocking feature 5055 on the firing member 5050 engages an unlocking ledge 4234 on the sled 4230 causing the firing member 5050 to be lifted upward so that the central pins 5058 on the firing member 5050 clear the blocking features in the frame 5010 was discussed above.

Figure 24:
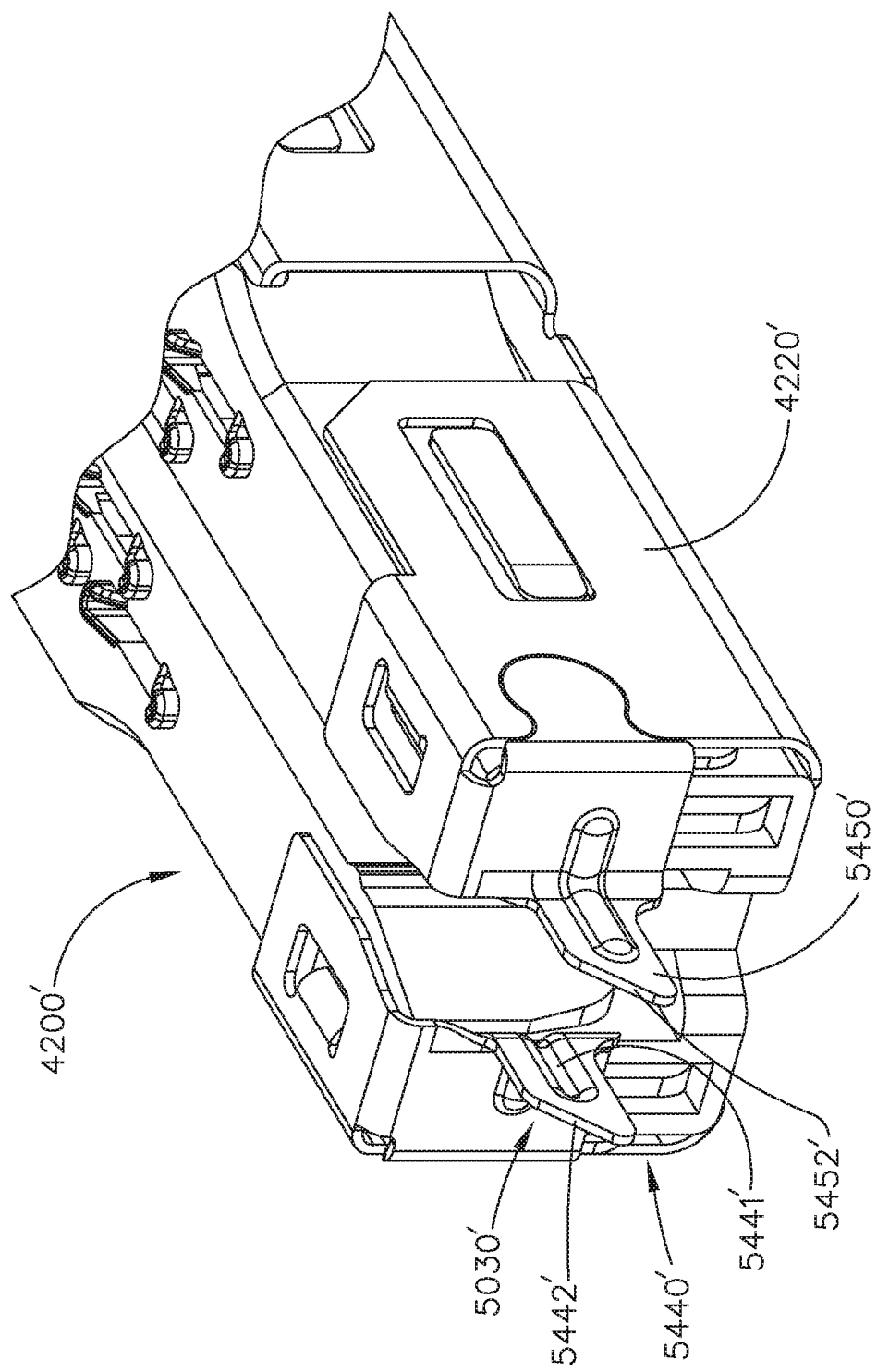
FIG. 24 is a perspective view of a proximal end of another staple cartridge.
Figure 25:
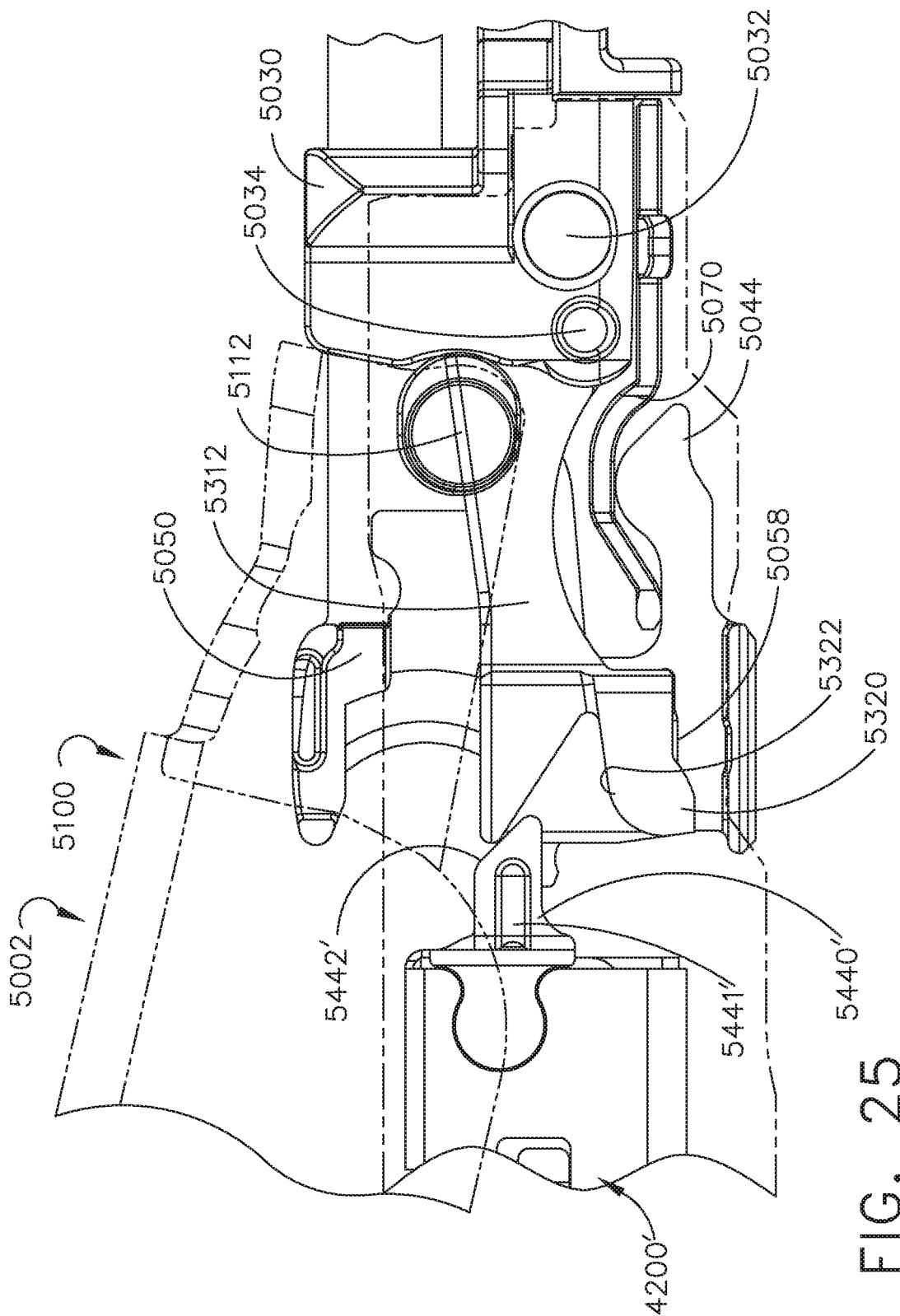
FIG. 25 is a partial side elevational view showing an initial insertion of the staple cartridge of FIG. 24 into a surgical stapling device with a first firing member lockout thereof in an engaged or locked position.
Figure 26:
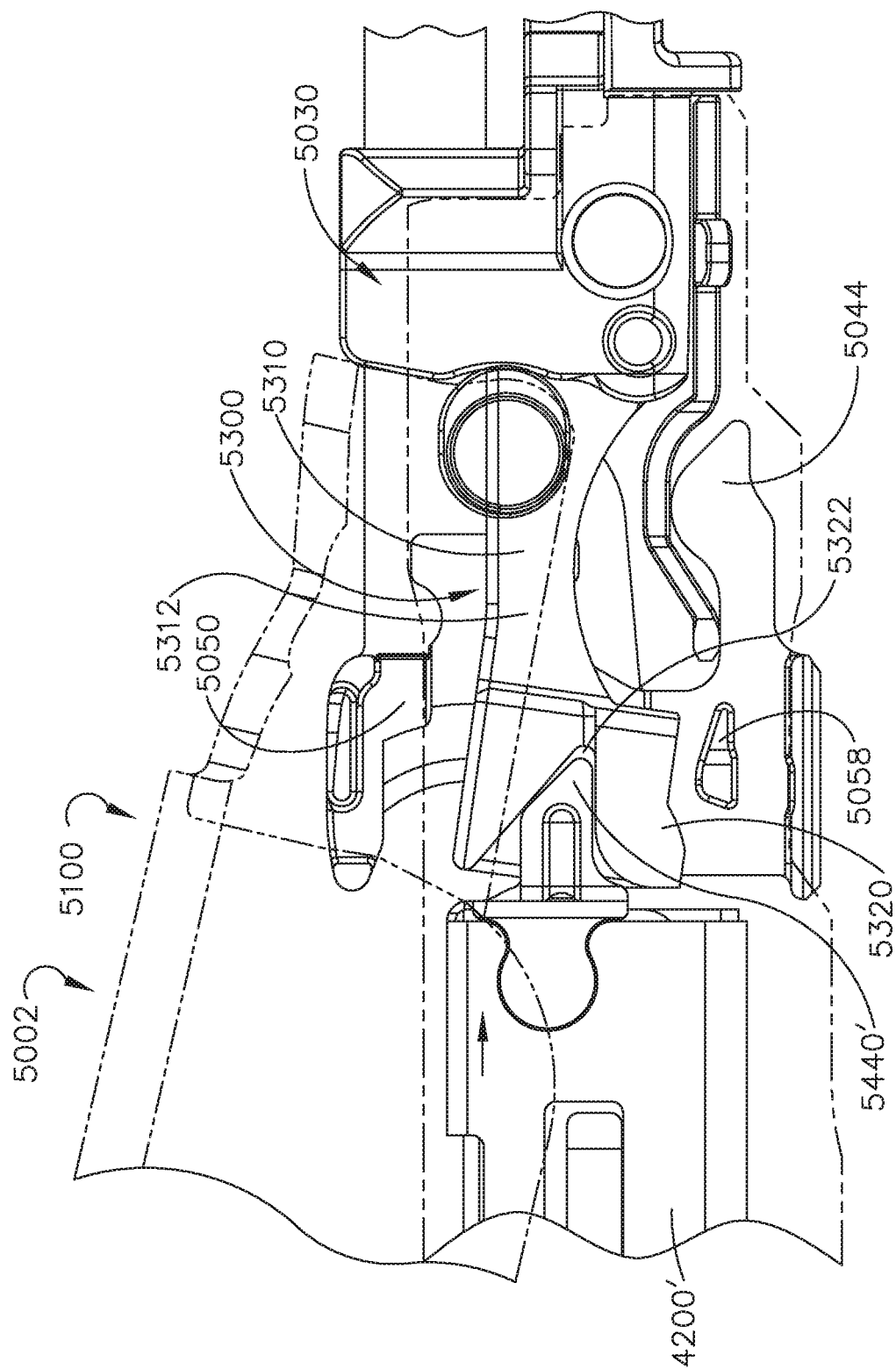
FIG. 26 is another partial side view of the surgical stapling device of FIG. 25, with the staple cartridge of FIG. 24 operably seated therein and the first firing member lockout in a disengaged or unlocked position.

FIGS. 24-26 illustrate an alternative compatible surgical staple cartridge 4200' that is configured to actuate the first lockout 5300 in the manner described above. In this arrangement, however, the authentication key 5030' is formed on the cartridge pan 4220'. As can be seen in FIG. 24, the authentication key 5030' comprises a right ramp feature 5440' and a left ramp feature 5450' that are bent into the cartridge pan 4220' to protrude proximally therefrom. A reinforcement rib 5441' may be embossed into each joint where the ramps 5440' and 5450' are formed to provide additional support and rigidity to each of the ramps 5440', 5450'. In the illustrated example, the ramp 5440' has an angled proximal tip 5442' and the ramp 5450' contains an angled proximal tip 5452'. The tips 5442', 5452' are each configured to enter the key pockets 5322 in the first and second lockout arms 5312, 5314 to pivot the first lockout 5300 in the above described manner. The first lockout 5300 otherwise operates in the manner described above.

Figure 27:
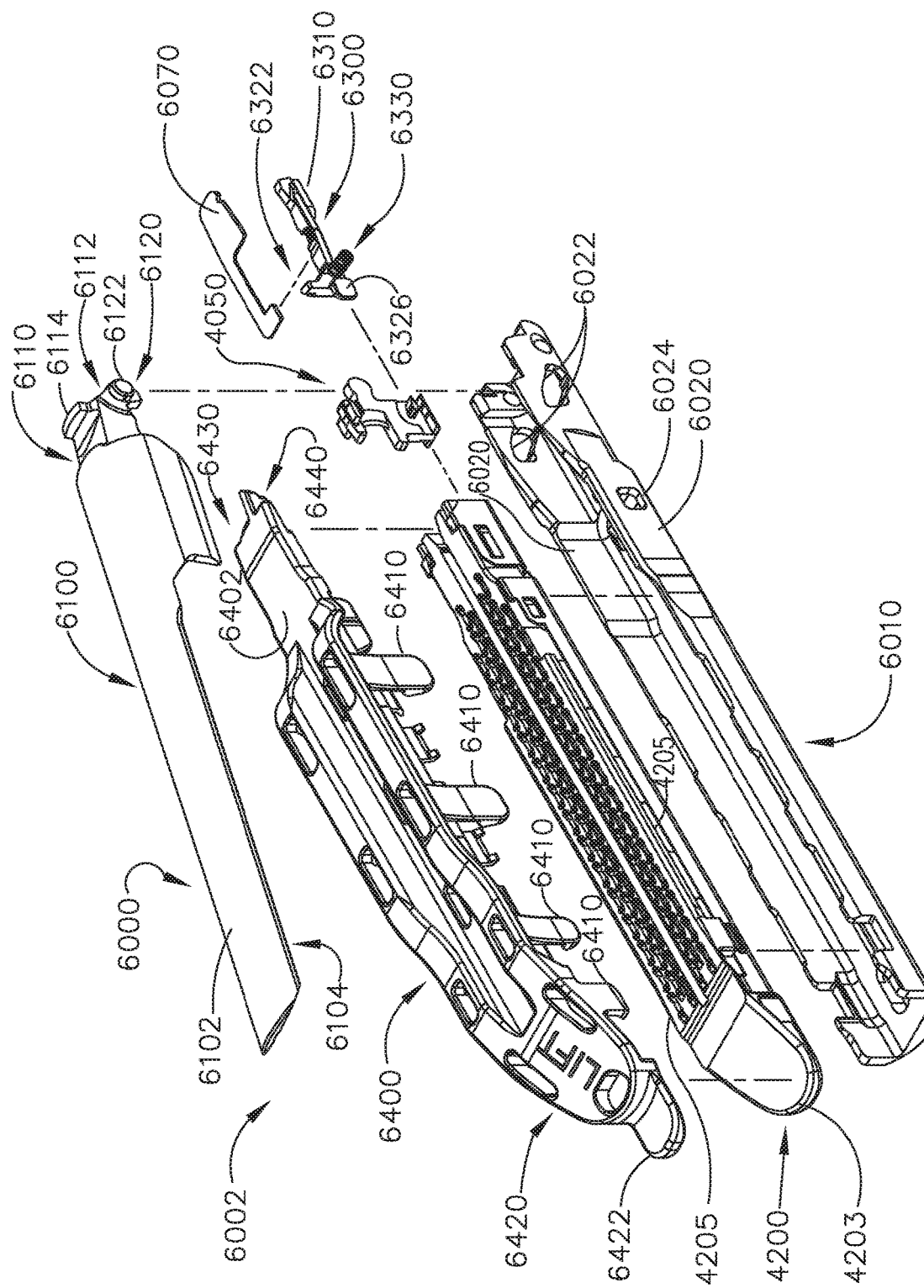
FIG. 27 is an exploded perspective assembly view of a surgical stapling device and staple cartridge of another surgical stapling assembly.

Referring to FIG. 27, an example of a surgical stapling assembly 6000 is shown. The surgical stapling assembly 6000 comprises a surgical stapling device 6002 that may be employed in connection with the surgical instrument 1010 described above or in connection with a variety of other surgical instruments or robots described in various disclosures that have been incorporated by reference herein. As can be seen in FIG. 27, the surgical stapling device 6002 comprises a first jaw, or frame 6010 that is configured to operably support a staple cartridge 4200 therein. The first jaw or frame 6010 is attached to a spine of the shaft assembly (not shown) by a shaft mount flange 4030 (FIG. 6) in the various manners described herein. The surgical stapling device 6002 further comprises a firing member assembly that comprises a knife bar that is attached to a knife member or firing member 4050 as was described above.

Further to the above, the surgical stapling device 6002 comprises a second jaw or anvil 6100 that is movable relative to the first jaw or frame 6010. The anvil 6100 is similar to anvil 4100 described above and comprises an anvil body 6102 and an anvil mounting portion 6110. The anvil body 6102 comprises a staple forming undersurface or tissue contacting surface 6104 that has a series of staple forming pockets (not shown) formed therein that are arranged to form corresponding staples as they are driven into forming contact therewith. The anvil mounting portion 6110 comprises a pair of laterally extending anvil pins or trunnion assemblies 6112. Each trunnion assembly 6112 comprises an outwardly and downwardly protruding lock lug portion 6120 that has a trunnion pin 6122 extending therefrom. Each trunnion pin 6122 is configured to be received in corresponding trunnion slots 6022 in the upstanding sidewalls 6020 of the first jaw 6010. In the illustrated arrangement, the trunnion slots 6022 are somewhat "kidney-shaped" and facilitate pivotal as well as axial travel of the corresponding trunnion pins 6122 therein.

As discussed above, as well as in several of the disclosures which have been incorporated by reference herein, the anvil 6100 may be movable from an open position wherein a used or spent surgical staple cartridge may either be removed from the frame 6010 or a fresh, new staple cartridge may be operably seated therein to a closed position by an axially movable closure member or end effector closure tube (not shown). For example, as the closure member is moved distally from a proximal position, the closure member may operably engage a cam surface on the anvil mounting portion 6110. Such interaction between the closure member and the anvil mounting portion 6110 causes the anvil mounting portion 6110 and the anvil trunnion pins 6122 to pivot and translate up the trunnion slots 6022 until the closure member moves the anvil 6100 to a closed position. When in the fully closed position, the staple-forming pockets in the anvil 6100 are properly aligned with the staples in a corresponding compatible staple cartridge that has been operably seated in the frame 6010. When the axially movable closure member is thereafter moved in a proximal direction, the closure member interfaces with an upstanding tab 6114 on the anvil mounting portion 6110 to return the anvil 6100 to the open position.

Further to the above, the surgical stapling device 6002 comprises a first lockout 6300 that is configured to prevent the second jaw or anvil 6100 from being movable from the open position to the closed position by the closure member. The first lockout 6300 may also be referred to herein as an "authentication" lockout. In the illustrated arrangement, the first lockout 6300 comprises a first lockout arm 6310 that is pivotally supported in the frame 6010 by a lockout pin 6312 that is attached thereto. In one example, the first lockout arm 6310 is fabricated from stainless steel or the like and the lockout pin 6312 is welded or otherwise attached thereto. The lockout pin 6312 is pivotally seated in a pivot hole 6013 in the frame 6010 to facilitate pivotal travel of the first lockout arm 6310 between a locked position and an unlocked position. See FIG. 28. In the illustrated example, a lockout feature 6316 is formed on the proximal end 6314 of the first lockout arm 6310 and is configured to blockingly engage the lock lug portion 6120 on the corresponding trunnion assembly 6112 when the first lockout arm 6310 is in an engaged position. When the lockout feature 6316 blockingly engages the lock lug portion 6120 on the trunnion assembly 6112, the lockout feature 6316 prevents the trunnion assembly 6112 from traveling within the corresponding trunnion slot 6022 in the first jaw or frame 6010 which effectively prevents the second jaw or anvil 6100 from moving from the open position to the closed position should a closure motion be applied thereto. This position of the first lockout arm 6310 may be referred to herein as a "jaw locking position". It will be appreciated that the lockout feature 6316, as well as the lock lug portion 6120, may be sufficiently robust so as to resist substantial closure motions that applied to the anvil 6100 to prevent closure of the anvil 6100.

Figure 28:
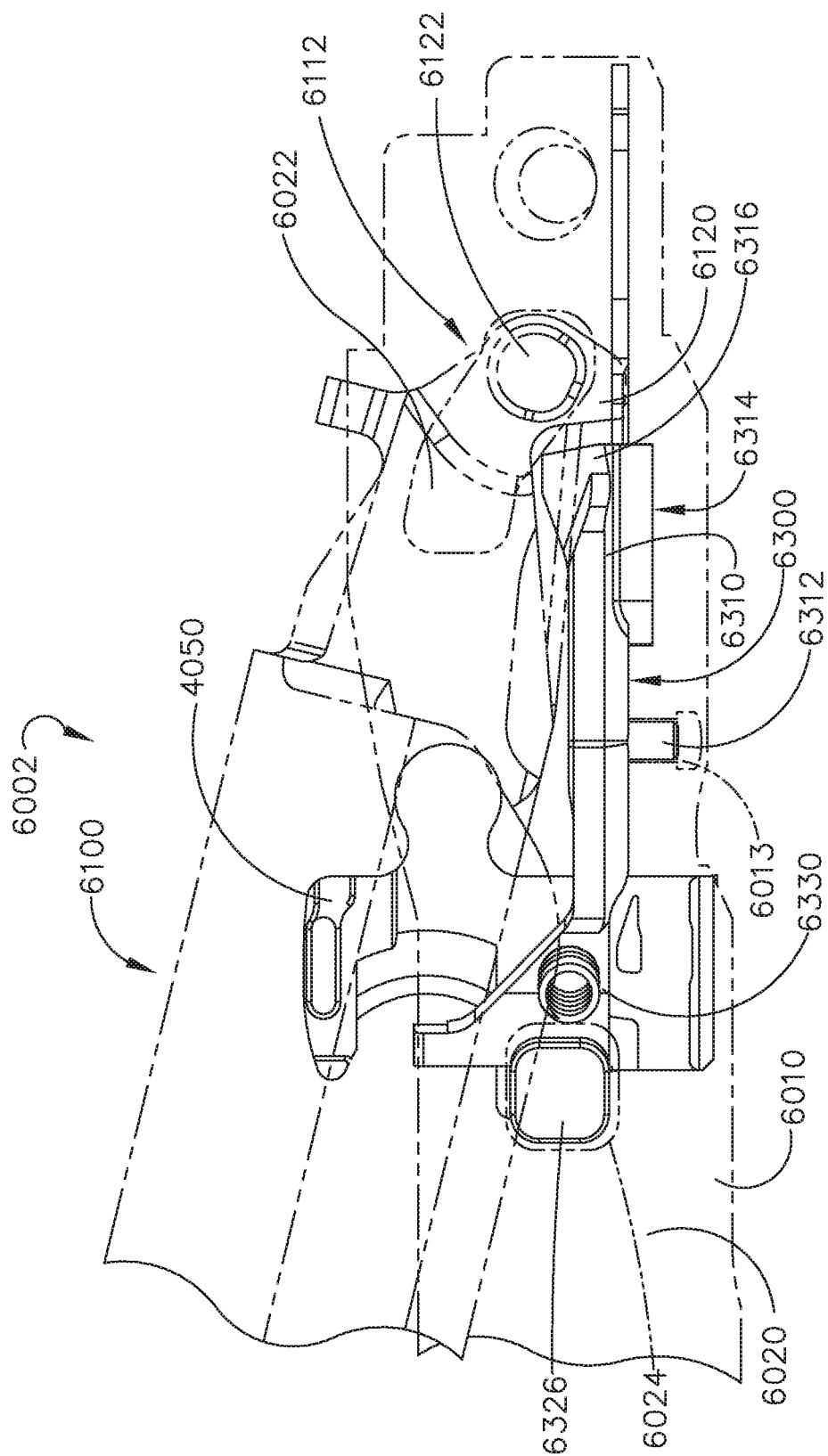
FIG. 28 is a partial side elevational view of a portion of the surgical stapling device of FIG. 27 illustrating a first lockout arm of a first lockout in a jaw locking position.
Figure 29:
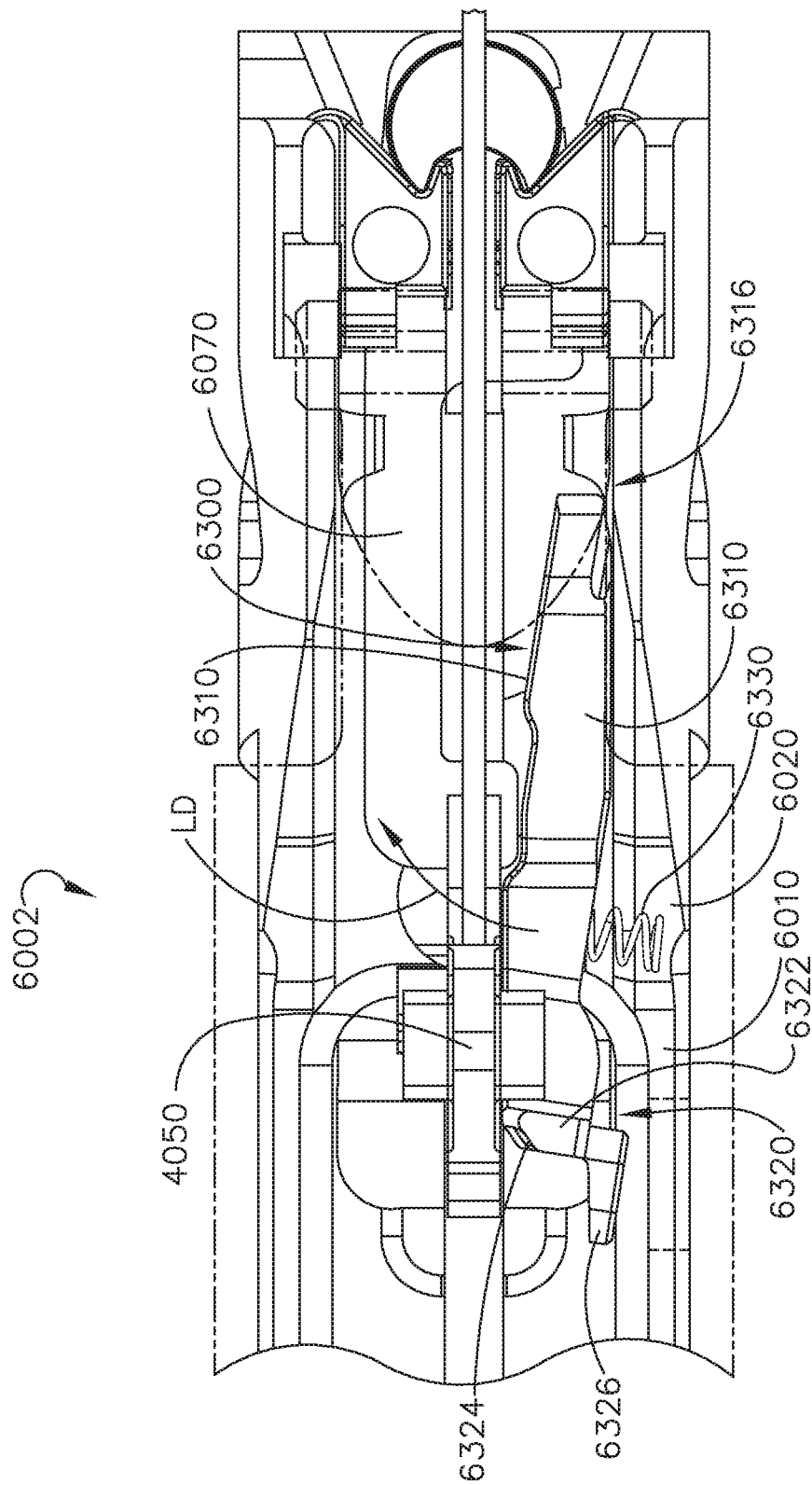
FIG. 29 is a top view of portions of the surgical stapling device of FIG. 28 with the first lockout arm in the jaw locking position.
Figure 30:
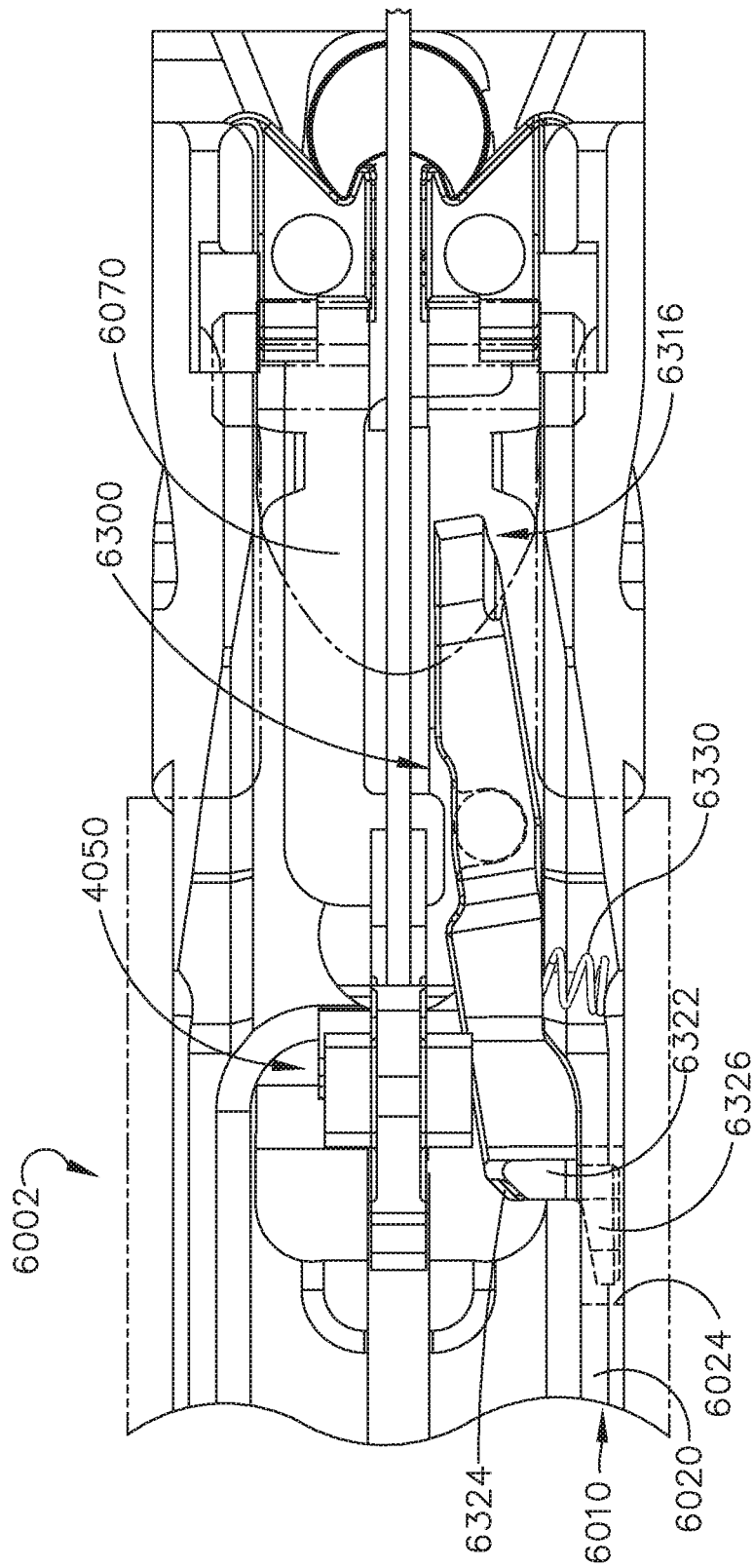
FIG. 30 is another top view of portions of the surgical stapling device of FIG. 29 with the first lockout arm in a jaw closure position.
Figure 31:
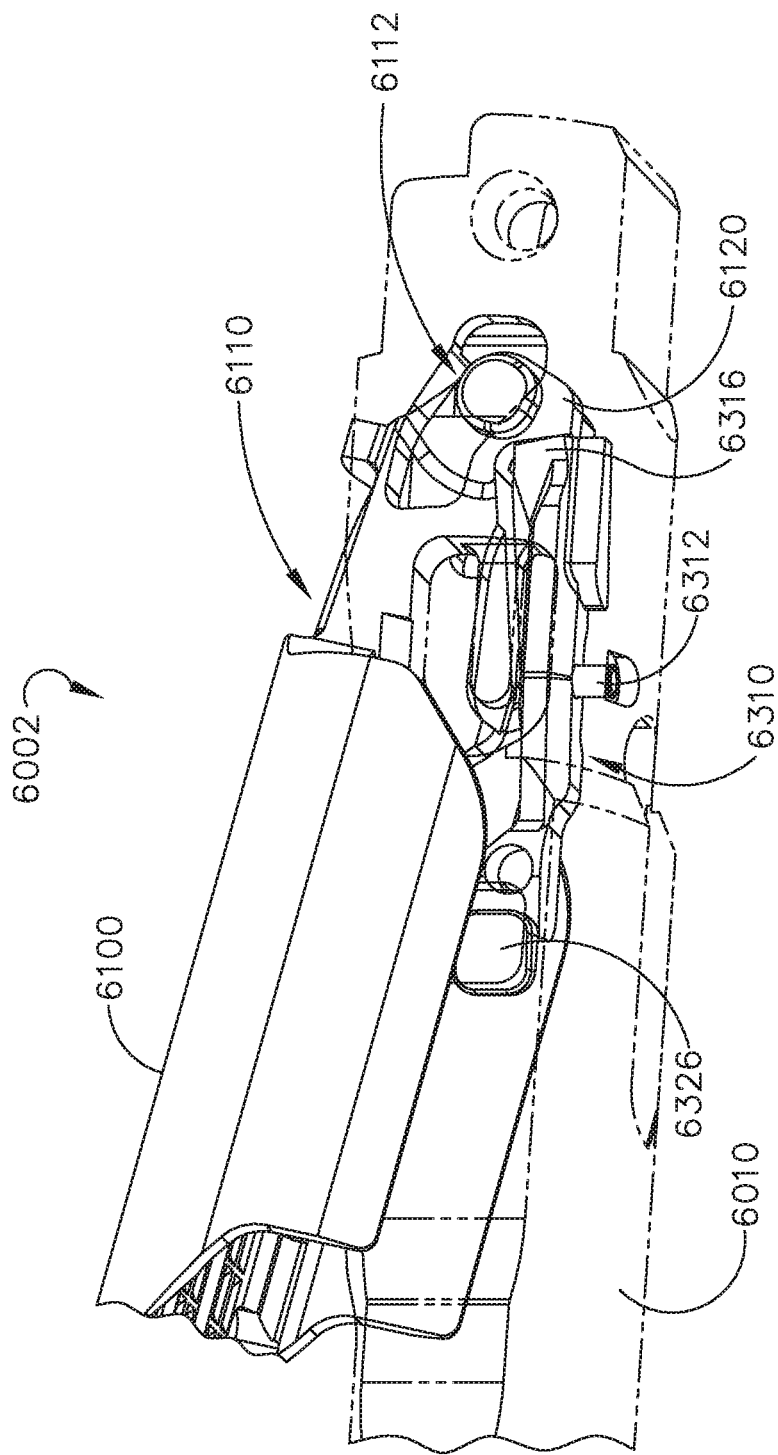
FIG. 31 is a partial bottom perspective view of the surgical stapling device of FIG. 29 with the first lockout arm in the jaw locking position.

Still referring to FIG. 28, a first lockout spring 6330 is supported in a corresponding sidewall 6020 of the first jaw or frame 6010 to bias the first lockout arm 6310 in a locking direction LD to the engaged, locked or "jaw locking" position wherein the first lockout arm 6310 prevents the anvil 6100 from moving from the open position to the closed position. A travel limiting plate or mounting plate 6070 is supported within the frame 6010 and attached to the shaft mounting assembly. The travel limiting plate 6070 also provides lateral support to the first lockout arm 6310 when in the jaw locking position. See FIG. 29. As can be seen in FIGS. 28 and 29, the first lockout arm 6310 further comprises an upstanding actuator cam arm 6322 that is formed on a distal end 6320 of the first lockout arm 6310. The actuator cam arm 6322 comprises an actuator cam surface 6324. The first lockout arm 6310 further comprises a retention tab 6326 that is configured to be received within a corresponding opening or tab window 6024 that is provided in a frame sidewall 6020.

Turning now to FIG. 27, the stapling assembly 6000 further comprises a retainer 6400 that is configured to be removably coupled to the surgical staple cartridge 4200. In various embodiments, the retainer 6400 is substantially similar to the retainer 4400 described above except for the authentication key 6430. In the illustrated arrangement, the retainer 6400 comprises a top portion 6402 that is coextensive with and configured to be received on the deck surface 4204 such that when the retainer 6400 is attached to the cartridge body 4202, the retainer 6400 covers all of the staple pockets 4208 in the cartridge body 4202. In alternative versions the retainer top may only cover some of the staple pockets or none at all. The retainer 6400 may be molded from a polymer material and include a plurality of retainer lugs 6410 that are configured to latchingly engage outwardly extending deck ledge portions 4205 that are formed on the staple cartridge body 4202. The retainer 6400 may further comprise an angled nose portion 6420 and a distal latch tab 6422 that that is configured to latching engage the distal nose 4203 of the staple cartridge body 4202. The retainer 6400 may be removably coupled to the surgical staple cartridge 4200 by engaging the latch tab 6422 with the end of the distal nose 4203 and aligning the retainer 6400 such that the underside of the top portion 6402 of the retainer 6400 confronts the cartridge deck surface 4204 and the retainer lugs 6410 are located above the deck ledge portions 4205 on each side of the cartridge body 4202. Thereafter, the retainer 6400 may be pressed toward the staple cartridge 4200 causing the retainer lugs 6410 to flex laterally outward and snap into latching engagement with the corresponding deck ledge portions 4205. Other retainer latching arrangements disclosed herein may also be employed to removably affix the retainer 6400 to the staple cartridge 4200. The retainer 6400 may be removed from the staple cartridge 4200 by applying a prying motion to the distal latch tab 6422 and lifting upward until the retainer lugs 6410 disengage the deck ledge portions 4205. In the illustrated example, the term "LIFT" is molded or embossed into the nose portion 6420 to provide removal instructions to the user.

Figure 32:
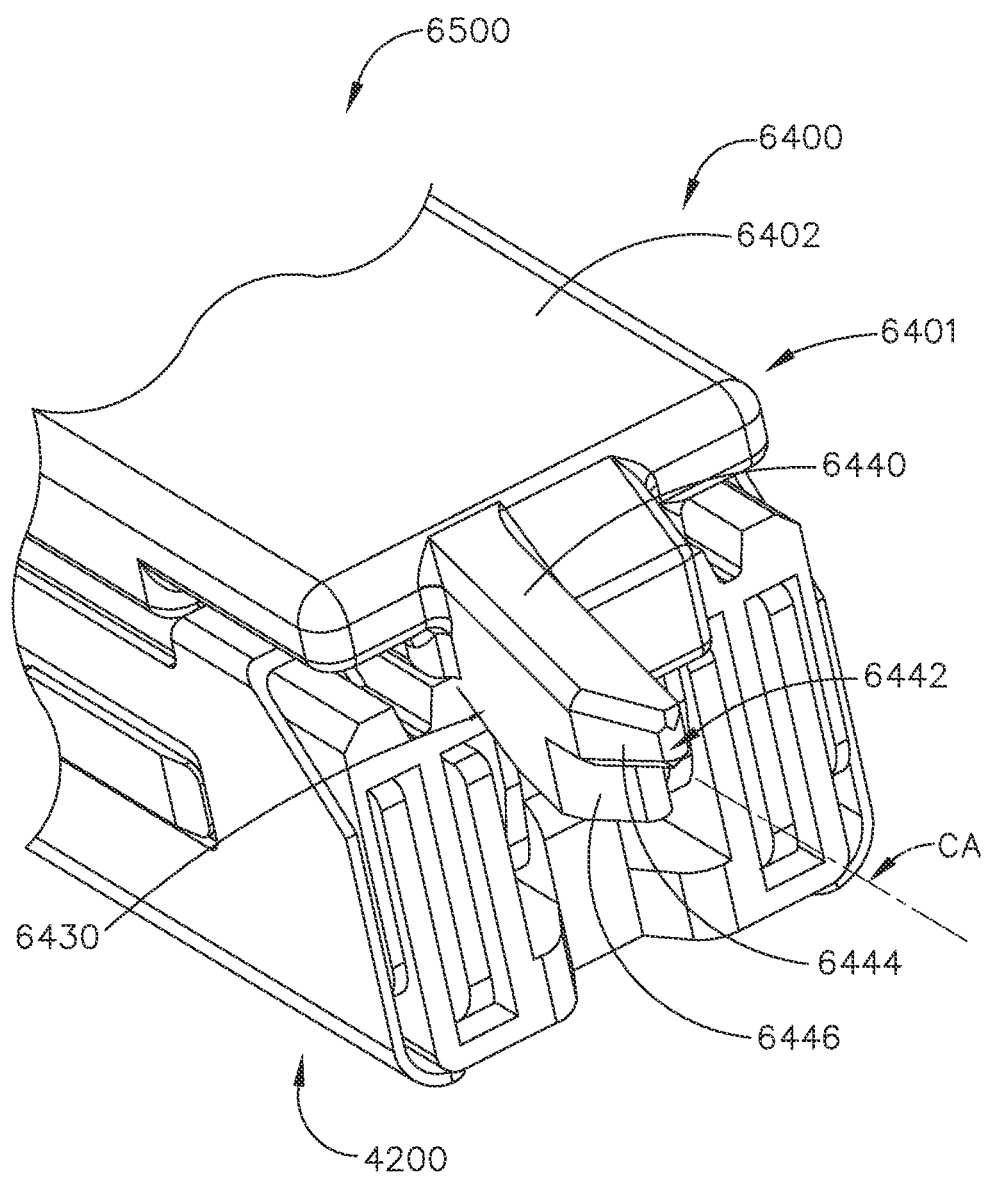
FIG. 32 is a partial perspective view of a proximal end of a cartridge assembly comprising another retainer attached to a staple cartridge.
Figure 33:
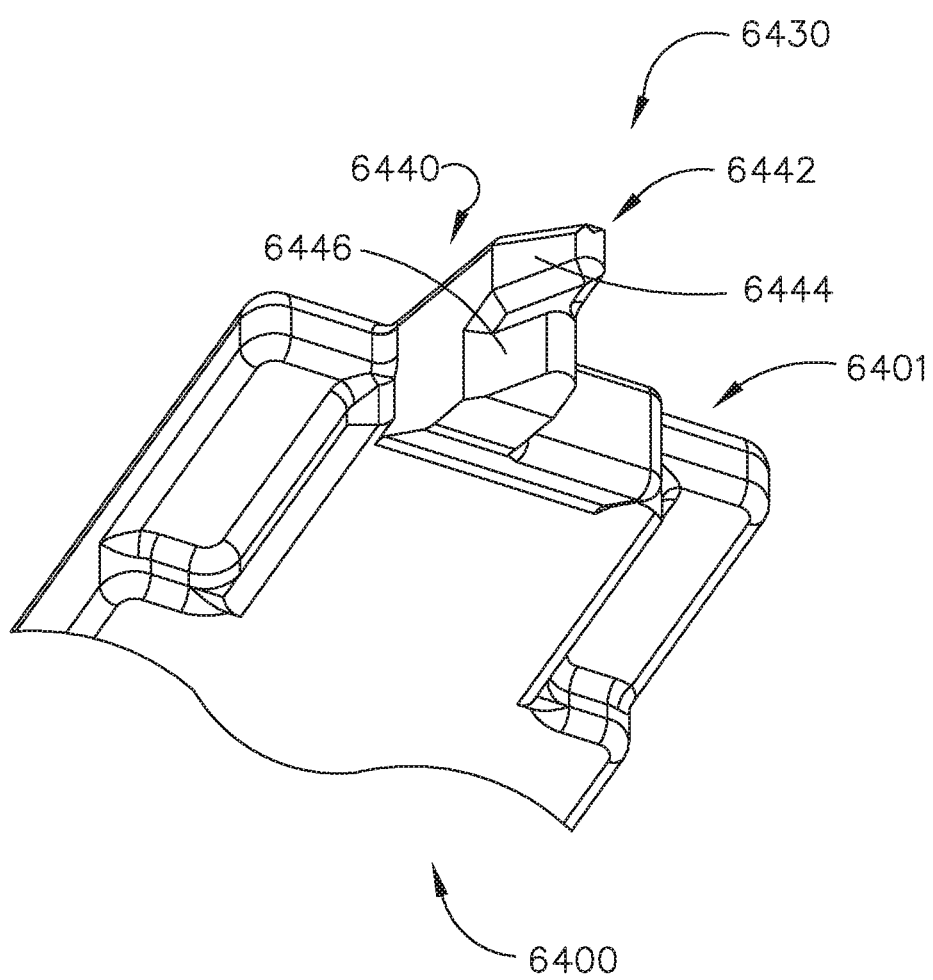
FIG. 33 is a bottom perspective view of a proximal end portion of the retainer of FIG. 32.
Figure 34:
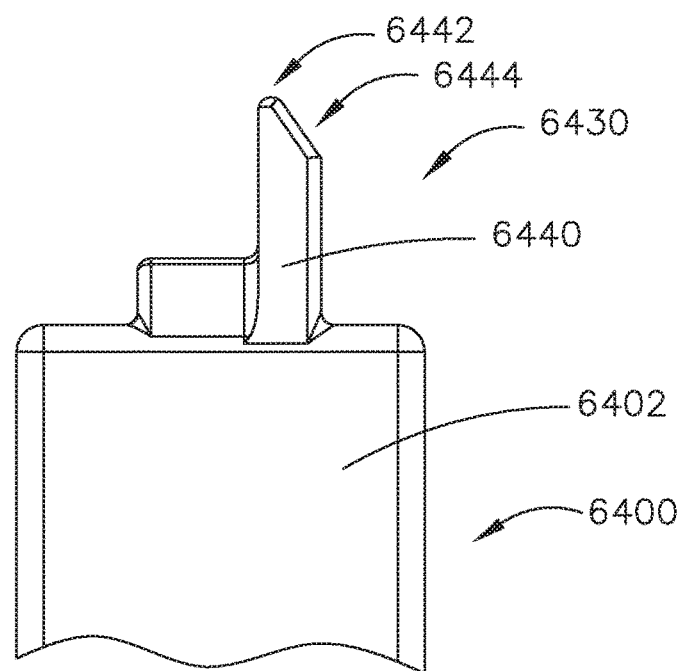
FIG. 34 is a top view of the proximal end of the retainer of FIG. 33.
Figure 35:
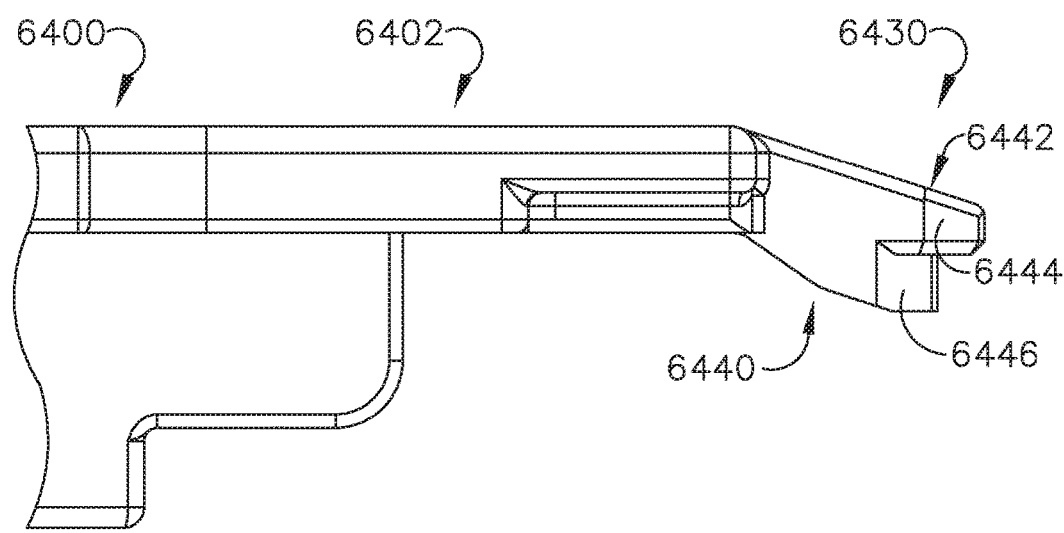
FIG. 35 is a side view of the proximal end of the retainer of FIG. 34.

Referring now to FIGS. 32-35, the retainer 6400 further comprises an authentication key 6430 that is configured to defeat, unlock or unlatch the first lockout 6300 when the retainer 6400 is attached to the surgical staple cartridge 4200 and the surgical staple cartridge 4200 has been operably seated in the first jaw or frame 6010. As can be seen in FIG. 32, the authentication key 6430 protrudes proximally from a proximal end 6401 of the top portion 6402 of the retainer 6400 and comprises an angled ramp feature 6440 that is positioned on one side of the cartridge axis CA when the retainer 6400 is attached to the staple cartridge 4200. In the illustrated example, the ramp 6440 angles downward from the top portion 6402 of the retainer 6400 and comprises a proximal tip 6442 that defines a first or proximal cam surface 6444 that angles inward at the tip. A second or distal cam surface 6446 is located below the first cam surface 6444. These dual sequential cam surfaces 6444, 6446 are configured to interface with the actuator cam surface 6324 on the actuator cam arm 6322 to move the first lockout arm 6310 from the locked or jaw locking position to the unlocked or jaw closure position. Such arrangement affords little room for the authentication key 6430 to unlockingly actuate the actuator cam arm 6322 when the staple cartridge supporting the retainer 6400 is operably seated in the first jaw or frame 6010. The dual cam surface arrangement facilitates pivotal actuation of the first lockout arm 6310 a sufficient pivotal distance required to place the first lockout arm 6310 in the disengaged or jaw closure position. This amount of pivotal travel may be more than twice the width of the ramp 6440, for example.

Figure 36:
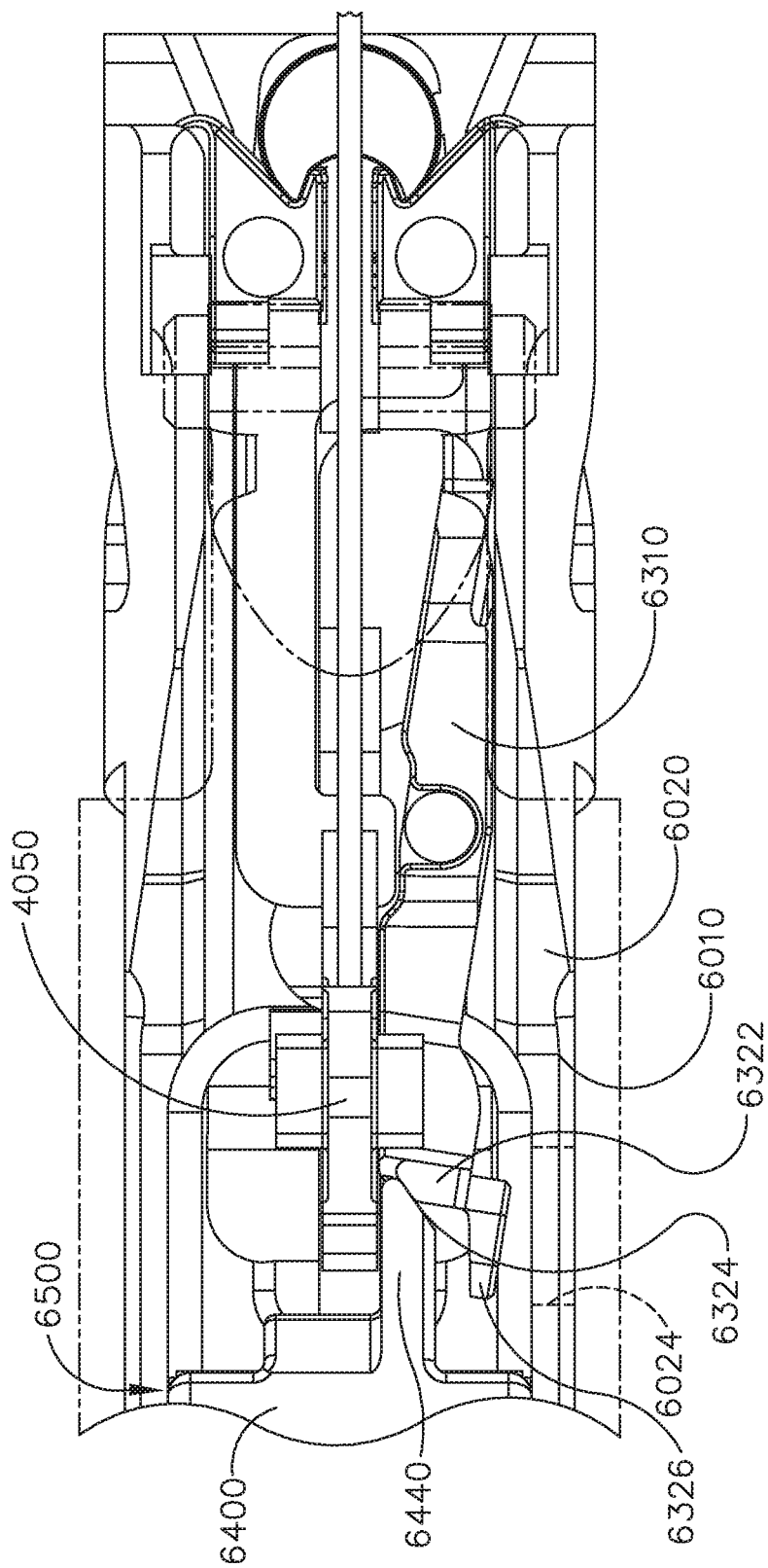
FIG. 36 is another top view of portions of the surgical stapling device of FIG. 29 during an initial insertion of the cartridge assembly of FIG. 32 therein.
Figure 37:
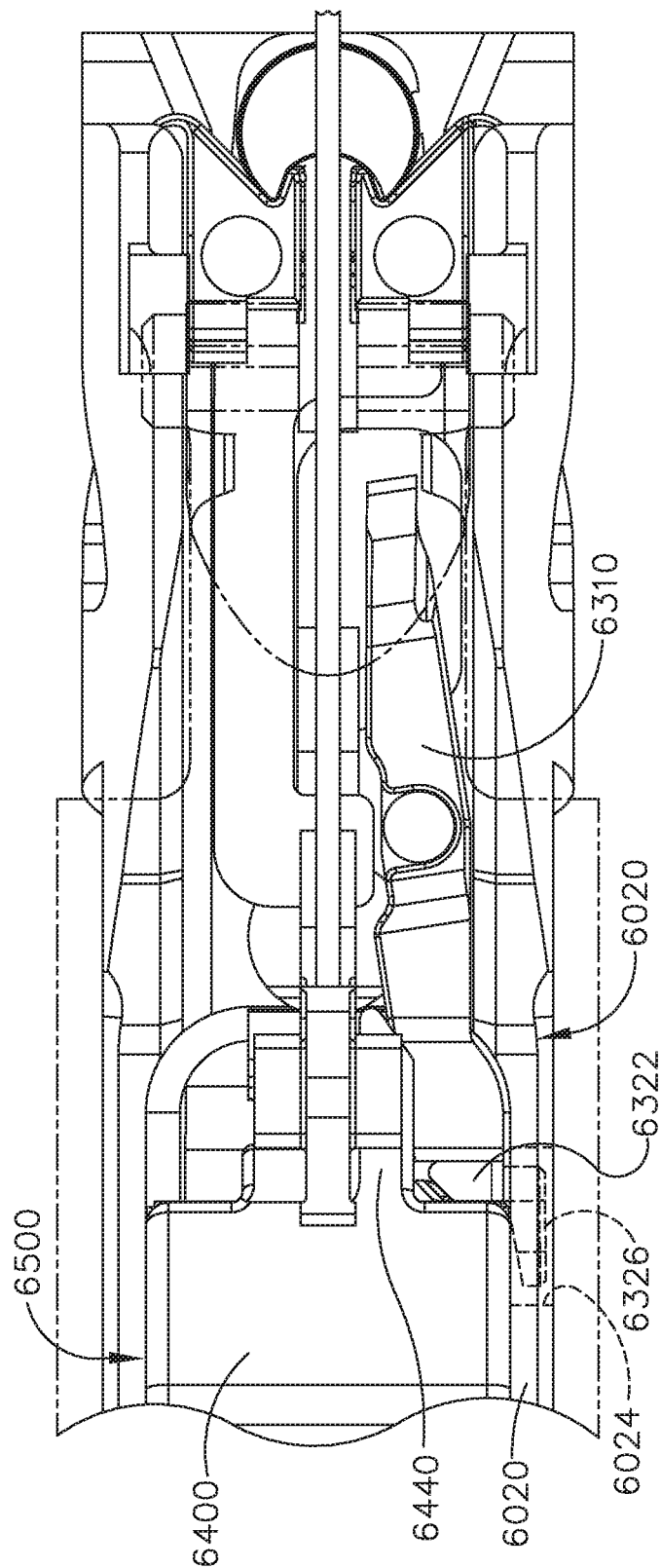
FIG. 37 is another top view of portions of the surgical stapling device of FIG. 36 after the cartridge assembly has been seated therein.

FIG. 29 illustrates the first lockout 6300 in the locked or jaw locking position wherein the first lockout arm 6310 is pivoted into position wherein the lockout feature 6316 is in blocking engagement with the lock lug portion 6120 on the trunnion assembly 6112 on the anvil 6100. Referring now to FIG. 36, after the retainer 6400 has been attached to the surgical staple cartridge 4200 to form a cartridge assembly 6500, the cartridge assembly 6500 may be inserted into the first jaw or frame 6010 such that the first cam surface 6444 engages the actuator cam surface 6324 on the actuator cam arm 6322 and begins to pivot the first lockout arm 6310 out of the locked or jaw locking position to an intermediate position. Continued longitudinal insertion of the assembled cartridge arrangement 6500 into the frame 6010 in a proximal direction causes the first cam surface 6444 to disengage the actuator cam surface 6324 and the lower, second cam surface 6446 to engage the actuator cam surface 6324 to move the first lockout arm 6310 from the intermediate position to the jaw closure position. See FIG. 37. When the first lockout arm 6310 is in the locked or jaw locking position, the actuator cam arm 6322 is located distal to the firing member 6050. The lower second cam surface 6446 completes the pivotal travel of the first lockout arm 6310 so that the actuator cam arm 6322 does not interfere with the operation of the firing member 6050 while allowing the anvil 6100 to move to a closed position. When the first lockout arm 6310 is in the unlocked or jaw closure position, the retention tab 6326 is received within the tab window 6024 in the frame sidewall 6020 and is retained therein by the staple cartridge 4200. When in that position, the first lockout 6300 is in the jaw closure position or stated another way is "defeated", unlocked or unlatched. The user may then remove the retainer 6400 from the surgical staple cartridge 4200 by prying the up the distal latch tab 6422 and lifting the retainer 6400 upward until the retainer lugs 6410 disengage the deck ledge portions 4205.

As can be appreciated from the foregoing, the space required to interface with the first lockout 6300 is available when the anvil 6100 is open, but is not available when the anvil 6100 is closed. The retainer 6400 is present on the cartridge 4200 only when the anvil 6100 is open during the cartridge insertion process. Thereafter, the retainer 6400 is removed from the staple cartridge 4200. The anvil 6100 cannot be closed when the retainer 6400 is in place. When closed, the anvil 6100 occupies the space that was occupied by the retainer 6400. This arrangement is very different from a cartridge-based authentication key arrangement that remains resident in the stapling device during the closing and firing of the device. Dual sequential ramps/camming surfaces are employed in this arrangement to move the first lockout arm 6310 laterally through a distance that is approximately at least twice as wide as the authentication key 6430. This may be an important aspect to this design.

The proximal high ramp or camming surface begins the unlocking movement and engages the upstanding actuator cam arm 6322 that is distal to the firing member 4050. It will be appreciated that a stationary locking feature that is unable to be moved or removed would not be able to reach this area without affecting the ability to move the firing member 4050 through the staple firing stroke. The second lower ramp/ camming surface completes the unlocking movement of the first unlocking arm 6310 so that it is completely clear for the anvil 6100 to close. The second ramp/camming surface is sequentially spaced behind the first ramp/camming surface so that it can only engage the distal end of the first lockout arm 6310 after the first ramp/camming surface has pivoted it to that intermediate position.

Figure 38:
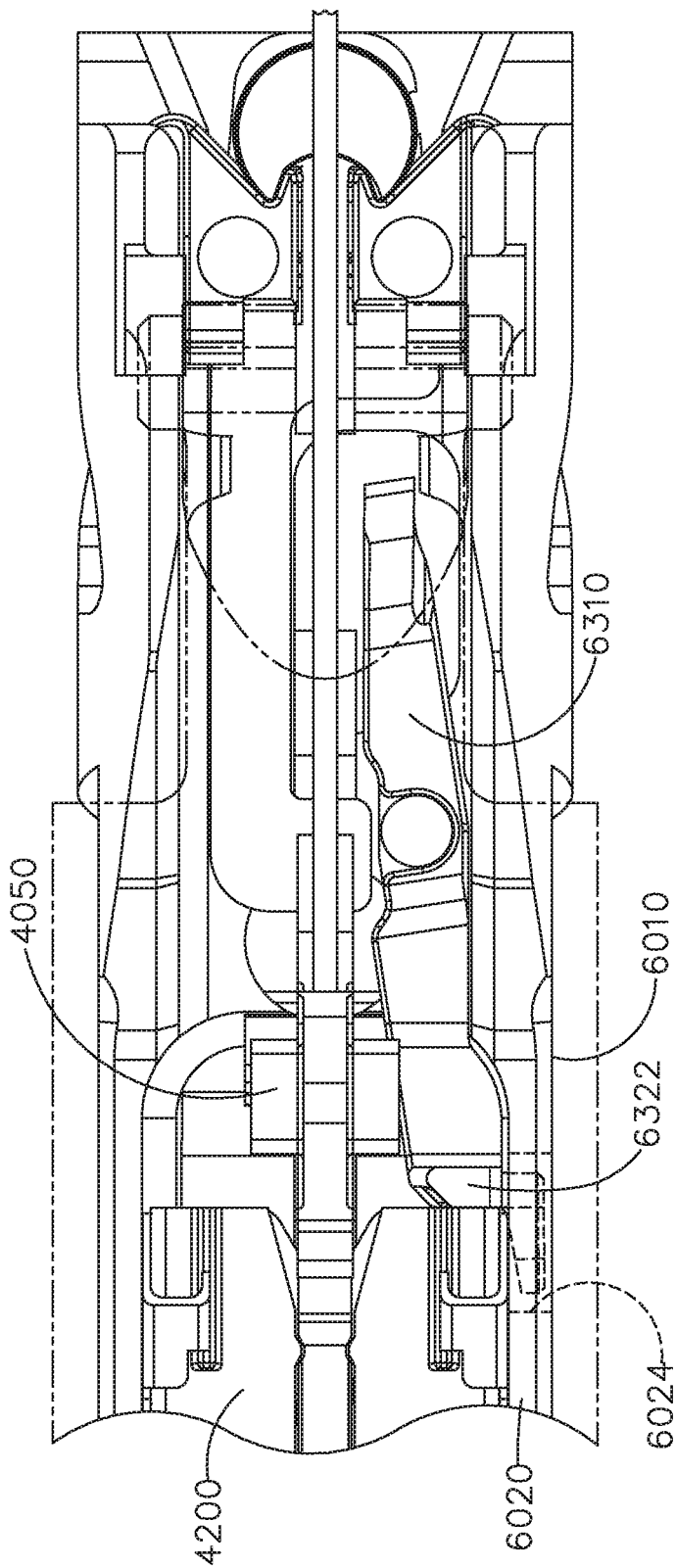
FIG. 38 is another top view of portions of the surgical stapling device of FIG. 37 after the retainer has been removed from the staple cartridge seated therein.

FIG. 38 illustrates the staple cartridge 4200 operably seated in the frame 6010 with the first lockout 6300 defeated and the retainer 6400 removed from the staple cartridge 4200. The anvil 6100 is now movable between the open and closed position and the surgical staple cartridge 4200 is otherwise capable of being fired. In at least one form, the surgical stapling device 6002 may also include a second lockout 4600 that is configured to prevent the firing member 4050 from distally advancing through the staple firing stroke when a spent staple cartridge is seated in the first jaw or frame 6010 in the various manners discussed above. After the staple cartridge 4200 has been fired, the firing member 4050 is retracted back to the starting position and the second jaw or anvil 6100 is pivoted back to the open position. The spent staple cartridge may then be removed from the first jaw or frame 6010. Once the spent staple cartridge 4200 has been removed from the first jaw or frame 6010, the first lockout spring biases the first lockout arm 6310 back to the jaw locking position wherein second jaw or anvil 6100 is prevented from moving from the open to closed position.

Figure 38A:
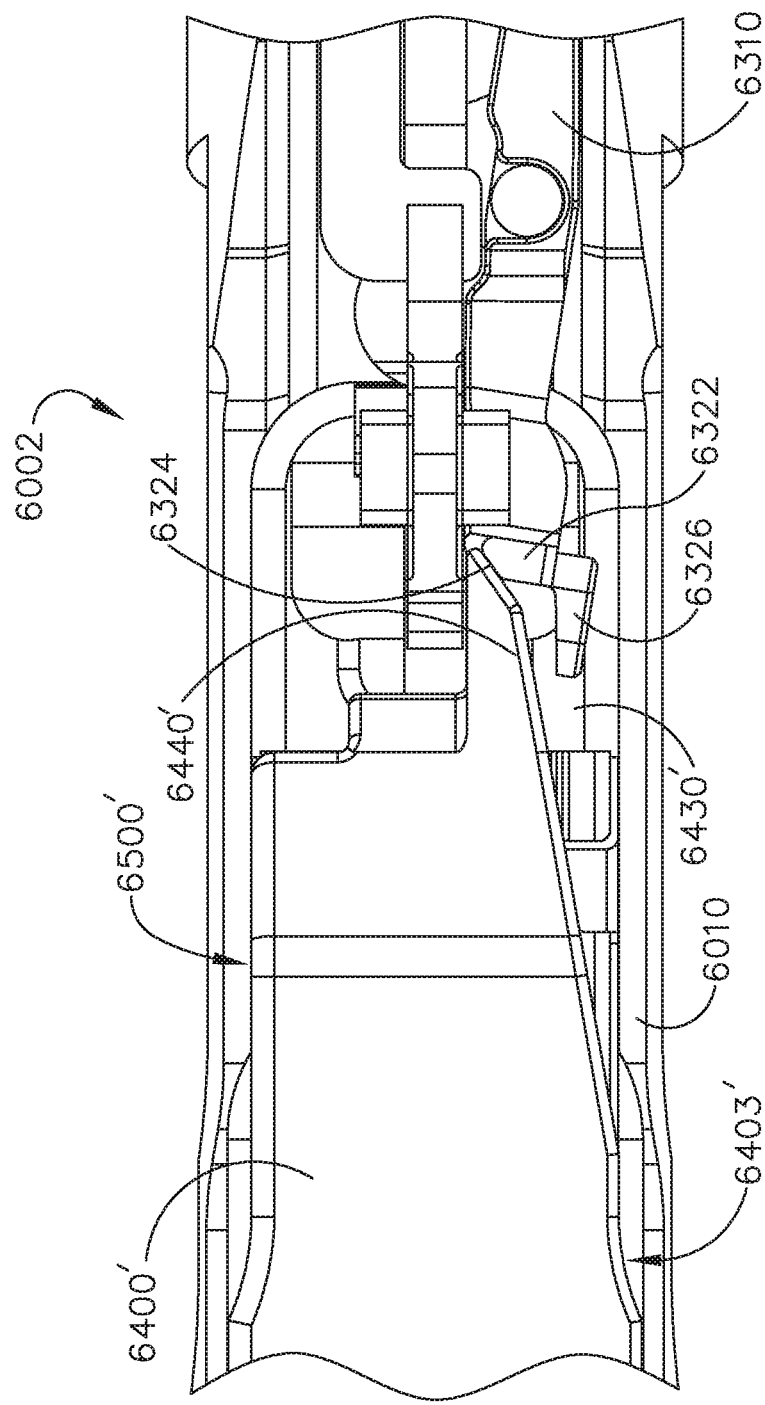
FIG. 38A is a top view of portions of the surgical stapling device of FIG. 37 with another cartridge assembly seated therein.

FIG. 38A is another top view of the surgical stapling device 6002 with a cartridge assembly 6500' seated therein that comprises a retainer 6400' that is attached to a staple cartridge 4200. The retainer 6400' is similar to retainer 6400 described above, except that the authentication key 6430' and ramp 6440' are blended into a side wall 6403' of the retainer 6400'. The retainer 6400' may otherwise operate in the same manner as retainer 6400 discussed above.

Figure 39:
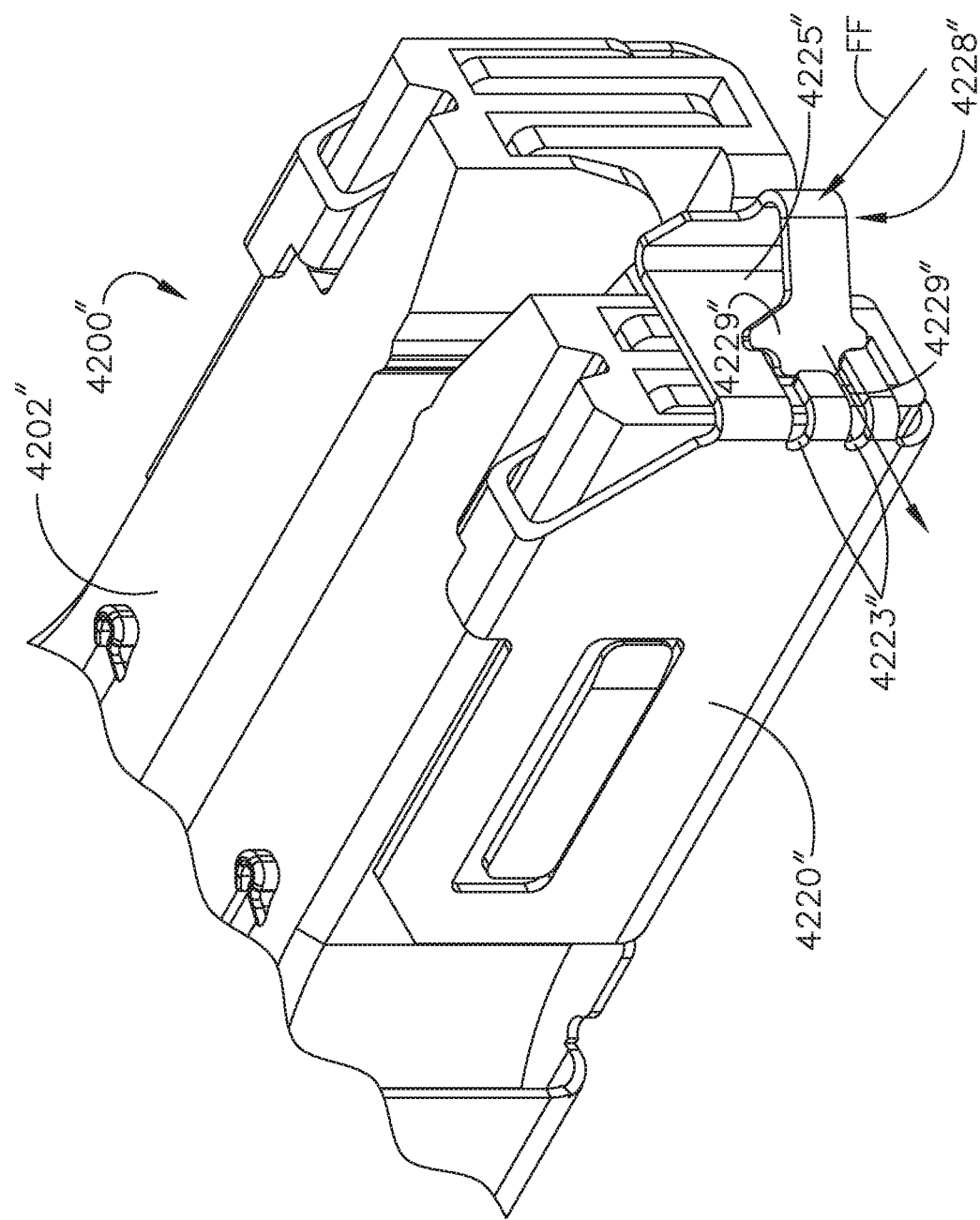
FIG. 39 is a partial perspective view of another staple cartridge with an authentication key folded into a cartridge pan of the staple cartridge.
Figure 40:
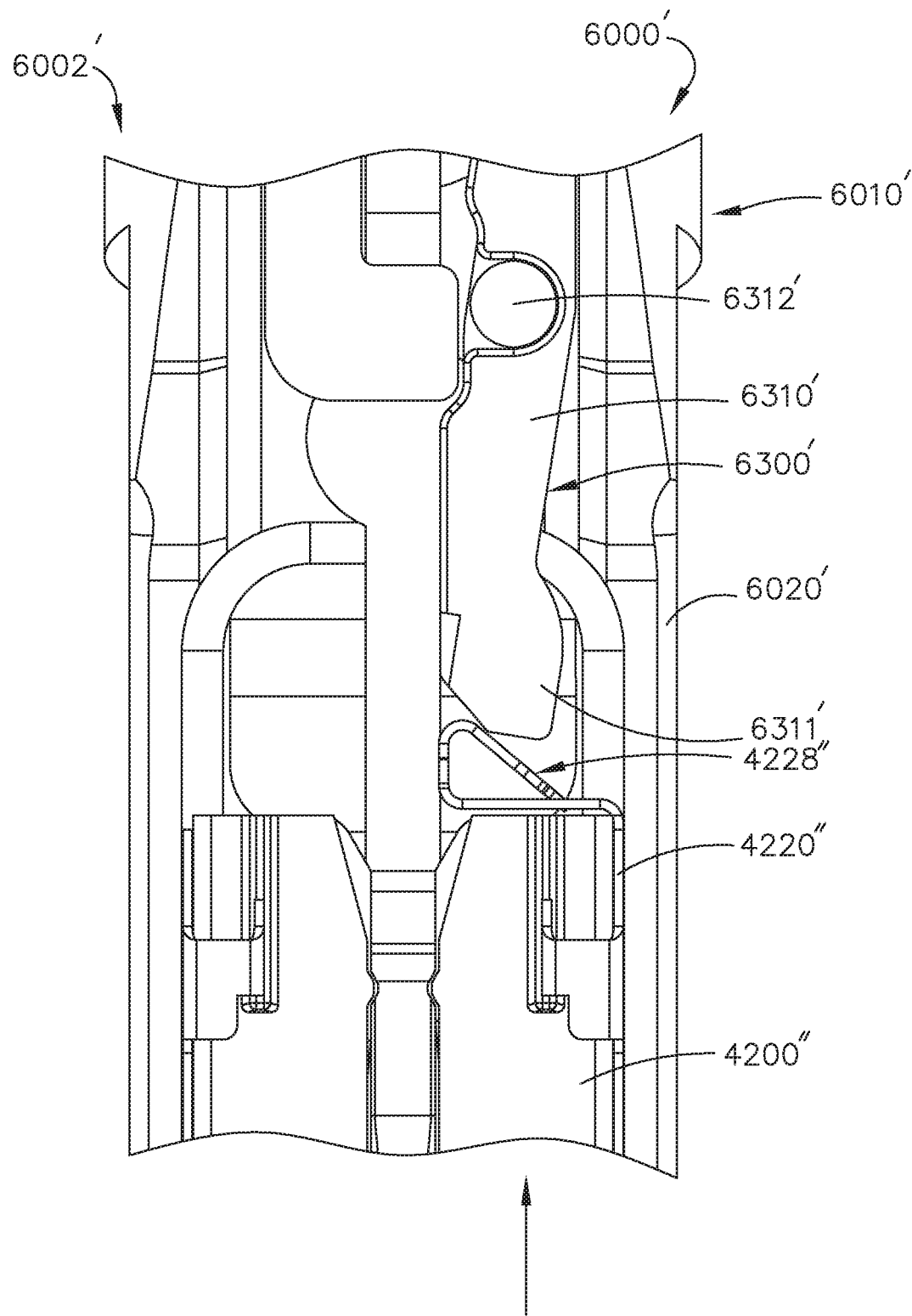
FIG. 40 is a top view of another surgical stapling device illustrating an initial insertion of the staple cartridge of FIG. 39 therein.
Figure 41:
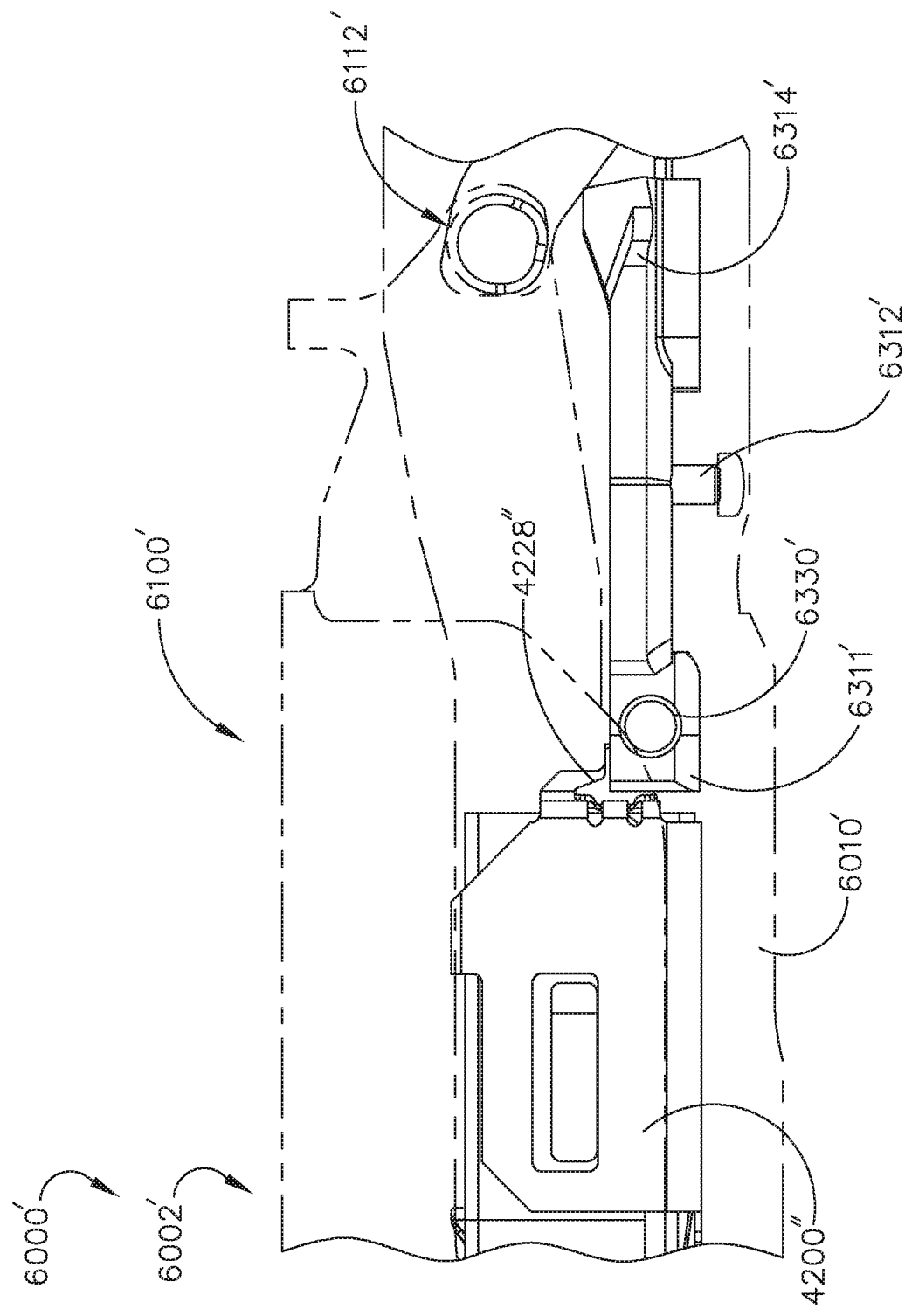
FIG. 41 is a side elevational view of the surgical stapling device and staple cartridge of FIG. 40.
Figure 42:
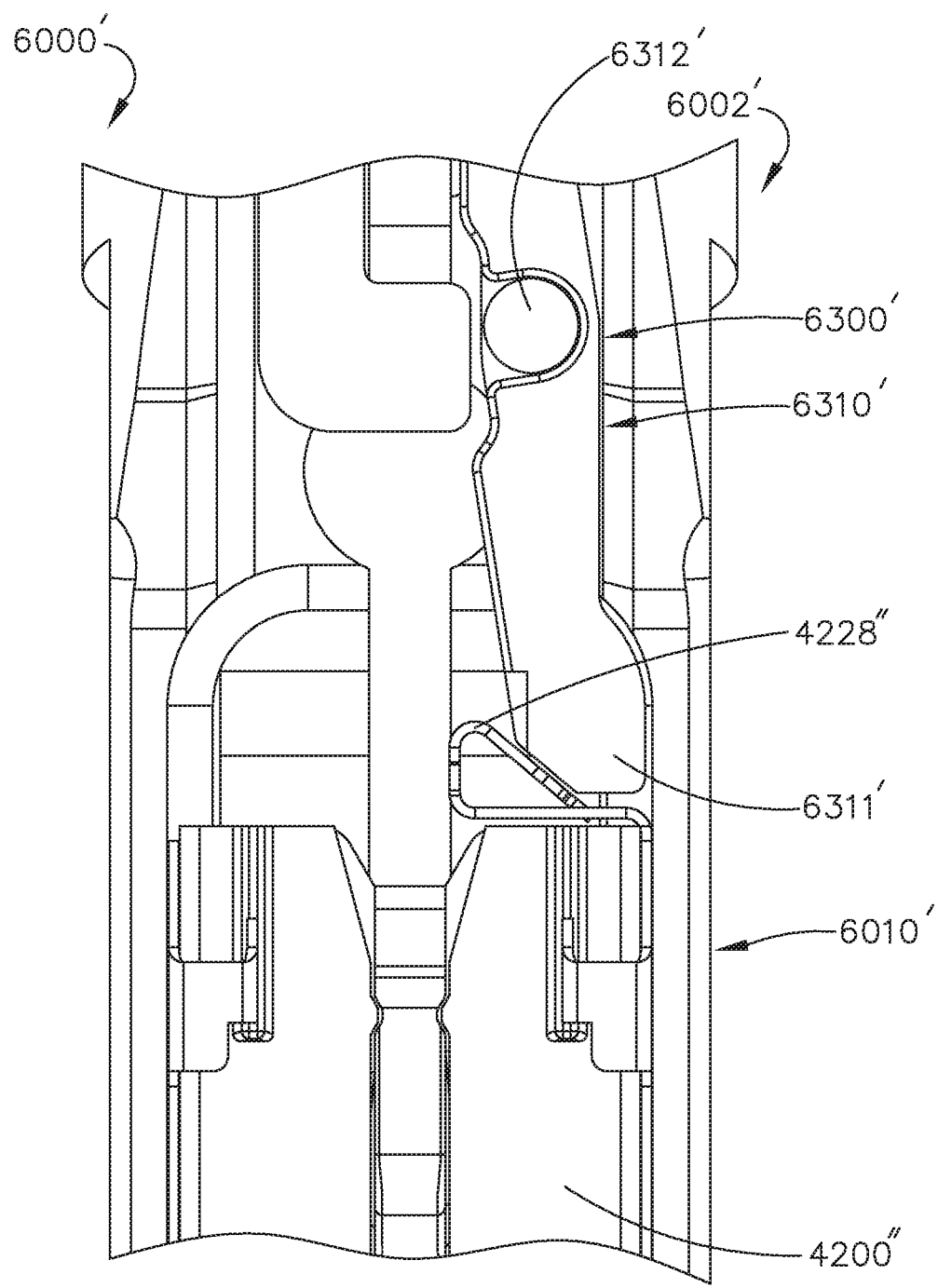
FIG. 42 is another top view of the surgical stapling device of FIG. 40 with the surgical staple cartridge of FIG. 39 operably seated therein.

FIG. 39 is a perspective view of a proximal end of a staple cartridge 4200" that is identical to staple cartridge 4200 described above, except that an authentication key 4228" is folded into a cartridge pan 4220" that is attached to a cartridge body 4202" as shown. As shown in FIGS. 40-42, the staple cartridge 4200" is configured to be used in connection with a surgical stapling assembly 6000' that comprises a surgical stapling device 6002' that comprises a first lockout 6300'. Surgical stapling device 6002' is substantially identical to surgical stapling device 6002 except for a distal end of 6311' of a first lockout arm 6310' that is pivotally supported in a frame 6010' by a lockout pin 6312' that is attached thereto. A proximal end 6314' of the first lockout arm 6310' is identical to the proximal end 6314 of the first lockout arm 6310 and is configured to blockingly engage a lock lug portion on the corresponding trunnion assembly 6112' of an anvil 6100' in the manner described in detail above. A lockout spring 6330' serves to pivot the first lockout arm 6310' to the locked position in the manner described above. FIG. 40 illustrates insertion of the staple cartridge 4200" into the frame 6010'. As can be seen in FIG. 40, the first lockout arm 6310' is in a locked or jaw locking position wherein the proximal end 6314' (FIG. 41) is in blocking engagement with the lock lug on the trunnion assembly 6112' to prevent closure of the anvil 6100'. FIGS. 41 and 42 illustrate the staple cartridge 4200" fully seated in the frame 6010'. As can be seen in FIGS. 41 and 42, the authentication key 4228" has pivoted the first lockout arm 6310' into a jaw closure position and retains the first lockout arm 6310' in that position. When in the jaw closure position, the anvil 6100 is free to be pivoted closed as illustrated in FIG. 41. In this arrangement, the authentication key 4228"

comprises a portion of the staple cartridge and is not mounted to a removable retainer. The authentication key 4228" retains the first lockout arm 6310' in the jaw closure position while the staple cartridge remains seated in the frame 6010' throughout the stapling procedure.

After the staple cartridge 4200' has been fired, the user returns a firing member of the surgical stapling device 6002' back to a starting position and the anvil 6100' is pivoted to the open position allowing the spent staple cartridge to be removed from the frame 6010'. When the spent staple cartridge 4200' is removed from the frame 6010', the lockout spring 6330' pivots the first lockout arm 6310' back to the jaw locking position. In some instances, the spent staple cartridge may be "reprocessed" for reuse in another stapling procedure and/or another stapling device. It is important for those reprocessing entities to install the proper surgical staples as well as the proper number of surgical staples into the reprocessed staple cartridge required to make that cartridge compatible with a particular stapling device to ensure the desired results during use. Unfortunately, some reprocessing entities at times fail to properly reprocess the spent cartridge, yet still offer the reprocessed spent cartridge as a new cartridge manufactured by the original manufacturer. The end user may unwittingly obtain the defective cartridge and use it in a surgical stapling device. In an effort to prevent such instances from occurring, once the spent cartridge has been removed from the surgical stapling device 6002', the authentication key 4228" may be irretrievably flattened. For example, as can be seen in FIG. 39, the authentication key 4228" is formed with a pair of lugs 4229" that are slidably received in slots 4223" provided in the cartridge pan 4220". By a applying a flattening force FF to the tip of the authentication key 4228" the key may be flattened against the proximal end 4225" of the cartridge pan 4220" rendering the authentication key 4228" inoperable for future use.

Figure 43:
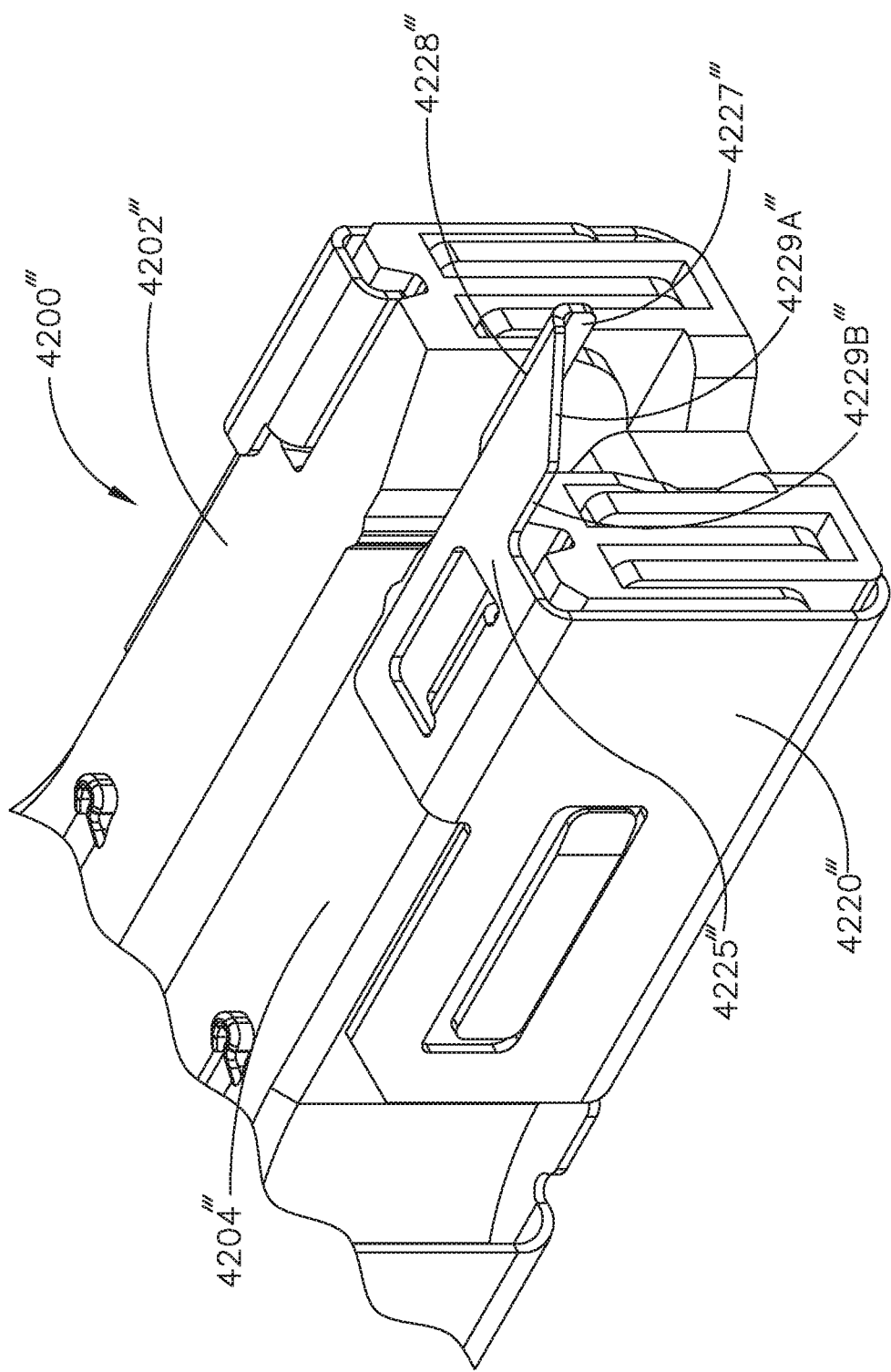
FIG. 43 is a partial perspective view of another staple cartridge with an authentication key folded into a cartridge pan of the staple cartridge.
Figure 44:
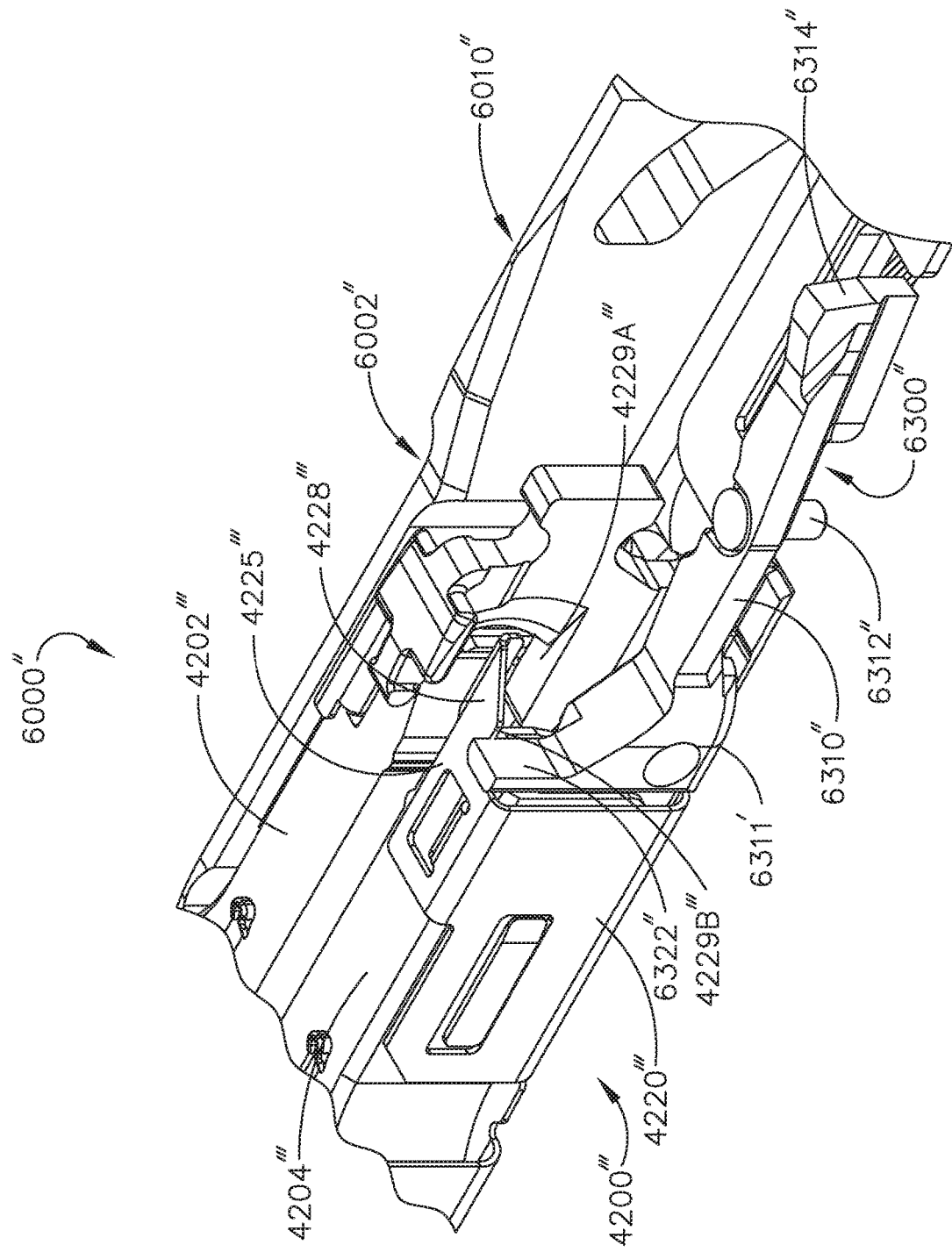
FIG. 44 is a partial perspective view showing the staple cartridge of FIG. 43 operably seated in another surgical stapling device.
Figure 45:
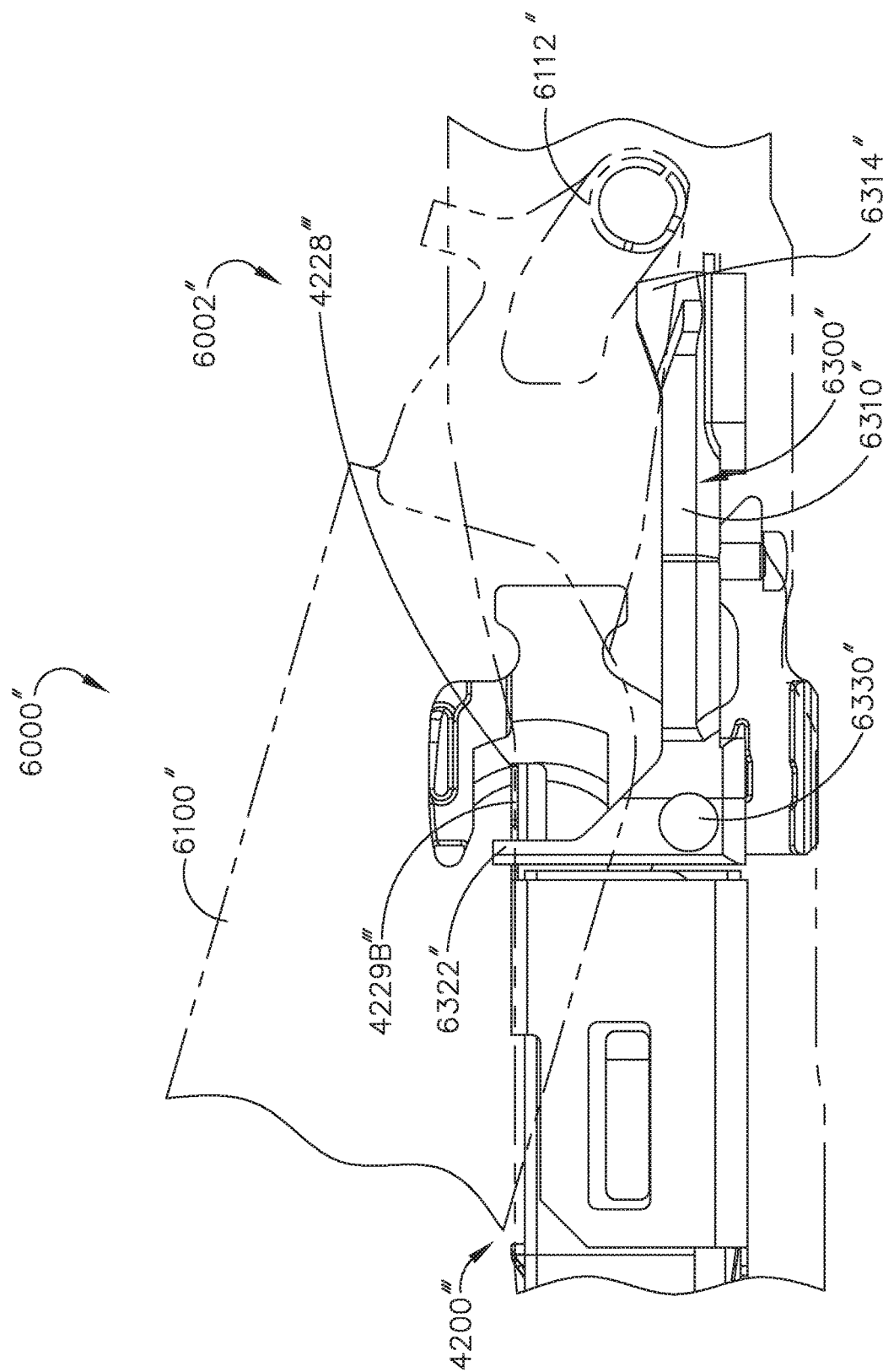
FIG. 45 is a side elevational view of the surgical stapling device and staple cartridge of FIG. 44 with a first lockout arm of the stapling device retained in a jaw closure position.
Figure 46:
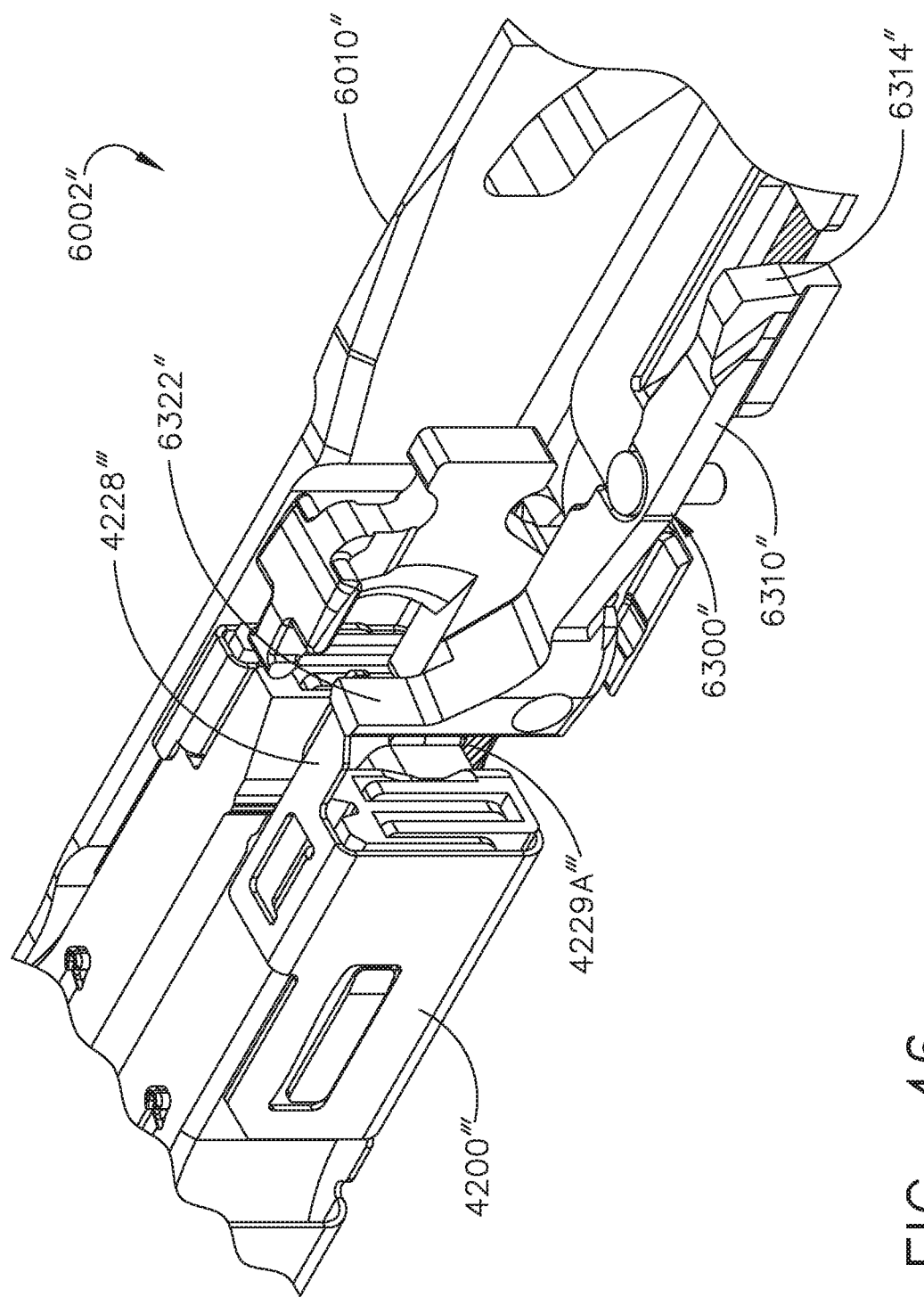
FIG. 46 is another perspective view of the surgical stapling device and staple cartridge of FIG. 44, during an initial insertion of the staple cartridge into the surgical stapling device.

FIG. 43 is a perspective view of a proximal end of a staple cartridge 4200''' that is identical to staple cartridge 4200 described above, except that an authentication key 4228''' is folded into a cartridge pan 4220''' that is attached to a cartridge body 4202''' as shown. In this embodiment, the authentication key 4228' protrudes from a top flap 4225''' of the cartridge pan 4220''' that is folded over a portion of a cartridge deck 4204''' which may serve to enhance the strength of the authentication key 4228'. The authentication key 4228' may further comprise a folded stiffener wall portion 4227' and have an angled actuation or cam surface 4229A''' and a latch surface 4229B'''. As shown in FIGS. 44-46, the staple cartridge 4200''' is configured to be used in connection with a surgical stapling assembly 6000" that comprises a surgical stapling device 6002" that comprises a first lockout 6300".

In many aspects, surgical stapling device 6002" is substantially identical to surgical stapling device 6002 and includes a first lockout arm 6310" that is pivotally supported in a frame 6010" by a lockout pin 6312" that is attached thereto. A proximal end 6314" of the first lockout arm 6310" may be identical to the proximal end 6314 of the first lockout arm 6310 and is configured to blockingly engage a lock lug portion on the corresponding trunnion assembly 6112" of an anvil 6100" in the manner described in detail above. A lockout spring 6330" serves to pivot the first lockout arm 6310" to the locked or jaw locking position in the manner described above. A distal end of the first lockout arm 6310" comprises an upstanding actuator cam arm 6322" that is configured to be engaged by the authentication key 4228''' on the staple cartridge 4200'''.

FIG. 46 illustrates insertion of the staple cartridge 4200''' into the frame 6010". The first lockout arm 6310" is in a jaw locking position wherein the proximal end 6314" is in blocking engagement with the lock lug on the trunnion assembly 6112' to prevent closure of the anvil 6100". During the initial insertion of the staple cartridge 4200''' into the frame 6010", the angled actuation or cam surface 4229A''' has contacted the upstanding actuator cam arm 6322" to begin to pivot the first lockout arm 6310" out of the jaw locking position. Continued insertion of the staple cartridge 4200''' into the frame 6010" causes the authentication key 4228''' to pivot the first lockout arm 6310" to the unlocked or jaw closure position wherein the actuator cam arm 6322" has disengaged the angled cam surface 4229A''' and is retained in that unlocked or jaw closure position by the latch surface 4229B''' on the authentication key 4228'''. See FIGS. 44 and 45. When in the unlocked or jaw closure position, the anvil 6100" is free to be pivoted closed. In this arrangement, the authentication key 4228''' comprises a portion of the staple cartridge and is not mounted to a removable retainer. The authentication key 4228''' retains the first lockout arm 6310" in the jaw closure position while the staple cartridge 4200''' remains seated in the frame 6010" throughout the stapling procedure.

Figure 47:
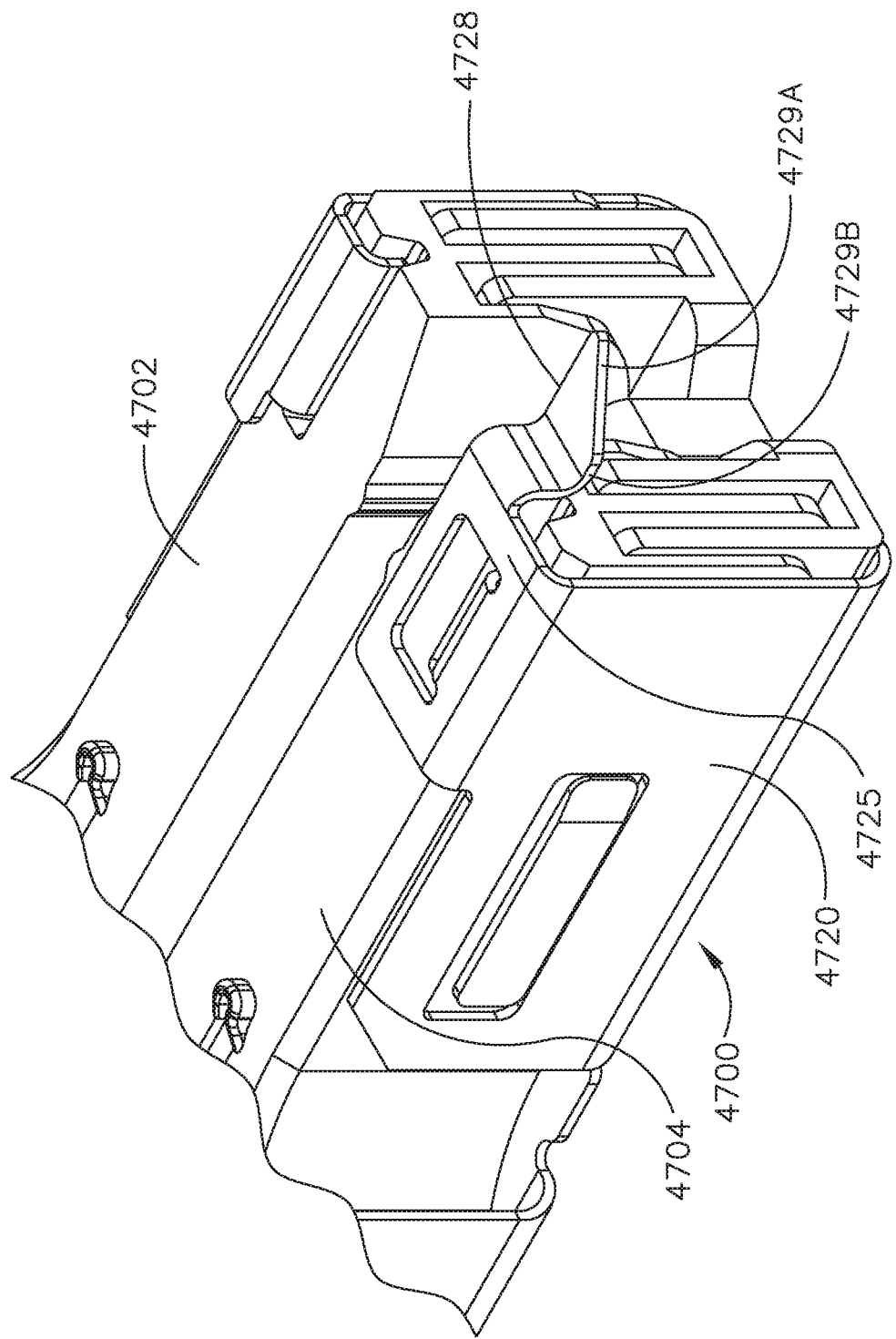
FIG. 47 is a partial perspective view of another staple cartridge with an authentication key folded into a cartridge pan of the staple cartridge.

FIG. 47 is a perspective view of a proximal end of a staple cartridge 4700 that, for the most part, is identical to staple cartridge 4200 described above, except that an authentication key 4728 is folded into a cartridge pan 4720 that is attached to a cartridge body 4702 as shown. In this embodiment, the authentication key 4728 protrudes from a top flap 4725 of the cartridge pan 4720 that is folded over a portion of a cartridge deck 4704 which may serve to enhance the strength of the authentication key 4728. The authentication key 4728 comprises an angled actuation or cam surface 4729A and a latch surface 4729B. The authentication key 4728 is folded to extend below a plane defined by the cartridge deck 4704 and may be employed, for example, with surgical stapling device 6002" in the above described manner or other surgical stapling devices with slightly shorter actuator cam arms.

Figure 48:
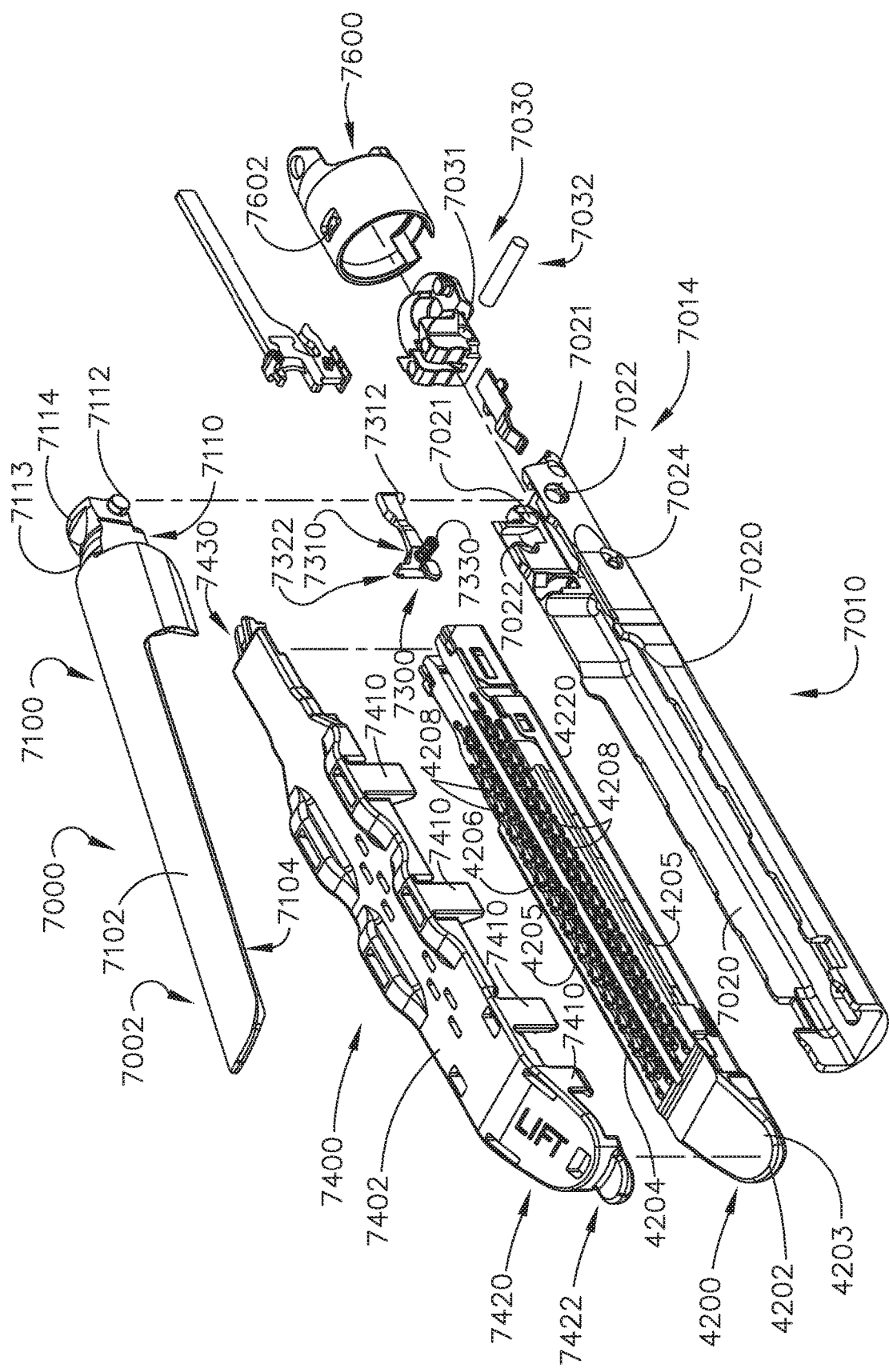
FIG. 48 is an exploded perspective assembly view of a surgical stapling device and staple cartridge of another surgical stapling assembly.
Figure 49:
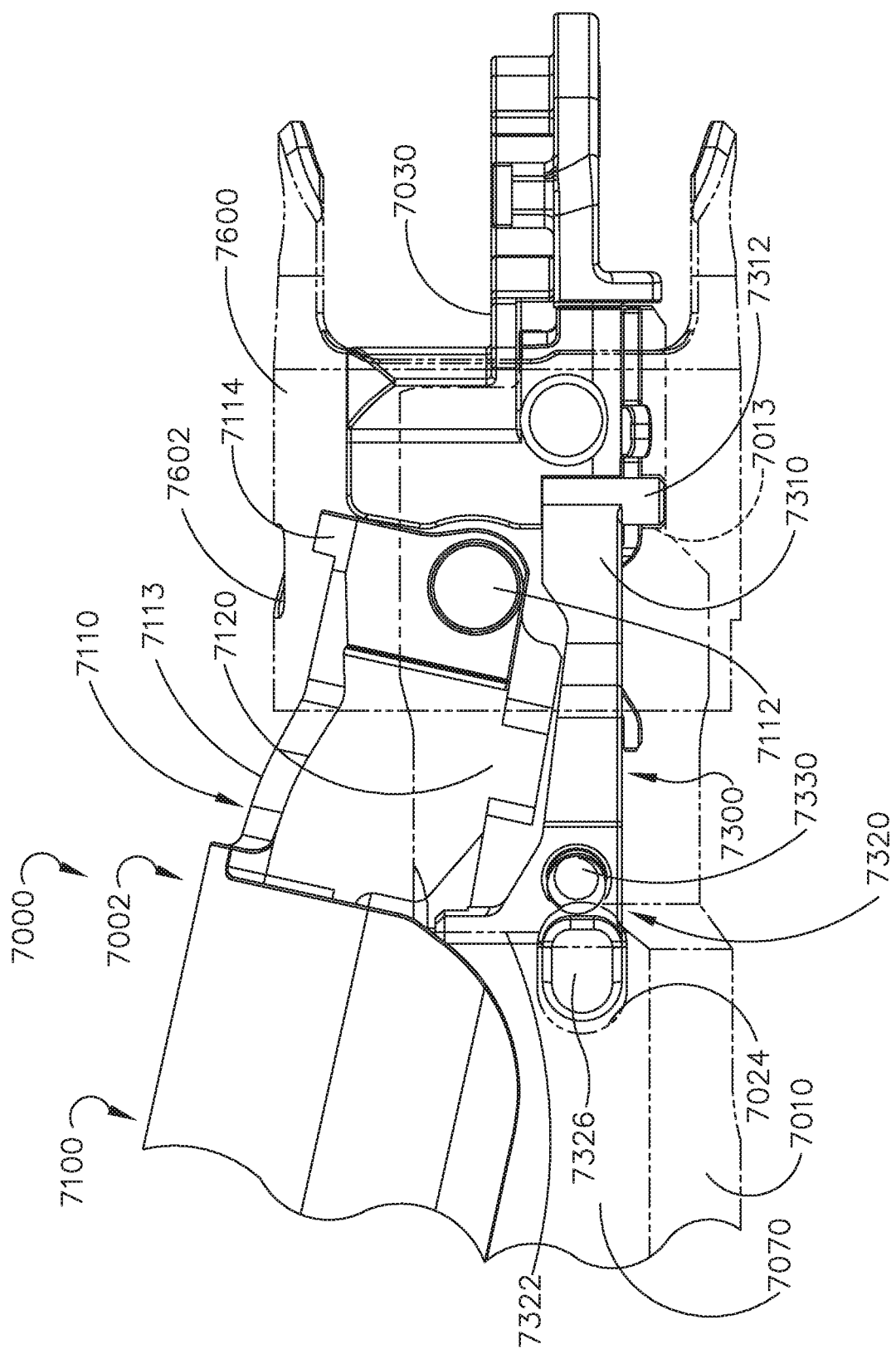
FIG. 49 is a side elevational view of the surgical stapling device of FIG. 48 with a first lockout arm of the surgical stapling device retained in a jaw locking position.

FIGS. 48-51 illustrate another surgical stapling assembly 7000 that is similar in many aspects to surgical stapling assembly 6000 discussed above. The surgical stapling assembly 7000 comprises a surgical stapling device 7002 that may be employed in connection with the surgical instrument 1010 described above or in connection with a variety of other surgical instruments or robots described in various disclosures that have been incorporated by reference herein. As can be seen in FIG. 48, the surgical stapling device 7002 comprises a first jaw, or frame, 7010 that is configured to operably support a staple cartridge 4200 therein. The first jaw or frame 7010 is attached to a spine of the shaft assembly in the various manners described herein. In the illustrated example, the first jaw or frame 7010 is attached to the spine of a shaft assembly (not shown in FIG. 48), by a shaft mount flange 7030 that is pinned by a pin 7032 or otherwise attached to a proximal end 7014 of the first jaw 7010. In particular, pin 7032 is configured to pass through aligned holes 7021 in upstanding sidewalls 7020 of the first jaw or frame 7010 as well as through hole 7031 in the shaft mount flange 7030. The shaft mount flange 7030 is configured to interface with an articulation joint arrangement (not shown) that is configured to facilitate articulation of the first jaw 7010 relative to the shaft assembly in various known configurations. The surgical stapling device 7002 may also be used in connection with shaft assemblies that do not facilitate articulation of the surgical stapling device 7002.

Still referring to FIG. 48, the surgical stapling device 7002 further comprises a firing member assembly 4040 that comprises a knife bar 4042 that is attached to a knife member or firing member 4050. Operation of the firing member 4050 and the knife bar 4042 were discussed in detail above. Further to the above, the surgical stapling device 7002 further comprises a second jaw or anvil 7100 that is movable relative to the first jaw or frame 7010. The anvil 7100 comprises an anvil body 7102 and an anvil mounting portion 7110. The anvil body 7102 comprises a staple forming undersurface or tissue contacting surface 7104 that has a series of staple forming pockets formed therein (not shown) that are arranged to form corresponding staples as they are driven into forming contact therewith. The anvil mounting portion 7110 comprises a pair of laterally extending anvil pins or trunnion pins 7112 that are configured to be received in corresponding trunnion holes 7022 in the upstanding sidewalls 7020 of the first jaw or frame 7010. Unlike the anvil 6100 described above, the anvil 7100 is pivotally pinned to the frame 7010 for pivotal travel relative thereto about a fixed pivot axis. Stated another way, unlike anvil 6100, anvil 7100 does not materially move axially or translate during the anvil closure process.

As discussed above, as well as in several of the disclosures which have been incorporated by reference herein, the anvil 7100 may be movable from an open position wherein a used or spent staple cartridge may either be removed from the first jaw or frame 7010 or an unfired staple cartridge may be operably seated therein to a closed position by an axially movable closure member or end effector closure tube 7600. For example, as the closure tube 7600 is moved distally from a proximal position, the closure tube 7600 may operably engage a cam surface 7113 on the anvil mounting portion 7110. Such interaction between the closure tube 7600 and the anvil mounting portion 7110 causes the anvil mounting portion 7110 and the trunnion pins 7112 to pivot until the closure member moves the anvil 7100 to a fully closed position. When in the fully closed position, the staple-forming pockets in the anvil 7100 are properly aligned with the staples in a corresponding compatible staple cartridge 4200 that has been operably seated in the first jaw or frame 7010. When the axially movable closure tube 7600 is thereafter moved in a proximal direction, a tab 7602 on the closure tube 7600 interfaces with a tab 7114 on the anvil mounting portion 7110 to cause the anvil 7100 to pivot back to the open position.

Further to the above, the surgical stapling device 7002 comprises a first lockout 7300 that is configured to prevent the second jaw or anvil 7100 from being movable from the open position to the closed position by the closure member 7600. The first lockout 7300 may also be referred to herein as an "authentication" lockout. In the illustrated arrangement, the first lockout 7300 comprises a first lockout arm 7310 that is pivotally supported in the first jaw or frame 7010 by a lockout pin 7312 that is attached thereto. In one example, the first lockout arm 7310 is fabricated from stainless steel or the like and the lockout pin 7312 may be machined into the proximal end thereof. The lockout pin 7312 is pivotally seated in a pivot hole 7013 in the frame 7010 to facilitate pivotal travel of the first lockout arm 7310 in a locking direction LD between a jaw locking position and a jaw closure position. See FIG. 50. In the illustrated example, the first lockout arm 7310 is configured to blockingly engage a lock lug portion 7120 protruding downward from the anvil mounting portion 7110 when the first lockout arm 7310 is the jaw locking position. When the first lockout arm 7310 is in that locked or engaged position, pivotal travel of the anvil 7100 is prevented when the lock lug portion 7120 contacts the first lockout arm 7310. It will be appreciated that the first lockout arm 7310, as well as the lock lug portion 7120, are each sufficiently robust so as to resist substantial closure motions that applied to the anvil 7100 to prevent closure of the anvil 7100.

Figure 50:
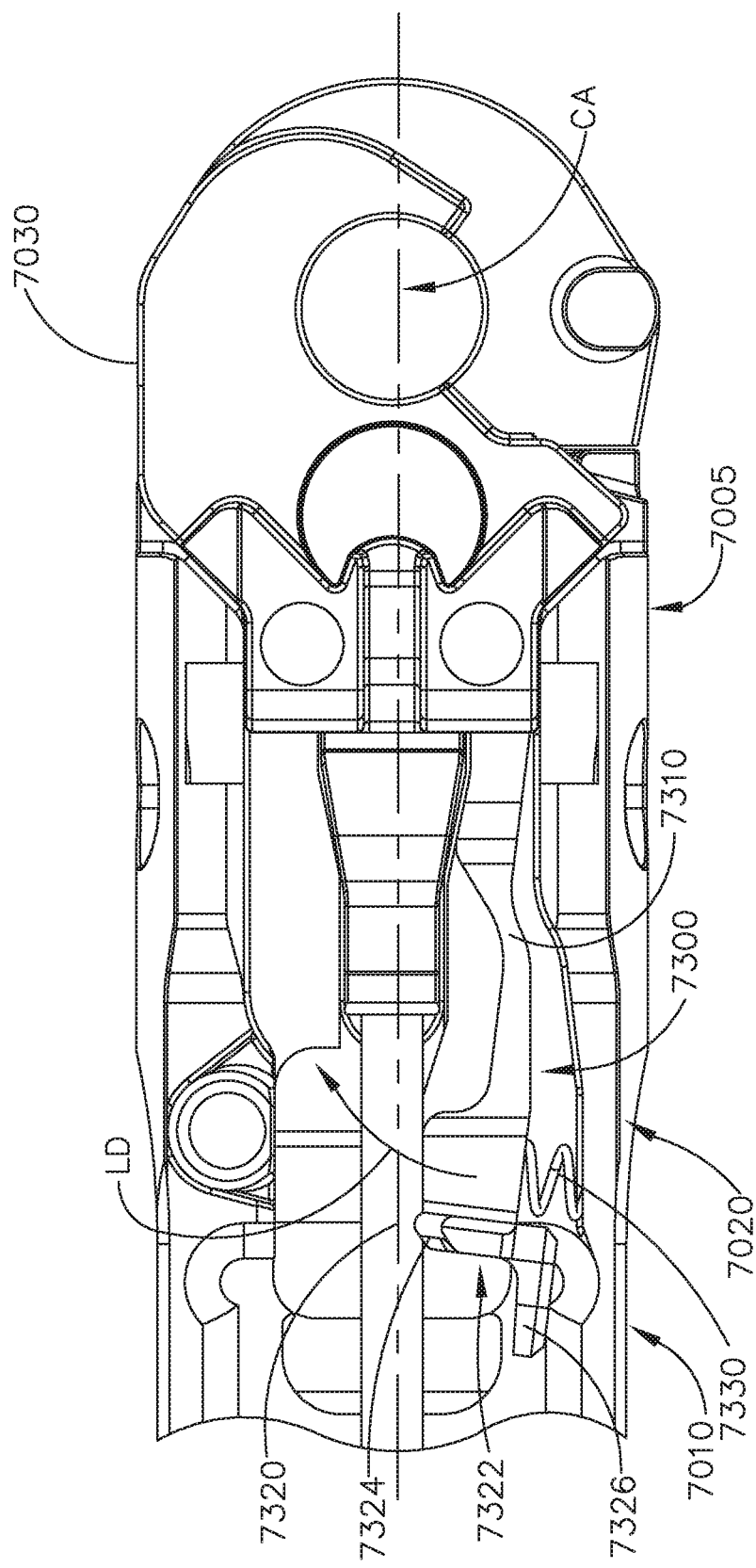
FIG. 50 is a top view of the surgical stapling device of FIG. 49, with the first lockout arm in the jaw locking position.

Referring now to FIG. 50, a first lockout spring 7330 is supported in a corresponding sidewall 7020 of the first jaw or frame 7010 to bias the first lockout arm 7310 in the locking direction LD to the locked or jaw locking position wherein the first lockout arm 7310 prevents the anvil 7100 from moving from the open position to the closed position. As can be seen in FIG. 50, the first lockout arm 7310 further comprises an upstanding actuator cam arm 7322 that is formed on a distal end 7320 of the first lockout arm 7310. The actuator cam arm 7322 comprises an actuator cam surface 7324 thereon. The first lockout arm 7310 further comprises a retention tab 7326 that is configured to be received within a corresponding opening or tab window 7024 provided in a frame sidewall 7020.

Turning again to FIG. 48, the stapling assembly 7000 further comprises a retainer 7400 that is configured to be removably coupled to the surgical staple cartridge 4200. In many aspects, the retainer 7400 is substantially similar to the retainer 4400 described above. In the illustrated arrangement, the retainer 7400 comprises a top portion 7402 that is coextensive with and configured to be received on the deck surface 4204 of the staple cartridge body 4202. When the retainer 7400 is attached to the cartridge body 4202, the retainer 7400 covers all of the staple pockets 4208 in the cartridge body 4202. In other versions only some or none of the staple pockets are covered. The retainer 7400 may be molded from a polymer material and include a plurality of retainer lugs 7410 that are configured to latchingly engage outwardly extending deck ledge portions 4205. The retainer 7400 may further comprise an angled nose portion 7420 and a distal latch tab 7422 that that is configured to latching engage the distal nose 4203 of the cartridge body 4202.

The retainer 7400 may be removably coupled to the surgical staple cartridge 4200 by engaging the distal latch tab 7422 with the end of the distal nose 4203 and aligning the retainer 7400 such that the underside of the top portion 7402 confronts the cartridge deck surface 4204 and the retainer lugs 7410 are located above the deck ledge portions 4205 on each side of the cartridge body 4202. Thereafter, the retainer 7400 may be pressed toward the staple cartridge 4200 causing the retainer lugs 7410 to flex laterally outward and snap into latching engagement with the corresponding deck ledge portions 4205. Other retainer latching arrangements disclosed herein may also be employed to removably affix the retainer 7400 to the staple cartridge 4200. The retainer 7400 may be removed from the staple cartridge 4200 by applying a prying motion to the distal latch tab 7422 and lifting upward until the retainer lugs 7410 disengage the deck ledge portions 4205. In the illustrated example, the term "LIFT" is molded or embossed into the nose portion 7420 to provide removal instructions to the user.

Figure 53:
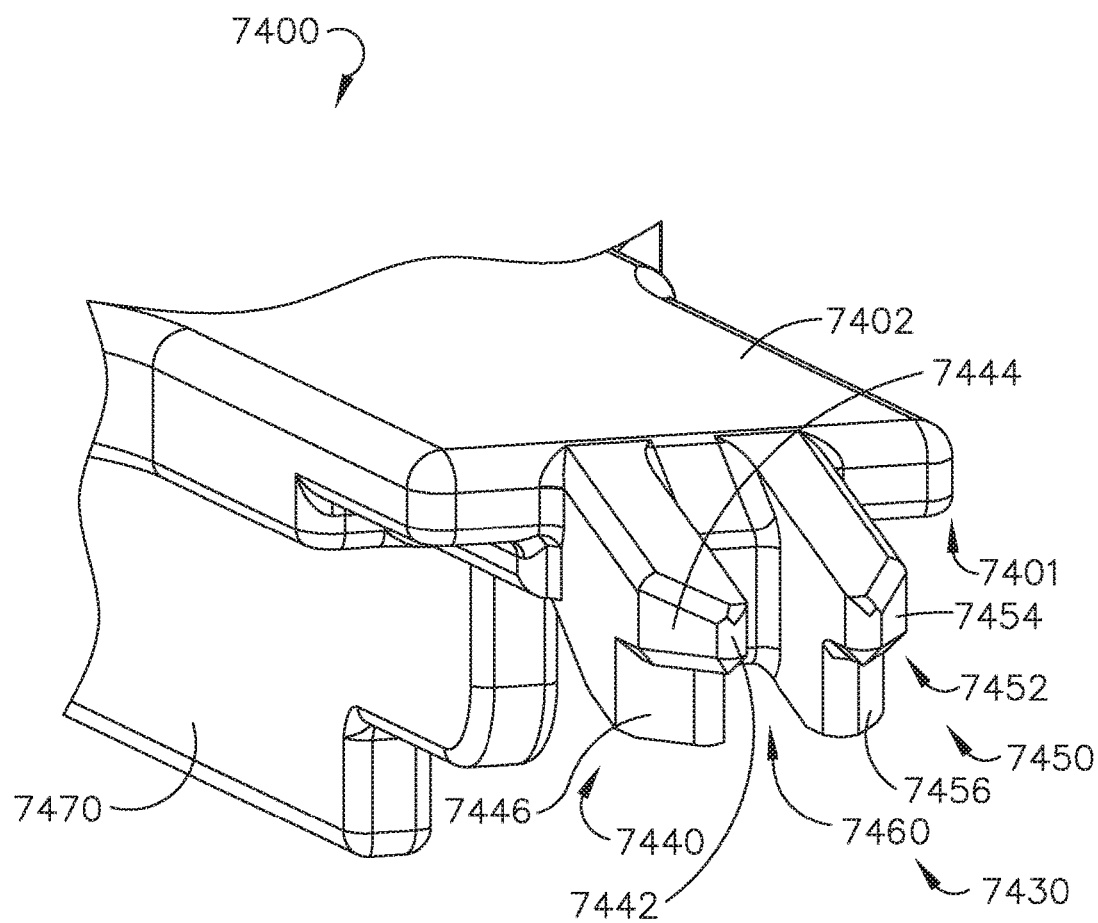
FIG. 53 is a partial perspective view of a proximal end of the retainer of the cartridge assembly of FIG. 52.
Figure 54:
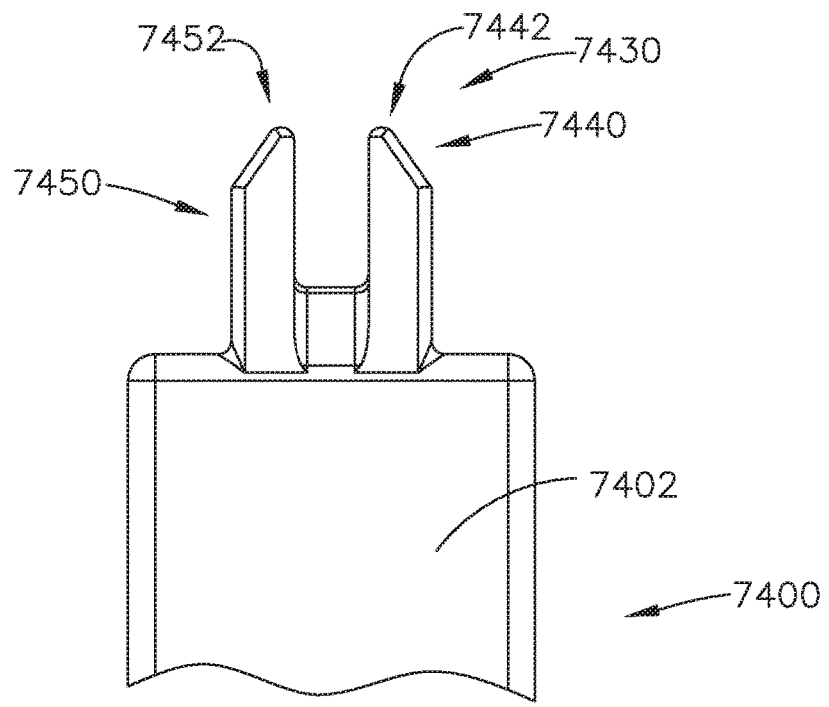
FIG. 54 is a top view of the proximal end of the retainer of FIG. 53.

Referring now to FIGS. 53-56, the retainer 7400 further comprises an authentication key 7430 that is configured to defeat the first lockout 7300 when the retainer 7400 is attached to the surgical staple cartridge 4200 and the surgical staple cartridge 4200 has been operably seated in the first jaw or frame 7010. As can be seen in FIG. 53, the authentication key 7430 protrudes proximally from a proximal end

7401 of the top portion 7402 of the retainer 7400 and comprises a right ramp feature 7440 and a left ramp feature 7450 that are separated by a space 7460 that is sized to receive the firing member body 4052 therebetween. In the illustrated example, the right ramp 7440 angles downward from the top portion 7402 of the retainer 7400 and comprises a proximal right tip 7442 that comprises a first right or proximal right cam surface 7444 that angles inward at the tip. A second right or distal right cam surface 7446 is located below the first right cam surface 7444. These dual sequential cam surfaces 7444, 7446 are configured to interface with the actuator cam surface 7324 on the actuator cam arm 7322 to move the first lockout arm 7310 from the jaw locking position to a "jaw closure position" in the various manners described above. Similarly, the left ramp 7450 angles downward from the top portion 7402 of the retainer 7400 and comprises a proximal left tip 7452 that comprises a first left or proximal left cam surface 7454 that angles inward at the tip. A second left or distal left cam surface 7456 is located below the first right cam surface 7444. These dual sequential cam surfaces 7454, 7456 are configured to interface with the actuator cam surface 7324 on the actuator cam arm 7322 of a first lockout arm 7310 that is mounted on the left or opposite side of a frame axis FA. The retainer 7400 additionally comprises a retainer keel 7470 that protrudes from the bottom surface of the top portion 7402 and is oriented to be received within the longitudinal slot 4206 in the surgical staple cartridge 4200. Retainer keel 7470 may serve to properly orient the retainer 7400 on the surgical staple cartridge 4200 so that the right and left ramps 7440 and 7450 extend on each side of the firing member 4050. The retainer keel 7470 may also be sized relative to the longitudinal slot 4206 to create a frictional retaining engagement therewith when the retainer 7400 is attached to the staple cartridge 4200 and also retain the sled 4230 in the unfired position with the staple cartridge 4200.

In use, the retainer 7400 is attached to the staple cartridge 4200 in the various manners disclosed herein to form a cartridge assembly 7500. The cartridge assembly 7500 may then be inserted into the first jaw or frame 7010 so as to bring the right ramp 7440 of the authentication key 7430 into engagement with the actuator cam surface 7324 on the actuator cam arm 7322. During the initial proximal insertion of the cartridge assembly 7500, the first right cam surface 7444 biases the actuator cam arm 7322 laterally outward to an intermediate position. Further longitudinal advancement of the cartridge assembly 7500 into the first jaw or frame 7010 in a proximal direction causes the first cam surface 7444 to disengage the actuator cam surface 7324 and the second right cam surface 7446 to engage the actuator cam surface 7324 to move the first lockout arm 7310 from the intermediate position into the fully disengaged or jaw closure position. When the first lockout arm 7310 is in the unlocked or jaw closure position, the retention tab 7326 is received within the tab window 7024 in the frame sidewall 7020 and is retained therein by the staple cartridge 4200. When in that position, the first lockout 7300 is in the unlocked or jaw closure position or stated another way is "defeated", unlocked or unlatched. The user may then remove the retainer 7400 from the surgical staple cartridge 4200 by prying the up the distal latch tab 7422 and lifting the retainer 7400 upward until the retainer lugs 7410 disengage the deck ledge portions 4205. The anvil 7100 is now movable between the open and closed position and the surgical staple cartridge 4200 is otherwise capable of being fired. In at least one version, the surgical stapling device 7002 may include a second lockout 4600 that is configured to prevent the firing member 4050 from distally advancing through the staple firing stroke when a spent staple cartridge is seated in the first jaw or frame 7010 in the various manners discussed above. After the staple cartridge 4200 has been fired, the firing member 4050 is retracted back to the starting position and the second jaw or anvil 7100 is pivoted back to the open position. The spent staple cartridge may then be removed from the first jaw or frame 7010. Once the spent staple cartridge 4200 has been removed from the first jaw or frame 7010, the first lockout spring biases the first lockout arm 7310 back to an engaged or jaw locking position wherein second jaw or anvil is prevented from moving from the open to closed position.

As can be seen in FIG. 52, the surgical stapling device 7002 employs a first lockout 7300 that is positioned within the first jaw or frame 7010 on a first side 7005 of a frame axis FA that lies on a common plane with the cartridge axis CA when a staple cartridge is operably seated in the frame 7010. FIG. 56 illustrates a second surgical stapling device 7002' that is identical to surgical stapling device 7002, except that the first lockout 7300' is positioned within the first jaw or frame 7010' on a second or opposite side 7007 of the center frame axis FA. In such instances, the left ramp 7450 of the authentication key 7430 serves to move the first lockout arm 7310' from the engaged or locked position to the disengaged or unlocked position when the cartridge assembly 7500' is seated into the first jaw of frame 7010' of the surgical stapling device 7002'. A 45 mm surgical stapling device may have the first lockout on a right side of the cartridge axis and a 60 mm surgical stapler may have the first lockout on a left side of the cartridge axis and visa versa. Or a certain specialty stapling device such as a vascular stapler or a thoracic staple may have the lockout on a different side than a multipurpose stapler.

Figure 57:
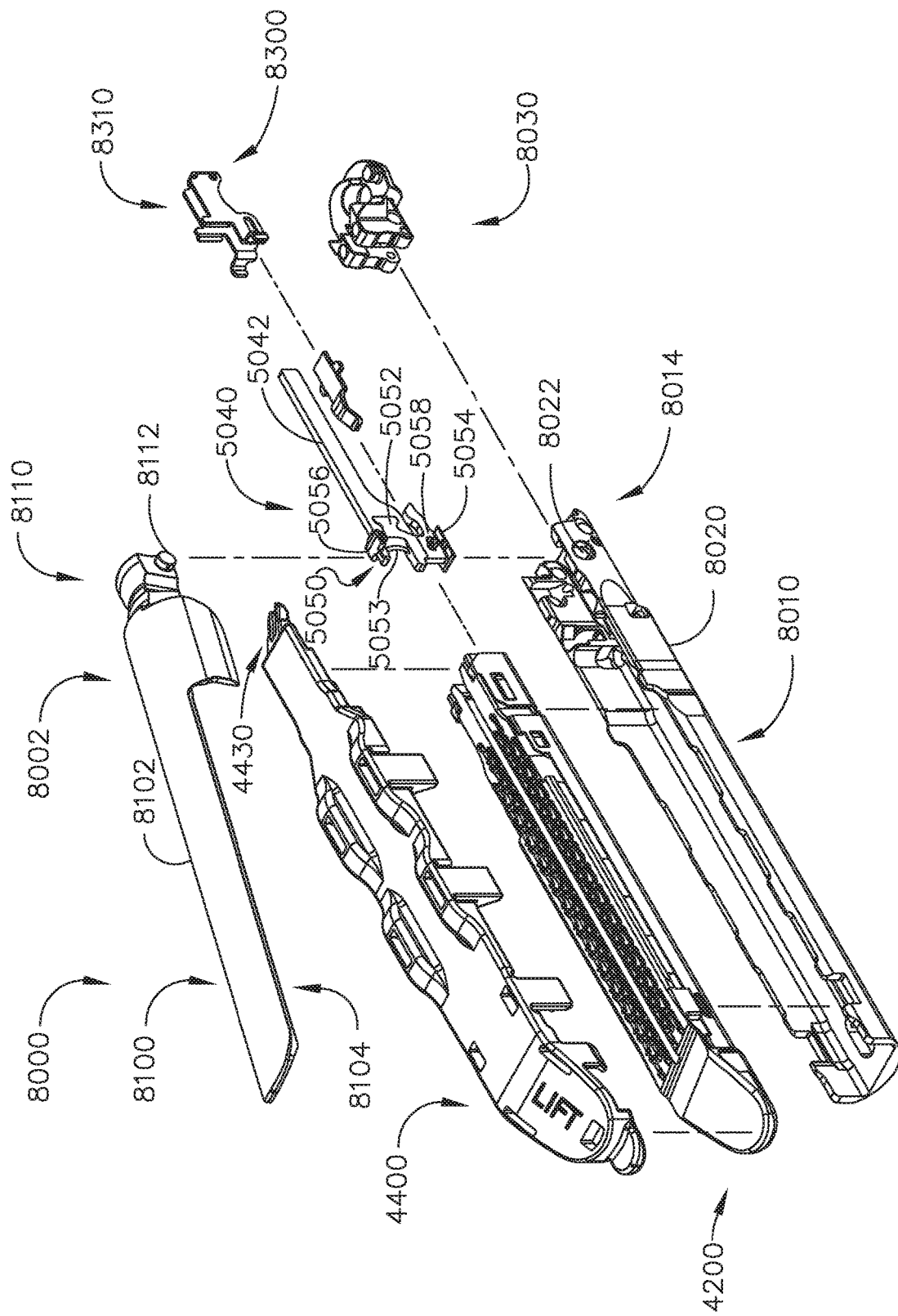
FIG. 57 is an exploded perspective assembly view of a surgical stapling device and staple cartridge of another surgical stapling assembly.

Referring to FIG. 57, an example of a surgical stapling assembly 8000 is shown. The surgical stapling assembly 8000 may be employed in connection with the surgical instrument 1010 described above or in connection with a variety of other surgical instruments or robots described in various disclosures that have been incorporated by reference herein. The surgical stapling assembly 8000 may be employed in connection with electrically controlled, battery powered manually powered and/or robotic controlled surgical instruments in the various forms disclosed in the aforementioned incorporated disclosures. As can be seen in FIG. 57, the surgical stapling assembly 8000 comprises a surgical stapling device generally designated as 8002 that comprises first jaw or frame 8010 that is configured to operably support a staple cartridge 4200 therein. The first jaw 8010 is attached to a spine of the shaft assembly of the surgical instrument or robot in the various manners described herein. In the illustrated example, the first jaw 8010 is attached to the spine portion of the shaft assembly (not shown in FIG. 57), by a shaft mount flange 8030 that is pinned by a pin or otherwise attached to a proximal end 8014 of the first jaw 8010. Other methods of attaching and operably interfacing the surgical device 8002 with a shaft of a surgical instrument may also be employed. For example, the stapling device 8002 may be attached to the shaft assembly such that the stapling device (sometimes also referred to as an "end effector") is not capable of articulating relative to the shaft assembly.

Still referring to FIG. 57, the surgical stapling assembly 8000 further comprises a firing member assembly 5040 that comprises a knife bar 5042 that is attached to a knife member 5050 or "firing member". The knife bar 5042 also interfaces with corresponding components and firing systems in the surgical instrument or robot to receive firing motions which can distally advance the knife bar 5042 and firing member 5050 through a staple firing stroke from a starting position to an ending position and also retract the knife bar 5042 and firing member 5050 proximally to return the firing member 5050 to the starting position. In the illustrated arrangement, the firing member 5050 comprises a firing member body 5052 that supports a cutting edge or knife edge 5053. The firing member 5050 further comprises a foot 5054 that is formed on the bottom of the firing member body 5052 and extends laterally from each side thereof. The firing member 5050 further comprises a pair of top pins or tabs 5056 that extend laterally from the firing member body 5052 that are adapted to engage ledges on an anvil as will be discussed further herein. Additionally, the firing member 5050 comprises a pair of central pins or tabs 5058 that protrude laterally from each side of the firing member body 5052. In some of the disclosures incorporated by reference herein, the firing member 5050 may also be referred to as an "E-Beam" firing member or cutting member.

Further to the above, the surgical stapling device 8002 further comprises a second jaw or anvil 8100 that is movable relative to the first jaw or frame 8010. The anvil 8100 comprises an anvil body 8102 and an anvil mounting portion 8110. The anvil body 8102 comprises a staple forming undersurface or tissue contacting surface 8104 that has a series of staple forming pockets (not shown) formed therein that are arranged to form corresponding staples as they are driven into forming contact therewith. The anvil mounting portion 8110 comprises a pair of laterally extending anvil pins or trunnion pins 8112 that are configured to be received in corresponding trunnion holes 8022 in the upstanding sidewalls 8020 of the first jaw or frame 8010. Unlike the anvil 4100 described above, the anvil 8100 is pivotally pinned to the frame 8010 for pivotal travel relative thereto about a fixed pivot axis. Stated another way, unlike anvil 4100, anvil 8100 does not materially move axially or translate during the anvil closure process.

As discussed above, as well as in several of the disclosures which have been incorporated by reference herein, the anvil 8100 may be movable from an open position wherein a used or spent staple cartridge may either be removed from the first jaw or frame 8010 or an unfired staple cartridge may be operably seated therein to a closed position by an axially movable closure member or end effector closure tube (not shown). For example, as the closure member is moved distally from a proximal position, the closure tube may operably engage a cam surface on the anvil mounting portion 8110. Such interaction between the closure member and the anvil mounting portion 8110 causes the anvil mounting portion 8110 and the trunnion pins 8112 to pivot until the closure member moves the anvil 8100 to a fully closed position. When in the fully closed position, the staple-forming pockets in the anvil 8100 are properly aligned with the staples in a corresponding compatible surgical staple cartridge that has been operably seated in the first jaw or frame 8010. When the axially movable closure member is thereafter moved in a proximal direction, the closure member causes the anvil 8100 to pivot back to the open position.

Figure 58:
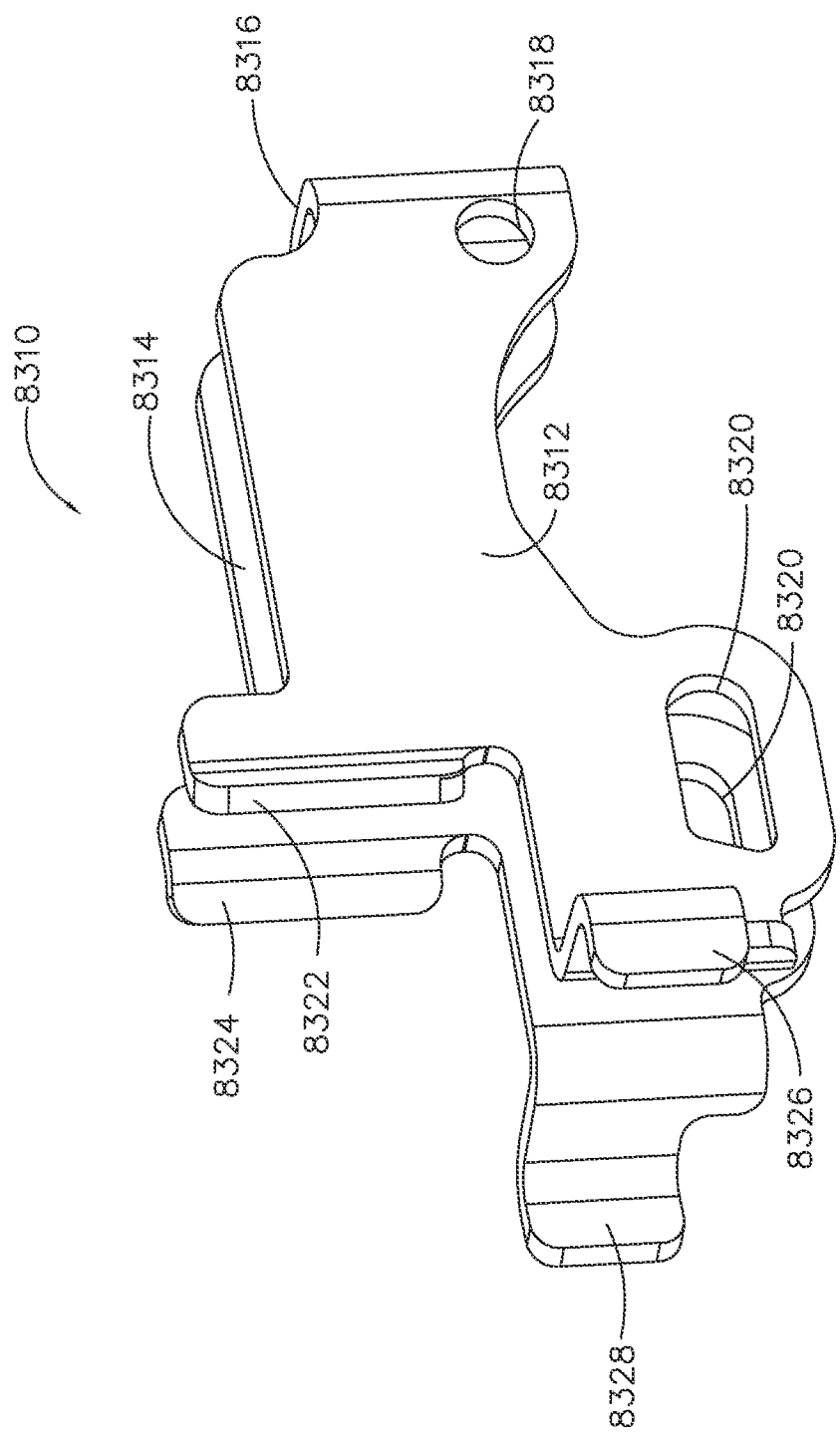
FIG. 58 is a perspective view of a first lockout spring of the surgical stapling device of FIG. 57.

Further to the above, the surgical stapling assembly 8000 further comprises a first lockout 8300 that is configured to prevent the firing member 5050 from moving distally from its proximal-most starting position when an authorized or compatible staple cartridge is not operably seated in the first jaw or frame 8010. The first lockout 8300 may also be referred to herein as an "authentication" lockout. In the illustrated arrangement, the first lockout 8300 comprises a single, bi-lateral first spring 8310 that is supported in the proximal end 8014 of the frame 8010 and attached to the shaft mount flange 8030. In one arrangement for example, the first spring 8310 comprises a first lockout arm 8312 that is located on one side of the cartridge axis CA and a second lockout arm 8314 that is located on an opposite side of the cartridge axis CA from the first lockout arm 8312. The first and second lockout arms 8312, 8314 are attached to a central body portion 8316. See FIG. 58. The spring 8310 is mounted in the first jaw or frame 8010 and affixed to the shaft mount flange 8030 by a pin 8034 that extends through holes 8036 in the shaft mount flange 8030 and through holes 8318 in the first lockout arm 8312 and the second lockout arm 8314. The first lockout arm 8312 and the second lockout arm 8314 each further comprise a lockout window or opening 8320 therein that are each adapted to receive therein the corresponding central pin 5058 protruding from the first and second sides of the firing member 5050 when the firing member 5050 is in its proximal-most or starting position. See FIGS. 59 and 61.

Figure 59:
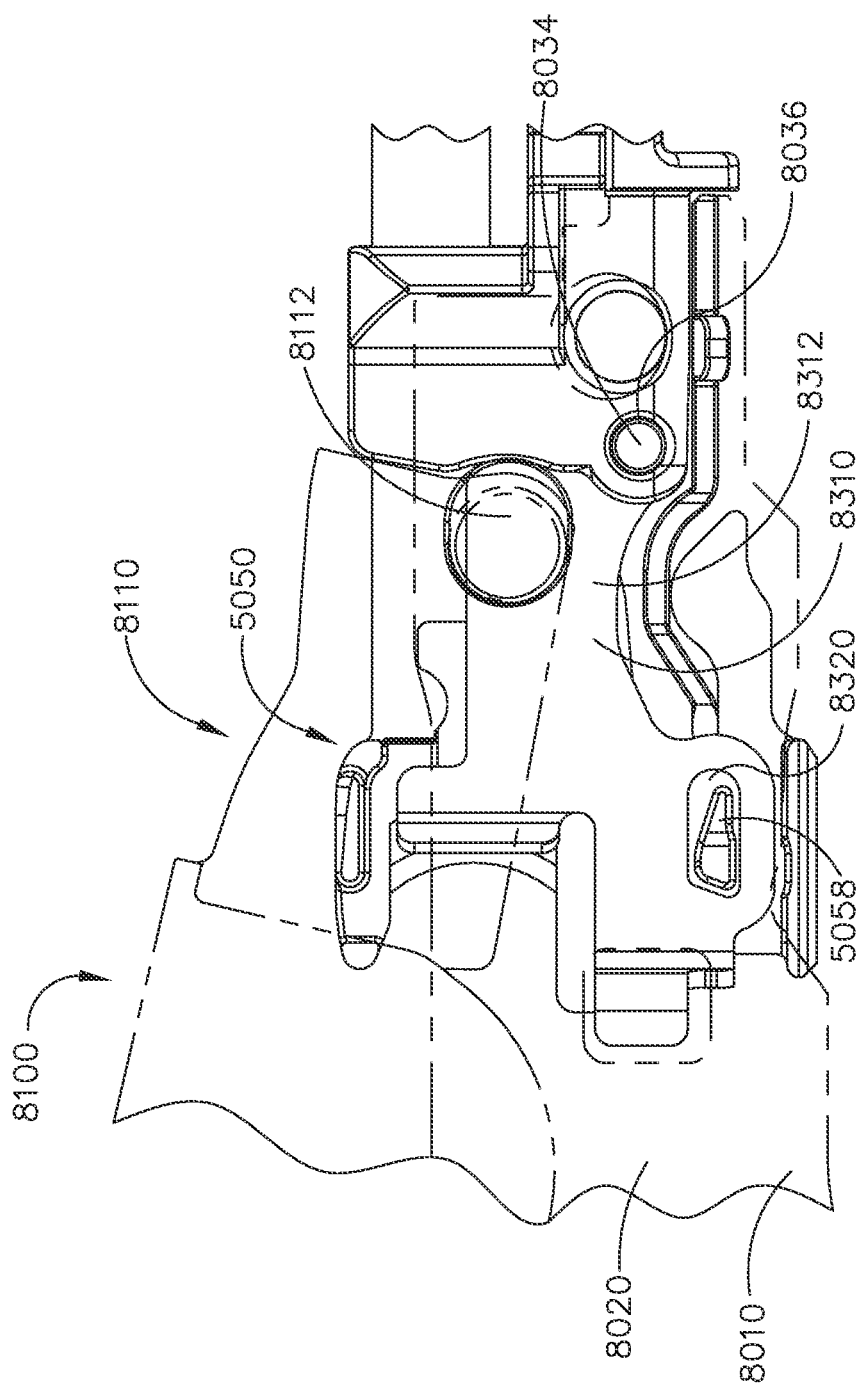
FIG. 59 is a partial side elevational view of the surgical stapling device of FIG. 57 with a first lockout spring thereof in locking engagement with a firing member of the surgical stapling device.
Figure 60:
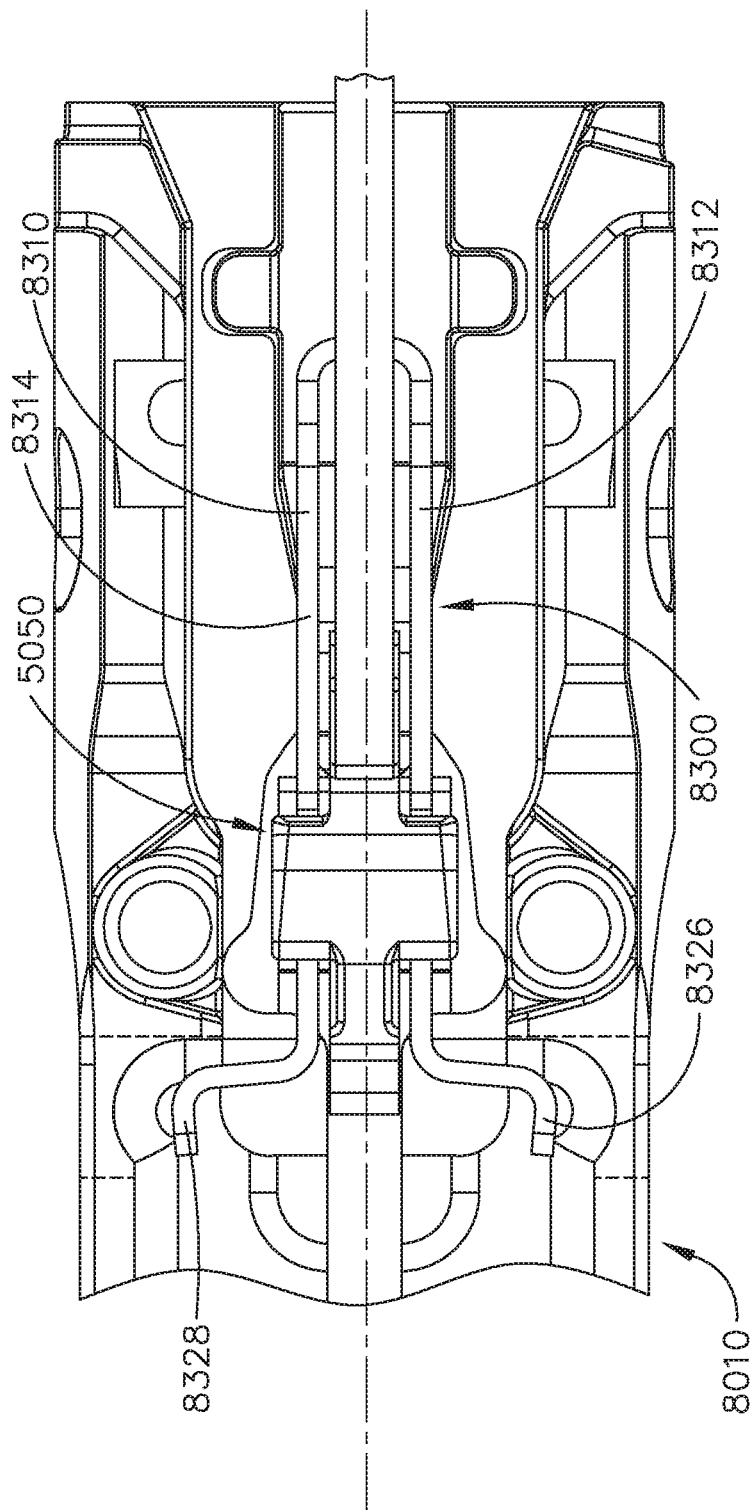
FIG. 60 is a top view of the surgical stapling device of FIG. 59 with the first lockout spring in the engaged or locked position.
Figure 61:
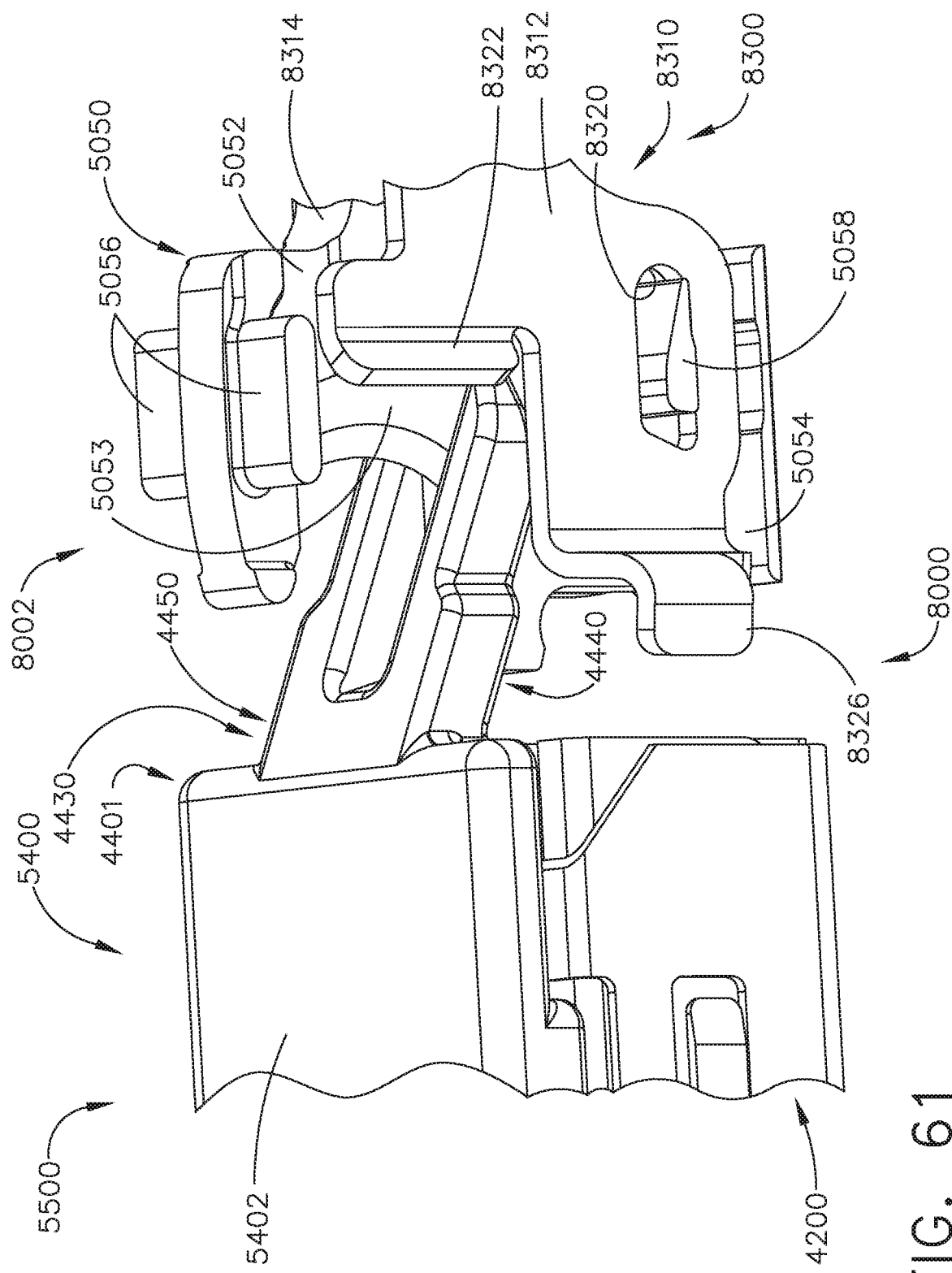
FIG. 61 is an exploded view of portions of the surgical stapling device of FIG. 60 showing an initial insertion of a cartridge assembly that comprises a retainer attached to a staple cartridge, wherein an authentication key on the retainer is engaging the first lockout spring of the surgical stapling device.

FIGS. 59-61 illustrate the first lockout 8300 in the locked position wherein the central pins 5058 are received within the lockout windows 8320 in the first and second lockout arms 8312, 8314. In some arrangements, those staple cartridges that are compatible with the surgical stapling device 8002 or, stated another way, those staple cartridges that have the proper number, size and arrangement of staples, may have one or more unlocking keys directly formed on the cartridge body and/or cartridge pan that are configured to defeat the first lockout when the compatible cartridge is operably seated in the first jaw or frame. Various cartridges that have unlocking keys protruding therefrom are disclosed in various disclosures which have been herein incorporated by reference. In other instances, however, the clinician may wish to use staple cartridges that are otherwise compatible with the surgical stapling assembly, but otherwise lack the unlocking keys. In such instances, the clinician would be unable to otherwise use those compatible staple cartridges in the surgical stapling device. The surgical stapling assembly 8000 includes features designed to facilitate use of such compatible staple cartridges that otherwise lack unlocking key features.

Figure 51:
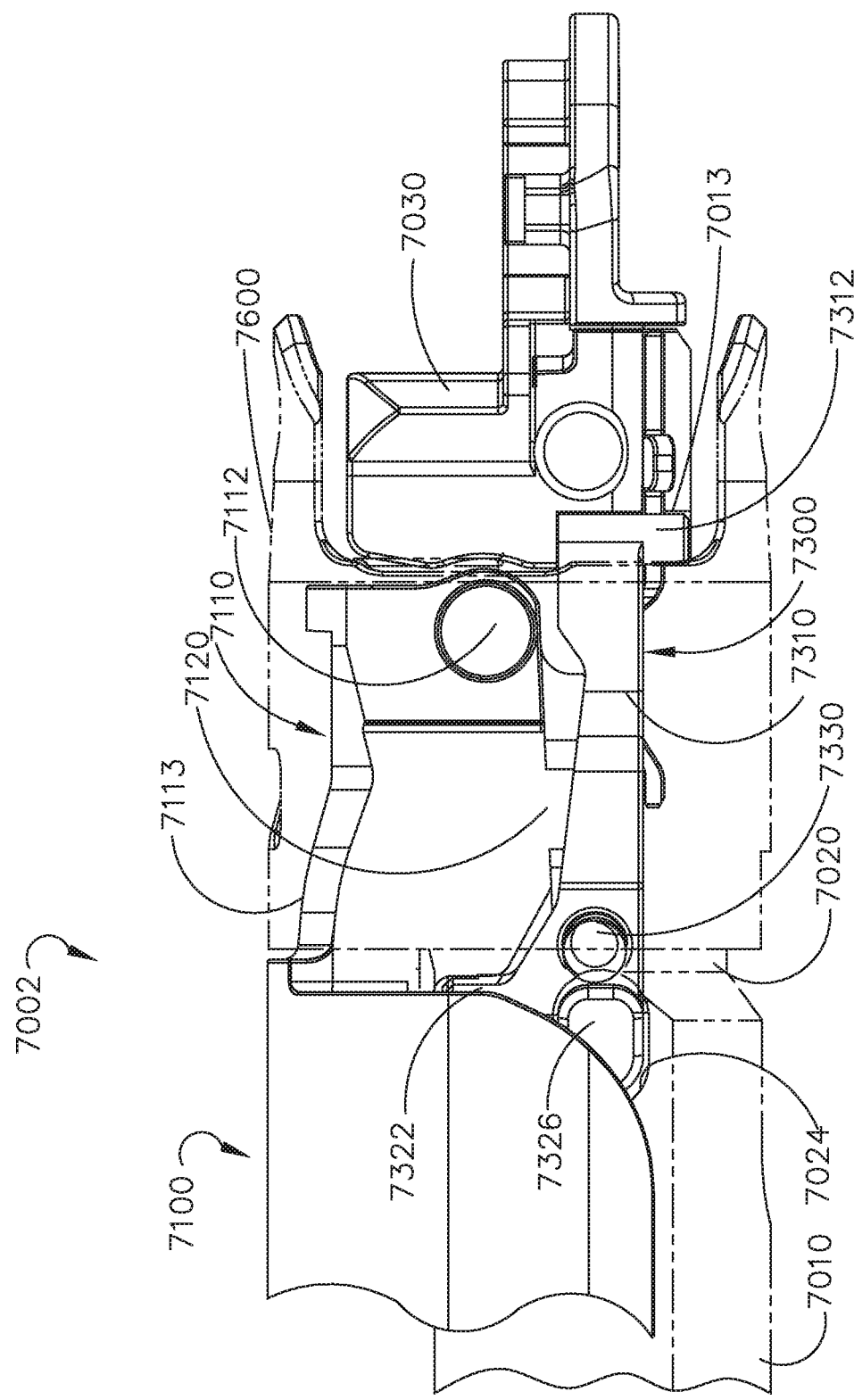
FIG. 51 is a side elevational view of the surgical stapling device of FIG. 49 with the first lockout arm in a jaw closure position and an anvil thereof in a closed position.
Figure 55:
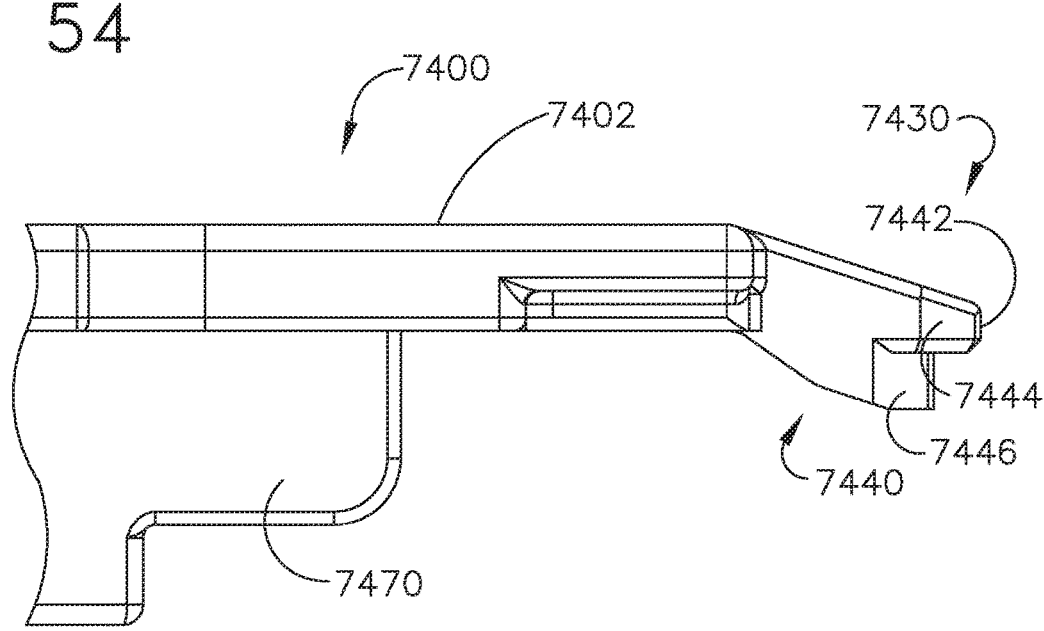
FIG. 55 is a side view of the proximal end of the retainer of FIG. 54.

Turning now to FIGS. 51 and 55, the stapling assembly 8000 further comprises a retainer 4400 that is configured to be removably coupled to the staple cartridge 4200. Specific details concerning the retainer 4400 were discussed above and will not be repeated here. As indicated above, the retainer 4400 further comprises an authentication key 4430 that is configured to defeat the first lockout 4300 when the retainer 4400 is attached to the staple cartridge 4200 and the staple cartridge 4200 has been operably seated in the first jaw or frame 8010. As can be seen in FIG. 11, the authentication key 4430 protrudes proximally from a proximal end 4401 of the top portion 4402 of the retainer 4400 and comprises a right ramp feature 4440 and a left ramp feature 4450 that are separated by a space 4460 that is sized to receive the firing member body 4052 therebetween. In the illustrated example, the right ramp 4440 angles downward from the top portion 4402 of the retainer 4400 and comprises a proximal right tip 4442. The proximal right tip 4442 defines a first right cam surface 4444 that angles inward at the tip and extends distally to a second right cam surface 4446. The second right cam surface 4446 extends from the first right cam surface 4444 to the top portion 4402. See FIG. 12. Similarly, the left ramp 4450 angles downward from the top portion 4402 of the retainer 4400 and comprises a proximal left tip 4452. The proximal left tip 4452 angles inward at the tip and extends distally to a second left cam surface 4456. The second left cam surface extends from the first left cam surface 4454 to the top portion 4402.

Figure 62:
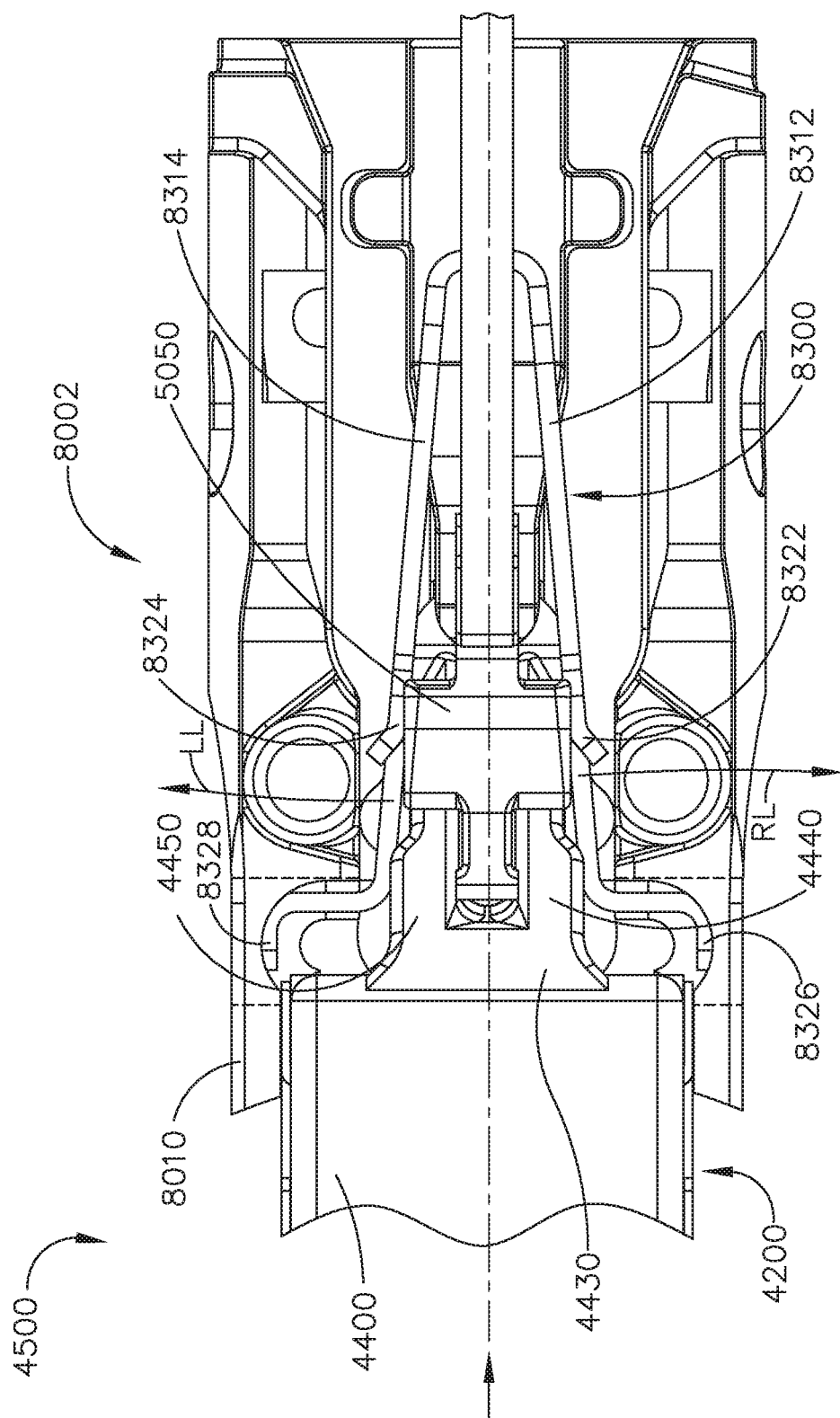
FIG. 62 is a top view of the surgical stapling device of FIG. 60 illustrating an initial insertion of the cartridge assembly of FIG. 61 therein.

Referring now to FIGS. 61 and 62, in use the retainer 4400 is removably attached to the staple cartridge 4200 to form a cartridge assembly 4500. The cartridge assembly 4500 is then inserted into the first jaw or frame 8010 so as to bring the right tip 4442 of the authentication key into contact with an upstanding unlocking tab 8322 on the first lockout arm 8312 and the left tip 4452 into contact with an upstanding unlocking tab 8324 on the second lockout arm 8314. During the initial proximal insertion of the cartridge assembly 4500, the first right cam surface 4444 biases the first lockout arm 8312 laterally outward (arrow RL in FIG. 62) and the first left cam surface 4454 biases the second lockout arm 8314 laterally outward (arrow LL). Further longitudinal advancement of the cartridge assembly 4500 into the first jaw or frame 8010 in a proximal direction causes the first lockout arm 8312 to attain a first intermediate position wherein the first lockout arm 8312 disengages the corresponding central pin 5058 on the firing member 5050 and also causes the second lockout arm 8314 to attain a second intermediate position wherein the second lockout arm 8314 disengages the corresponding central pin 5058 on the firing member 5050. Continued longitudinal insertion of the cartridge assembly 4500 into the first jaw or frame 8010 in a proximal direction causes the second right cam surface 4446 to further bias the first lockout arm 8312 laterally outward and the second left cam surface 4456 to further bias the second lockout arm 8314 laterally outward until the cartridge assembly 4500 is completely operably seated in the first jaw or frame 8010. See FIG. 63.

Figure 63:
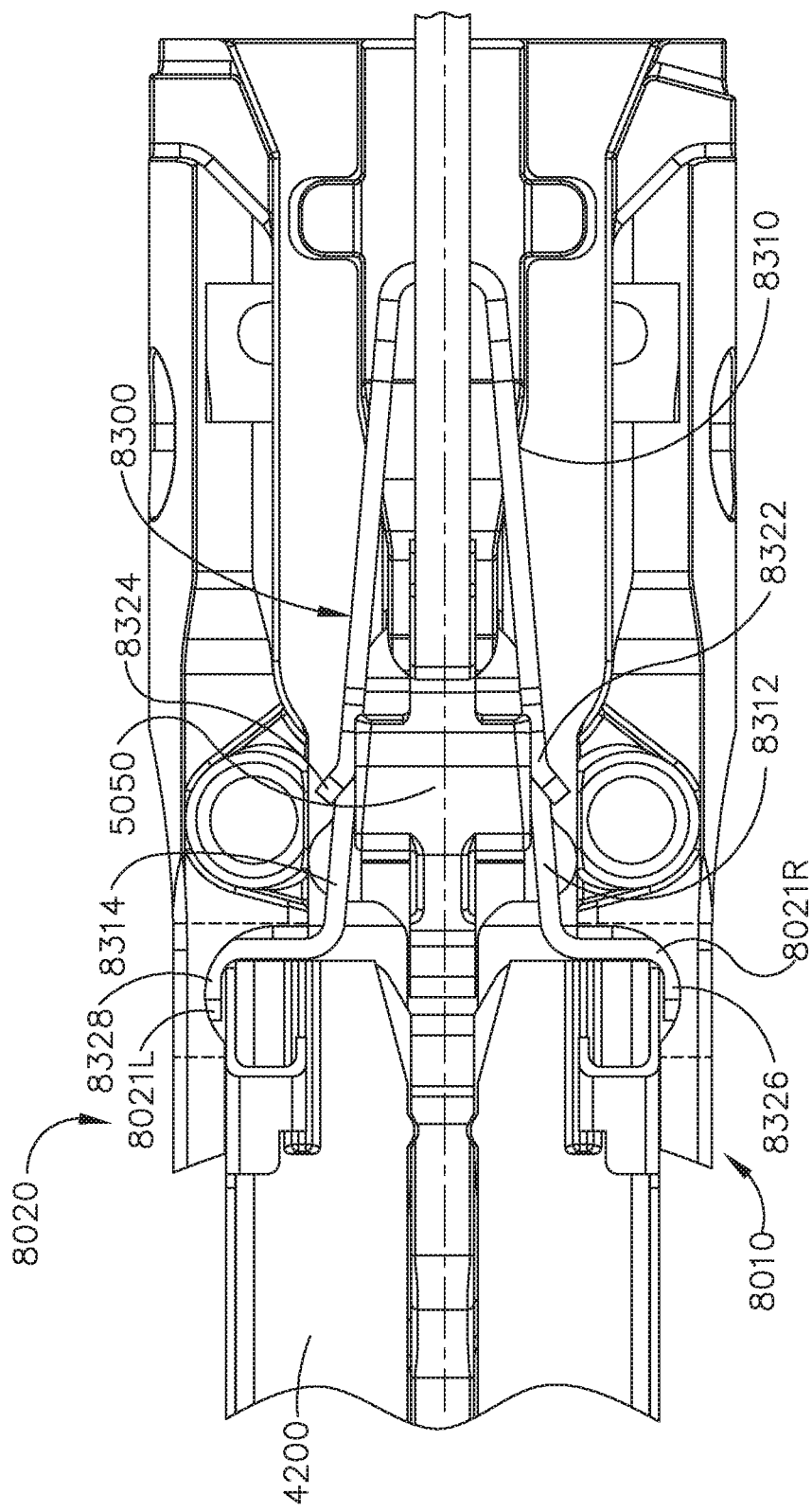
FIG. 63 is another top view of the surgical stapling device of FIG. 62 after the retainer has been removed from the staple cartridge seated in the surgical stapling device.

When the cartridge assembly 4500 has been operably seated in the first jaw or frame 5010, a distal first retention tab 8326 on the first lockout arm 8312 engages a corresponding side of the staple cartridge 4200 to retain the first lockout arm 8312 in that unlocked position. As can be seen in FIG. 63, a clearance pocket 8021R is provided in the sidewall 8020 to accommodate the first retention tab 8326 in that position. Likewise a distal second retention tab 8328 formed on the second lockout arm 8314 engages another corresponding side of the staple cartridge 4200 to retain the second lockout arm 8314 in that unlocked position. A clearance pocket 8021L is provided in the sidewall 8020 to accommodate the second retention tab 8328 in that position. When in that position, the first lockout 8300 is in the unlocked position or, stated another way, is "defeated". The user may then remove the retainer 4400 from the staple cartridge 4200 in the above-described manner. With the first lockout 8300 defeated or unlocked, the firing member 5050 may be distally advanced from the starting position and is in a "ready state".

After the staple cartridge 4200 has been fired, the firing member 5050 is retracted back to the starting position and the second jaw or anvil 8100 is pivoted back to the open position. The spent staple cartridge may then be removed from the first jaw or frame 8010. Once the spent staple cartridge 4200 has been removed from the first jaw or frame 8010, the first and second lockout arms 8312, 8314 spring back into engagement with the corresponding central pins 5058 on the firing member 5050 to once again retain the firing member 5050 in the starting position. Also, in at least one version, the surgical stapling device 8002 also includes a second lockout 5600 that is configured to prevent the firing member 5050 from distally advancing through the staple firing stroke when a spent staple cartridge is seated in the first jaw or frame 8010. Details concerning the operation of the second lockout were provided above and will not be repeated here.

Figure 64:
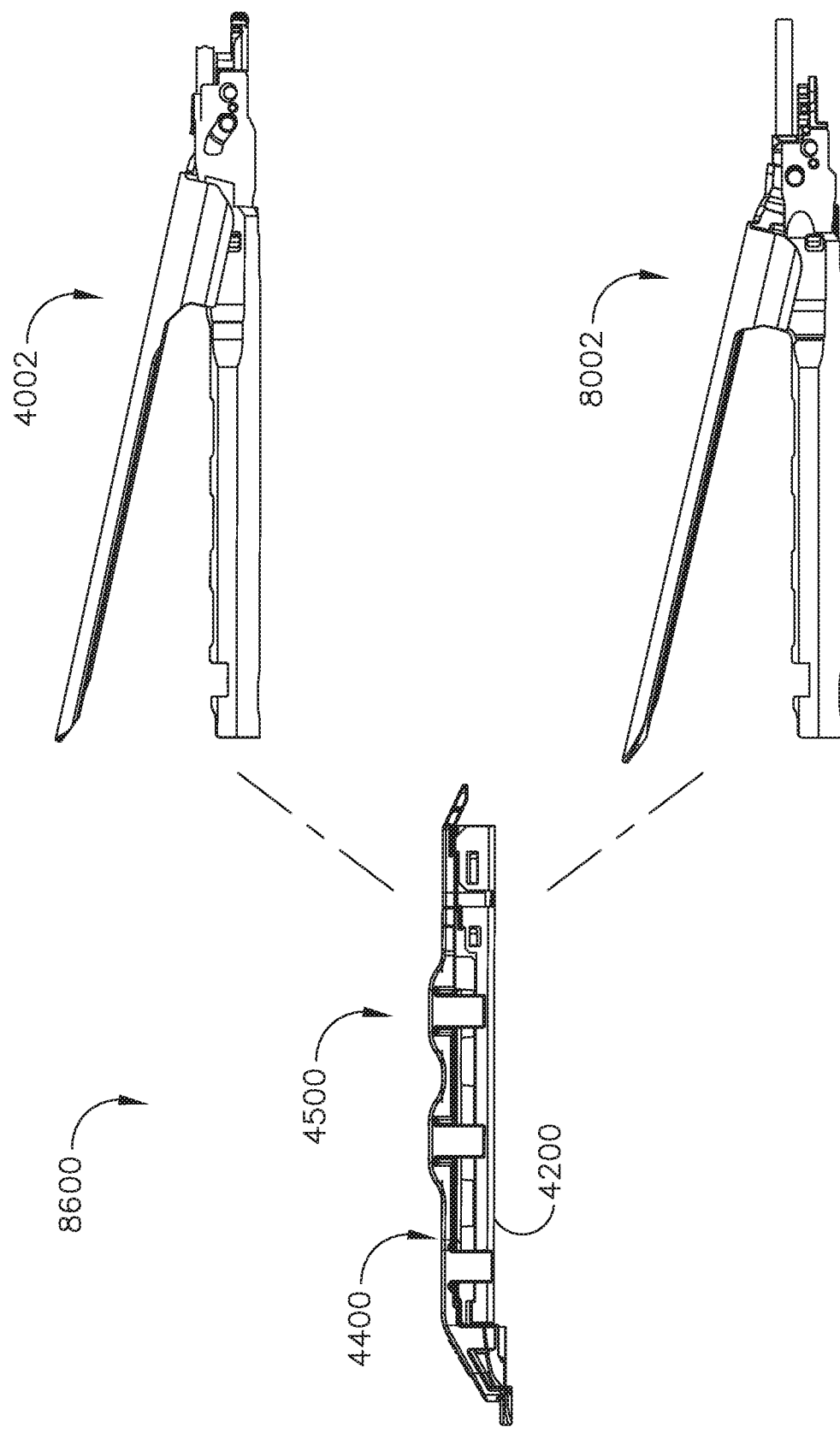
FIG. 64 is an exploded view of a surgical system.

Further to the above, at least one form of the retainer 4400 may be attached to various staple cartridges that are adapted to be used with (compatible with) different forms of surgical stapling devices. Stated another way, the retainer 4400 may be used on staple cartridges that can be seated in different stapling devices to defeat the various lockout mechanisms of those stapling devices. Staple cartridge 8200 may similarly be used with different stapling devices that have different forms of lockouts. For example, FIG. 64 illustrates a surgical stapling system generally designated as 8600 which comprises a first stapling device 4002 and at least a second stapling device 8002. The retainer 4400 may be coupled to surgical staple cartridges 4200 to form a cartridge assembly 4500 that is compatible with one of both of the surgical stapling devices 4002, 8002. When the retainer 4400 is attached to a compatible staple cartridge 4200 to form an assembled cartridge arrangement 4500, the assembled cartridge arrangement may be used in either of the devices 4002, 8002. Likewise, the staple cartridge 4200 may also be used in either of the stapling devices 4002, 8002. Surgical stapling device 4002 employs a translating anvil 4100; stapling device 8002 employs a pivoting anvil 8100. These devices offer very different amounts of space for the authentication key arrangements to operate due to the different amounts of space required for the anvils of each device to move between the open and closed positions. Thus, in various applications, the authentication ramp features may need to be rather narrow and employ staged and vertically displaced camming surfaces in order to actuate the lockout configurations of both types of stapling devices.

In connection with another general aspect, the various authentication keys and authentication ramps disclosed herein may be mixed and matched with retainer body configurations disclosed herein such that one retainer/authentication key/ramp configuration may be employed with staple cartridges that can be used in a plurality of stapling devices disclosed herein. Such retainer authentication key/ramp configurations may be used to defeat a plurality of the lockout systems in those various stapling devices. Stated another way, one retainer/authentication key/authentication ramp configuration may be employed to unlock the jaw blocking lockouts and/or the firing member lockouts on several of the stapling devices disclosed herein.

As discussed herein, the authentication key arrangement may be provided on a detachable retainer, on the cartridge pan, on the cartridge body, on the sled or on another ancillary attached part. These authentication keys may be fashioned such that they could defeat the various first lockout systems of those surgical stapling devices disclosed herein that employ a translating jaw arrangement as well as the first lockout systems of those surgical stapling devices that employ a jaw arrangement that is pivotable about a fixed pivot axis. The design of such "universal" authentication keys may be limited and dictated by the amount of available space in such devices when the movable jaw or anvil is in the closed position (for those keys designed to be resident in the device throughout the stapling firing operation) as well as in the open position.

When designing authentication key configurations that may be employed to defeat lockouts in surgical stapling devices that employ a translating jaw as well lockouts in surgical stapling devices that employ a movable jaw that pivots about a fixed axis, the amount of available space that is available in each surgical stapling device will necessarily dictate a particular shape of a "universal" authentication key. Because the jaw shapes and travel paths are different in these types of surgical stapling devices, the amount of available space for the authentication keys when the jaws are open and closed differ.

Figure 64A:
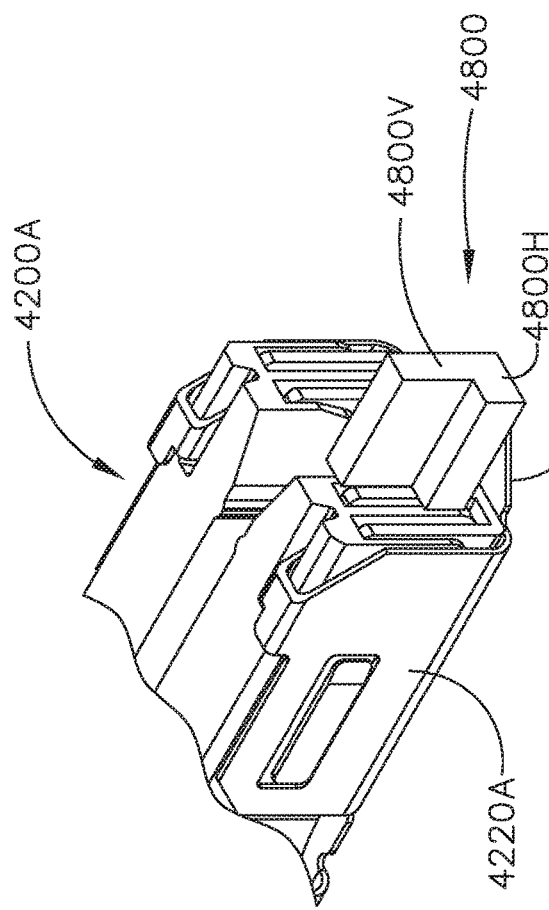
FIGS. 64A-64ZZ illustrate examples of various amounts of spaces that are available for authentication key arrangements of various staple cartridges as used in connection with different surgical stapling devices.
Figure 64C:
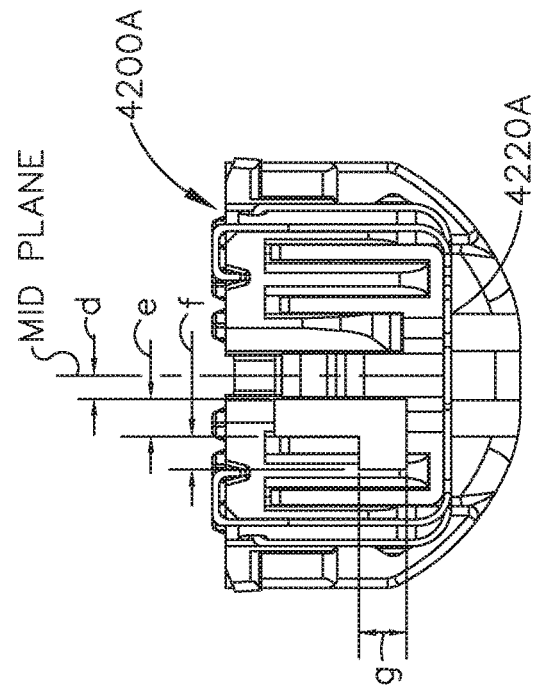
Figure 64B:
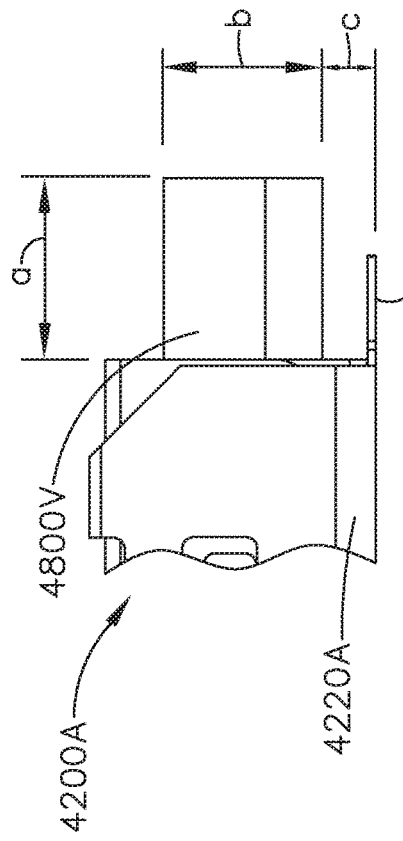
Figure 64D:
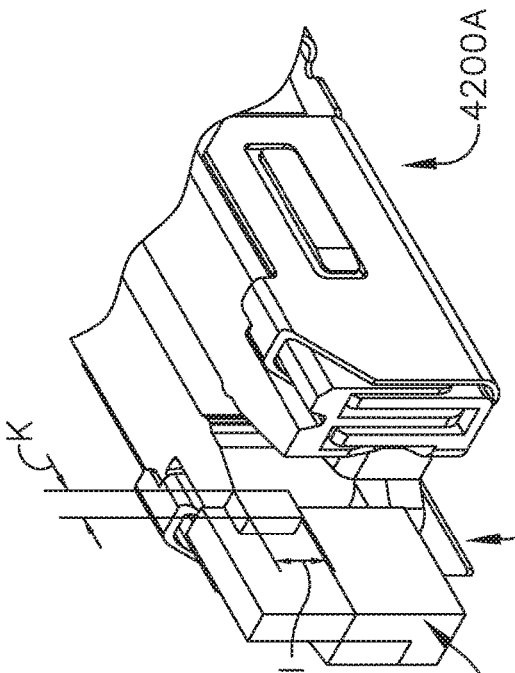
Figure 64F:
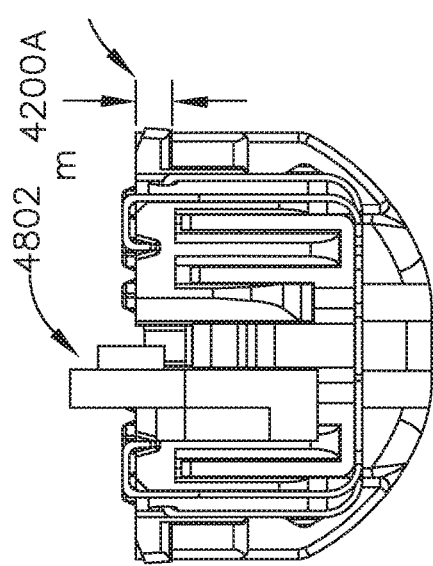
Figure 64E:
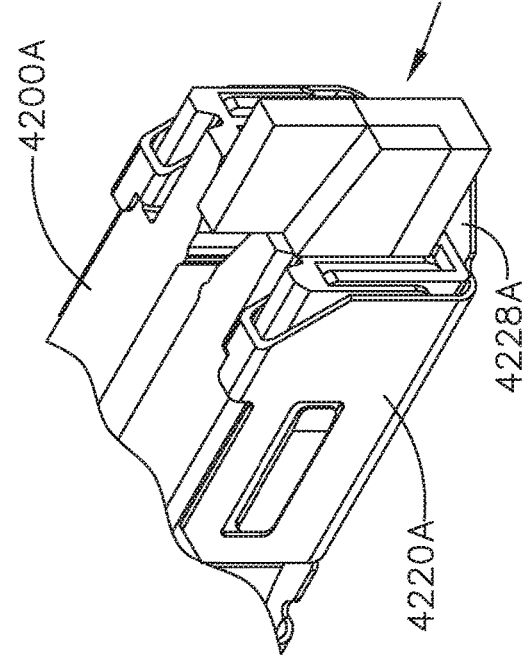
Figure 64G:
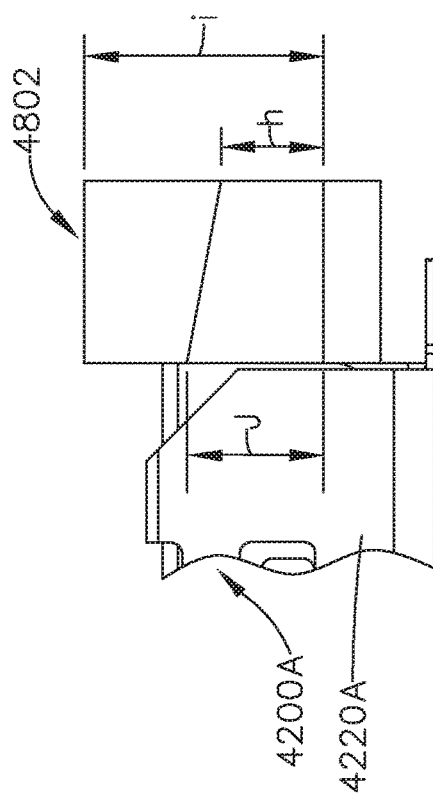

FIGS. 64A-C illustrate an example of an amount of space that is available to accommodate an authentication key 4228A of a staple cartridge 4200A, wherein the authentication key feature 4228A formed on a bottom portion of the cartridge pan 4220A and when the staple cartridge 4200A is seated in, for example, a surgical stapling device 4002 that has a translating anvil 4100 that is in the closed position. As can be seen in those Figures, a "closed" space envelop 4800 has a vertical leg 4800V and a horizontal leg 4800H, wherein when used in connection with one surgical stapling device: a is approximately 0.16 inches, b is approximately 0.14 inches, c is approximately 0.047 inches, d is approximately 0.025 inches, e is approximately 0.04 inches, f is approximately 0.035 inches, and g is approximately 0.05 inches, for example. FIGS. 64D-64G illustrate an "open" space envelope 4802 for the staple cartridge 4200A when the jaws of the surgical stapling device are open, wherein: h is approximately 0.14 inches, i is approximately 0.26 inches, j is approximately 0.17 inches, k is approximately 0.04 inches, L is approximately 0.0.07 inches, and M is approximately 0.03 inches, for example.

Figure 64H:
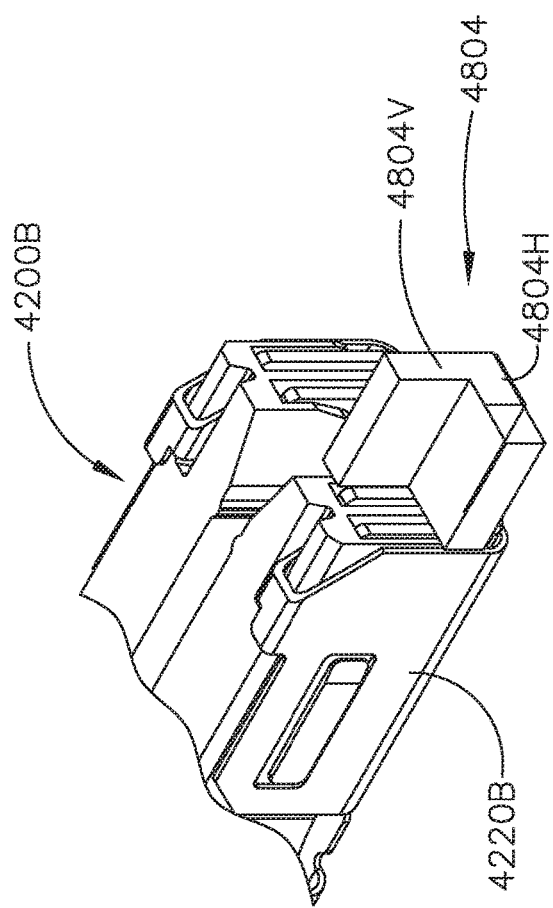
Figure 64J:
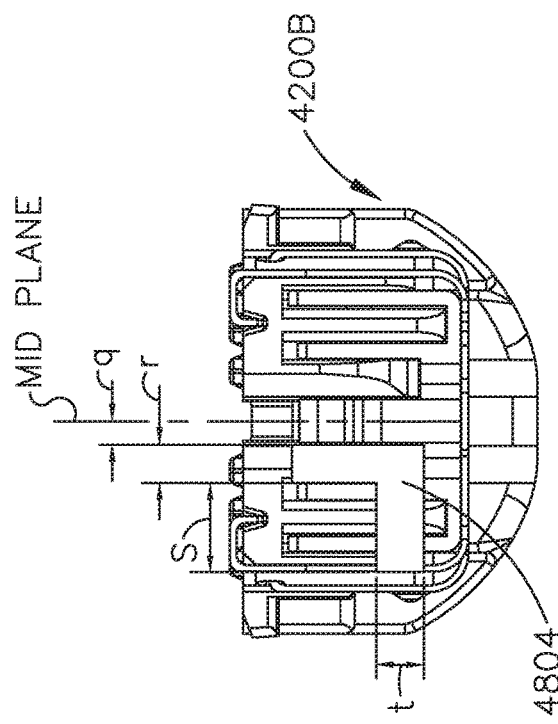
Figure 64I:
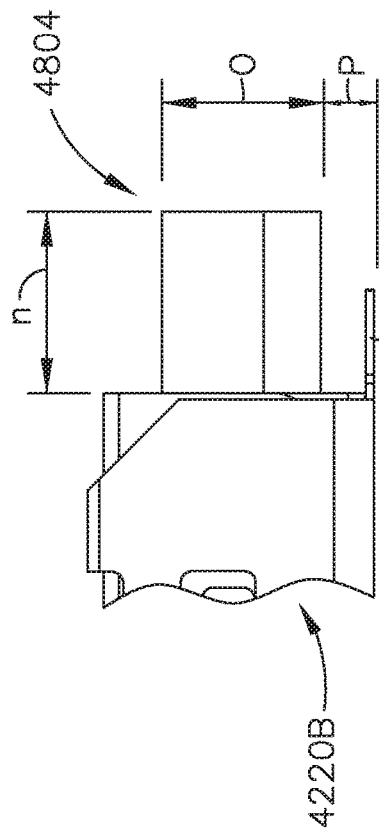

FIGS. 64H-J illustrate an example of an amount of space that is available to accommodate an authentication key 4228B of another staple cartridge 4200B, wherein the authentication key feature 4228B formed on a bottom portion of the cartridge pan 4220B and when the staple cartridge 4200B is seated in, for example, a surgical stapling device 4002 that has a translating anvil 4100 that is in the closed position. As can be seen in those Figures, a "closed" space envelop 4804 has a vertical leg 4804V and a horizontal leg 4804H, wherein when used in connection with one surgical stapling device: n is approximately 0.16 inches, o is approximately 0.16 inches, p is approximately 0.14 inches, q is approximately 0.025 inches, r is approximately 0.04 inches, s is approximately 0.095 inches, t is approximately 0.05 inches, for example.

Figure 64K:
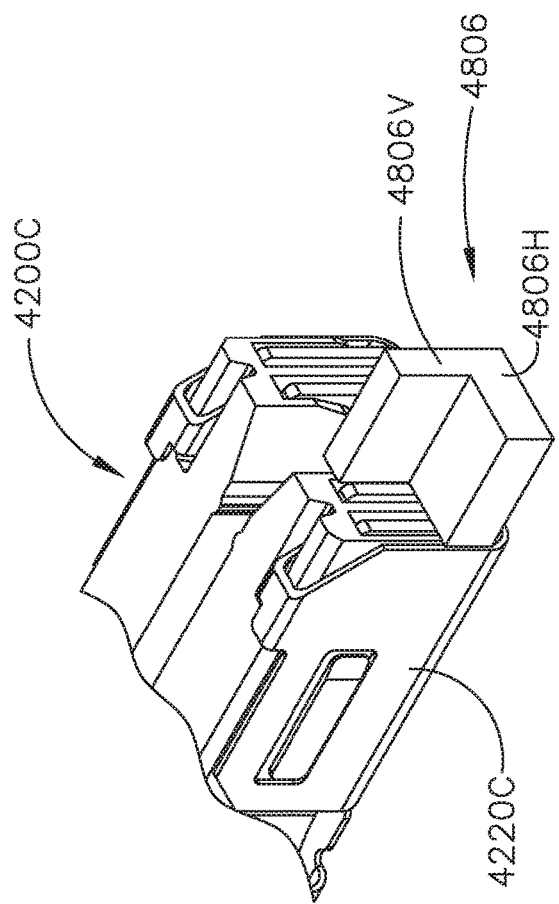
Figure 64L:
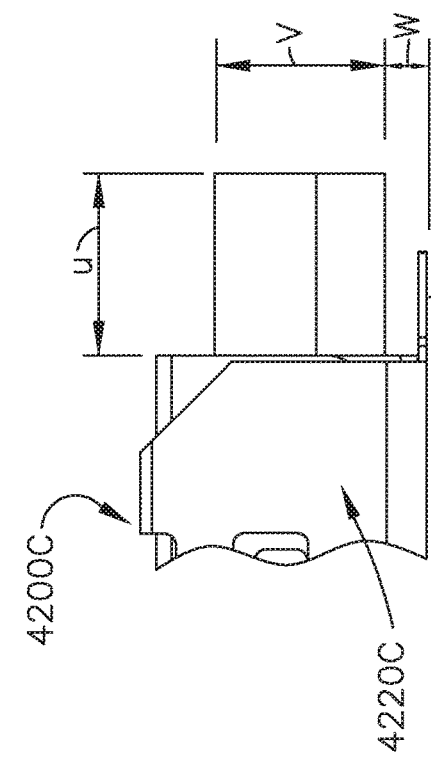
Figure 64M:
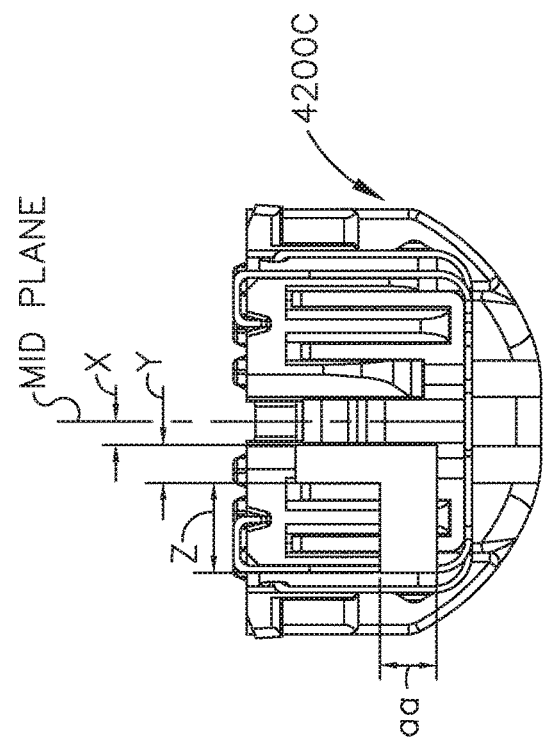

FIGS. 64K-M illustrate an example of an amount of space that is available to accommodate an authentication key 4228C of a staple cartridge 4200C, wherein the authentication key feature 4228C formed on a bottom portion of the cartridge pan 4220C and when the staple cartridge 4200C is seated in, for example, a surgical stapling device 4002 that has a translating anvil 4100 that is in the closed position. As can be seen in those Figures, a "closed" space envelop 4806 has a vertical leg 4806V and a horizontal leg 4806H, wherein when used in connection with one surgical stapling device: u is approximately 0.16 inches, v is approximately 0.15 inches, w is approximately 0.037 inches, x is approximately 0.025 inches, y is approximately 0.04 inches, z is approximately 0.095 inches, and aa is approximately 0.06 inches, for example. FIGS. 64N-Q illustrate an "open" space envelope 4808 for the staple cartridge 4200C when the jaws of the surgical stapling device are open, wherein: bb is approximately 0.26 inches, cc is approximately 0.23 inches, dd is approximately 0.12 inches, ee is approximately 0.12 inches, ff is approximately 0.08 inches, and gg is approximately 0.04 inches, for example.

FIGS. 64R-T illustrate an example of an amount of space that is available to accommodate an authentication key 4228D of a staple cartridge 4200D, wherein the authentication key feature 4228D formed on a bottom portion of the cartridge pan 4220D and when the staple cartridge 4200D is seated in, for example, a surgical stapling device 8002 that has an anvil 8100 that movable between an open and closed position about a fixed pivot axis. As can be seen in those Figures, a "closed" space envelop 4810 has a vertical leg 4810V and a horizontal leg 4810H, wherein when used in connection with one surgical stapling device: hh is approximately 0.16 inches, ii is approximately 0.20 inches, jj is approximately 0.047 inches, kk is approximately 0.025 inches, ll is approximately 0.05 inches, mm is approximately 0.025 inches, and nn is approximately 0.09 inches, for example. FIGS. 64U-64X illustrate an "open" space envelope 4812 for the staple cartridge 4200D when the jaws of the surgical stapling device are open, wherein: oo is approximately 0.09 inches, pp is approximately 0.08 inches, qq is approximately 0.05 inches, rr is approximately 0.06 inches, ss is approximately 0.10 inches, and tt is approximately 0.03 inches, and uu is approximately 0.09 inches, for example.

FIGS. 64Y-64ZZ illustrate an example of an amount of space that is available to accommodate an authentication key 4228E of a staple cartridge 4200E, wherein the authentication key feature 4228E formed on a bottom portion of the cartridge pan 4220E and when the staple cartridge 4200E is seated in, for example, a surgical stapling device 8002 that has an anvil 8100 that movable between an open and closed position about a fixed pivot axis. As can be seen in those Figures, a "closed" space envelop 4814 has a vertical leg 4814V and a horizontal leg 4814H, wherein when used in connection with one surgical stapling device: vv is approximately 0.16 inches, ww is approximately 0.20 inches, xx is approximately 0.047 inches, yy is approximately 0.025 inches, zz is approximately 0.05 inches, aaa is approximately 0.085 inches, and bbb is approximately 0.09 inches, for example.

Figure 65:
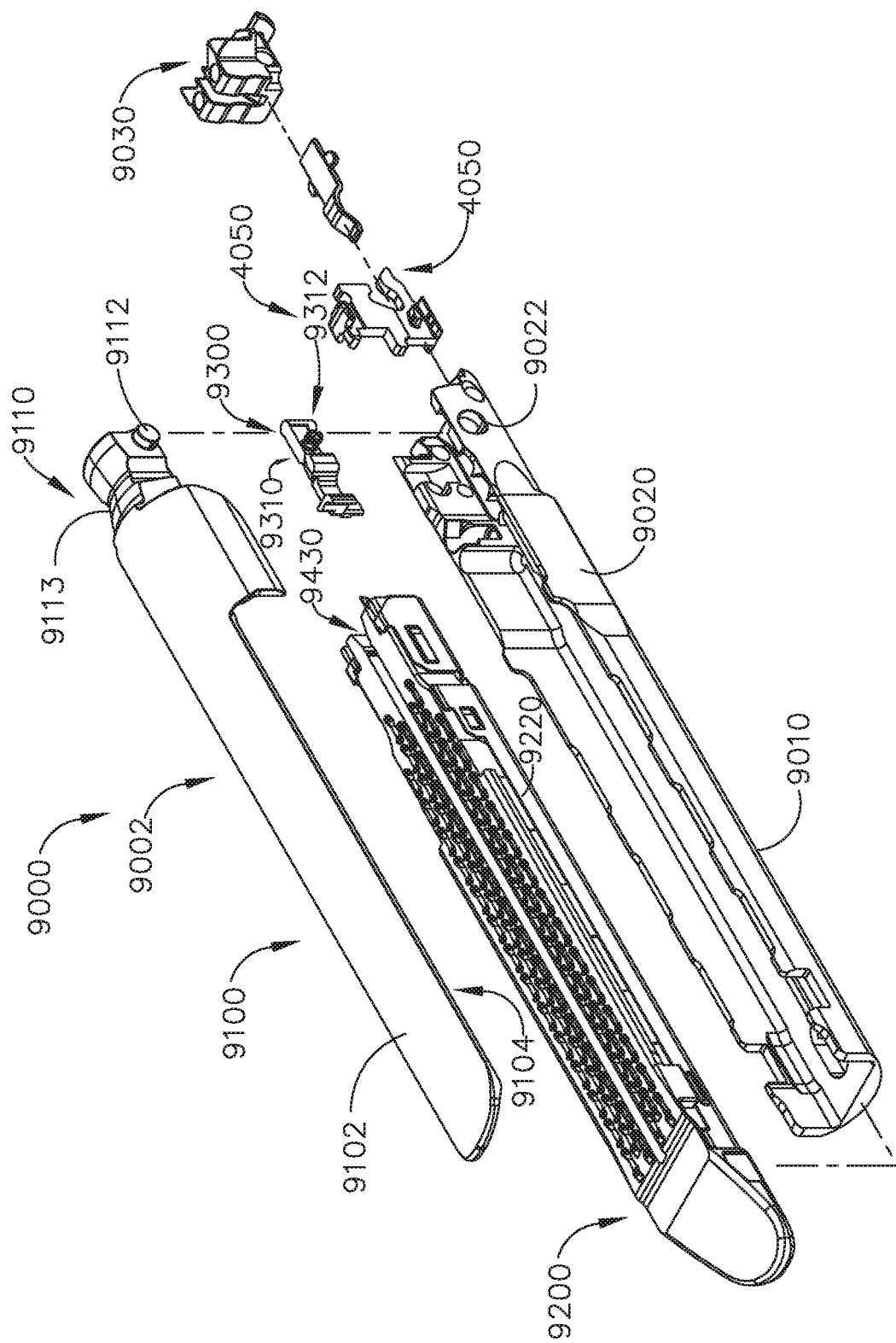
FIG. 65 is an exploded perspective assembly view of a surgical stapling device and staple cartridge of another surgical stapling assembly.

FIGS. 65-71 illustrate another surgical stapling assembly 9000 that is similar in many aspects to surgical stapling assembly 7000 discussed above. The surgical stapling assembly 9000 comprises a surgical stapling device 9002 that may be employed in connection with the surgical instrument 1010 described above or in connection with a variety of other surgical instruments and robots described in various disclosures that have been incorporated by reference herein. As can be seen in FIG. 65, the surgical stapling device 9002 comprises a first jaw or frame 9010 that is configured to operably support a staple cartridge 9200 therein. The first jaw or frame 9010 is attached to a spine of the shaft assembly in the various manners described herein. In the illustrated example, the first jaw or frame 9010 is attached to the spine of a shaft assembly (not shown in FIG. 65), by a shaft mount flange 9030. The surgical stapling device 9002 may also be used in connection with shaft assemblies that do not facilitate articulation of the surgical stapling device 9002.

Still referring to FIG. 65, the surgical stapling device 9002 further comprises a firing member assembly 4040 that comprises a knife bar (not shown) that is attached to a knife member 4050 or "firing member". Operation of the firing member 4050 and the knife bar were discussed in detail above and will not be repeated here. The surgical stapling device 9002 further comprises a second jaw or anvil 9100 that is movable relative to the first jaw or frame 9010. The anvil 9100 comprises an anvil body 9102 and an anvil mounting portion 9110. The anvil body 9102 comprises a staple forming undersurface or tissue contacting surface 9104 that has a series of staple forming pockets (not shown) formed therein that are arranged to form corresponding staples as they are driven into forming contact therewith.

The anvil mounting portion 9110 comprises a pair of laterally extending anvil pins or trunnion pins 9112 that are configured to be received in corresponding trunnion holes 9022 in the upstanding sidewalls 9020 of the first jaw or frame 9010. Unlike the anvil 6100 described above, the anvil 9100 is pivotally pinned to the frame 9010 for pivotal travel relative thereto about a fixed pivot axis. Stated another way, unlike anvil 6100, anvil 9100 does not materially move axially or translate during the anvil closure process.

Figure 69:
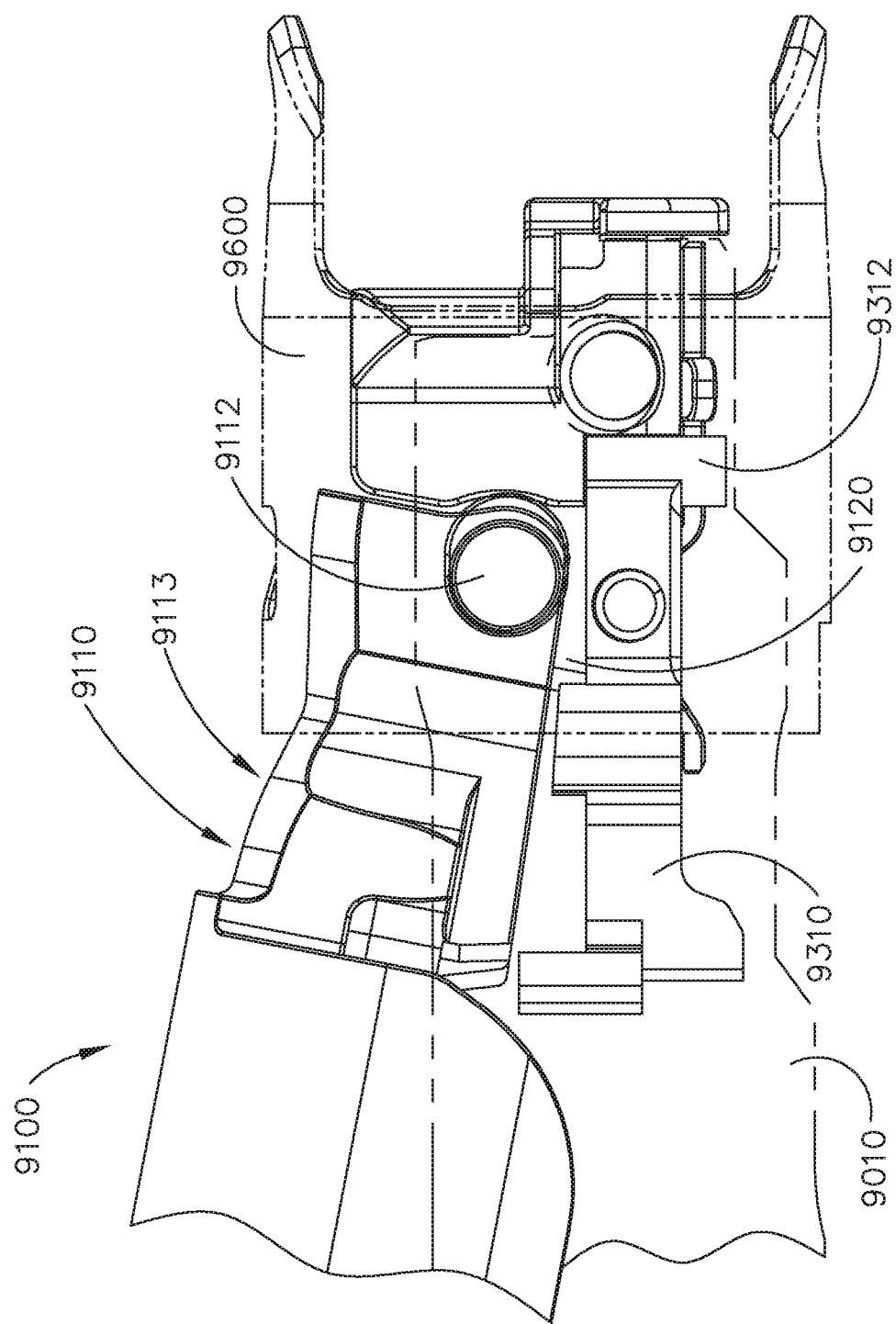
FIG. 69 is a side elevational view of the surgical stapling device of FIG. 68 with the first lockout arm in the jaw locking position.
Figure 70:
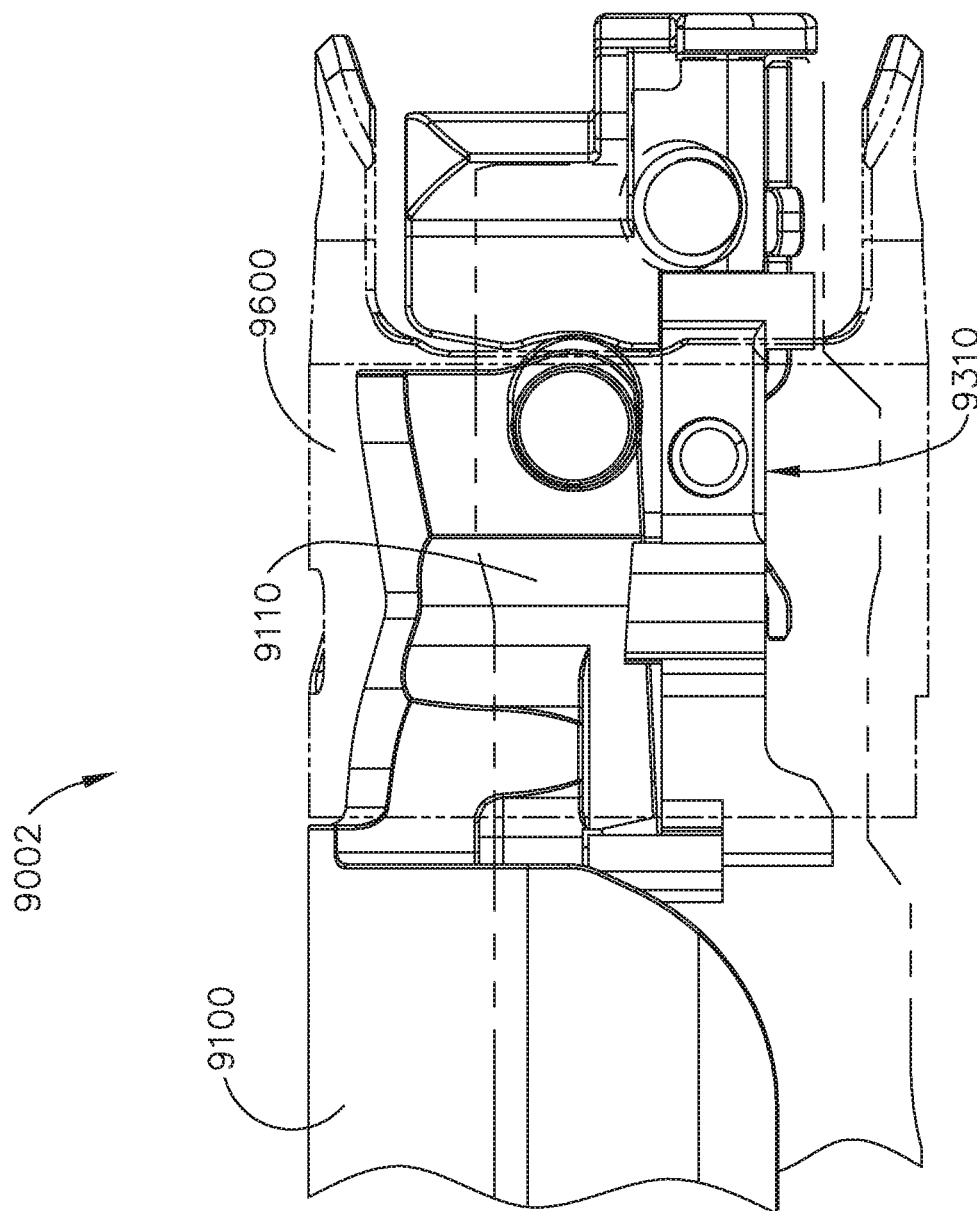
FIG. 70 is another side elevational view of the surgical stapling device of FIG. 69 with the first lockout arm in a jaw closure position and an anvil thereof in a closed position.

As discussed above, as well as in several of the disclosures which have been incorporated by reference herein, the anvil 9100 may be movable from an open position wherein a used or spent staple cartridge may either be removed from the first jaw or frame 9010 or an unfired staple cartridge may be operably seated therein to a closed position by an axially movable closure member or end effector closure tube 9600 (FIG. 69). For example, as the closure tube 9600 is moved distally from a proximal position, the closure tube 9600 may operably engage a cam surface 9113 on the anvil mounting portion 9110. Such interaction between the closure tube 9600 and the anvil mounting portion 9110 causes the anvil mounting portion 9110 and the anvil trunnion pins 9112 to pivot until the closure member moves the anvil 9100 to a fully closed position. When in the fully closed position, the staple-forming pockets in the anvil 9100 are properly aligned with the staples in a corresponding compatible staple cartridge 9200 that has been operably seated in the first jaw or frame 9010. When the axially movable closure tube 9600 is thereafter moved in a proximal direction, features on the closure tube 9600 interface with the anvil mounting portion 9110 to cause the anvil 9100 to pivot back to the open position.

Further to the above, the surgical stapling device 9002 comprises a first lockout 9300 that is configured to prevent the second jaw or anvil 9100 from being movable from the open position to the closed position by the closure tube 9600. The first lockout 9300 may also be referred to herein as an "authentication" lockout. In the illustrated arrangement, the first lockout 9300 comprises a first lockout arm 9310 that is pivotally supported in the first jaw or frame 9010 by a lockout pin 9312 that is attached thereto. See FIG. 66. In one example, the first lockout arm 9310 is fabricated from stainless steel or the like and the lockout pin 9312 may be machined into the proximal end thereof. The lockout pin 9312 is pivotally seated in a pivot hole 9013 in the frame 9010 to facilitate pivotal travel of the first lockout arm 9310 between a jaw locking position and a jaw closure position. See FIG. 68. In the illustrated example, the first lockout arm 9310 is configured to blockingly engage a lock lug portion 9120 protruding downward from the anvil mounting portion 9110 when the first lockout arm 9310 is the locked or jaw locking position. See FIG. 69. When the first lockout arm 9310 is in that locked or engaged position, pivotal travel of the anvil 9100 is prevented when the lock lug portion 9120 contacts the first lockout arm 9310. It will be appreciated that the first lockout arm 9310, as well as the lock lug portion 9120, are each sufficiently robust so as to resist substantial closure motions that applied to the anvil 9100 to prevent closure of the anvil 9100.

Figure 66:
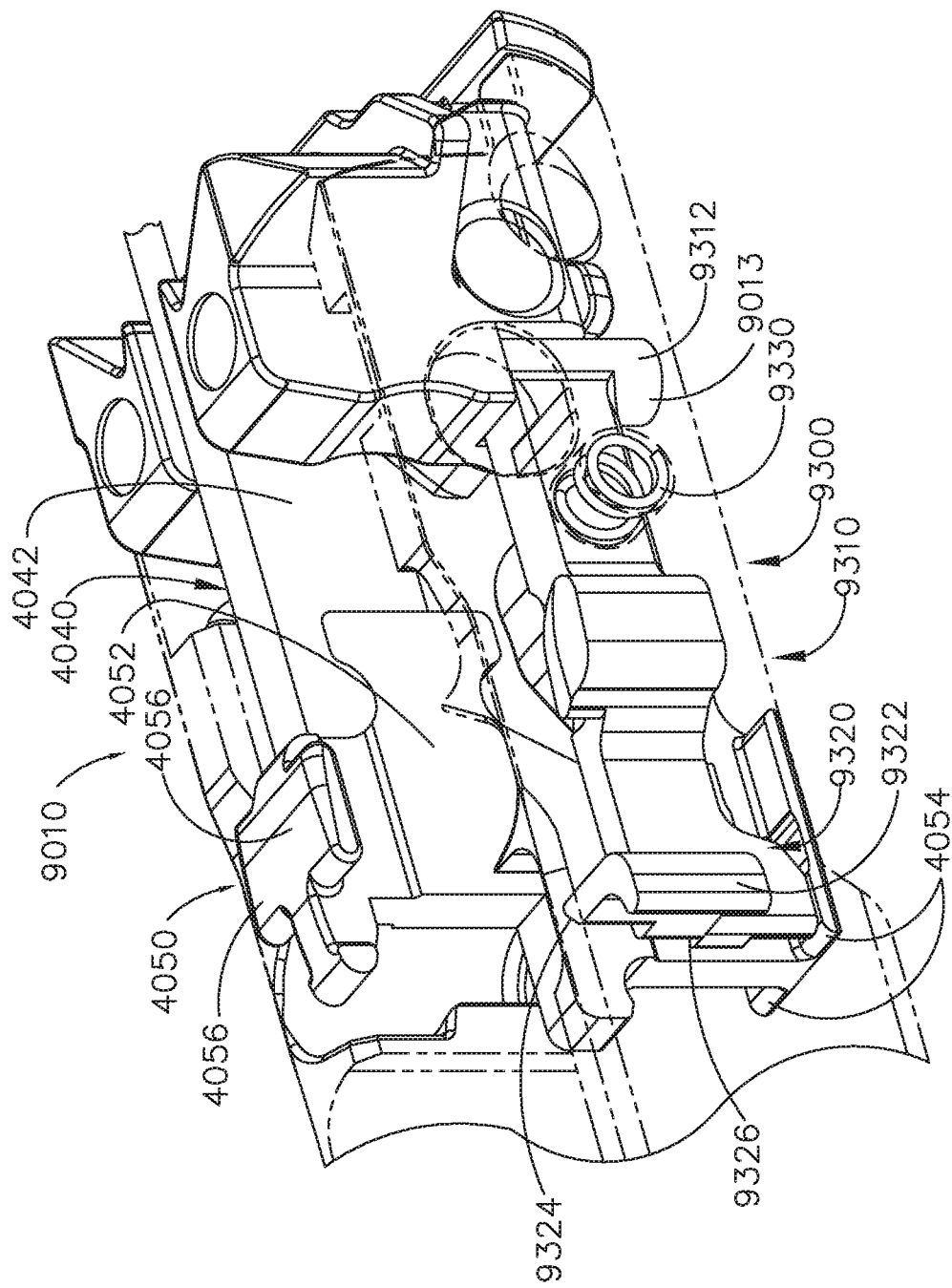
FIG. 66 is a partial perspective view of portions of the surgical stapling device of FIG. 65.
Figure 67:
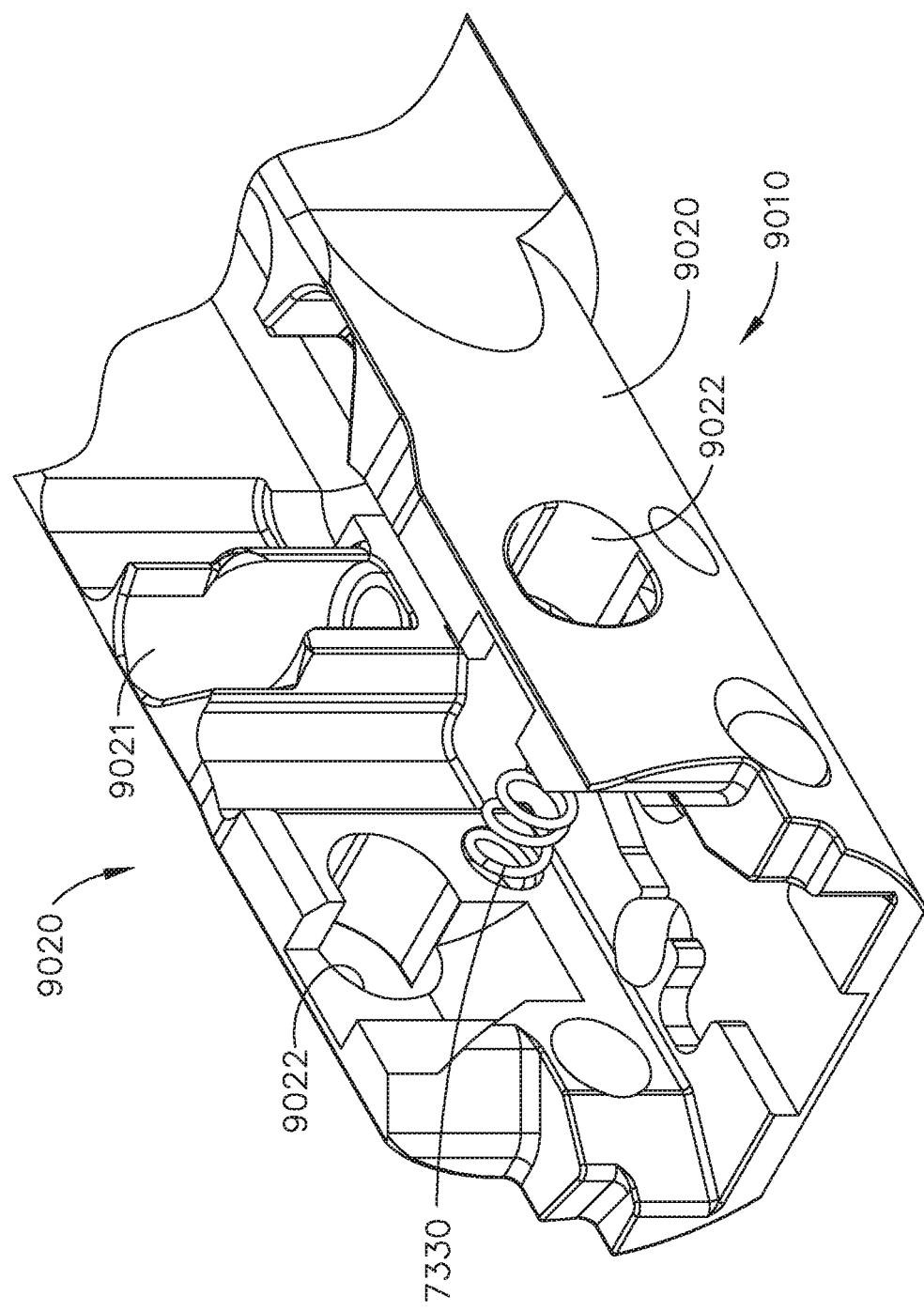
FIG. 67 is a perspective view of a proximal end portion of a first jaw of the surgical stapling device of FIG. 65.
Figure 68:
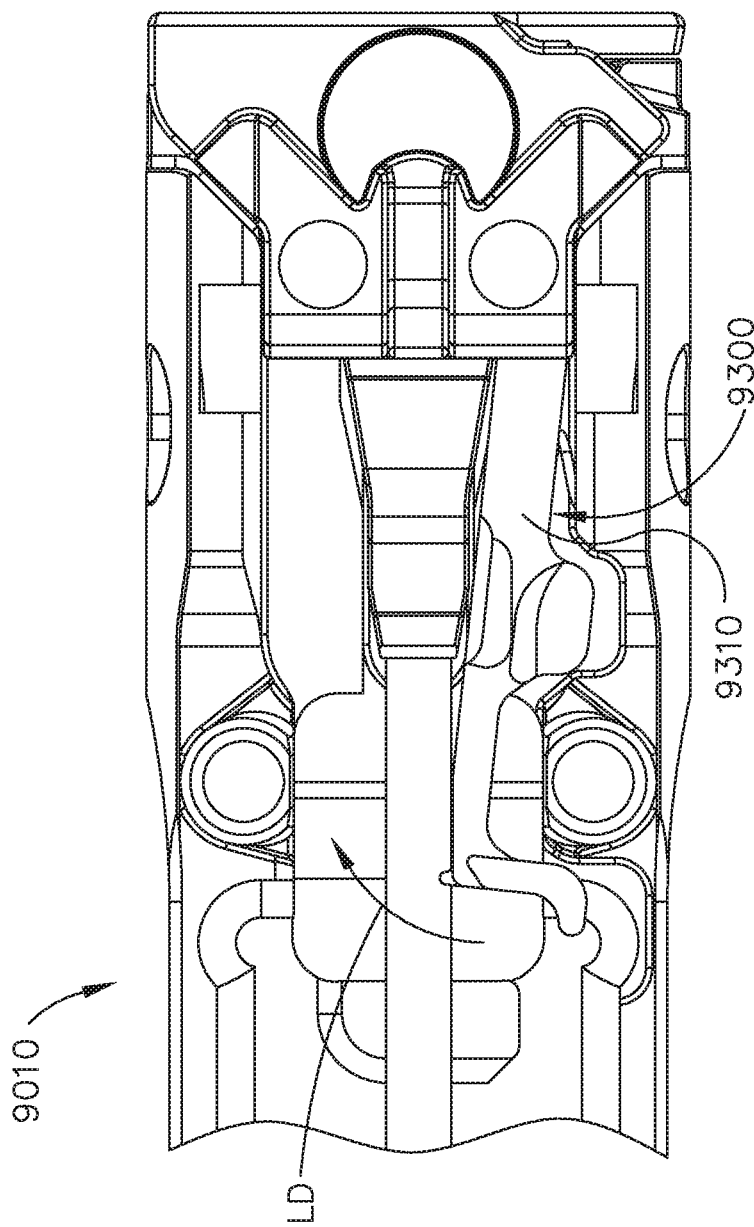
FIG. 68 is a top view of the surgical stapling device of FIG. 65 with a first lockout arm thereof in a jaw locking position.
Figure 71:
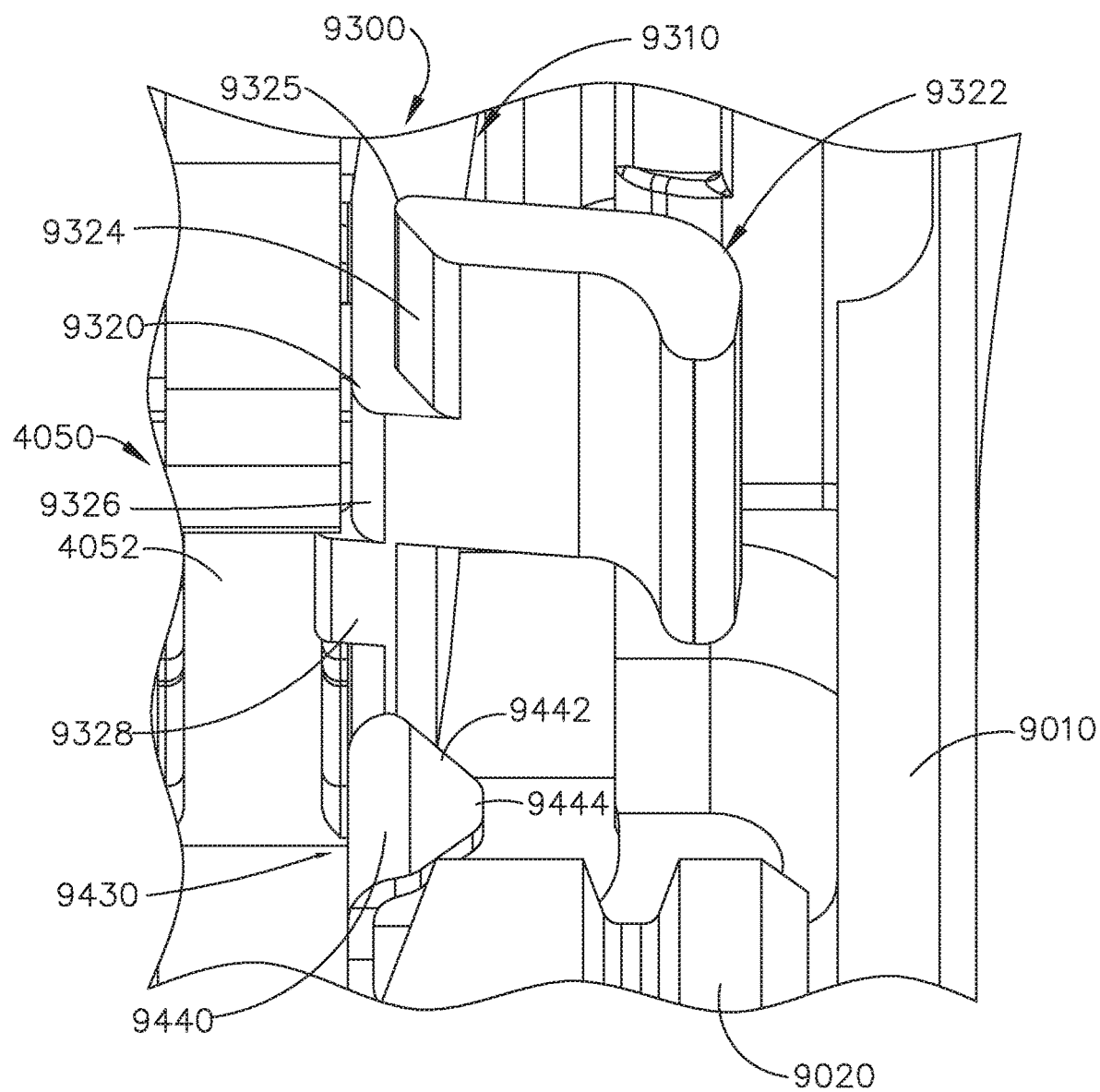
FIG. 71 is an end elevational view of a portion of the surgical stapling device with the first lockout arm thereof in the jaw locking position.

Referring now to FIG. 66, a first lockout spring 9330 is supported in a corresponding sidewall 9020 of the first jaw or frame 9010 to apply a lateral biasing force to the first lockout arm 9310 to bias the first lockout arm 9310 in the locked direction LD (FIG. 68) to the locked or jaw locking position wherein the first lockout arm 9310 prevents the anvil 9100 from moving from the open position to the closed position. As can be seen in FIG. 66, the first lockout arm 9310 further comprises an upstanding cam actuator tab 9322 that is formed on a distal end 9320 of the first lockout arm 9310. As can be seen in FIG. 71, the cam actuator tab 9322 comprises an upper actuator cam surface 9324. In addition, a lower actuator cam member 9326 is formed on the distal end 9320 of the first lockout arm 9310.

Figure 72:
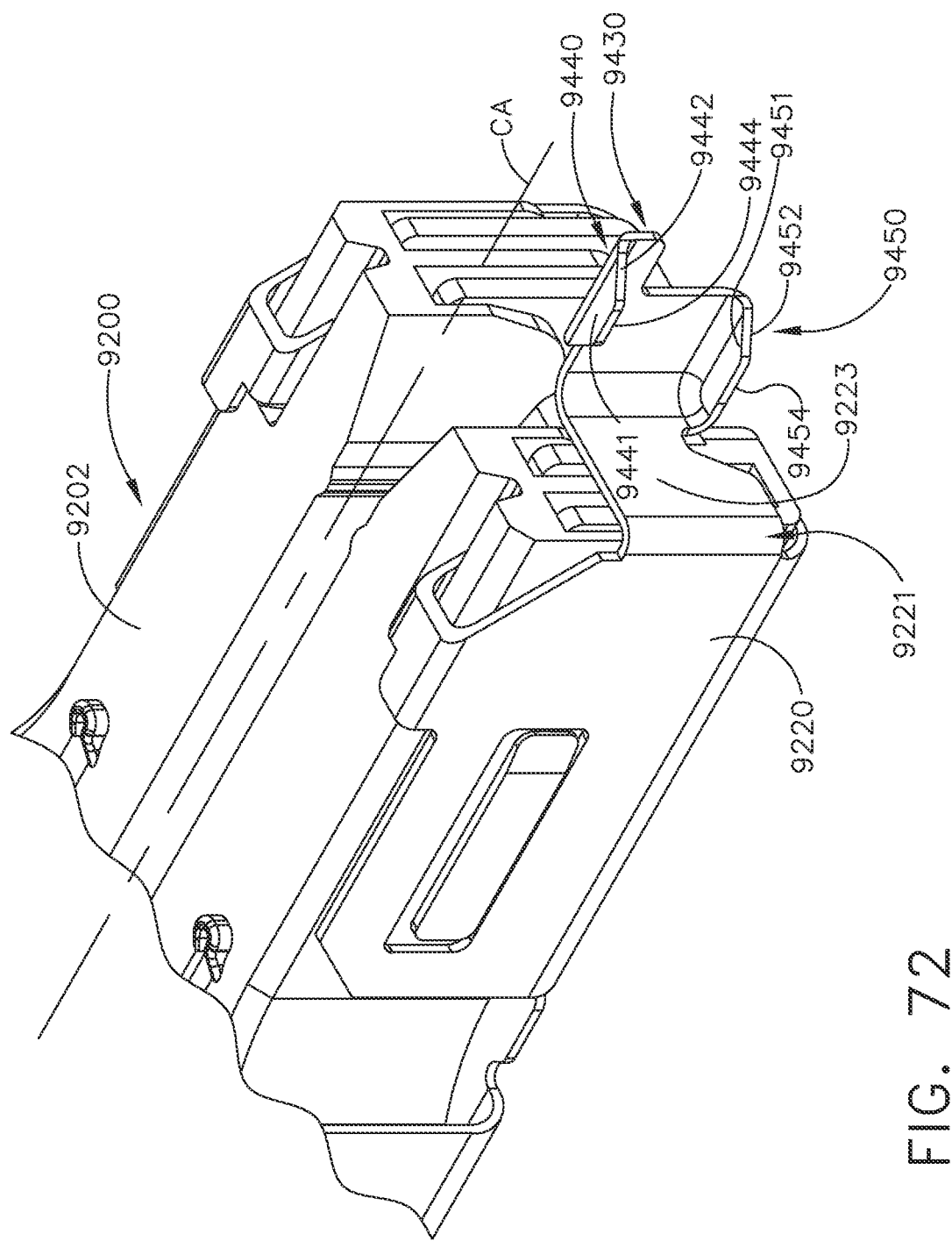
FIG. 72 is a perspective view of a staple cartridge that may be employed in connection with the surgical stapling device of FIG. 65.

In at least one example, the stapling assembly 9000 comprises a staple cartridge 9200 that is identical to staple cartridge 4200 described above except that an authentication key 9430 is formed into a cartridge pan 9220. See FIG. 72. The authentication key 9430 is configured to defeat, unlock or unlatch the first lockout 9300 when the staple cartridge 9200 is operably seated in the frame 9010. As can be seen in FIG. 72, the authentication key 9430 protrudes proximally from a proximal end 9221 of the cartridge pan 9220 and comprises an upper ramp feature 9440 and a lower ramp feature 9450 that is vertically displaced from the upper ramp feature 9440. The authentication key 9430 is bent in a generally right angle from a portion 9223 of the cartridge pan 9220 that extends across a portion of a distal end of the cartridge body 9202. The upper ramp feature 9440 comprises an upper ramp tab 9441 that is bent into the authentication key 9430 and the lower ramp feature 9450 comprises a lower ramp tab 9451 that is bent into the authentication key 9430. As can be seen in FIG. 72, both the upper ramp feature 9440 and the lower ramp feature 9450 are located on a same side of a cartridge axis CA that is defined by the cartridge body 9202. The upper ramp feature 9440 is formed so that is its also proximal to the lower ramp feature 9450. As indicated above, the upper and lower ramp features 9440, 9450 are bent out of the cartridge pan 9220. Stated another way, the upper and lower ramp features 9440, 9450 are integrally formed in the cartridge pan 9220. In the illustrated example, the upper ramp feature 9440 comprises a first upper cam surface 9442 and a second upper cam surface 9444. The first upper cam surface 9442 is proximal to the second upper cam surface and is also angled relative to the second upper cam surface 9444. The lower ramp feature 9450 comprises a first lower cam surface 9452 and a second lower cam surface 9454. The first lower cam surface 9452 is proximal to the second lower cam surface 9454 and is also angled relative to the first lower cam surface 9452.

Figure 73:
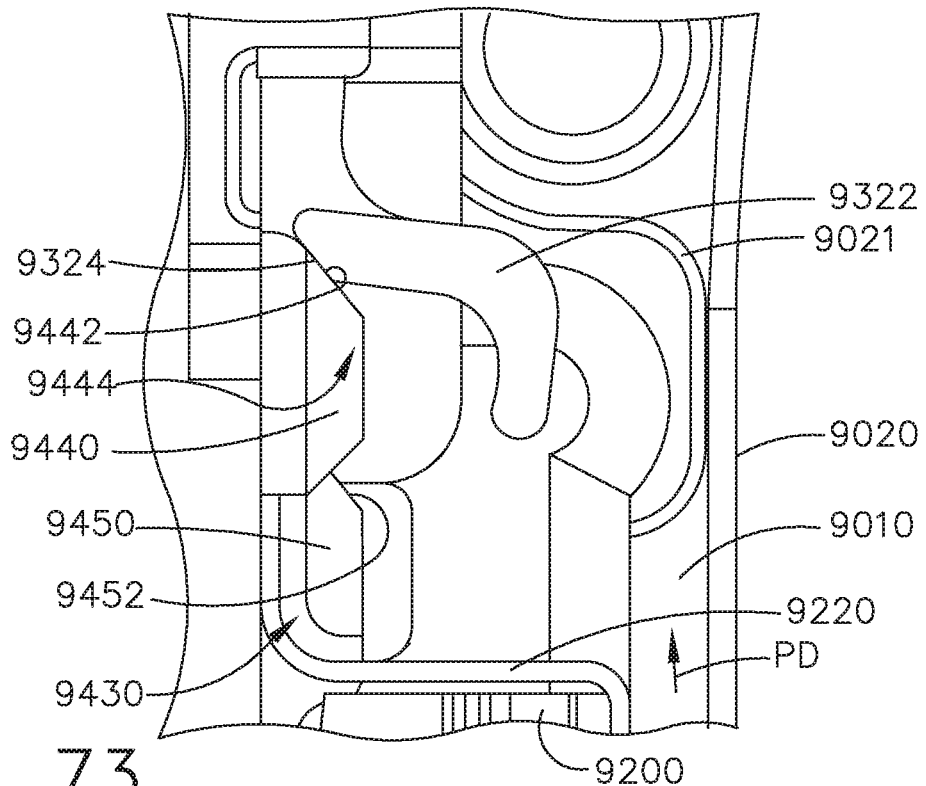
FIG. 73 is a top view of a portion of the first lockout arm of the surgical stapling device of FIG. 65 illustrating an initial insertion of the staple cartridge of FIG. 72 therein.

FIGS. 73-77 illustrate the interaction between the upper and lower ramp features 9440, 9450 of the authentication key 9430 and the upper actuator cam surface 9324 on the cam actuator tab 9322 and the lower actuator cam member 9326. FIG. 73 illustrates the position of the authentication key 9430 relative to the cam actuator tab 9322 when the staple cartridge 9200 is initially longitudinally inserted (direction PD) into the frame 9010. As can be seen in FIG. 73, the first upper cam surface 9442 of the upper ramp feature 9440 is in camming engagement with the upper actuator cam surface 9324 on the cam actuator tab 9322 and begins to bias the cam actuator tab 9322, as well as the first lockout arm 9310 laterally. As can be further seen in FIG. 73, a lockout pocket 9021 is provided in the adjacent upstanding side wall 9020 of the frame 9010 to accommodate the cam actuator tab 9322 as the first lockout arm 9310 is moved from the locked or jaw locking position to the unlocked or jaw closure position.

Figure 74:
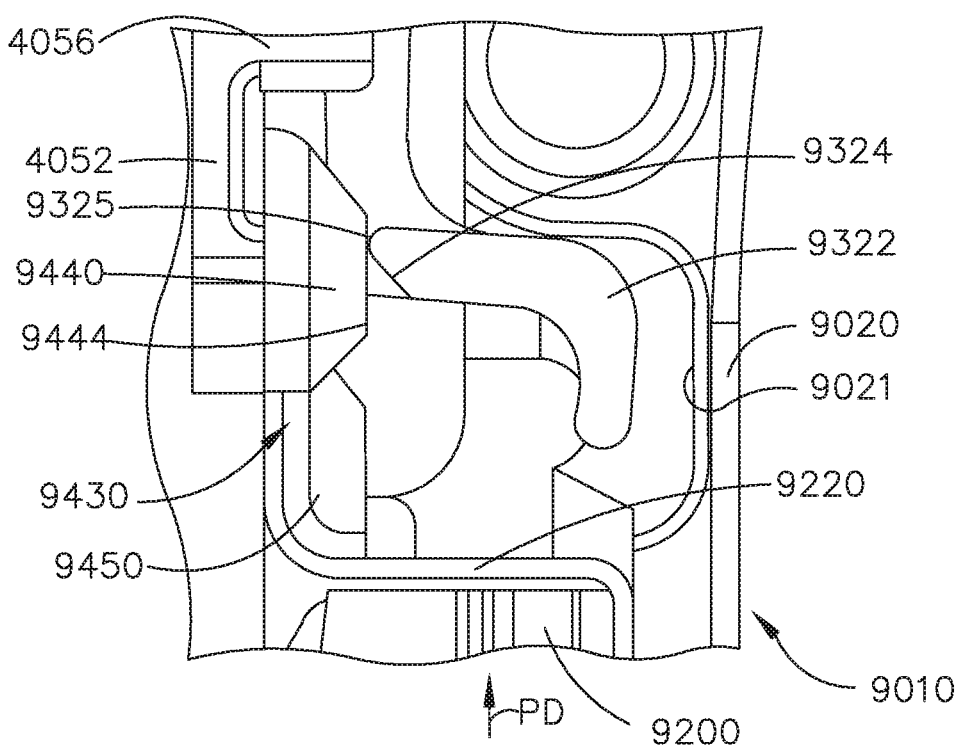
FIG. 74 is another top view of the first lockout arm in engagement with an upper ramp feature of an authentication key of the staple cartridge.

FIG. 74 illustrates the continued longitudinal insertion of the staple cartridge 9200 into the frame 9010 in a proximal direction. As can be seen in FIG. 74, the staple cartridge 9200 has been inserted to a point wherein the first upper cam surface 9442 has proceeded past the upper actuator cam surface 9324 allowing a tip 9325 of the cam actuator tab 9322 to engage the second upper cam surface 9444 on the upper ramp feature 9440 of the authentication key 9430. Such sequential interaction continues to move the cam actuator tab 9322 and the first lockout arm 9310 laterally to an intermediate position between the locked or jaw locking position and the unlocked or jaw closure position.

Figure 75:
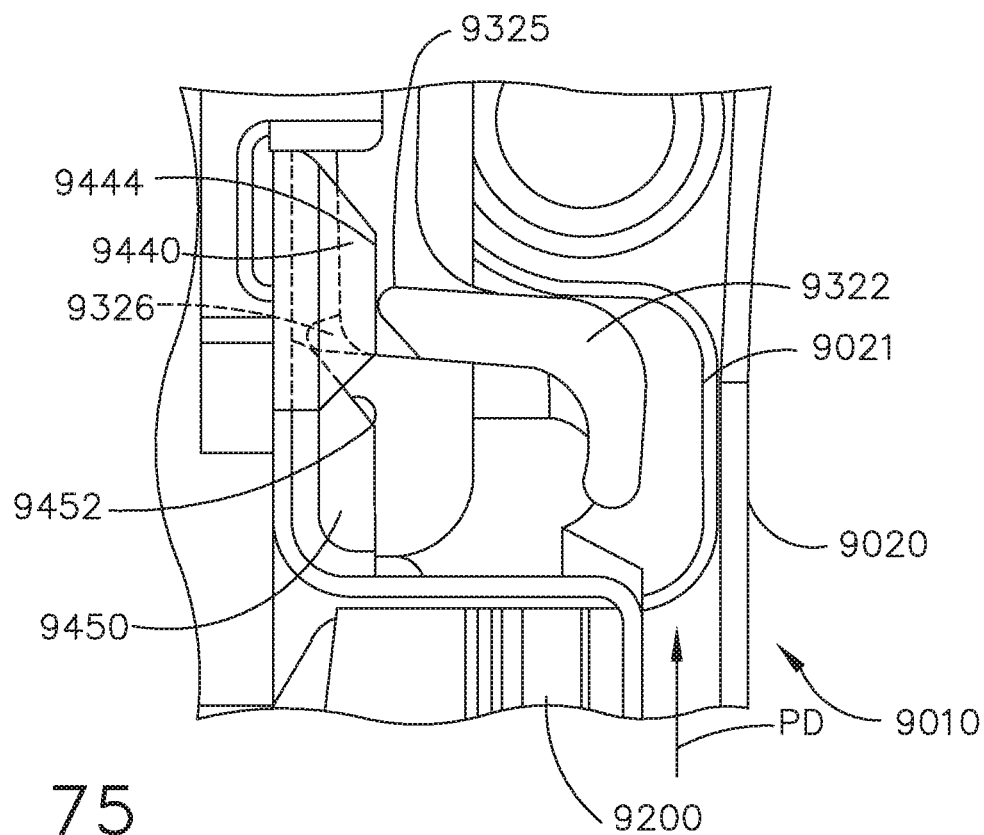
FIG. 75 is another top view of the first lockout arm of the surgical stapling device of FIG. 65 during further insertion of the staple cartridge of FIG. 72 therein.

FIG. 75 illustrates a position of the staple cartridge 9200 as it continues to be longitudinally inserted into the frame 9010 in the proximal direction PD. As can be seen in FIG. 75, the tip 9325 of the cam actuator tab 9322 remains in engagement with the second upper cam surface 9444 on the upper ramp feature 9440 and the lower actuator cam member 9326 has now engaged the first lower cam surface 9452 on the lower ramp feature 9450. This sequential interaction continues to move the cam actuator tab 9322 as well as the first lockout arm 9310 laterally.

Figure 76:
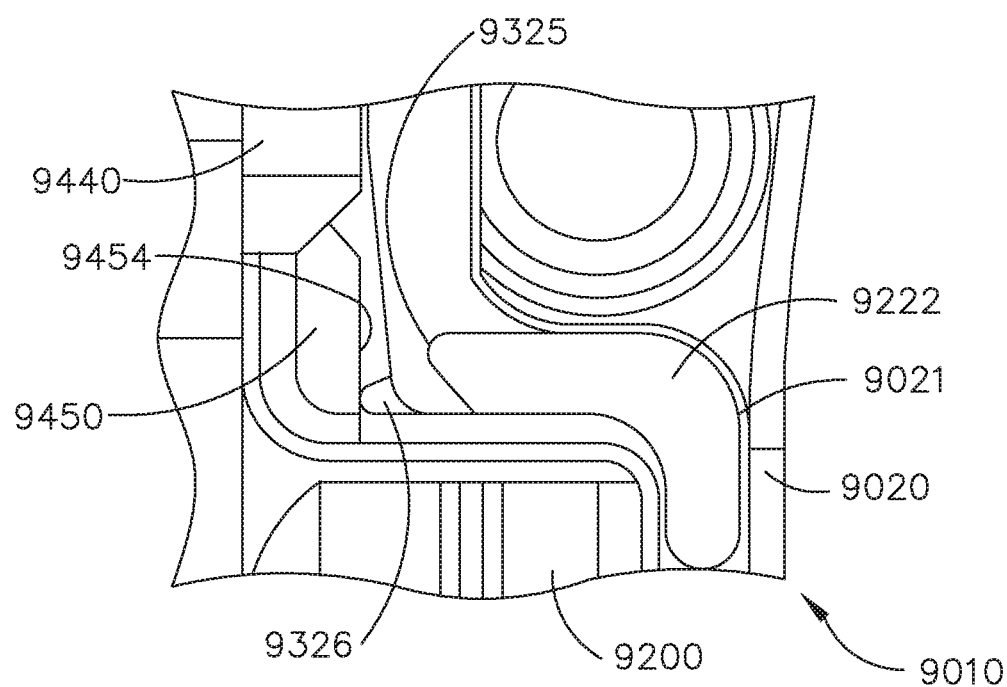
FIG. 76 is another top view of the first lockout arm of the surgical stapling device of FIG. 65 in the jaw closure position after the staple cartridge has been operably seated in the surgical stapling device.
Figure 77:
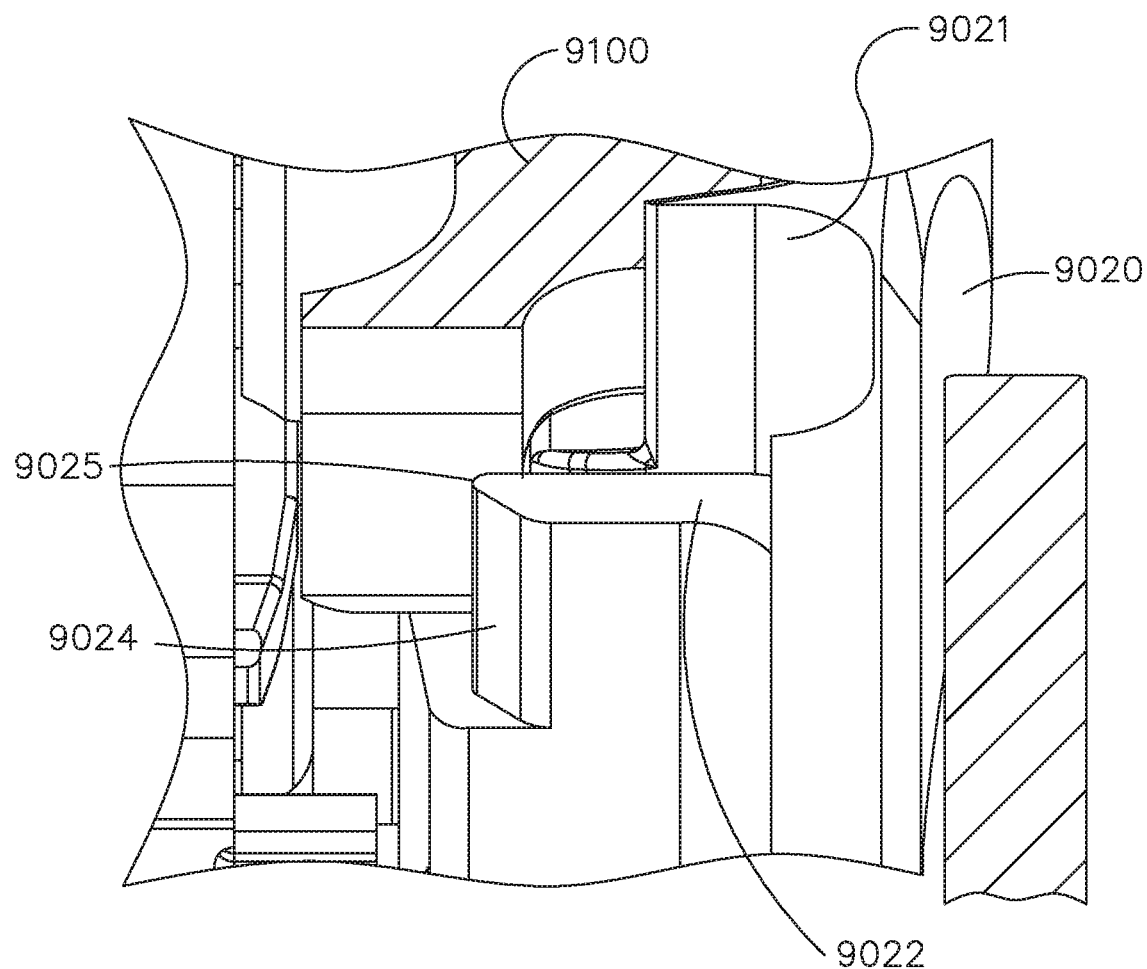
FIG. 77 is a partial perspective view of a portion of the first lockout arm of FIG. 76 during closure of an anvil of the surgical stapling device of FIG. 65.
Figure 78:
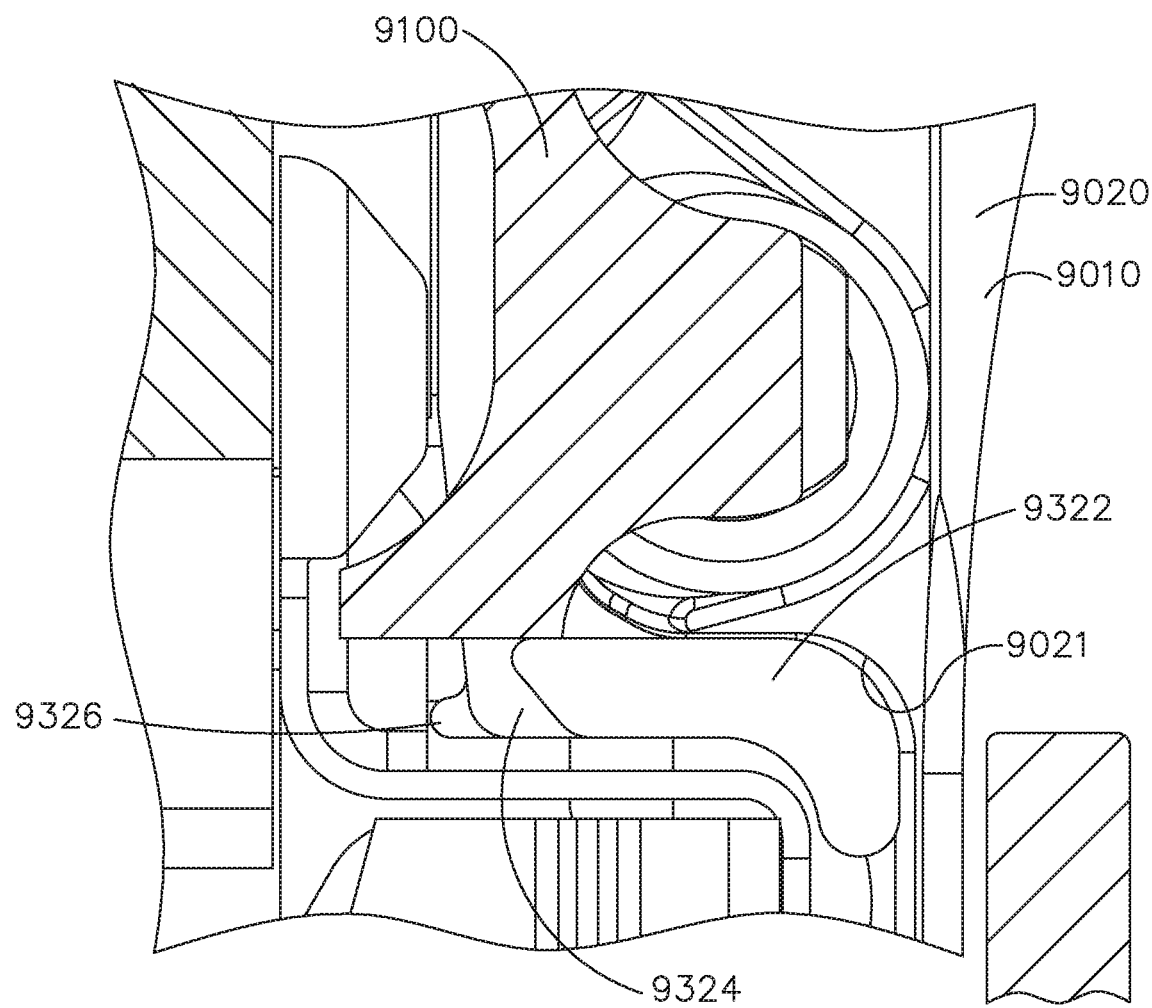
FIG. 78 is a partial top view of the surgical stapling device of FIG. 77 with a portion of the anvil shown in cross-section.

FIG. 76 illustrates the position of the actuator tab 9322 after the staple cartridge 9200 has been operably (fully) seated in the frame 9010. As can be seen in FIG. 76, the lower actuator cam member 9326 remains engaged with the second lower cam surface 9454 on the lower ramp feature 9450 and has moved the cam actuator tab 9322 laterally to be seated in the lockout pocket 9021 in the upstanding side wall 9020 of the frame 9010. When the first lockout arm 9310 is in that unlocked or jaw closure position shown in FIG. 76, the anvil 9100 may be pivoted from the open position to the closed position without being blocked by the first lockout arm 9310. When the first lockout arm 9310 is in the locked or jaw locking position, the lower actuator cam member 9326 is located in front of the firing member body 4052 so that the jaw unlocking procedure cannot be commenced by distally advancing the firing member. The lower actuator cam member 9326 is positioned above the central pins 4058 of the firing member 4050 to provide adequate clearance therebetween during the unlocking procedure. FIGS. 77 and 78 illustrate position of the first lockout arm 6310 relative to a portion of the anvil 9100 after the anvil 9100 has been pivoted to the closed position.

The surgical stapling device 9002 may further comprise a second lockout similar to second lockout 4600 for preventing the firing member 4050 from advancing through the firing stroke when a spent staple cartridge is seated in the first jaw of frame 9010. The second lockout 4600 was described in detail above and will not be repeated here.

Figure 78A:
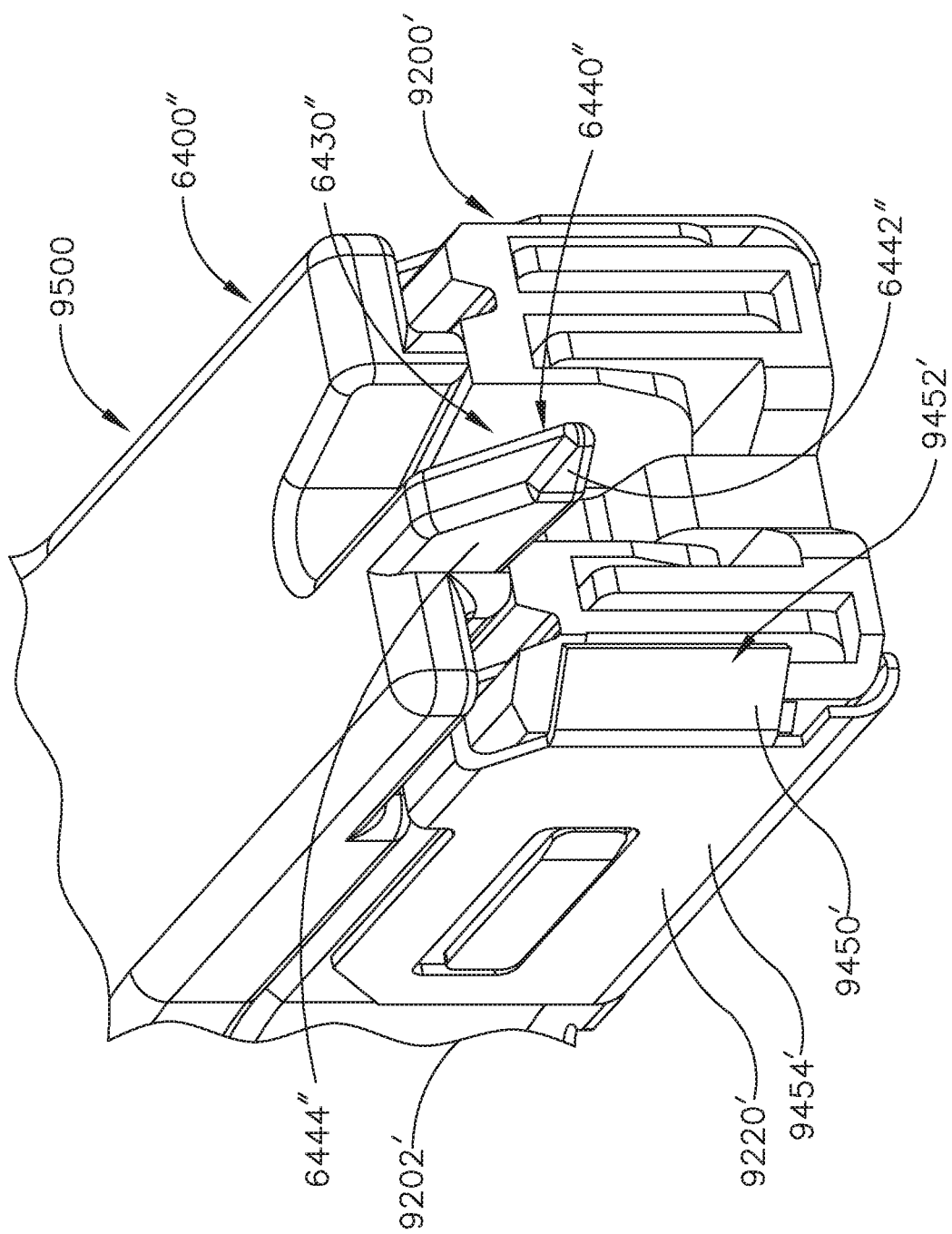
FIG. 78A is a perspective view of another retainer embodiment attached to another staple cartridge embodiment.

FIG. 78A illustrates an alternative cartridge assembly 9500 that may be used in connection with the surgical stapling device 9002 in the above-described manner. In the illustrated example, the cartridge assembly 9500 comprises a staple cartridge 9200' that has a retainer a 6400" attached thereto. Retainer 6400" is similar to retainer 6400 described above, except for the shape and configuration of the authentication key 6430" and ramp 6440". The retainer 6400" may in many aspects be identical to retainer 6400 discussed above.

Still referring to FIG. 78A, the cartridge assembly 9500 comprises a staple cartridge 9200' that is similar to staple cartridge 4200 described above except that a second authentication ramp 9450' is formed into a cartridge pan 9220' that is attached to the cartridge body 9202'. When the retainer 6400" is attached to the staple cartridge 9200' as shown, the ramp 6440" comprises a "first" ramp that comprises a first upper cam surface 6442" and a second upper cam surface 6444". The first upper cam surface 6442" is proximal to the second upper cam surface 6444" and is also angled relative to the second upper cam surface 6444". The second authentication ramp 9450' which is located on the cartridge pan 9220' comprises a first lower cam surface 9452' and a second lower cam surface 9454'. The second ramp 9450' is positioned below the first ramp 6440" on the retainer 6400" and is positioned distal to the first upper cam surface 6442". When the cartridge assembly 9500 is operably seated into the frame 9010 of the surgical stapling device 9002, the combination of the first ramp 6440" on the retainer 6400" and the second ramp 9450" on the cartridge pan 9220' operates in the same manner as the upper ramp feature 9440 and the second ramp feature 9450 on cartridge 9200 to sequentially defeat, unlock or unlatch the first lockout 9300 in the manner described in detail above. Once the first lockout arm 9310 has been moved to the unlocked or "jaw closure position", the second ramp 9450' retains the first lockout arm 9310 in that position. The user may then remove the retainer 6400" from the staple cartridge 9200' and the anvil 9100 may be pivoted from the open position to the closed position.

Figure 78B:
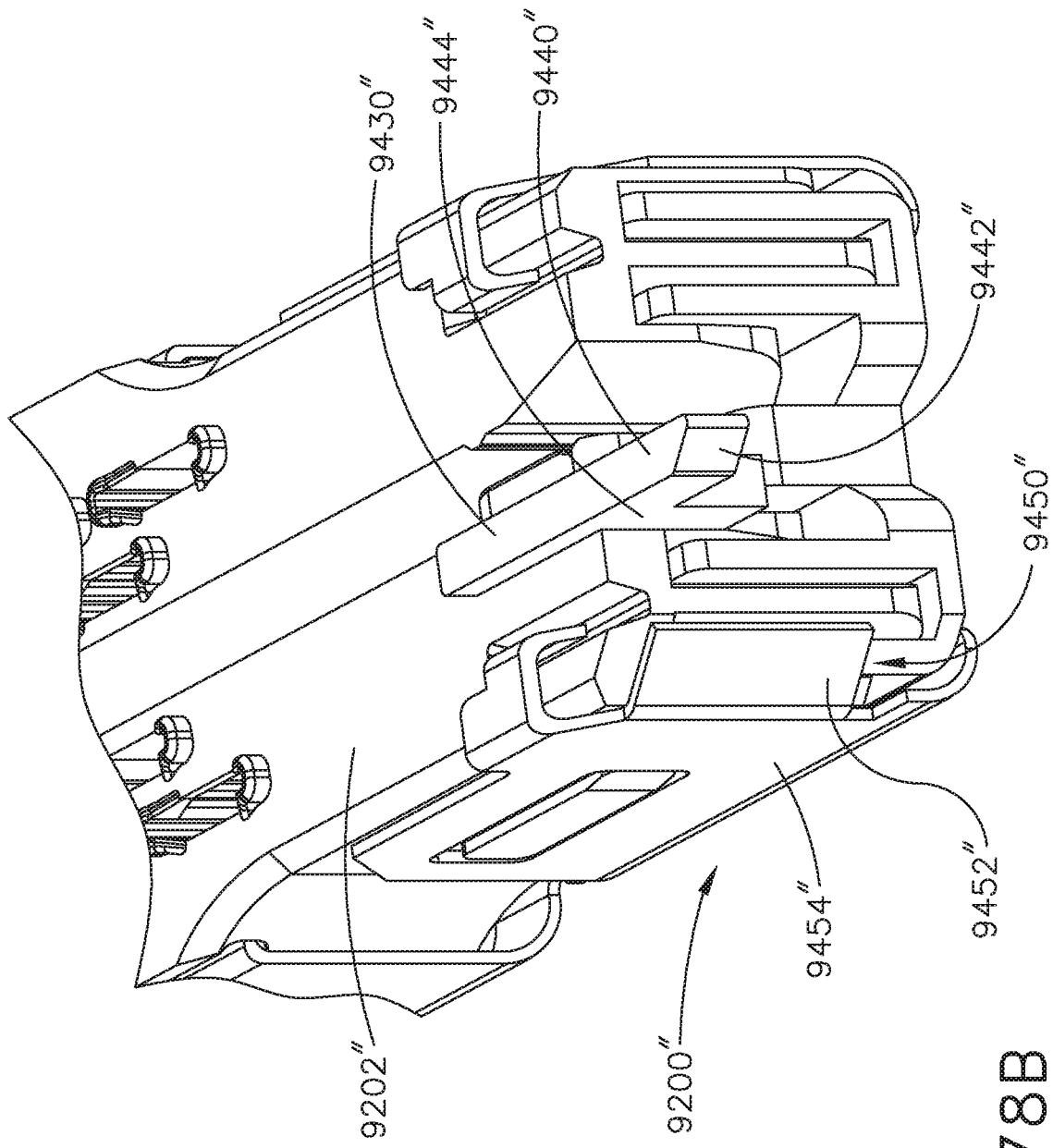
FIG. 78B is a perspective view of another staple cartridge embodiment.
Figure 78C:
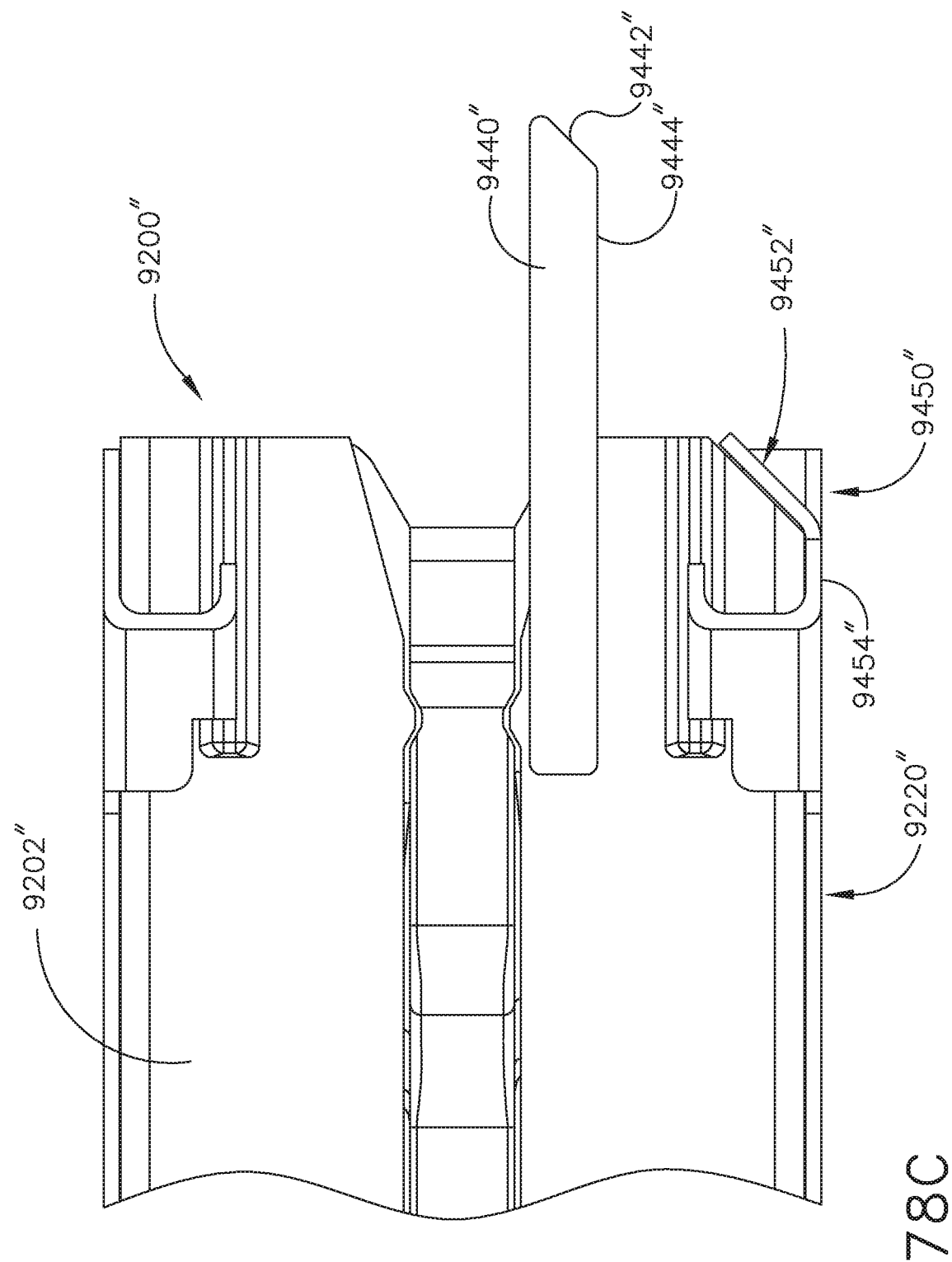
FIG. 78C is a top view of the staple cartridge embodiment of FIG. 78B.

FIGS. 78B-78C illustrate an alternative staple cartridge 9200" that is similar to staple cartridge 9200 described above except that a first authentication key 9430" is formed or molded into the cartridge body 9202". The first authentication key 9430" comprises a first ramp 9440" that has a first upper cam surface 9442" and a second upper cam surface 9444" formed thereon. The first upper cam surface 9442" is proximal to the second upper cam surface 9444" and is also angled relative to the second upper cam surface 9444". The second authentication ramp 9450" which comprises a portion of the cartridge pan 9220" comprises a first lower cam surface 9452" and a second lower cam surface 9454". The second authentication ramp 9450" is located below the first ramp 9440" and is positioned distal to the first upper cam surface 9442". When the cartridge assembly 9200" is operably seated into the frame 9010 of the surgical stapling device 9002, the combination of the first ramp 9440" and the second ramp 9450" operate in the same manner as the upper ramp feature 9440 and the lower ramp features 9450 on cartridge 9200 to defeat the first lockout 9300 in the manner described in detail above.

Various aspects of the subject matter described herein are set out in the following examples.

EXAMPLE 1

A surgical stapling assembly configured to receive a staple cartridge. The staple cartridge comprises a cartridge body comprising a longitudinal slot, a deck surface, a plurality of staple pocket opening through the deck surface, a staple removably stored within each staple pocket, and a sled configured to fire the staples from the cartridge body during a staple firing stroke. The surgical stapling assembly comprises a stapling device comprising a first jaw, a second jaw movable relative to the first jaw between an open position and a closed position, a firing member, a first lockout, and a second lockout. The firing member is movable between a starting position and an ending position within the longitudinal slot during the staple firing stroke. The firing member is configured to actuate the sled to fire the staples during the staple firing stroke. The first lockout is configured to prevent the second jaw from being movable from the open position to the closed position. The first lockout comprises a lockout arm configured to releasably retain the second jaw in the open position. The second lockout is configured to prevent the firing member from advancing through the staple firing stroke when a spent staple cartridge is seated in the stapling device. The surgical stapling assembly further comprises a retainer removably mounted to the cartridge body. The retainer is supported on the deck surface to form a cartridge assembly. The retainer comprises an authentication key that is configured to defeat the first lockout by moving the lockout arm from a jaw locking position wherein the lockout arm prevents the second jaw from being moved from the open position to the closed position to a jaw closure position wherein the second jaw is movable from the open position to the closed position when the cartridge assembly is seated in the stapling device.

EXAMPLE 2

The surgical stapling assembly of Example 1, wherein the retainer covers the staple pockets in the deck surface when the retainer is attached to the cartridge body, and wherein the staple pockets are exposed when the retainer is removed from the cartridge body.

EXAMPLE 3

The surgical stapling assembly of Examples 1 or 2, wherein the first jaw defines a jaw axis, and wherein the authentication key is positioned on only one lateral side of the jaw axis.

EXAMPLE 4

The surgical stapling assembly of Examples 1, 2, or 3, wherein the first lockout is proximal to the second lockout.

EXAMPLE 5

The surgical stapling assembly of Examples 1, 2, 3, or 4, wherein the authentication key extends proximally from a proximal end of the retainer.

EXAMPLE 6

The surgical stapling assembly of Examples 1, 2, 3, 4, or 5, wherein the lockout arm is pivotally movable between the jaw locking position and the jaw closure position.

EXAMPLE 7

The surgical stapling assembly of Examples 1, 2, 3, 4, 5, or 6, wherein the authentication key comprises a proximal cam surface and a distal cam surface. The proximal cam surface is configured to engage the lockout arm when the cartridge assembly is initially inserted into the first jaw. The proximal cam surface moves the lockout arm from the jaw locking position to an intermediate position. The distal cam surface is configured to engage the lockout arm when the lockout arm is in the intermediate position. The distal cam surface moves the lockout arm to the jaw closure position when the cartridge assembly is seated in the first jaw.

EXAMPLE 8

The surgical stapling assembly of Example 7, wherein the proximal cam surface is proximal to the distal cam surface and vertically offset therefrom.

EXAMPLE 9

The surgical stapling assembly of Examples 1, 2, 3, 4, 5, 6, 7 or 8, wherein the second lockout comprises an abutment portion on one of the first and second jaws configured to be contacted by the firing member when the spent staple cartridge is seated in the stapling device.

EXAMPLE 10

The surgical stapling assembly of Example 9, wherein the firing member is movable between an unlocked position where the firing member is distally movable from the starting position to the ending position during the staple firing stroke and a locked position where the abutment portion prevents the firing member from moving distally.

EXAMPLE 11

The surgical stapling assembly of Example 10, wherein the sled in the staple cartridge is configured to move the firing member from the locked position to the unlocked position when the sled is in an unfired position within the staple cartridge and the staple cartridge is seated in the surgical stapling device.

EXAMPLE 12

The surgical stapling assembly of Examples 10 or 11, wherein the lockout arm is configured to move in a first plane between the jaw locking position and the jaw closure position, and wherein the firing member is movable in a second plane between the locked position and the unlocked position, and wherein the first plane is orthogonal relative to the second plane.

EXAMPLE 13

The surgical stapling assembly of Example 11, wherein the first lockout is proximal to the sled of the staple cartridge when the staple cartridge is seated in the surgical stapling assembly when the sled is in the unfired position.

EXAMPLE 14

The surgical stapling assembly of Examples 1, 2, 3, 4, 5, 6, 7, 8, 9, 10, 11, 12, or 13, wherein the first jaw defines a first jaw axis, and wherein the lockout arm is pivotally supported on one side of the first jaw axis.

EXAMPLE 15

A surgical stapling system comprising a first stapling device, a second stapling device, a staple cartridge, and a retainer. The first stapling device comprises a first frame, a first jaw movable relative to the first frame between a first open position and a first closed position, a first firing member movable between a first starting position and a first ending position during a first staple firing stroke, and a first jaw lockout configured to prevent the first jaw from being moved from the first open position to the first closed position. The first jaw lockout comprises a first jaw lockout arm configured to releasably retain the first jaw in the first open position. The second stapling device comprises a second frame, a second jaw movable relative to the second frame between a second open position and a second closed position, a second firing member movable between a second starting position and a second ending position during a second staple firing stroke, and a second jaw lockout configured to prevent the second jaw from being moved from the second open position to the second closed position. The second jaw lockout comprises a second jaw lockout arm configured to releasably retain the second jaw in the second open position. The staple cartridge is configured for use in either of the first and second stapling devices. The staple cartridge comprises a cartridge body comprising a longitudinal slot and a deck surface, a plurality of staple pockets opening through the deck surface, a staple removably stored in each staple pocket, and a sled movable through the cartridge body during the first and second staple firing strokes to fire the staples. The retainer is removably mounted to the cartridge body. The retainer is supported on the deck surface when attached to the cartridge body to form a cartridge assembly. The retainer comprises an authentication key that is configured to defeat the first jaw lockout by moving the first jaw lockout arm out of a first jaw locking position to a first jaw closure position wherein the first jaw is movable from the first open position to the first closed position when the cartridge assembly is seated in the first stapling device. The authentication key is further configured to defeat the second jaw lockout by moving the second jaw lockout arm out of a second jaw locking position to a second jaw closure position wherein the second jaw is movable from the second open position to the second closed position when the cartridge assembly is seated in the second stapling device.

EXAMPLE 16

The surgical stapling system of Example 15, wherein the first frame defines a first frame axis, wherein the first jaw lockout arm is pivotally supported on a first side of the first frame axis, wherein the second frame defines a second frame axis, and wherein the second jaw lockout arm is pivotally supported on an opposite side of the second frame axis that is opposite from the first side of the first frame axis.

EXAMPLE 17

The surgical stapling system of Examples 15 or 16, wherein the authentication key comprises a first lockout ramp and a second lockout ramp. The first lockout ramp protrudes from a proximal end of the retainer and is configured to move the first jaw lockout arm from the first jaw locking position to the first jaw closure position when the cartridge assembly is seated in the first stapling device. The second lockout ramp protrudes from the proximal end of the retainer and is configured to move the second jaw lockout arm from the second jaw locking position to the second jaw closure position when the cartridge assembly is seated in the second stapling device.

EXAMPLE 18

The surgical stapling system of Example 17, wherein the first lockout ramp comprises a first proximal cam surface and a first distal cam surface. The first proximal cam surface is configured to move the first jaw lockout arm from the first jaw locking position to a first intermediate position when the cartridge assembly is initially inserted into the first stapling device. The first distal cam surface is configured to engage the first jaw lockout arm when the first jaw lockout arm is in the first intermediate position. The first distal cam surface moves the first jaw lockout arm from the first intermediate position to the first jaw closure position when the cartridge assembly is fully seated in the first stapling device. The second lockout ramp comprises a second proximal cam surface and a second distal cam surface. The second proximal cam surface is configured to move the second jaw lockout arm from the second jaw locking position to a second intermediate position when the cartridge assembly is initially inserted into the second stapling device. The second distal cam surface is configured to engage the second jaw lockout arm when the second jaw lockout arm is in the second intermediate position. The second distal cam surface moves the second jaw lockout arm from the second intermediate position to the second jaw closure position when the cartridge assembly is fully seated in the second stapling device.

EXAMPLE 19

The surgical stapling system of Example 18, wherein the first proximal cam surface is proximal to the first distal cam surface and vertically offset therefrom, and wherein the second proximal cam surface is proximal to the second distal cam surface and vertically offset therefrom.

EXAMPLE 20

A retainer for use with a surgical staple cartridge configured for use with a first surgical stapling device comprising a first jaw and a first frame. The first jaw is movable relative to the first frame between a first open position and a first closed position. The staple cartridge comprises a cartridge body comprising a longitudinal slot, a deck surface, a plurality of staple pockets opening through the deck surface, a staple removably stored within each staple pocket, and a sled configured to fire the staples from the cartridge body when driven by a first firing member of the first surgical stapling device. The first surgical stapling device further comprises a first lockout arm movable from a first jaw locking position wherein the first lockout arm prevents the first jaw from being moved from the first open position to the first closed position to a first jaw closure position wherein the first jaw is movable from the first open position to the first closed position. The retainer comprises a retainer body and a first authentication ramp. The retainer body is configured for removable attachment to the cartridge body. The retainer body is sized to cover the deck surface and the staple pockets to form a cartridge assembly. The first authentication ramp is configured to move the first lockout arm from the first jaw locking position to the first jaw closure position when the cartridge assembly is seated in the first surgical stapling device and the retainer is removed from the cartridge body.

EXAMPLE 21

The retainer of Example 20, wherein the first authentication ramp comprises a first proximal cam surface and a first distal cam surface. The first proximal cam surface is configured to engage the first lockout arm when the cartridge assembly is initially inserted into the first surgical stapling device. The first proximal cam surface moves the first lockout arm from the first jaw locking position to a first intermediate position. The first distal cam surface is configured to engage the first lockout arm when the first lockout arm is in the first intermediate position. The first distal cam surface moves the first lockout arm from the first intermediate position to the first jaw closure position when the cartridge assembly is seated in the first frame.

EXAMPLE 22

The retainer of Examples 20 or 21, wherein the staple cartridge is configured for use with a second surgical stapling device comprising a second jaw, a second frame, and a second lockout arm, wherein the second jaw is movable relative to the second frame between a second open position and a second closed position, wherein the second lockout arm is movable from a second jaw locking position to a second jaw closure position wherein the second jaw is movable from the second open position to the second closed position, wherein the retainer further comprises a second authentication ramp protruding from a proximal end of the retainer body, and wherein the second authentication ramp is configured to move the second lockout arm from the second jaw locking position to the second jaw closure position when the cartridge assembly is seated in the second surgical stapling device and the retainer is removed from the cartridge body.

EXAMPLE 23

The retainer of Example 22, wherein the first frame defines a first frame axis, wherein the first lockout arm is pivotally supported on a first side of the first frame axis, wherein the second frame defines a second frame axis, wherein the second lockout arm is pivotally supported on an opposite second side of the second frame axis, wherein the retainer defines a retainer axis that is vertically aligned with the first frame axis when the cartridge assembly is supported in the first frame, wherein the retainer axis is vertically aligned with the second frame axis when the cartridge assembly is supported in the second frame, wherein the first authentication ramp is located on a first side of the retainer axis, and wherein the second authentication ramp is located on a second side of the retainer axis.

EXAMPLE 24

The retainer of Examples 22 or 23, wherein the first authentication ramp comprises a first proximal cam surface and a first distal cam surface. The first proximal cam surface is configured to engage the first lockout arm when the staple cartridge is initially inserted into the first surgical stapling device. The first proximal cam surface moves the first lockout arm from the first jaw locking position to a first intermediate position. The first distal cam surface is configured to engage the first lockout arm when the first lockout arm is in the first intermediate position. The first distal cam surface moves the first lockout arm from the first intermediate position to the first jaw closure position when the cartridge assembly is seated in the first frame. The second authentication ramp comprises a second proximal cam surface and a second distal cam surface. The second proximal cam surface is configured to engage the second lockout arm when the staple cartridge is initially inserted into the second surgical stapling device. The second proximal cam surface moves the second lockout arm from the second jaw locking position to a second intermediate position. The second distal cam surface is configured to engage the second lockout arm when the second lockout arm is in the second intermediate position. The second distal cam surface moves the second lockout arm from the second intermediate position to the second jaw closure position when the cartridge assembly is seated in the second frame.

EXAMPLE 25

The retainer of Example 24, wherein the first proximal cam surface is proximal to the first distal cam surface and vertically offset therefrom, and wherein the second proximal cam surface is proximal to the second distal cam surface and vertically offset therefrom.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical stapling assembly configured to receive a staple cartridge, wherein the staple cartridge comprises a cartridge body comprising a longitudinal slot, a deck surface, a plurality of staple pockets opening through the deck surface, a staple removably stored within each staple pocket, and a sled configured to fire the staples from the cartridge body during a staple firing stroke, and wherein said surgical stapling assembly comprises:

a stapling device, comprising:
a first jaw;
a second jaw movable relative to said first jaw between an open position and a closed position;
a firing member movable between a starting position and an ending position within the longitudinal slot during the staple firing stroke, wherein said firing member is configured to actuate the sled to fire the staples during the staple firing stroke;
a first lockout configured to prevent said second jaw from being movable from said open position to said closed position, wherein said first lockout comprises a lockout arm configured to releasably retain said second jaw in said open position; and
a second lockout configured to prevent said firing member from advancing through the staple firing stroke when a spent staple cartridge is seated in said stapling device; and
a retainer removably mounted to the cartridge body, wherein said retainer is supported on the deck surface to form a cartridge assembly, and wherein said retainer comprises an authentication key that is configured to defeat said first lockout by moving said lockout arm from a jaw locking position wherein said lockout arm prevents said second jaw from being moved from said open position to said closed position to a jaw closure position wherein said second jaw is movable from said open position to said closed position when said cartridge assembly is seated in said stapling device.

2. The surgical stapling assembly of claim 1, wherein said retainer covers the staple pockets in the deck surface when said retainer is attached to the cartridge body, and wherein the staple pockets are exposed when said retainer is removed from the cartridge body.

3. The surgical stapling assembly of claim 1, wherein said first jaw defines a jaw axis, and wherein said authentication key is positioned on only one lateral side of said jaw axis.

4. The surgical stapling assembly of claim 1, wherein said first lockout is proximal to said second lockout.

5. The surgical stapling assembly of claim 1, wherein said authentication key extends proximally from a proximal end of said retainer.

6. The surgical stapling assembly of claim 1, wherein said lockout arm is pivotally movable between said jaw locking position and said jaw closure position.

7. The surgical stapling assembly of claim 6, wherein said authentication key comprises:
 a proximal cam surface configured to engage said lockout arm when said cartridge assembly is initially inserted into said first jaw, wherein said proximal cam surface moves said lockout arm from said jaw locking position to an intermediate position; and
 a distal cam surface configured to engage said lockout arm when said lockout arm is in said intermediate position, wherein said distal cam surface moves said lockout arm to said jaw closure position when said cartridge assembly is seated in said first jaw.

8. The surgical stapling assembly of claim 7, wherein said proximal cam surface is proximal to said distal cam surface and vertically offset therefrom.

9. The surgical stapling assembly of claim 1, wherein said second lockout comprises an abutment portion on one of said first and second jaws configured to be contacted by said firing member when the spent staple cartridge is seated in said stapling device.

10. The surgical stapling assembly of claim 9, wherein said firing member is movable between an unlocked position where said firing member is distally movable from the starting position to the ending position during the staple firing stroke and a locked position where said abutment portion prevents said firing member from moving distally.

11. The surgical stapling assembly of claim 10, wherein the sled in the staple cartridge is configured to move said firing member from said locked position to said unlocked position when the sled is in an unfired position within the staple cartridge and the staple cartridge is seated in said stapling device.

12. The surgical stapling assembly of claim 11, wherein said lockout arm is configured to move in a first plane between said jaw locking position and said jaw closure position, and wherein said firing member is movable in a second plane between said locked position and said unlocked position, and wherein said first plane is orthogonal relative to said second plane.

13. The surgical stapling assembly of claim 11, wherein said first lockout is proximal to the sled of the staple cartridge when the staple cartridge is seated in said surgical stapling assembly when the sled is in the unfired position.

14. The surgical stapling assembly of claim 1, wherein said first jaw defines a first jaw axis, and wherein said lockout arm is pivotally supported on one side of said first jaw axis.

15. A surgical stapling system, comprising:
 a first stapling device, comprising:
  a first frame;
  a first jaw movable relative to said first frame between a first open position and a first closed position;
  a first firing member movable between a first starting position and a first ending position during a first staple firing stroke; and
  a first jaw lockout configured to prevent said first jaw from being moved from said first open position to said first closed position, wherein said first jaw lockout comprises a first jaw lockout arm configured to releasably retain said first jaw in said first open position; and
 a second stapling device, comprising:
  a second frame;
  a second jaw movable relative to said second frame between a second open position and a second closed position;
  a second firing member movable between a second starting position and a second ending position during a second staple firing stroke; and
  a second jaw lockout configured to prevent said second jaw from being moved from said second open position to said second closed position, wherein said second jaw lockout comprises a second jaw lockout arm configured to releasably retain said second jaw in said second open position; and
 a staple cartridge configured for use in either of said first and second stapling devices, wherein said staple cartridge comprises:
  a cartridge body comprising a longitudinal slot and a deck surface;
  a plurality of staple pockets opening through said deck surface;
  a staple removably stored in each said staple pocket; and
  a sled movable through said cartridge body during said first and second staple firing strokes to fire said staples; and
 a retainer removably mounted to said cartridge body, wherein said retainer is supported on said deck surface when attached to said cartridge body to form a cartridge assembly, wherein said retainer comprises an authentication key that is configured to defeat said first jaw lockout by moving said first jaw lockout arm out of a first jaw locking position to a first jaw closure position wherein said first jaw is movable from said first open position to said first closed position when said cartridge assembly is seated in said first stapling device, and wherein said authentication key is further configured to defeat said second jaw lockout by moving said second jaw lockout arm out of a second jaw locking position to a second jaw closure position wherein said second jaw is movable from said second open position to said second closed position when said cartridge assembly is seated in said second stapling device.

16. The surgical stapling system of claim 15, wherein said first frame defines a first frame axis, wherein said first jaw lockout arm is pivotally supported on a first side of said first frame axis, wherein said second frame defines a second frame axis, and wherein said second jaw lockout arm is pivotally supported on an opposite side of said second frame axis that is opposite from said first side of said first frame axis.

17. The surgical stapling system of claim 16, wherein said authentication key comprises:
 a first lockout ramp protruding from a proximal end of said retainer, wherein said first lockout ramp is configured to move said first jaw lockout arm from said first jaw locking position to said first jaw closure position when said cartridge assembly is seated in said first stapling device; and a second lockout ramp protruding from said proximal end of said retainer, wherein said second lockout ramp is configured to move said second jaw lockout arm from said second jaw locking position to said second jaw closure position when said cartridge assembly is seated in said second stapling device.

18. The surgical stapling system of claim 17, wherein said first lockout ramp comprises:

a first proximal cam surface configured to move said first jaw lockout arm from said first jaw locking position to a first intermediate position when said cartridge assembly is initially inserted into said first stapling device; and a first distal cam surface configured to engage said first jaw lockout arm when said first jaw lockout arm is in said first intermediate position, wherein said first distal cam surface moves said first jaw lockout arm from said first intermediate position to said first jaw closure position when said cartridge assembly is fully seated in said first stapling device, and wherein said second lockout ramp comprises:

a second proximal cam surface configured to move said second jaw lockout arm from said second jaw locking position to a second intermediate position when said cartridge assembly is initially inserted into said second stapling device; and a second distal cam surface configured to engage said second jaw lockout arm when said second jaw lockout arm is in said second intermediate position, wherein said second distal cam surface moves said second jaw lockout arm from said second intermediate position to said second jaw closure position when said cartridge assembly is fully seated in said second stapling device.

19. The surgical stapling system of claim 18, wherein said first proximal cam surface is proximal to said first distal cam surface and vertically offset therefrom, and wherein said second proximal cam surface is proximal to said second distal cam surface and vertically offset therefrom.

20. A retainer for use with a surgical staple cartridge configured for use with a first surgical stapling device comprising a first jaw and a first frame, wherein the first jaw is movable relative to the first frame between a first open position and a first closed position, wherein the staple cartridge comprises a cartridge body comprising a longitudinal slot, a deck surface, a plurality of staple pockets opening through the deck surface, a staple removably stored within each staple pocket, and a sled configured to fire the staples from the cartridge body when driven by a first firing member of the first surgical stapling device, wherein the first surgical stapling device further comprises a first lockout arm movable from a first jaw locking position wherein the first lockout arm prevents the first jaw from being moved from the first open position to the first closed position to a first jaw closure position wherein the first jaw is movable from the first open position to the first closed position, and wherein said retainer comprises:

a retainer body configured for removable attachment to the cartridge body, wherein said retainer body is sized to cover the deck surface and the staple pockets to form a cartridge assembly; and a first authentication ramp configured to move the first lockout arm from the first jaw locking position to the first jaw closure position when the cartridge assembly is seated in the first surgical stapling device.

21. The retainer of claim 20, wherein said first authentication ramp comprises:

a first proximal cam surface configured to engage the first lockout arm when the cartridge assembly is initially inserted into the first surgical stapling device, wherein said first proximal cam surface moves the first lockout arm from the first jaw locking position to a first intermediate position; and a first distal cam surface configured to engage the first lockout arm when the first lockout arm is in the first intermediate position, wherein said first distal cam surface moves the first lockout arm from the first intermediate position to the first jaw closure position when the cartridge assembly is seated in the first frame.

22. The retainer of claim 20, wherein the staple cartridge is configured for use with a second surgical stapling device comprising a second jaw, a second frame, and a second lockout arm, wherein the second jaw is movable relative to the second frame between a second open position and a second closed position, wherein the second lockout arm is movable from a second jaw locking position to a second jaw closure position wherein the second jaw is movable from the second open position to the second closed position, wherein said retainer further comprises a second authentication ramp protruding from a proximal end of said retainer body, and wherein said second authentication ramp is configured to move the second lockout arm from the second jaw locking position to the second jaw closure position when the cartridge assembly is seated in the second surgical stapling device.

23. The retainer of claim 22, wherein the first frame defines a first frame axis, wherein the first lockout arm is pivotally supported on a first side of the first frame axis, wherein the second frame defines a second frame axis, wherein the second lockout arm is pivotally supported on an opposite second side of the second frame axis, wherein said retainer defines a retainer axis that is vertically aligned with the first frame axis when the cartridge assembly is supported in the first frame, wherein said retainer axis is vertically aligned with the second frame axis when the cartridge assembly is supported in the second frame, wherein said first authentication ramp is located on a first side of said retainer axis, and wherein said second authentication ramp is located on a second side of said retainer axis.

24. The retainer of claim 22, wherein said first authentication ramp comprises:

a first proximal cam surface configured to engage the first lockout arm when the cartridge assembly is initially inserted into the first surgical stapling device, wherein said first proximal cam surface moves the first lockout arm from said first jaw locking position to a first intermediate position; and a first distal cam surface configured to engage the first lockout arm when the first lockout arm is in the first intermediate position, wherein said first distal cam surface moves the first lockout arm from the first intermediate position to the first jaw closure position when the cartridge assembly is seated in the first frame, and wherein said second authentication ramp comprises:

a second proximal cam surface configured to engage the second lockout arm when the cartridge assembly is initially inserted into the second surgical stapling device, wherein said second proximal cam surface moves the second lockout arm from the second jaw locking position to a second intermediate position; and a second distal cam surface configured to engage the second lockout arm when the second lockout arm is in the second intermediate position, wherein said second distal cam surface moves the second lockout arm from the second intermediate position to the second jaw closure position when the cartridge assembly is seated in the second frame.

25. The retainer of claim 24, wherein said first proximal cam surface is proximal to said first distal cam surface and vertically offset therefrom, and wherein said second proximal cam surface is proximal to said second distal cam surface and vertically offset therefrom.

* * * * *